(12) United States Patent
Wilcox et al.

(10) Patent No.: US 11,221,340 B2
(45) Date of Patent: Jan. 11, 2022

(54) LUNG CANCER BIOMARKERS AND USES THEREOF

(71) Applicant: SomaLogic, Inc., Boulder, CO (US)

(72) Inventors: Sheri K. Wilcox, Longmont, CO (US);
Deborah Ayers, Broomfield, CO (US);
Nebojsa Janjic, Boulder, CO (US);
Larry Gold, Boulder, CO (US);
Michael Riel-Mehan, San Marcos, CA (US); Thale Jarvis, Boulder, CO (US)

(73) Assignee: SomaLogic, Inc., Boulder, CO (US)

( * ) Notice: Subject to any disclaimer, the term of this patent is extended or adjusted under 35 U.S.C. 154(b) by 326 days.

(21) Appl. No.: 15/993,132

(22) Filed: May 30, 2018

(65) Prior Publication Data
US 2018/0275143 A1    Sep. 27, 2018

Related U.S. Application Data

(63) Continuation of application No. 13/808,751, filed as application No. PCT/US2011/043595 on Jul. 11, 2011, now abandoned.
(Continued)

(51) Int. Cl.
*G01N 33/68* (2006.01)
*C12Q 1/6886* (2018.01)
(Continued)

(52) U.S. Cl.
CPC ....... *G01N 33/6893* (2013.01); *C12Q 1/6886* (2013.01); *G01N 33/57423* (2013.01);
(Continued)

(58) Field of Classification Search
CPC ......... G01N 33/6893; G01N 33/57423; C12Q 1/6886; C12Q 2600/106; C12Q 2600/112; C12Q 2600/156; C12Q 2600/16
See application file for complete search history.

(56) References Cited

U.S. PATENT DOCUMENTS 5,660,985 A    8/1997 Pieken et al.
6,004,267 A    12/1999 Tewari et al.
(Continued)

FOREIGN PATENT DOCUMENTS

CA    2648382    4/2008
CA    2734535    8/2018
(Continued)

OTHER PUBLICATIONS

Acosta et al. (2000) PNAS 97(10):5450-5455 "Molecular basis for a link between complement and the vascular complications of diabetes".
(Continued)

*Primary Examiner* — Jeremy C Flinders
(74) *Attorney, Agent, or Firm* — Leydig, Voit & Mayer, Ltd.

(57) ABSTRACT

The present application includes biomarkers, methods, devices, reagents, systems, and kits for the detection and diagnosis of lung cancer. In one aspect, the application provides biomarkers that can be used alone or in various combinations to diagnose lung cancer or permit the differential diagnosis of pulmonary nodules as benign or malignant. In another aspect, methods are provided for diagnosing lung cancer in an individual, where the methods include detecting, in a biological sample from an individual, at least one biomarker value corresponding to at least one biomarker selected from the group of biomarkers provided in Table 18, Table 20, or Table 21, wherein the individual is classified as having lung cancer, or the likelihood of the individual having lung cancer is determined, based on the at least one biomarker value.

5 Claims, 36 Drawing Sheets

Related U.S. Application Data

(60) Provisional application No. 61/444,947, filed on Feb. 21, 2011, provisional application No. 61/363,122, filed on Jul. 9, 2010.

(51) Int. Cl.
*G01N 33/574* (2006.01)
*G16B 20/00* (2019.01)
*G16B 99/00* (2019.01)
*G16B 20/20* (2019.01)
*G16B 25/10* (2019.01)
*G16B 40/30* (2019.01)
*G16B 25/00* (2019.01)
*G16B 40/00* (2019.01)

(52) U.S. Cl.
CPC ............ *G16B 20/00* (2019.02); *G16B 20/20* (2019.02); *G16B 25/10* (2019.02); *G16B 40/30* (2019.02); *G16B 99/00* (2019.02); *C12Q 2600/106* (2013.01); *C12Q 2600/112* (2013.01); *C12Q 2600/156* (2013.01); *C12Q 2600/16* (2013.01); *G16B 25/00* (2019.02); *G16B 40/00* (2019.02)

(56) References Cited

U.S. PATENT DOCUMENTS

| | | |
|---|---|---|
| 6,335,170 B1 | 1/2002 | Orntoft et al. |
| 6,631,330 B1 | 10/2003 | Poynard |
| 7,081,340 B2 | 7/2006 | Baker et al. |
| 7,090,983 B1 | 8/2006 | Muramatsu et al. |
| 7,189,507 B2 | 3/2007 | Mack et al. |
| 7,521,195 B1 | 4/2009 | Joseloff et al. |
| 7,526,387 B2 | 4/2009 | Baker et al. |
| 7,569,345 B2 | 8/2009 | Cobleigh et al. |
| 7,582,441 B1 | 9/2009 | Ruben et al. |
| 7,622,251 B2 | 11/2009 | Baker et al. |
| 7,695,913 B2 | 4/2010 | Cowens et al. |
| 7,723,033 B2 | 5/2010 | Baker et al. |
| 7,767,391 B2 | 8/2010 | Scott et al. |
| 7,807,392 B1 | 10/2010 | Domon |
| 7,838,224 B2 | 11/2010 | Baker et al. |
| 7,858,304 B2 | 12/2010 | Baker et al. |
| 7,862,995 B2 | 1/2011 | Bacus et al. |
| 7,871,769 B2 | 1/2011 | Baker et al. |
| 7,888,019 B2 | 2/2011 | Kiefer et al. |
| 7,892,760 B2 | 2/2011 | Birse et al. |
| 7,930,104 B2 | 4/2011 | Baker et al. |
| 7,939,261 B2 | 5/2011 | Baker et al. |
| 7,947,447 B2 | 5/2011 | Zichi et al. |
| 8,008,003 B2 | 8/2011 | Baker et al. |
| 8,014,957 B2 | 9/2011 | Radich et al. |
| 8,019,552 B2 | 9/2011 | Dai et al. |
| 8,026,060 B2 | 9/2011 | Watson et al. |
| 8,029,995 B2 | 10/2011 | Watson et al. |
| 8,034,565 B2 | 10/2011 | Cobleigh et al. |
| 8,067,178 B2 | 11/2011 | Baker et al. |
| 8,071,286 B2 | 12/2011 | Baker et al. |
| 8,450,069 B2 | 5/2013 | Goix et al. |
| 8,541,183 B2 | 9/2013 | Streeper et al. |
| 8,632,983 B2 | 1/2014 | Haab et al. |
| 9,103,837 B2 | 8/2015 | Nikrad et al. |
| 9,423,403 B2 | 8/2016 | Nikrad et al. |
| 2003/0134343 A1 | 7/2003 | Batra et al. |
| 2003/0144476 A1 | 7/2003 | Agarwal et al. |
| 2003/0215895 A1 | 11/2003 | Wennerberg et al. |
| 2003/0224501 A1 | 12/2003 | Young et al. |
| 2004/0009489 A1 | 1/2004 | Golub et al. |
| 2004/0219572 A1 | 11/2004 | Chen et al. |
| 2004/0241653 A1 | 12/2004 | Feinstein et al. |
| 2005/0069963 A1 | 3/2005 | Loskin et al. |
| 2005/0095611 A1 | 5/2005 | Chan et al. |
| 2005/0181375 A1 | 8/2005 | Aziz et al. |
| 2005/0214826 A1 | 9/2005 | Mor et al. |
| 2005/0260639 A1 | 11/2005 | Nakamura et al. |
| 2005/0260697 A1 | 11/2005 | Wang et al. |
| 2006/0019256 A1 | 1/2006 | Clarke et al. |
| 2006/0223127 A1 | 10/2006 | Yip et al. |
| 2007/0099209 A1 | 5/2007 | Clarke et al. |
| 2007/0105142 A1 | 5/2007 | Wilhelm et al. |
| 2007/0178108 A1 | 8/2007 | Dillion et al. |
| 2007/0178504 A1 | 8/2007 | Colpitts et al. |
| 2007/0212721 A1 | 9/2007 | Fischer et al. |
| 2007/0275422 A1 | 11/2007 | Lowe et al. |
| 2008/0057590 A1 | 3/2008 | Urdea et al. |
| 2008/0090258 A1 | 4/2008 | Lokshin |
| 2008/0171319 A1 | 7/2008 | Urdea et al. |
| 2008/0305962 A1 | 12/2008 | Wirtz et al. |
| 2009/0004667 A1* | 1/2009 | Zichi .................. C12Q 1/6816 435/6.11 |
| 2009/0005268 A1 | 1/2009 | Berlin |
| 2009/0023149 A1 | 1/2009 | Knudsen et al. |
| 2009/0042229 A1 | 2/2009 | Folkman et al. |
| 2009/0053189 A1 | 2/2009 | Glimcher et al. |
| 2009/0098549 A1* | 4/2009 | Schneider ............ C12Q 1/6811 435/6.11 |
| 2009/0104617 A1 | 4/2009 | Gordon et al. |
| 2009/0176228 A1 | 7/2009 | Birse et al. |
| 2009/0197285 A1* | 8/2009 | Hirschowitz .... G01N 33/57423 435/7.23 |
| 2009/0233286 A1 | 9/2009 | Segara et al. |
| 2010/0009386 A1* | 1/2010 | Streeper ........... G01N 33/57423 435/7.2 |
| 2010/0070191 A1 | 3/2010 | Gold et al. |
| 2010/0130527 A1 | 5/2010 | Lehrer et al. |
| 2010/0131432 A1 | 5/2010 | Kennedy et al. |
| 2010/0184034 A1 | 7/2010 | Bankaitis-Davis et al. |
| 2010/0221752 A2 | 9/2010 | Gold et al. |
| 2010/0267041 A1 | 10/2010 | Shuber et al. |
| 2010/0279419 A1 | 11/2010 | Streckfus et al. |
| 2011/0003707 A1 | 1/2011 | Goix et al. |
| 2011/0015865 A1 | 1/2011 | Rosenberg et al. |
| 2011/0059103 A1 | 3/2011 | Briessen et al. |
| 2011/0144914 A1 | 6/2011 | Harrington et al. |
| 2011/0236903 A1 | 9/2011 | McClelland et al. |
| 2011/0256545 A1* | 10/2011 | Guo ..................... C12Q 1/6886 435/6.13 |
| 2012/0040861 A1 | 2/2012 | Williams et al. |
| 2012/0077695 A1 | 3/2012 | Ostroff et al. |
| 2012/0101002 A1 | 4/2012 | Riel-Mehan et al. |
| 2012/0143805 A1 | 6/2012 | Gold et al. |
| 2012/0165217 A1 | 6/2012 | Gold et al. |
| 2012/0252039 A1* | 10/2012 | Cho ................. G01N 33/57423 435/7.92 |
| 2013/0085079 A1 | 4/2013 | Gill et al. |
| 2014/0073521 A1 | 3/2014 | Ostroff et al. |
| 2014/0073522 A1 | 3/2014 | Williams et al. |
| 2018/0201641 A1 | 7/2018 | Rohloff et al. |

FOREIGN PATENT DOCUMENTS

| | | |
|---|---|---|
| CN | 102762743 A | 10/2012 |
| EP | 2771692 | 4/2018 |
| JP | 2006-53113 A | 2/2006 |
| JP | 2010-534852 | 11/2010 |
| JP | 2011-510297 | 3/2011 |
| KR | 10-2006-0031809 | 4/2006 |
| RU | 2376372 | 12/2009 |
| WO | WO 2002/086443 | 10/2002 |
| WO | WO 2004/031412 | 4/2004 |
| WO | WO 2004/075713 | 9/2004 |
| WO | WO 2005/043163 | 5/2005 |
| WO | WO 2005/103281 | 11/2005 |
| WO | WO 2006/016697 A1 | 2/2006 |
| WO | WO 2006/022895 | 3/2006 |
| WO | WO 2007/013665 A2 | 2/2007 |
| WO | WO 2007/045996 A1 | 4/2007 |
| WO | WO 2007/109571 | 9/2007 |
| WO | WO 2008/046911 A2 | 4/2008 |
| WO | WO 2008/048371 | 4/2008 |
| WO | WO 2008/063413 A2 | 5/2008 |
| WO | WO 2008/117067 | 10/2008 |

(56) References Cited

FOREIGN PATENT DOCUMENTS

| | | |
|---|---|---|
| WO | WO 2008/144034 | 11/2008 |
| WO | WO 2009/036123 | 3/2009 |
| WO | WO 2009/091581 | 7/2009 |
| WO | WO 2009/103542 A1 | 8/2009 |
| WO | WO 2010/030697 | 3/2010 |
| WO | WO 2010/049538 | 5/2010 |
| WO | WO 2010/142713 | 12/2010 |
| WO | WO 2010/144358 | 12/2010 |
| WO | WO 2011/022552 | 2/2011 |
| WO | WO 2011/050328 | 4/2011 |
| WO | WO 2011/059721 | 5/2011 |
| WO | WO 2011/068839 | 6/2011 |
| WO | WO 2011/072177 | 6/2011 |
| WO | WO 2011/094483 | 8/2011 |
| WO | WO 2011/100472 A1 | 8/2011 |
| WO | WO 2011/109440 | 9/2011 |
| WO | WO 2011/127219 | 10/2011 |
| WO | WO 2012/021795 | 2/2012 |
| WO | WO 2012/149550 | 11/2012 |
| WO | WO 2013/049674 | 4/2013 |
| WO | WO 2013/062515 | 5/2013 |

OTHER PUBLICATIONS

Arikan et al. (2005) Journal of Cellular Physiology 204:139-145 "Induction of Macrophage Elastase (MMP-12) Gene Expression by Statins".
Bagnato et al. (2007) Molecular & Cellular Proteomics 6.6 1088-1102 "Proteomics Analysis of Human Coronary Atherosclerotic Plaque".
Boroumand et al., (2011) "Association between angiographically assessed coronary artery disease and serum levels of prostate specific antigen", PSA and CAD, Abstract, Clin.Lab. 57(11-12):975-81.
Carter (2012) Scientifica vol. 2012, Article ID 402783: 1-14 "Complement Activation: An Emerging Player in the Pathogenesis of Cardiovascular Disease."
Chiao et al., (publicly available Apr. 2010) "In vivo Matrix Metalloproteinase-7 Substrates Identified in the Left Ventricle Post-Myocardial Infarction Using Proteomics", J Proteome Res. (May 2010) 9(5):2649-2657.
Chieng-Yane et al., (2010) "Protease activated Receptor-1 antagonist, F 16618 reduces arterial restenosis by down-regulation of TNFα and MMP7 expression, and migration and proliferation of vascular smooth muscle cells", JPET #175182.
Clark et al. (2001) American Heart Journal 141(4):684-690 "Serum complement activation in congestive heart failure".
Das et al., (May 2010) "Plasminogen and Its Receptors as Regulators of Cardiovascular Inflammatory Responses", Trends Cardiovasc Med. 20(4):120-124.
De Sutter et al. (publicly available Jul. 2010) Journal of Molecular and Cellular Cardiology (Nov. 2010) 49:894-896 "Cardiovascular determinants and prognostic significance of CC Chemokine Ligand-18 (CCL18/PARC) in patients with stable coronary artery disease".
De Weger et al., (May 2011) "Proteomic profiling of the human failing heart after left ventricular assist device support", The Journal of Heart and Lung Transplantation, 30(5):497-506.
Farlow et al., (Sep. 2010) British Journal of Cancer 103, "A Multi-analtye Serum Test for the Detection of Non-small Cell Lung Cancer", pp. 1221-1228.
Fischetti et al. (2006) Autoimmunity 39(5):417-428 "Cross-talk between the complement system and endothelial cells in physiologic conditions and in vascular diseases".
Gold et al. (Posted Jun. 2010) Nature Proceedings "Aptamer-based multiplexed proteomic technology for biomarker discovery," Available online at http://precedings.nature.com/documents/4538/version/1/files/npre20104538-1.pdf, 77 pp.
Gronski et al. (1997) The Journal of Biological Chemistry 272(18):12189-12194 "Hydrolysis of a Broad Spectrum of Extracellular Matrix Proteins by Human Macrophage Elastase".
Hak et al. (2001) The Journal of Clinical Endocrinology & Metabolism 86(9): 4398-4405 "Markers of Inflammation and Cellular Adhesion Molecules in Relation to Insulin Resistance in Nondiabetic Elderly: The Rotterdam Study".
Halberg et al. (2008) Endocrinol. Metab. Clin. North Am. 37(3):1-15 "The Adipocyte as an Endocrine Cell".
Hanash et al. (2008) Nature 452:571-579 "Mining the plasma proteome for cancer biomarkers".
Haskard et al. (2008) Current Opinion in Lipidology 19:478-482 "The role of complement in atherosclerosis".
Human Protoarray (2009) V2.0 Content List.
Invitrogen (2009) Immune Response Biomarker Profiling Service Report, p. 1-33, "Immune Response Biomarker Profiling on ProtoArray Human Protein Microarrays for Our Favorite Customer".
Iribarren et al., (Jun. 2011) "Circulating Angiopoietins-1 and -2, Angiopoietin Receptor Tie-2 and Vascular Endothelial Growth Factor-A as Biomarkers of Acute Myocardial Infarction: a Prospective Nested Case-Control Study", BMC Cardiovascular Disorders 11:31, 9 pp.
Jguirim-Souissi et al. (2007) American Journal of Cardiology 100:23-27 "Plasma Metalloproteinase-12 and Tissue Inhibitor of Metalloproteinase-1 Levels and Presence, Severity, and Outcome of Coronary Artery Disease".
Keefe et al. (Jul. 2010) Nature Reviews Drug Discovery 9:537-550 "Aptamers as therapeutics".
Kim et al. (2006) Clinical Immunology 118:127-136 "Membrane complement regulatory proteins".
Kraaijeveld et al. (2007) Circulation 116:1931-1941 "CC Chemokine Ligand-5 (CCL5/RANTES) and CC Chemokine Ligand-18 (CCL18/PARC) Are Specific Markers of Refractory Unstable Angina Pectoris and Are Transiently Raised During Severe Ischemic Symptoms".
Langeggen et al. (2000) Clin. Exp. Immunol. 121:69-76 "The endothelium is an extrahepatic site of synthesis of the seventh component of the complement system".
Lee et al., (publicly available Sep. 2010) "Simvastatin suppresses expression of angiogenic factors in the retinas of rats with streptozotocin-induced diabetes", Graefes Arch Clin Exp Ophthalmol (2011) 249:389-397.
Liang et al. (2006) Circulation 113:1993-2001 "Macrophage Metalloelastase Accelerates the Progression of Atherosclerosis in Transgenic Rabbits".
Mason et al. (2002) Circulation Research 91:696-703 "Statin-Induced Expression of Decay-Accelerating Factor Protects Vascular Endothelium Against Complement-Mediated Injury".
McNeill et al. (publicly available Mar. 2010) Clinical Science (Jun. 2010) 118:641-655 "Inflammatory cell recruitment in cardiovascular disease: murine models and potential clinical applications".
Monahan et al. (1980) The Journal of Biological Chemistry 255(22):10579-10582 "Binding of the Eighth Component of Human Complement to the Soluble Cytolytic Complex Is Mediated by Its β Subunit".
Nagase et al. (2006) Cardiovascular Research 69:562-573 "Structure and function of matrix metalloproteinases and TIMPs".
Page-McCaw et al. (2007) Molecular Cell Biology 8:221-233 "Matrix metalloproteinases and the regulation of tissue remodelling".
Peden et al., (publicly available Mar. 2011) "A genome-wide association study in Europeans and South Asians identifies five new loci for coronary artery disease", Nature Genetics (Apr. 2011) 43(4) 339-344.
Peden et al., "A genome-wide association study in Europeans and South Asians identifies five novel loci for coronary artery disease", Nature Genetics doi:10.1038/ng.782.
Podack et al. (1978) The Journal of Immunology 120(6):1841-1848 "The C5b-6 Complex: Formation, Isolation, and Inhibition of its Activity by Lipoprotein and the S-Protein of Human Serum".
ProtoArray (2009) Human ProtoArray 2.0 Content List, 1.
Raitoharju et al., (Jul. 2011) "miR-21, miR-210, miR-34a, and miR-146a/b are up-regulated in human atherosclerotic plaques in the Tampere Vascular Study", Atherosclerosis (Nov. 2011) 219:211-217.

(56) References Cited

OTHER PUBLICATIONS

Raitoharju et al., (2011) Supplementary tables "miR-21, miR-210, miR-34a, and miR-146a/b are up-regulated in human atherosclerotic plaques in the Tampere Vascular Study", Atherosclerosis 219:211-217.
Razuvaev et al., (publicly available Jul. 2011) "Correlations Between Clinical Variables and Gene-expression Profiles in Carotid Plaque Instability", Eur. J. Vasc. Endovasc. Surg. (Dec. 2011) 42:722-730.
Reape et al. (1999) American Journal of Pathology 154(2):365-374 "Expression and Cellular Localization of the CC Chemokines PARC and ELC in Human Atherosclerotic Plaques".
Robertson et al. (2012) BBRC 427:568-573 "Synexpression group analyses identify new functions of FSTL3, a TGFβ ligand inhibitor".
Rohatgi et al., (Oct. 2009) "Differential Associations between Soluble Cellular Adhesion Molecules and Atherosclerosis in the Dallas Heart Study: a Distinct Role for Soluble Endothelial Cell-Selective Adhesion Molecule", Arterioscler. Thromb. Vasc. Biol. 29(10):1684-1690.
Scholtes et al. (2012) J. Am. Heart Assoc. 1-12 "Carotid Atherosclerotic Plaque Matrix Metalloproteinase—12-Postive Macrophage Subpopulation Predicts Adverse Outcome After Endarterectomy".
Shlipak et al. (2008) Am. J. Med. 121(1):50-57 "Biomarkers to Predict Recurrent Cardiovascular Disease: The Heart and Soul Study."
Souza et al. (2008) Molecular Endocrinology 22(12):2689-2702 "Proteomic Identification and Functional Validation of Activins and Bone Morphogenetic Protein 11 as Candidate Novel Muscle Mass Regulators".
Speidl et al. (publicly available Dec. 2010) Journal of Thrombosis and Haemostasis (Mar. 2011) 9:428-440 "Complement in atherosclerosis: friend or foe?".
Swinnen et al., (Oct. 2009) "Absence of Thrombospondin-2 Causes Age-Related Dilated Cardiomyopathy", Circulation, Journal of the American Heart Association 120:1585-1597.
Tanner et al. (Aug. 2011) Plos One 6(8), e23609: 1-12 "Pharmacogenetic Associations of MMP9 and MMP12 Variants with Cardiovascular Disease in Patients with Hypertension."
Tedesco et al. (1997) J. Exp. Med 185(9):1619-1627 "The Cytolytically Inactive Terminal Complement Complex Activates Endothelial Cells to Express Adhesion Molecules and Tissue Factor Procoagulant Activity".
Théroux et al. (2006) Can. J. Cardiol. 22(Suppl B):18B-24B "Complement activity and pharmacological inhibition in cardiovascular disease".
Van Almen et al., (publicly available May 2011) "Absence of thromospondin-2 increases cardiomyocyte damage and matrix disruption in doxorubicin-induced cardiomyopathy", Journal of Molecular and Cellular Cardiology (Sep. 2011) 51:318-328.
Wagsater et al. (2012) International Journal of Molecular Medicine 30:288-294 "Serine protease inhibitor A3 in atherosclerosis and aneurysm disease".
Wang et al., (publicly available Apr. 2009) "Matrix Metalloproteinase-7 and ADAM-12 (a Disintegrin and Metalloproteinase-12) Define a Signaling Axis in Agonist-Induced Hypertension and Cardiac Hypertrophy", Circulation, Journal of the American Heart Association (May 2009) 119:2480-2489.
Wang et al., (2009) MMP-7 and ADAM 12 define a signaling axis in agonist-induced hypertension and cardiac hypertrophy, Supplemental Material, pp. 1-15.
Wang et al. (publicly available Dec. 2010) Biomedicine & Pharmacotherapy (Mar. 2011) 65:118-122 "The effect of atorvastatin on mRNA levels of inflammatory genes expression in human peripheral blood lymphocytes by DNA microarray".
Yasojima et al. (2001) American Journal of Pathology 158(3): 1039-1051 "Generation of C-Reactive Protein and Complement Components in Atherosclerotic Plaques".
Yasojima et al., (2001) "Complement Components, but Not Complement Inhibitors, Are Upregulated in Atherosclerotic Plaques", Arterioscler Thromb Vasc Biol. 21:1214-1219.
Zeng et al. (publicly available Oct. 2010) Journal of Proteome Research (Dec. 2010) 9(12):6440-6449 "Lung Cancer Serum Biomarker Discovery Using Glycoprotein Capture and Liquid Chromatography Mass Spectrometry".
ADAPT website by the Patterson Institute for Cancer Research, pro besets for MMP7, printed May 22, 2013.
ADAPT website by the Patterson Institute for Cancer Research, probesets for Cadherin-5 (CDH5), printed May 22, 2013.
ADAPT website by the Patterson Institute for Cancer Research, probesets for ERBB1 (EGFR), printed May 22, 2013.
ADAPT website, The Paterson Institute for Cancer Research, probesets for CDH1, printed Jan. 29, 2014.
ADAPT website, The Paterson Institute for Cancer Research, probesets for EGFR, printed Jan. 29, 2014.
ADAPT website, The Paterson Institute for Cancer Research, probesets for VEGF, printed Jan. 29, 2014.
Amonkar et al. (Feb. 2009) PLoS. One, 4(2):e4599, "Development and preliminary evaluation of a multivariate index assay for ovarian cancer".
Aspinall-O'Dea et al. (2007) Proteomics Clin. Appl. 1:1066-1079 "The pancreatic cancer proteome—recent advances and future promise".
Balasenthil et al. (2011) Cancer Prev Res 4:137-149 "A Migration Signature and Plasma Biomarker Panel for Pancreatic Adenocarcinoma".
Baron et al. (Feb. 1999) Cancer Epidemiology; Biomarkers & Prevention 8:129-137, "Serum sErB1 and Epidermal Growth Factor Levels as Tumor Biomarkers in Women with Stage III or IV Epithelial Ovarian Cancer".
Bignotti et al. (2006) Gynecol. Oncol.103:405-416, "Differential gene expression profiles between tumor biopsies and short-term primary cultures of ovarian serous carcinomas: Identification of novel molecular biomarkers for early diagnosis and therapy".
Bock et al. (Mar. 1, 2004) Proteomics 4(3):609-618 "Photoaptamer arrays applied to multiplexed proteomic analysis".
Borrebaeck (2006) Expert Opin. Biol. Ther. 6(8):833-838 "Antibody microarray-based oncoproteomics ".
Brand et al. (2007) Gut 56:1460-1469 "Advances in counselling and surveillance of patients at risk for pancreatic cancer".
Brody and Gold (2005) Reviews in Molecular Biotechnology 74:5-13, "Aptamers as therapeutic and diagnostic agents".
Bünger et al. (2010) J Cancer Res Clin Oncol "Serum biomarkers for improved diagnostic of pancreatic cancer: a current overview".
Burgess (2008) Proteomics Clin. Appl 2:1223-1233 "Prostate cancer serum biomarker discovery through proteomic analysis of alpha-2 macroglobulin protein complexes".
Cecconi et al. (2011) Proteomics 11:816-828 "Proteomics in pancreatic cancer research".
Chang et al. (Dec. 2009) Journal of Translational Medicine, 7(1):105, "Identification of a biomarker panel using a multiplex proximity ligation assay improves accuracy of pancreatic cancer diagnosis".
Charalabopoulos et al. (Mar. 2006) Experimental Oncolology 28(1):83-85, "The Clinical Significance of Soluble E-Cadherin in Nonsmall Cell Lung Cancer".
Chen et al. (2002) Molecular and Cellular Proteomics 1:304-323 "Discordant Protein and mRNA Expression in Lung Adenocarcinomas*".
Chen et al. (2005) Gastroenterology 129:1187-1197 "Pancreatic Cancer Proteome: The Proteins That Underlie Invasion, Metastasis, and Immunologic Escape".
Chen, et al. (2008) Proteome. Sci. 6:20, pp. 1-11, "Profiling of serum and tissue high abundance acute-phase proteins of patients with epithelial and germ line ovarian carcinoma".
Chu et al. (2011) Cancer Biology & Therapy 11(12):995-1000 "Diagnostic values of SCC, CEA, Cyfra21-1 and NSE for lung cancer in patients with suspicious pulmonary masses".
Diamandis, et al. (2000) Clin. Biochem. 33(7):579-583, "Human Kallikrein 6 (Zyme/Protease M/Neurosin): A new serum biomarker of ovarian carcinoma".
Douglas et al. (2010) Cancer Epidemiol Biomarkers Prev 19(9):2298-2306 "Serum IGF-I, IGF-II, IGFBP-3, and IGF-I/IGFBP-3 Molar Ratio and Risk of Pancreatic Cancer in the Prostate, Lung, Colorectal, and Ovarian Cancer Screening Trial".

(56) References Cited

OTHER PUBLICATIONS

Dowling et al. (2007) Electrophoresis 28(23):4302-4310 "2D difference gel electrophoresis of the lung squamous cell carcinoma versus normal sera demonstrates consistent alterations in the levels of ten specific proteins".
Ehmann et al. (2007) Pancreas 34:205-214 "Identification of Potential Markers for the Detection of Pancreatic Cancer Through Comparative Serum Protein Expression Profiling".
Erdogan et al. (2007) APMIS, 115, 204-209, "C-kit protein expression in uterine and ovarian mesenchymal tumours".
European Search Report dated Jan. 17, 2012 in EP 09813557.7.
European Search Report dated May 7, 2012 in EP 09819761.9.
European Search Report dated Dec. 4, 2013 in EP 11804482.5.
Fuji et al. (2004) Journal of Proteome Research 3:712-718 "Multidimensional Protein Profiling Technology and Its Application to Human Plasma Proteome".
Gao et al. (Aug. 2005) BMC Cancer 5:110 (internet pp. 1-10) "Distinctive serum protein profiles involving abundant proteins in lung cancer patients based upon antibody microarray analysis".
Gold, L., et al. (Dec. 2010) PLoS One, 5(12): p. e15004, "Aptamer-based multiplexed proteomic technology for biomarker discovery".
Gortzak-Uzan et al. (2008) J. Proteome. Res., 7:339-351, "A proteome resource of ovarian cancer ascites: Integrated proteomic and bioinformatic analyses to identify putative biomarkers".
Granville et al. (2005) Am. J. Respir. Cell. Mol. Biol. 32:169-176, "An Overview of Lung Cancer Genomics and Proteomics".
Gray et al. (2009) J Thorac Oncol 4(3):411-425, "In arrayed ranks: array technology in the study of mesothelioma".
Great Britain Examination Report dated Feb. 7, 2012 in GB 1106053.0.
Great Britain Examination Report dated Sep. 20, 2011 in GB 1106053.0.
Great Britain Search Report dated Feb. 7, 2012 in GB 1106053.0.
Greenbaum (Sep. 1, 2001) Genome Research, Cold Spring Harbor Laboratory 11(9):1463-1468, "Interrelating different types of genomic data, from proteome to secretome: 'Oming in on function'".
Grønborg et al. (2004) Journal of Proteome Research 3:1042-1055 "Comprehensive Proteomic Analysis of Human Pancreatic Juice".
Havrilesky et al. (2008) Gynecol. Oncol. 110:374-382, "Evaluation of biomarker panels for early stage ovarian cancer detection and monitoring for disease recurrence".
Heo et al. (2007) Proteomics. 7(23):4292-4302, "Identification of putative serum glycoprotein biomarkers for human lung adenocarcinoma by multilectin affinity chromatography and LC-MS/MS".
Herszényi et al. (2008) European Journal of Cancer Prevention 17(5):438-445 "Serum cathepsin B and plasma urokinase-type plasminogen activator levels in gastrointestinal tract cancers".
Hofmann (2005) Clin Cancer Res 11(3):1086-1092, "Matrix metalloproteinase-13 expression correlates with local recurrence and metastic disease in non-small cell lung cancer patients".
Hoffman (2006) Oncology Reports 16(3):587-595, "Identification and classification of differentially expressed genes in non-small cell lung, cancer by expression profiling on a global human 59.620 element oligonucleotide array".
Honda et al. (2013) Jpn J Clin Oncol 43(2)103-109, "Proteomic Approaches to the Discovery of Cancer Biomarkers for Early Detection and Personalized Medicine".
Hongsachart (2009) Electrophoresis 30:1206-1220, "Glycoproteomic analysis of WGA-bound glycoprotein biomarkers in sera from patents with lung adenocarcinoma".
Hough et al. (May 15, 2001) Cancer Research 61:3869-3876, "Coordinately Up-Regulated Genes in Ovarian Cancer".
HUGO Gene Nomenclature Committee, Symbol Report for "CNDP1", printed May 2015.
HUGO Gene Nomenclature Committee, Symbol Report for "MMP7", printed May 2015.
Ingvarsson et al. (2008) Proteomics 8:2211-2219 "Detection of pancreatic cancer using antibody microarray-based serum protein profiling".

International Preliminary Report on Patentability dated Sep. 30, 2010 in PCT/US2009/056399.
International Preliminary Report on Patentability dated Jan. 15, 2013 PCT/US2011/043595.
International Preliminary Report on Patentability dated Apr. 29, 2014 in PCT/US2011/057499.
International Search Report and Written Opinion dated Feb. 28, 2012 in PCT/US2011/057499.
International Search Report and Written Opinion dated Mar. 26, 2012 in PCT/US2011/043595.
International Search Report and Written Opinion dated Nov. 20, 2009 in PCT/US2009/056399.
Jackson et al. (Dec. 15, 2007) Clin. Cancer Res. 13(24), "Proteomic Profiling Identifies Afamin as a Potential Biomarker for ovarian cancer".
Jäger et al. (2002) British Journal of Cancer 86:858-863, "Serum levels of the angiogenic factor pleiotrophin in relation to disease stage in lung cancer patients".
Jamieson et al. (2011) Clin Cancer Res 17:3316-3331 "Tissue Biomarkers for Prognosis in Pancreatic Ductal Adenocarcinoma: A Systematic Review and Meta-analysis".
Kim et al. (2006) J. Korean Med. Sci., 21:81-85, "Expression and mutational analysis of c-kit in ovarian surface epithelial tumors".
Kioi et al. (Sep. 2006) Cancer 107(6):1407-1418, "Interleukin-13 receptor alpha2 chain: a potential biomarker and molecular target for ovarian cancer therapy".
Kojima et al. (2008) J Gastrointest Surg 12:1683-1690, "Applying Proteomic-Based Biomarker Tools for the Accurate Diagnosis of Pancreatic Cancer".
Kosanam et al. (2011) Proteomics 11:4551-4558 "Mining the malignant ascites proteome for pancreatic cancer biomarkers".
Kuhlmann et al. (2007) Cancer Epidemiol Biomarkers Prev 16(5):886-91 "Evaluation of Matrix Metalloproteinase 7 in Plasma and Pancreatic Juice as a Biomarker for Pancreatic Cancer".
Kuk et al. (2009) Mol. Cell Proteomics 8:661-669, "Mining the ovarian cancer ascites proteome for potential ovarian cancer biomarkers".
Lassus et al. (2004) Br. J. Cancer, 91:2048-2055, "Genetic alterations and protein expression of KIT and PDGFRA in serous ovarian carcinoma".
Lemos-González (Apr. 2007) British Journal of Cancer 96:1569-1578, "Alteration of the serum levels of the epidermal growth factor receptor and its ligands in patients with non-small cell lung cancer and head and neck carcinoma".
Li et al. (2006) Journal of Clinical Oncology, 24:1754-1760, "Serum Circulating Human mRNA Profiling and Its Utility for Oral Cancer Detection".
Louhimo et al. (2004) Oncology 66:126-131 "Serum HCGβ and CA 72-4 Are Stronger Prognostic Factors than CEA, CA 19-9 and CA 242 in Pancreatic Canter".
Lowe et al. (2007) PLoS ONE 2(3):e323 "Gene Expression Patterns in Pancreatic Tumors, Cells and Tissues".
Maciel et al. (2005) J. Exp. Ther. Oncol. 5:31-38, "Differential proteomic serum pattern of low molecular weight proteins expressed by adenocarcinoma lung cancer patients".
McCauley et al. (2003) Analytical Biochemistry 319:244-250 "Aptamer-based biosensor arrays for detection and quantification of biological macromolecules".
Mercer (1990) Immunol. Ser., 1990;53:39-54, "Use of Multiple Markers to Enhance Clinical Utility".
Mikolajczyk et al. (2004) Clinical Biochemistry 37:519-528, "Are multiple markers the future of prostate cancer diagnostics?".
Miller et al. (2003) Proteomics 3:56-63, "Antibody microarray profiling of human prostate cancer sera: Antibody screening and identification of potential biomarkers".
Mithani et al. (2011) Melanoma Res. 21(4):298-307 "Use of integrative epigenetic and cytogenetic analyses to identify novem tumor suppressor genes in malignant melanoma".
Mohr et al. (2004) Biochim Biophys Acta. 1688(1):43-60, "Cell protection, resistance and invasiveness of two malignant mesotheliomas as assessed by 10K-microarray".

(56) References Cited

OTHER PUBLICATIONS

Moore et al. (2008) Gynecol. Oncol.108:402-408, "The use of multiple novel tumor biomarkers for the detection of ovarian carcinoma in patients with a pelvic mass".
Mor et al. (May 24, 2005) PNAS 102(21):7677-7682, "Serum protein markers for early detection of ovarian cancer".
Niedergethmann et al. (2004) Pancreas 29(3):204-211 "Prognostic Impact of Cysteine Proteases Cathepsin B and Cathepsin L in Pancreatic Adenocarcinoma".
Nolen et al. (Jan. 2009) Gynecol. Oncol. 112(1):47-54, "A serum based analysis of ovarian epithelial tumorigenesis".
Office Action dated Apr. 25, 2013 in U.S. Appl. No. 12/556,480.
Ogata et al. (2006) J. Proteome.Res. 5:3318-3325, "Elevated levels of phosphorylated fibrinogen-alpha-isoforms and differential expression of other post-translationally modified proteins in the plasma of ovarian cancer patients".
Ohta et al. (1995) Gallbladder and Pancreas 16(5):407-412 "Mechanism and Control of Metastasis of Pancreatic Cancer—New Discovery".
Okada et al. (2006) Clin Cancer Res 12(1): 191-197 "A Novel Cancer Testis Antigen That Is Frequently Expressed in Pancreatic, Lung, and Endometrial Cancers".
Olchovsky et al. (2002) Acta Oncologica 41(2):182-187, "Elevated Insulin-Like Growth Factor-1 and Insulin-Line Growth Factor Binding Protein-2 in Malignant Pleural Effusion".
Orchekowski (2005) Cancer Res 65(23):11193-11202 "Antibody Microarray Profiling Reveals Individual and Combined Serum Proteins Associated with Pancreatic Cancer".
Orchekowski (2005) Cancer Res 65(23) Supplemental "Antibody Microarray Profiling Reveals Individual and Combined Serum Proteins Associated with Pancreatic Cancer".
Ostroff, R. (2010) Clin Cancer Res-American Assoc, for Cancer Research Journals 16(A3) "Detection of rare cancers with aptamer proteomic technology".
Ostroff et al. (2010) PLoS ONE 5(12): e15003. doi:10.1371/journal. pone.0015003, "Unlocking Biomarker Discovery: Large Scale Application of Aptamer Proteomic Technology for Early Detection of Lung Cancer".
Palmer et al. (Jul. 2008) PLoS. One., 3(7):e2633, "Systematic evaluation of candidate blood markers for detecting ovarian cancer".
Park et al. (2007) Chest 132:200-206 "Serum Angiopoietin-2 as a Clinical Marker for Lung Cancer".
Park et al. (2008) Journal of Proteome Research 7:1138-1150, "Proteomic Profiling of Endothelial Cells in Human Lung Cancer".
Patz et al. (Dec. 10, 2007) Journal of Clinical Oncology, 25(35):5578-5583, "Panel of Serum Biomarkers for the Diagnosis of Lung Cancer".
Planque et al. (Mar. 1, 2008) Clin. Cancer Res. 14(5):1355-1362, "A Multiparametric Serum Kallikrein Panel for Diagnosis of Non-Small Cell Lung Carcinoma".
Polanski et al. (2006) Biomark. Insights. 1-48, "A list of candidate cancer biomarkers for targeted proteomics".
Polanski et al. (2006) Supplement—Biomark. Insights. 1-48, "A list of candidate cancer biomarkers for targeted proteomics".
Pouniotis et al. (2005) British Society for Immunology, Clinical and Experimental Immunology 143:363-372, "Alveolar macrophage function is altered in patients with lung cancer".
Ransohoff (Feb. 16, 2005) Journal of the National Cancer Institute 97(4):315-319, "Lessons from Controversy: Ovarian Cancer Screening and Serum Proteomics".
Rosen et al. (2005) Gynecol. Oncol. 99:267-277, "Potential markers that complement expression of CA125 in epithelial ovarian cancer".
Saad et al. (2008) Cancer 113:2129-38 "Immunohistochemical Markers Associated With Brain Metastases in Patients With Nonsmall Cell Lung Carcinoma".
Salam et al. (2009) Med. Oncol. 26:161-166, "Serum levels of epidermal growth factor and HER-2 neu in non small-cell lung cancer: prognostic correlation".

Santin et al. (2004) Int. J. Cancer 112:14-25, "Gene Express Profiles in Primary Ovarian Serous papillary Tumors and Normal Ovarian Epithelium: Identification of Candidate Molecule Markers for Ovarian Cancer Diagnosis and Therapy".
Schwartz (1995) Clinica Chimica Acta 237:67-78 "Tissue cathepsins as tumor markers".
Shah et al. (Apr. 2010) J. Thorac. Cardiovasc. Surg. 139(4):984-990, "Differential matrix metalloproteinase levels in adenocarcionoma and squamous cell carcinoma of the lung".
Shen (2004) Cancer Research 64:9018-9026 "Protein Expression Profiles in Pancreatic Adenocarcinoma Compared with Normal Pancreatic Tissue and Tissue Affected by Pancreatitis as Detected by Two-Dimensional Gel Electrophoresis and Mass Spectrometry".
Shen et al. (Dec. 1, 2006) Cancer Res 2006:66(23):11194-11206, Identification and Validation of Differences in Protein Levels in Normal, Premalignant, and Malignant Lung Cells and Tissues Using High-Throughput Western Array and Immunohisochemistry.
Shih et al. (2007) Gynecol. Oncol. 105:501-507, "Ovarian cancer specific kallikrein profile in effusions".
Spira et al. (Mar. 2007) "Airwayepithelial gene expression in the diagnostic evaluation of smokers with suspect lung cancer" Nature Medicine, 13(3):361-366.
Suzuki et al. (2002) Lung Cancer 35(1): 29-34, "Serum endostatin correlates with progression and prognosis of non-small cell lung cancer".
Swidzińska et al. (2005) Rocz. Akad. Med. Bialymst 50:197-2000, "Serum endostatin levels in patients with lung carcinoma" (abstract only).
Tamura et al. (2002) The International Journal of Biological Markers 17(4):275-279, "Diagnostic value of plasma vascular endothelial growth factor as a tumor marker in patients with non-small cell lung cancer".
Tas et al. (2006) Cancer Investigation 24:576-580 "Serum Vascular Endothelial Growth Factor (VEGF) and Bcl-2 Levels in Advanced Stage Non-Small Cell Lung Cancer".
Tchagang et al. (Jan. 2008) Mol. Cancer Ther. 7(1):27-37, "Early detection of ovarian cancer using group biomarkers".
Tonary et al. (2000) Int. J. Cancer, 89:242-250, "Lack of expression of c-KIT in ovarian cancers is associated with poor prognosis".
Tsukishiro et al. (2004) Gynecol.Oncol. 96:516-519, "Use of serum secretory leukocyte protease inhibitor levels in patients to improve specificity of ovarian cancer diagnosis".
Wang et al. (2010) Zhongguo Shi Yan Xue Ye Xue Za Zhi 18(3):753-756 "Correlation of inflammatory marker and coagulation factors with deep vein thrombosis" [abstract only].
Welsh et al. (Mar. 2003) PNAS 100(6):3410-3415, "Large-scale delineation of secreted protein biomarkers overexpressed in cancer tissue and serum".
Xu et al. (2010) PLoS ONE 5(1):e13696 "A Comparative Analysis of Gene-Expression Data of Multiple Cancer Types".
Yaziji et al. (Apr. 2006) Modern pathology 19(4):514-523, "Evaluation of 12 antibodies for distinguishing epithelioid mesothelioma from adenocarcinoma: identification of a three-antibody immunohistochemical panel with maximal sensitivity and specificity".
Zeh (2005) Cancer Biomarkers 1:259-269 "Multianalyte profiling of serum cytokines for detection of pancreatic cancer".
Zelan et al. (2008) The Practical Journal of Cancer 23(4) "Common tumor biomarkers and researches on their use in detecting and diagnosing non-small cell lung cancer" [in Chinese and English translation].
Zhong et al. (2003) Cancer Detection and Prevention 27:285-290, "Antibodies to HSP70 and HSP90 in serum in non-small cell lung cancer patients".
Zhonghua (Jul. 18, 2006) Yi Xue Za Zhi. 86(27):1916-18, "The value of serum endostatin level in early diagnosis of lung cancer" (abstract only).
Ganz, et al. (2016) "Development and Validation of a Protein-Based Risk Score for Cardiovascular Outcomes Among Patients with Stable Coronary Heart Disease", *Innovations in Health Care Delivery*. 315(23): 2532-2541.
Liu et al., "Overexpression of matrix metalloproteinase-7(MMP-7) correlates with tumor proliferation,and a poor prognosis in non-small cell lung cancer", Lung Cancer, 58, pp. 384-391, 2007.

(56) References Cited

OTHER PUBLICATIONS

Prudkin et al., "Epidermal growth factor receptor abnormalities in lung cancer. Pathogenetic and clinical implications", Annals of Diagnostic Pathology, 10, pp. 306-315, 2006.

* cited by examiner

FIG. 7

```
┌─────────────────────────────────────────────────┐
│ RETRIEVE ON A COMPUTER BIOMARKER INFORMATION    │
│ FOR AN INDIVIDUAL, WHEREIN THE BIOMARKER        │
│ INFORMATION COMPRISES BIOMARKER VALUES THAT     │
│ EACH CORRESPOND TO ONE OF AT LEAST N            │
│ BIOMARKERS SELECTED FROM THE BIOMARKERS         │
│ LISTED IN TABLE 1                               │
└─────────────────────────────────────────────────┘ — 3004
                        │
                        ▼
        ┌────────────────────────────────┐
        │ PERFORM WITH THE COMPUTER A    │
        │ CLASSIFICATION OF EACH OF THE  │
        │ BIOMARKER VALUES               │
        └────────────────────────────────┘ — 3008
                        │
                        ▼
        ┌────────────────────────────────┐
        │ INDICATE A LIKELIHOOD THAT THE │
        │ INDIVIDUAL HAS LUNG CANCER     │
        │ BASED UPON A PLURALITY OF      │
        │ CLASSIFICATIONS                │
        └────────────────────────────────┘ — 3012
```

3000

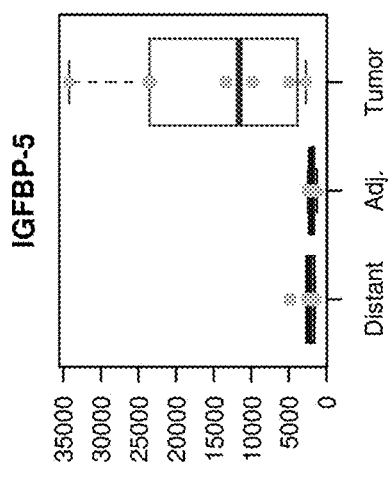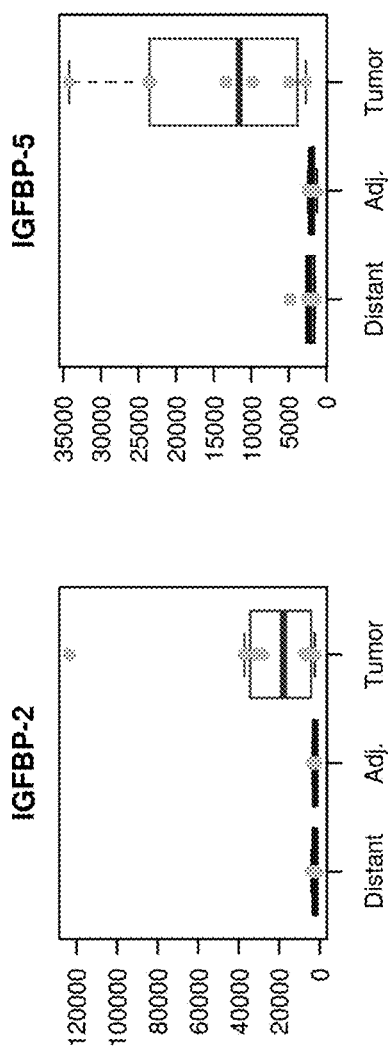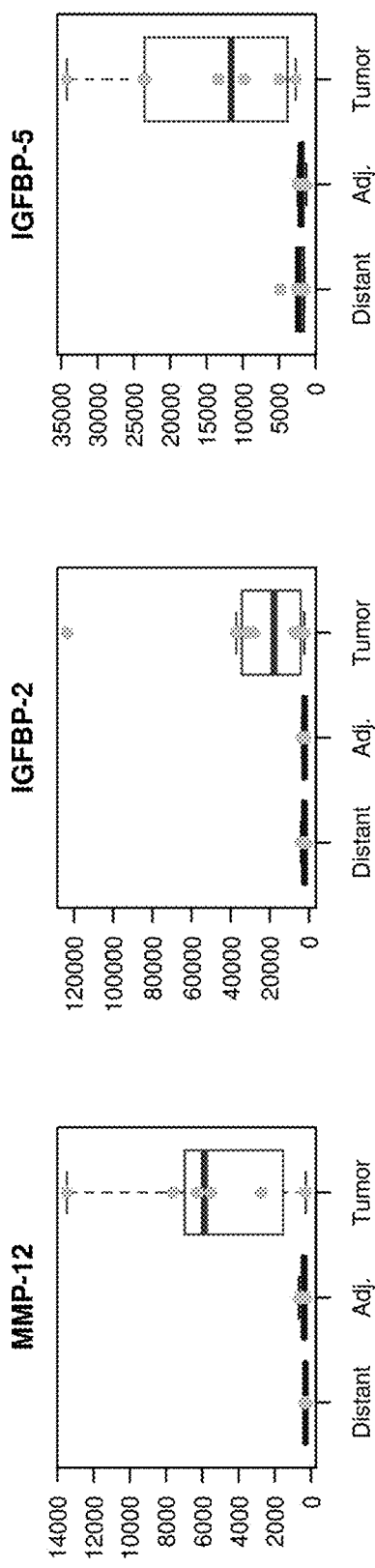
FIG. 23A
FIG. 23B
FIG. 23C
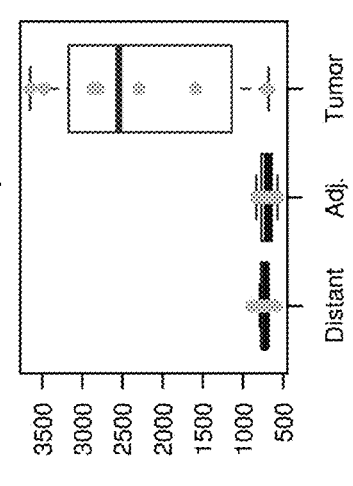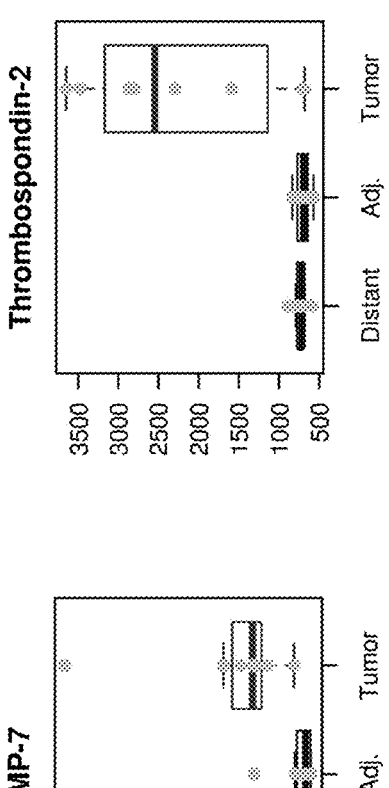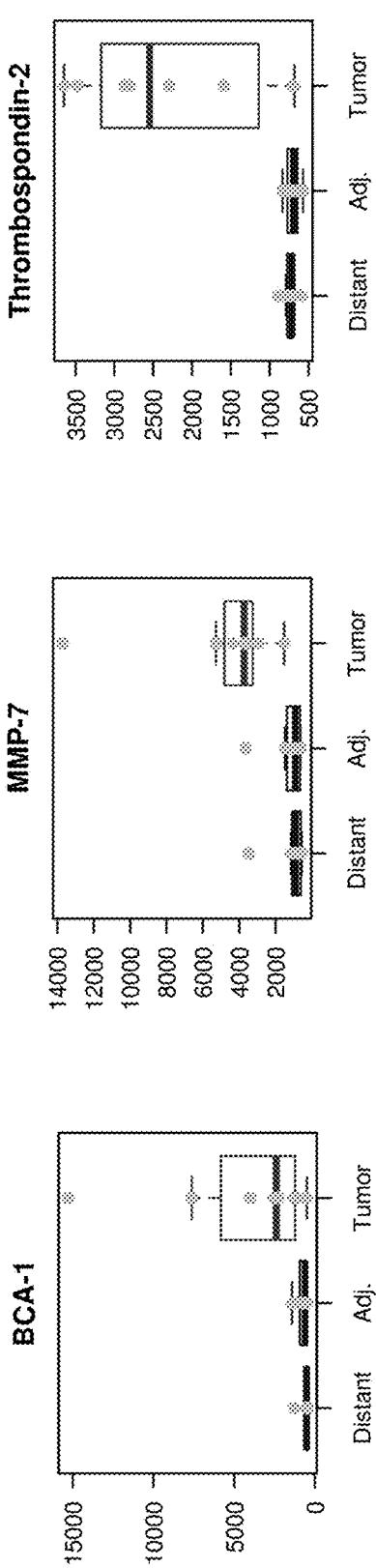
FIG. 23D
FIG. 23E
FIG. 23F

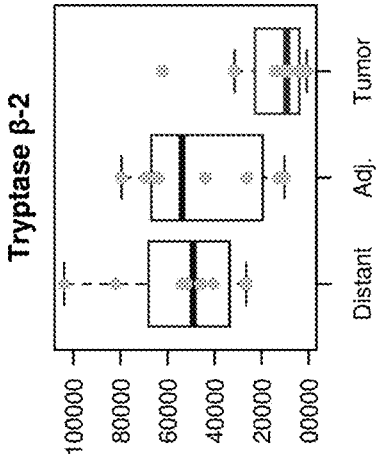
FIG. 24A
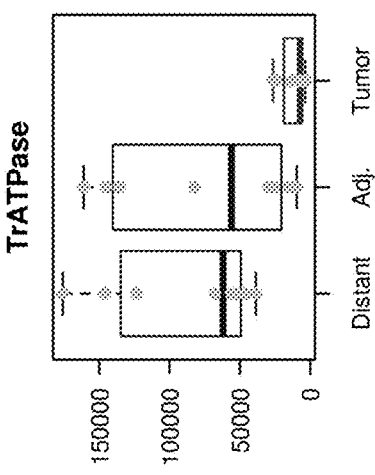
FIG. 24B
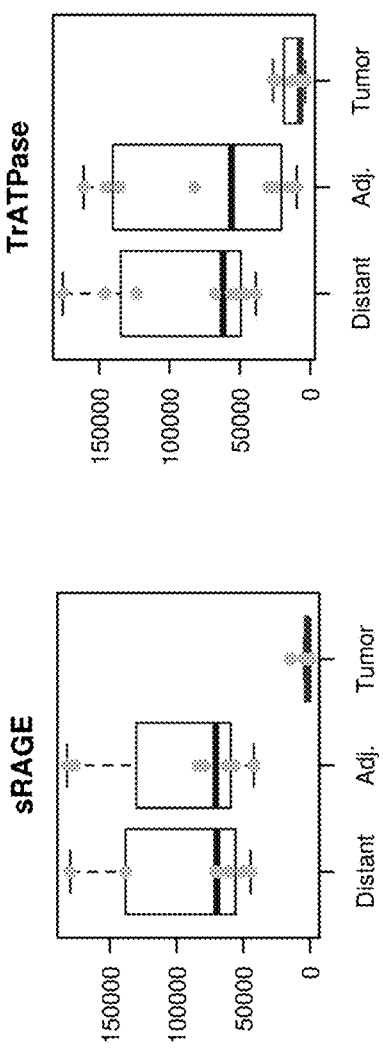
FIG. 24C
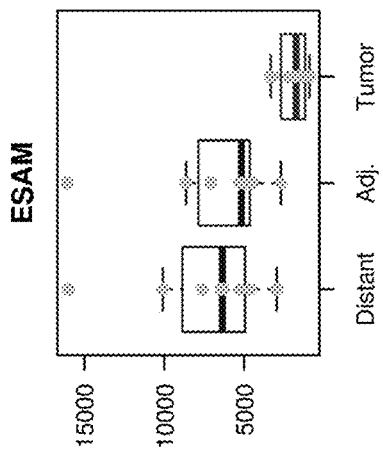
FIG. 24D
FIG. 24E
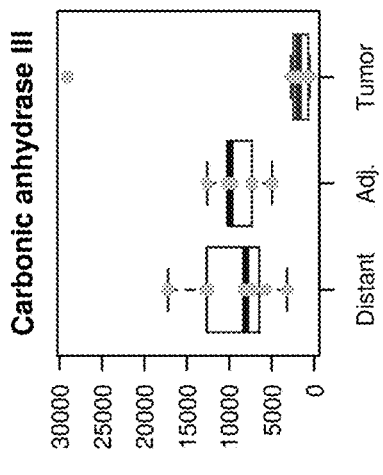
FIG. 24F

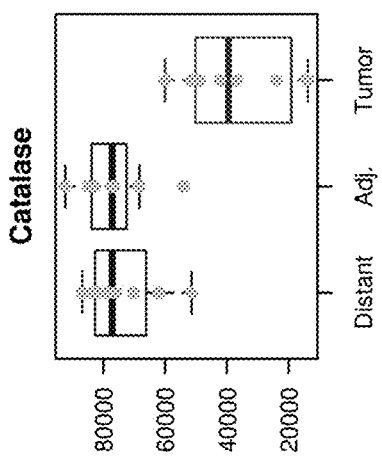
FIG. 24M
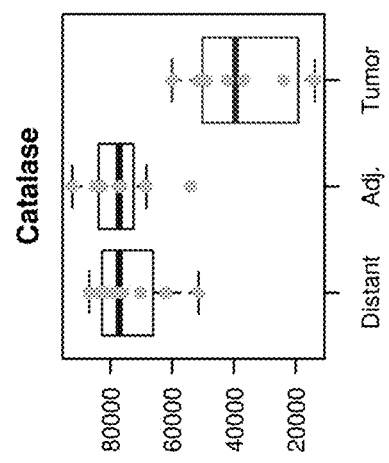
FIG. 24N
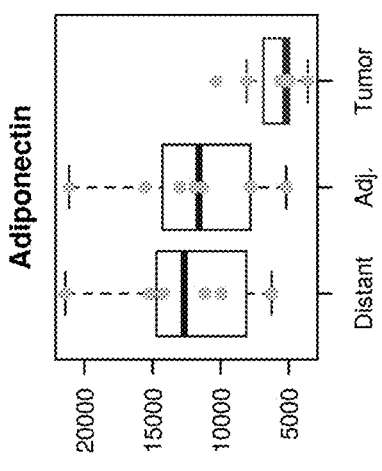
FIG. 24O
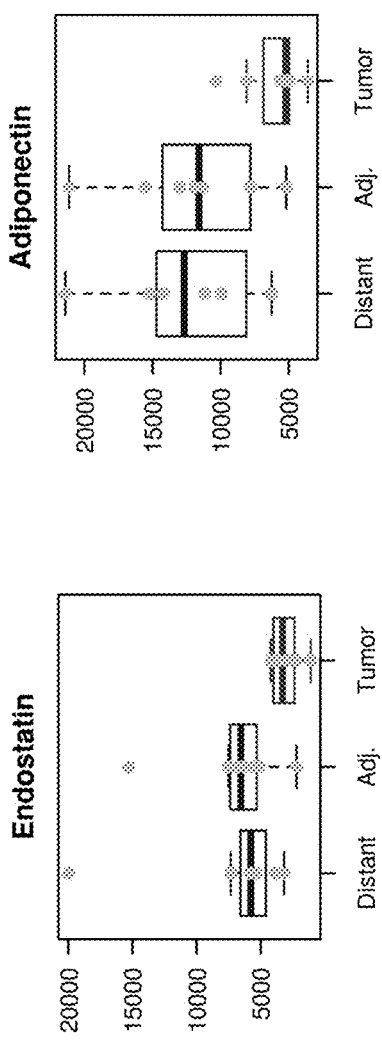
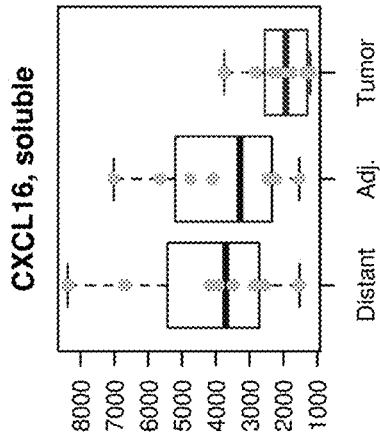
FIG. 24P

LUNG CANCER BIOMARKERS AND USES THEREOF

RELATED APPLICATIONS

This application is a continuation application of U.S. application Ser. No. 13/808,751, filed Jan. 7, 2013, which is a 35 U.S.C. § 371 national phase application of PCT/US2011/043595, filed Jul. 11, 2011, which claims the benefit of U.S. Provisional Application Ser. No. 61/363,122, filed Jul. 9, 2010 and U.S. Provisional Application Ser. No. 61/444,947, filed Feb. 21, 2011, each of which is entitled "Lung Cancer Biomarkers and Uses Thereof". Each of these applications are incorporated herein by reference in its entirety for all purposes.

FIELD OF THE INVENTION

The present application relates generally to the detection of biomarkers and the diagnosis of cancer in an individual and, more specifically, to one or more biomarkers, methods, devices, reagents, systems, and kits for diagnosing cancer, more particularly lung cancer, in an individual.

BACKGROUND

The following description provides a summary of information relevant to the present application and is not an admission that any of the information provided or publications referenced herein is prior art to the present application.

Lung cancer remains the most common cause of cancer-related mortality. This is true for both men and women. In 2005 in the United States lung cancer accounted for more deaths than breast cancer, prostate cancer, and colon cancer combined. In that year, 107,416 men and 89,271 women were diagnosed with lung cancer, and 90,139 men and 69,078 women died from lung cancer. Among men in the United States, lung cancer is the second most common cancer among white, black, Asian/Pacific Islander, American Indian/Alaska Native, and Hispanic men. Among women in the United States, lung cancer is the second most common cancer among white, black, and American Indian/Alaska Native women, and the third most common cancer among Asian/Pacific Islander and Hispanic women. For those who do not quit smoking, the probability of death from lung cancer is 15% and remains above 5% even for those who quit at age 50-59. The annual healthcare cost of lung cancer in the U.S. alone is $95 billion.

Ninety-one percent of lung cancer caused by smoking is non-small cell lung cancer (NSCLC), which represents approximately 87% of all lung cancers. The remaining 13% of all lung cancers are small cell lung cancers, although mixed-cell lung cancers do occur. Because small cell lung cancer is rare and rapidly fatal, the opportunity for early detection is small.

There are three main types of NSCLC: squamous cell carcinoma, large cell carcinoma, and adenocarcinoma. Adenocarcinoma is the most common form of lung cancer (30%-40% and reported to be as high as 50%) and is the lung cancer most frequently found in both smokers and non-smokers. Squamous cell carcinoma accounts for 25-30% of all lung cancers and is generally found in a proximal bronchus. Early stage NSCLC tends to be localized, and if detected early it can often be treated by surgery with a favorable outcome and improved survival. Other treatment options include radiation treatment, drug therapy, and a combination of these methods.

NSCLC is staged by the size of the tumor and its presence in other tissues including lymph nodes. In the occult stage, cancer cells are found in sputum samples or lavage samples and no tumor is detectable in the lungs. In stage 0, only the innermost lining of the lungs exhibit cancer cells and the tumor has not grown through the lining. In stage IA, the cancer is considered invasive and has grown deep into the lung tissue but the tumor is less than 3 cm across. In this stage, the tumor is not found in the bronchus or lymph nodes. In stage IB, the tumor is either larger than 3 cm across or has grown into the bronchus or pleura, but has not grown into the lymph nodes. In stage IIA, the tumor is more than 3 cm across and has grown into the lymph nodes. In stage IIB, the tumor has either been found in the lymph nodes and is greater than 3 cm across or grown into the bronchus or pleura; or the cancer is not in the lymph nodes but is found in the chest wall, diaphragm, pleura, bronchus, or tissue that surrounds the heart. In stage IIIA, cancer cells are found in the lymph nodes near the lung and bronchi and in those between the lungs but on the side of the chest where the tumor is located. Stage IIIB, cancer cells are located on the opposite side of the chest from the tumor and in the neck. Other organs near the lungs may also have cancer cells and multiple tumors may be found in one lobe of the lungs. In stage IV, tumors are found in more than one lobe of the same lung or both lungs and cancer cells are found in other parts of the body.

Current methods of diagnosis for lung cancer include testing sputum for cancerous cells, chest x-ray, fiber optic evaluation of airways, and low dose spiral computed tomography (CT). Sputum cytology has a very low sensitivity. Chest X-ray is also relatively insensitive, requiring lesions to be greater than 1 cm in size to be visible. Bronchoscopy requires that the tumor is visible inside airways accessible to the bronchoscope. The most widely recognized diagnostic method is CT, but in common with X-ray, the use of CT involves ionizing radiation, which itself can cause cancer. CT also has significant limitations: the scans require a high level of technical skill to interpret and many of the observed abnormalities are not in fact lung cancer and substantial healthcare costs are incurred in following up CT findings. The most common incidental finding is a benign lung nodule.

Lung nodules are relatively round lesions, or areas of abnormal tissue, located within the lung and may vary in size. Lung nodules may be benign or cancerous, but most are benign. If a nodule is below 4 mm the prevalence is only 1.5%, if 4-8 mm the prevalence is approximately 6%, and if above 20 mm the incidence is approximately 20%. For small and medium-sized nodules, the patient is advised to undergo a repeat scan within three months to a year. For many large nodules, the patient receives a biopsy (which is invasive and may lead to complications) even though most of these are benign.

Therefore, diagnostic methods that can replace or complement CT are needed to reduce the number of surgical procedures conducted and minimize the risk of surgical complications. In addition, even when lung nodules are absent or unknown, methods are needed to detect lung cancer at its early stages to improve patient outcomes. Only 16% of lung cancer cases are diagnosed as localized, early stage cancer, where the 5-year survival rate is 46%, compared to 84% of those diagnosed at late stage, where the 5-year survival rate is only 13%. This demonstrates that relying on symptoms for diagnosis is not useful because many of them are common to other lung disease. These symptoms include a persistent cough, bloody sputum, chest pain, and recurring bronchitis or pneumonia.

Where methods of early diagnosis of cancer exist, the benefits are generally accepted by the medical community. Cancers that have widely utilized screening protocols have the highest 5-year survival rates, such as breast cancer (88%) and colon cancer (65%) versus 16% for lung cancer. However, 88% of lung cancer patients survive ten years or longer if the cancer is diagnosed at Stage 1 through screening. This demonstrates the clear need for diagnostic methods that can reliably detect early-stage NSCLC.

Progression from healthy state to disease is accompanied by changes in protein expression in affected tissues. Comparative interrogation of the human proteome in healthy and diseased tissues can offer insights into the biology of disease and lead to discovery of biomarkers for diagnostics, new targets for therapeutic intervention, and identification of patients most likely to benefit from targeted treatment. Biomarker selection for a specific disease state involves first the identification of markers that have a measurable and statistically significant difference in a disease population compared to a control population for a specific medical application. Biomarkers can include secreted or shed molecules that parallel disease development or progression and readily diffuse into the blood stream from lung tissue or from distal tissues in response to a lesion. The biomarker or set of biomarkers identified are generally clinically validated or shown to be a reliable indicator for the original intended use for which it was selected. Biomarkers can include small molecules, peptides, proteins, and nucleic acids. Some of the key issues that affect the identification of biomarkers include over-fitting of the available data and bias in the data.

A variety of methods have been utilized in an attempt to identify biomarkers and diagnose disease. For protein-based markers, these include two-dimensional electrophoresis, mass spectrometry, and immunoassay methods. For nucleic acid markers, these include mRNA expression profiles, microRNA profiles, FISH, serial analysis of gene expression (SAGE), and large scale gene expression arrays.

The utility of two-dimensional electrophoresis is limited by low detection sensitivity; issues with protein solubility, charge, and hydrophobicity; gel reproducibility; and the possibility of a single spot representing multiple proteins. For mass spectrometry, depending on the format used, limitations revolve around the sample processing and separation, sensitivity to low abundance proteins, signal to noise considerations, and inability to immediately identify the detected protein. Limitations in immunoassay approaches to biomarker discovery are centered on the inability of antibody-based multiplex assays to measure a large number of analytes. One might simply print an array of high-quality antibodies and, without sandwiches, measure the analytes bound to those antibodies. (This would be the formal equivalent of using a whole genome of nucleic acid sequences to measure by hybridization all DNA or RNA sequences in an organism or a cell. The hybridization experiment works because hybridization can be a stringent test for identity. Even very good antibodies are not stringent enough in selecting their binding partners to work in the context of blood or even cell extracts because the protein ensemble in those matrices have extremely different abundances.) Thus, one must use a different approach with immunoassay-based approaches to biomarker discovery—one would need to use multiplexed ELISA assays (that is, sandwiches) to get sufficient stringency to measure many analytes simultaneously to decide which analytes are indeed biomarkers. Sandwich immunoassays do not scale to high content, and thus biomarker discovery using stringent sandwich immunoassays is not possible using standard array formats. Lastly, antibody reagents are subject to substantial lot variability and reagent instability. The instant platform for protein biomarker discovery overcomes this problem.

Many of these methods rely on or require some type of sample fractionation prior to the analysis. Thus the sample preparation required to run a sufficiently powered study designed to identify/discover statistically relevant biomarkers in a series of well-defined sample populations is extremely difficult, costly, and time consuming. During fractionation, a wide range of variability can be introduced into the various samples. For example, a potential marker could be unstable to the process, the concentration of the marker could be changed, inappropriate aggregation or disaggregation could occur, and inadvertent sample contamination could occur and thus obscure the subtle changes anticipated in early disease.

It is widely accepted that biomarker discovery and detection methods using these technologies have serious limitations for the identification of diagnostic biomarkers. These limitations include an inability to detect low-abundance biomarkers, an inability to consistently cover the entire dynamic range of the proteome, irreproducibility in sample processing and fractionation, and overall irreproducibility and lack of robustness of the method. Further, these studies have introduced biases into the data and not adequately addressed the complexity of the sample populations, including appropriate controls, in terms of the distribution and randomization required to identify and validate biomarkers within a target disease population.

Although efforts aimed at the discovery of new and effective biomarkers have gone on for several decades, the efforts have been largely unsuccessful. Biomarkers for various diseases typically have been identified in academic laboratories, usually through an accidental discovery while doing basic research on some disease process. Based on the discovery and with small amounts of clinical data, papers were published that suggested the identification of a new biomarker. Most of these proposed biomarkers, however, have not been confirmed as real or useful biomarkers primarily because the small number of clinical samples tested provide only weak statistical proof that an effective biomarker has in fact been found. That is, the initial identification was not rigorous with respect to the basic elements of statistics. In each of the years 1994 through 2003, a search of the scientific literature shows that thousands of references directed to biomarkers were published. During that same time frame, however, the FDA approved for diagnostic use, at most, three new protein biomarkers a year, and in several years no new protein biomarkers were approved.

Based on the history of failed biomarker discovery efforts, mathematical theories have been proposed that further promote the general understanding that biomarkers for disease are rare and difficult to find. Biomarker research based on 2D gels or mass spectrometry supports these notions. Very few useful biomarkers have been identified through these approaches. However, it is usually overlooked that 2D gel and mass spectrometry measure proteins that are present in blood at approximately 1 nM concentrations and higher, and that this ensemble of proteins may well be the least likely to change with disease. Other than the instant biomarker discovery platform, proteomic biomarker discovery platforms that are able to accurately measure protein expression levels at much lower concentrations do not exist.

Much is known about biochemical pathways for complex human biology. Many biochemical pathways culminate in or are started by secreted proteins that work locally within the pathology, for example growth factors are secreted to stimulate the replication of other cells in the pathology, and other factors are secreted to ward off the immune system, and so on. While many of these secreted proteins work in a paracrine fashion, some operate distally in the body. One skilled in the art with a basic understanding of biochemical pathways would understand that many pathology-specific proteins ought to exist in blood at concentrations below (even far below) the detection limits of 2D gels and mass spectrometry. What must precede the identification of this relatively abundant number of disease biomarkers is a proteomic platform that can analyze proteins at concentrations below those detectable by 2D gels or mass spectrometry.

Accordingly, a need exists for biomarkers, methods, devices, reagents, systems, and kits that enable (a) the differentiation of benign pulmonary nodules from malignant pulmonary nodules; (b) the detection of lung cancer biomarkers; and (c) the diagnosis of lung cancer.

To fulfill this need, a novel aptamer-based proteomic technology for biomarker discovery, which is capable of simultaneously measuring thousands of proteins from small sample volumes of plasma or serum has been developed (see e.g., U.S. Pub. No. 2010/0070191; U.S. Pub. No. 2010/0086948, Ostroff et al., "Unlocking biomarker discovery: Large scale application of aptamer proteomic technology for early detection of lung cancer," Nature Precedings, (2010); Gold et al., "Aptamer-based multiplexed proteomic technology for biomarker discovery," Nature Precedings, (2010)). This technology, referred to as SOMAscan, is enabled by a new generation of slow off-rate aptamers (SOMAmers) that contain chemically modified nucleotides, which greatly expand the physicochemical diversity of the large randomized nucleic acid libraries from which the aptamers are selected (see U.S. Pat. No. 7,947,447). Such modifications, which are compatible with SELEX, introduce functional groups into aptamers that are often found in protein-protein interaction, antibody-antigen interactions and interactions between small-molecule drugs with their protein targets. Overall, the use of these modifications expands the range of possible aptamer targets, improves their binding properties and facilitates selection of aptamers with slow dissociation rates.

Specifically, proteins in complex matrices such as plasma are measured with a process that transforms a signature of protein concentrations into a corresponding signature of DNA aptamer concentrations, which is then quantified using a DNA microarray platform (Gold et al., "Aptamer-based multiplexed proteomic technology for biomarker discovery," Nature Precedings, (2010)). The assay leverages equilibrium binding and kinetic challenge. Both are carried out in solution, not on a surface, to take advantage of more favorable kinetics of binding and dissociation. In essence, the assay takes advantage of the dual nature of aptamers as both folded binding entities with defined shapes and unique sequences recognizable by specific hybridization probes.

The assay is capable of simultaneously measuring large numbers of proteins ranging from low to high abundance in serum. For example, samples from 1,326 subjects from four independent studies of non-small cell lung cancer (NSCLC) have been analyzed in long-term tobacco-exposed populations. More than 800 proteins in 15 µL of serum were measured and a 12-protein panel was developed that distinguishes NSCLC from controls with 91% sensitivity and 84% specificity in a training set and 89% sensitivity and 83% specificity in a blinded, independent verification set. Importantly, performance was similar for early and late stage NSCLC (Ostroff et al., Unlocking biomarker discovery: Large scale application of aptamer proteomic technology for early detection of lung cancer," Nature Precedings, (2010)).

To date, several clinical biomarker studies of human diseases, including lung cancer (U.S. Pub. No. 2010/0070191), ovarian cancer (U.S. Pub. No. 2010/0086948), and chronic kidney disease have been conducted using this method. These studies have identified novel potential disease biomarkers to each of these diseases as well as to cancer in general.

SUMMARY

The present application demonstrates the utility of the newly discovered microarray platform technology to identify disease-related biomarkers from tissue. The present application includes biomarkers, methods, reagents, devices, systems, and kits for the detection and diagnosis of cancer and more particularly, lung cancer from tissue. The biomarkers of the present application were identified using a multiplex aptamer-based assay which is described in detail in Example 6. By using the aptamer-based biomarker identification method described herein, this application describes a surprisingly large number of lung cancer biomarkers from tissue that are useful for the detection and diagnosis of lung cancer. In identifying these biomarkers, over 800 proteins from a number of individual samples were measured, some of which were at concentrations in the low femtomolar range. This is about four orders of magnitude lower than biomarker discovery experiments done with 2D gels and/or mass spectrometry.

While certain of the described lung cancer biomarkers are useful alone for detecting and diagnosing lung cancer, methods are described herein for the grouping of multiple subsets of the lung cancer biomarkers that are useful as a panel of biomarkers. Once an individual biomarker or subset of biomarkers has been identified, the detection or diagnosis of lung cancer in an individual can be accomplished using any assay platform or format that is capable of measuring differences in the levels of the selected biomarker or biomarkers in a biological sample.

However, it was only by using the aptamer-based biomarker identification method described herein, wherein over 800 separate potential biomarker values were individually screened from a large number of individuals having previously been diagnosed either as having or not having lung cancer that it was possible to identify the lung cancer biomarkers disclosed herein. This discovery approach is in stark contrast to biomarker discovery from conditioned media or lysed cells as it queries a more patient-relevant system that requires no translation to human pathology.

Thus, in one aspect of the instant application, one or more biomarkers are provided for use either alone or in various combinations to diagnose lung cancer, particularly non-small cell lung cancer (NSCLC) or permit the differential diagnosis of pulmonary nodules as benign or malignant. Exemplary embodiments include the biomarkers provided in Table 18, which as noted above, were identified using a multiplex aptamer-based assay, as described generally in Example 1 and more specifically in Example 6. The markers provided in Table 18 are useful in distinguishing benign nodules from cancerous nodules. The markers provided in Table 18 are also useful in distinguishing asymptomatic smokers from smokers having lung cancer. In one aspect the biomarker is MMP-7. In another aspect the biomarker is MMP-12.

While certain of the described lung cancer biomarkers are useful alone for detecting and diagnosing lung cancer, methods are also described herein for the grouping of multiple subsets of the lung cancer biomarkers that are each useful as a panel of two or more biomarkers. Thus, various embodiments of the instant application provide combinations comprising N biomarkers, wherein N is at least two biomarkers. In other embodiments, N is selected to be any number from 2-36 biomarkers.

In yet other embodiments, N is selected to be any number from 2-7, 2-10, 2-15, 2-20, 2-25, 2-30, 2-36. In other embodiments, N is selected to be any number from 3-7, 3-10, 3-15, 3-20, 3-25, 3-30, 3-36. In other embodiments, Nis selected to be any number from 4-7, 4-10, 4-15, 4-20, 4-25, 4-30, 4-36. In other embodiments, N is selected to be any number from 5-7, 5-10, 5-15, 5-20, 5-25, 5-30, 5-36. In other embodiments, N is selected to be any number from 6-10, 6-15, 6-20, 6-25, 6-30, 6-36. In other embodiments, N is selected to be any number from 7-10, 7-15, 7-20, 7-25, 7-30, 7-36. In other embodiments, N is selected to be any number from 8-10, 8-15, 8-20, 8-25, 8-30, 8-36. In other embodiments, N is selected to be any number from 9-15, 9-20, 9-25, 9-30, 9-36. In other embodiments, N is selected to be any number from 10-15, 10-20, 10-25, 10-30, 10-36. It will be appreciated that N can be selected to encompass similar, but higher order, ranges.

In another aspect, a method is provided for diagnosing lung cancer in an individual, the method including detecting, in a biological sample from an individual, at least one biomarker value corresponding to at least one biomarker selected from the group of biomarkers provided in Table 18, wherein the individual is classified as having lung cancer based on the at least one biomarker value.

In another aspect, a method is provided for diagnosing lung cancer in an individual, the method including detecting, in a biological sample from an individual, biomarker values that each correspond to one of at least N biomarkers selected from the group of biomarkers set forth in Table 18, wherein the likelihood of the individual having lung cancer is determined based on the biomarker values.

In another aspect, a method is provided for diagnosing lung cancer in an individual, the method including detecting, in a biological sample from an individual, biomarker values that each correspond to one of at least N biomarkers selected from the group of biomarkers set forth in Table 18, wherein the individual is classified as having lung cancer based on the biomarker values, and wherein N=2-10.

In another aspect, a method is provided for diagnosing lung cancer in an individual, the method including detecting, in a biological sample from an individual, biomarker values that each correspond to one of at least N biomarkers selected from the group of biomarkers set forth in Table 18, wherein the likelihood of the individual having lung cancer is determined based on the biomarker values, and wherein N=2-10.

In another aspect, a method is provided for screening smokers for lung cancer, the method including detecting, in a biological sample from an individual who is a smoker, at least one biomarker value corresponding to at least one biomarker selected from the group of biomarkers set forth in Table 18, wherein the individual is classified as having lung cancer, or the likelihood of the individual having lung cancer is determined, based on the at least one biomarker value.

In another aspect, a method is provided for screening smokers for lung cancer, the method including detecting, in a biological sample from an individual who is a smoker, biomarker values that each correspond to one of at least N biomarkers selected from the group of biomarkers set forth in Table 18, wherein the individual is classified as having lung cancer, or the likelihood of the individual having lung cancer is determined, based on said biomarker values, wherein N=2-10.

In another aspect, a method is provided for diagnosing that an individual does not have lung cancer, the method including detecting, in a biological sample from an individual, at least one biomarker value corresponding to at least one biomarker selected from the group of biomarkers set forth in Table 18, wherein the individual is classified as not having lung cancer based on the at least one biomarker value.

In another aspect, a method is provided for diagnosing that an individual does not have lung cancer, the method including detecting, in a biological sample from an individual, biomarker values that each corresponding to one of at least N biomarkers selected from the group of biomarkers set forth in Table 18, wherein the individual is classified as not having lung cancer based on the biomarker values, and wherein N=2-10.

In another aspect, a method is provided for diagnosing lung cancer, the method including detecting, in a biological sample from an individual, biomarker values that each correspond to a biomarker on a panel of N biomarkers, wherein the biomarkers are selected from the group of biomarkers set forth in Table 18, wherein a classification of the biomarker values indicates that the individual has lung cancer, and wherein N=3-10.

In another aspect, a method is provided for diagnosing lung cancer, the method including detecting, in a biological sample from an individual, biomarker values that each correspond to a biomarker on a panel of N biomarkers, wherein the biomarkers are selected from the group of biomarkers set forth in Table 18, wherein a classification of the biomarker values indicates that the individual has lung cancer, and wherein N=3-15.

In another aspect, a method is provided for screening smokers for lung cancer, the method including detecting, in a biological sample from an individual who is a smoker, biomarker values that each correspond to a biomarker on a panel of N biomarkers, wherein the biomarkers are selected from the group of biomarkers set forth in Table 18, wherein the individual is classified as having lung cancer, or the likelihood of the individual having lung cancer is determined, based on the biomarker values, and wherein N=3-10.

In another aspect, a method is provided for screening smokers for lung cancer, the method including detecting, in a biological sample from an individual who is a smoker, biomarker values that each correspond to a biomarker on a panel of N biomarkers, wherein the biomarkers are selected from the group of biomarkers set forth in Table 18, wherein the individual is classified as having lung cancer, or the likelihood of the individual having lung cancer is determined, based on the biomarker values, wherein N=3-15.

In another aspect, a method is provided for diagnosing an absence of lung cancer, the method including detecting, in a biological sample from an individual, biomarker values that each correspond to a biomarker on a panel of N biomarkers, wherein the biomarkers are selected from the group of biomarkers set forth in Table 18, wherein a classification of the biomarker values indicates an absence of lung cancer in the individual, and wherein N=3-10.

In another aspect, a method is provided for diagnosing an absence of lung cancer, the method including detecting, in a biological sample from an individual, biomarker values that each correspond to a biomarker on a panel of N biomarkers, wherein the biomarkers are selected from the group of biomarkers set forth in Table 18, wherein a classification of the biomarker values indicates an absence of lung cancer in the individual, and wherein N=3-15.

In another aspect, a method is provided for diagnosing lung cancer in an individual, the method including detecting, in a biological sample from an individual, biomarker values that correspond to one of at least N biomarkers selected from the group of biomarkers set forth in Table 18, wherein the individual is classified as having lung cancer based on a classification score that deviates from a predetermined threshold, and wherein N=2-10.

In another aspect, a method is provided for screening smokers for lung cancer, the method including detecting, in a biological sample from an individual who is a smoker, biomarker values that each correspond to a biomarker on a panel of N biomarkers, wherein the biomarkers are selected from the group of biomarkers set forth in Table 18, wherein the individual is classified as having lung cancer, or the likelihood of the individual having lung cancer is determined, based on a classification score that deviates from a predetermined threshold, wherein N=3-10.

In another aspect, a method is provided for screening smokers for lung cancer, the method including detecting, in a biological sample from an individual who is a smoker, biomarker values that each correspond to a biomarker on a panel of N biomarkers, wherein the biomarkers are selected from the group of biomarkers set forth in Table 18, wherein the individual is classified as having lung cancer, or the likelihood of the individual having lung cancer is determined, based on a classification score that deviates from a predetermined threshold, wherein N=3-15.

In another aspect, a method is provided for diagnosing an absence of lung cancer in an individual, the method including detecting, in a biological sample from an individual, biomarker values that correspond to one of at least N biomarkers selected from the group of biomarkers set forth in Table 18, wherein said individual is classified as not having lung cancer based on a classification score that deviates from a predetermined threshold, and wherein N=2-10.

In another aspect, a computer-implemented method is provided for indicating a likelihood of lung cancer. The method comprises: retrieving on a computer biomarker information for an individual, wherein the biomarker information comprises biomarker values that each correspond to one of at least N biomarkers, wherein N is as defined above, selected from the group of biomarkers set forth in Table 18; performing with the computer a classification of each of the biomarker values; and indicating a likelihood that the individual has lung cancer based upon a plurality of classifications.

In another aspect, a computer-implemented method is provided for classifying an individual as either having or not having lung cancer. The method comprises: retrieving on a computer biomarker information for an individual, wherein the biomarker information comprises biomarker values that each correspond to one of at least N biomarkers selected from the group of biomarkers provided in Table 18; performing with the computer a classification of each of the biomarker values; and indicating whether the individual has lung cancer based upon a plurality of classifications.

In another aspect, a computer program product is provided for indicating a likelihood of lung cancer. The computer program product includes a computer readable medium embodying program code executable by a processor of a computing device or system, the program code comprising: code that retrieves data attributed to a biological sample from an individual, wherein the data comprises biomarker values that each correspond to one of at least N biomarkers, wherein N is as defined above, in the biological sample selected from the group of biomarkers set forth in Table 18; and code that executes a classification method that indicates a likelihood that the individual has lung cancer as a function of the biomarker values.

In another aspect, a computer program product is provided for indicating a lung cancer status of an individual. The computer program product includes a computer readable medium embodying program code executable by a processor of a computing device or system, the program code comprising: code that retrieves data attributed to a biological sample from an individual, wherein the data comprises biomarker values that each correspond to one of at least N biomarkers in the biological sample selected from the group of biomarkers provided in Table 18; and code that executes a classification method that indicates a lung cancer status of the individual as a function of the biomarker values.

In another aspect, a computer-implemented method is provided for indicating a likelihood of lung cancer. The method comprises retrieving on a computer biomarker information for an individual, wherein the biomarker information comprises a biomarker value corresponding to a biomarker selected from the group of biomarkers set forth in Table 18; performing with the computer a classification of the biomarker value; and indicating a likelihood that the individual has lung cancer based upon the classification.

In another aspect, a computer-implemented method is provided for classifying an individual as either having or not having lung cancer. The method comprises retrieving from a computer biomarker information for an individual, wherein the biomarker information comprises a biomarker value corresponding to a biomarker selected from the group of biomarkers provided in Table 18; performing with the computer a classification of the biomarker value; and indicating whether the individual has lung cancer based upon the classification.

In still another aspect, a computer program product is provided for indicating a likelihood of lung cancer. The computer program product includes a computer readable medium embodying program code executable by a processor of a computing device or system, the program code comprising: code that retrieves data attributed to a biological sample from an individual, wherein the data comprises a biomarker value corresponding to a biomarker in the biological sample selected from the group of biomarkers set forth in Table 18; and code that executes a classification method that indicates a likelihood that the individual has lung cancer as a function of the biomarker value.

In still another aspect, a computer program product is provided for indicating a lung cancer status of an individual. The computer program product includes a computer readable medium embodying program code executable by a processor of a computing device or system, the program code comprising: code that retrieves data attributed to a biological sample from an individual, wherein the data comprises a biomarker value corresponding to a biomarker in the biological sample selected from the group of biomarkers provided in Table 18; and code that executes a classification method that indicates a lung cancer status of the individual as a function of the biomarker value.

In another embodiment of the instant application, exemplary embodiments include the biomarkers provided in Table 20, which as noted above, were identified using a multiplex aptamer-based assay, as described generally in Example 1 and more specifically in Example 6. The markers provided in Table 20 are useful in distinguishing benign nodules from cancerous nodules. The markers provided in Table 20 are also useful in distinguishing asymptomatic smokers from smokers having lung cancer. With reference to Table 20, N is selected to be any number from 2-25 biomarkers. The markers provided in Table 20 have been determined to be useful in both tissue and serum samples.

In yet other embodiments, N is selected to be any number from 2-7, 2-10, 2-15, 2-20, 2-25. In other embodiments, N is selected to be any number from 3-7, 3-10, 3-15, 3-20, 3-25. In other embodiments, N is selected to be any number from 4-7, 4-10, 4-15, 4-20, 4-25. In other embodiments, N is selected to be any number from 5-7, 5-10, 5-15, 5-20, 5-25. In other embodiments, N is selected to be any number from 6-10, 6-15, 6-20, 6-25. In other embodiments, N is selected to be any number from 7-10, 7-15, 7-20, 7-25. In other embodiments, N is selected to be any number from 8-10, 8-15, 8-20, 8-25. In other embodiments, N is selected to be any number from 9-15, 9-20, 9-25. In other embodiments, N is selected to be any number from 10-15, 10-20, 10-25. It will be appreciated that N can be selected to encompass similar, but higher order, ranges.

In another aspect, a method is provided for diagnosing lung cancer in an individual, the method including detecting, in a biological sample from an individual, at least one biomarker value corresponding to at least one biomarker selected from the group of biomarkers provided in Table 20, wherein the individual is classified as having lung cancer based on the at least one biomarker value.

In another aspect, a method is provided for diagnosing lung cancer in an individual, the method including detecting, in a biological sample from an individual, biomarker values that each correspond to one of at least N biomarkers selected from the group of biomarkers set forth in Table 20, wherein the likelihood of the individual having lung cancer is determined based on the biomarker values.

In another aspect, a method is provided for diagnosing lung cancer in an individual, the method including detecting, in a biological sample from an individual, biomarker values that each correspond to one of at least N biomarkers selected from the group of biomarkers set forth in Table 20, wherein the individual is classified as having lung cancer based on the biomarker values, and wherein N=2-10.

In another aspect, a method is provided for diagnosing lung cancer in an individual, the method including detecting, in a biological sample from an individual, biomarker values that each correspond to one of at least N biomarkers selected from the group of biomarkers set forth in Table 20, wherein the likelihood of the individual having lung cancer is determined based on the biomarker values, and wherein N=2-10.

In another aspect, a method is provided for screening smokers for lung cancer, the method including detecting, in a biological sample from an individual who is a smoker, at least one biomarker value corresponding to at least one biomarker selected from the group of biomarkers set forth in Table 20, wherein the individual is classified as having lung cancer, or the likelihood of the individual having lung cancer is determined, based on the at least one biomarker value.

In another aspect, a method is provided for screening smokers for lung cancer, the method including detecting, in a biological sample from an individual who is a smoker, biomarker values that each correspond to one of at least N biomarkers selected from the group of biomarkers set forth in Table 20, wherein the individual is classified as having lung cancer, or the likelihood of the individual having lung cancer is determined, based on said biomarker values, wherein N=2-10.

In another aspect, a method is provided for diagnosing that an individual does not have lung cancer, the method including detecting, in a biological sample from an individual, at least one biomarker value corresponding to at least one biomarker selected from the group of biomarkers set forth in Table 20, wherein the individual is classified as not having lung cancer based on the at least one biomarker value.

In another aspect, a method is provided for diagnosing that an individual does not have lung cancer, the method including detecting, in a biological sample from an individual, biomarker values that each corresponding to one of at least N biomarkers selected from the group of biomarkers set forth in Table 20, wherein the individual is classified as not having lung cancer based on the biomarker values, and wherein N=2-10.

In another aspect, a method is provided for diagnosing lung cancer, the method including detecting, in a biological sample from an individual, biomarker values that each correspond to a biomarker on a panel of N biomarkers, wherein the biomarkers are selected from the group of biomarkers set forth in Table 20, wherein a classification of the biomarker values indicates that the individual has lung cancer, and wherein N=3-10.

In another aspect, a method is provided for diagnosing lung cancer, the method including detecting, in a biological sample from an individual, biomarker values that each correspond to a biomarker on a panel of N biomarkers, wherein the biomarkers are selected from the group of biomarkers set forth in Table 20, wherein a classification of the biomarker values indicates that the individual has lung cancer, and wherein N=3-15.

In another aspect, a method is provided for screening smokers for lung cancer, the method including detecting, in a biological sample from an individual who is a smoker, biomarker values that each correspond to a biomarker on a panel of N biomarkers, wherein the biomarkers are selected from the group of biomarkers set forth in Table 20, wherein the individual is classified as having lung cancer, or the likelihood of the individual having lung cancer is determined, based on the biomarker values, and wherein N=3-10.

In another aspect, a method is provided for screening smokers for lung cancer, the method including detecting, in a biological sample from an individual who is a smoker, biomarker values that each correspond to a biomarker on a panel of N biomarkers, wherein the biomarkers are selected from the group of biomarkers set forth in Table 20, wherein the individual is classified as having lung cancer, or the likelihood of the individual having lung cancer is determined, based on the biomarker values, wherein N=3-15.

In another aspect, a method is provided for diagnosing an absence of lung cancer, the method including detecting, in a biological sample from an individual, biomarker values that each correspond to a biomarker on a panel of N biomarkers, wherein the biomarkers are selected from the group of biomarkers set forth in Table 20, wherein a classification of the biomarker values indicates an absence of lung cancer in the individual, and wherein N=3-10.

In another aspect, a method is provided for diagnosing an absence of lung cancer, the method including detecting, in a biological sample from an individual, biomarker values that each correspond to a biomarker on a panel of N biomarkers, wherein the biomarkers are selected from the group of biomarkers set forth in Table 20, wherein a classification of the biomarker values indicates an absence of lung cancer in the individual, and wherein N=3-15.

In another aspect, a method is provided for diagnosing lung cancer in an individual, the method including detecting, in a biological sample from an individual, biomarker values that correspond to one of at least N biomarkers selected from the group of biomarkers set forth in Table 20, wherein the individual is classified as having lung cancer based on a classification score that deviates from a predetermined threshold, and wherein N=2-10.

In another aspect, a method is provided for screening smokers for lung cancer, the method including detecting, in a biological sample from an individual who is a smoker, biomarker values that each correspond to a biomarker on a panel of N biomarkers, wherein the biomarkers are selected from the group of biomarkers set forth in Table 20, wherein the individual is classified as having lung cancer, or the likelihood of the individual having lung cancer is determined, based on a classification score that deviates from a predetermined threshold, wherein N=3-10.

In another aspect, a method is provided for screening smokers for lung cancer, the method including detecting, in a biological sample from an individual who is a smoker, biomarker values that each correspond to a biomarker on a panel of N biomarkers, wherein the biomarkers are selected from the group of biomarkers set forth in Table 20, wherein the individual is classified as having lung cancer, or the likelihood of the individual having lung cancer is determined, based on a classification score that deviates from a predetermined threshold, wherein N=3-15.

In another aspect, a method is provided for diagnosing an absence of lung cancer in an individual, the method including detecting, in a biological sample from an individual, biomarker values that correspond to one of at least N biomarkers selected from the group of biomarkers set forth in Table 20, wherein said individual is classified as not having lung cancer based on a classification score that deviates from a predetermined threshold, and wherein N=2-10.

In another aspect, a computer-implemented method is provided for indicating a likelihood of lung cancer. The method comprises: retrieving on a computer biomarker information for an individual, wherein the biomarker information comprises biomarker values that each correspond to one of at least N biomarkers, wherein N is as defined above, selected from the group of biomarkers set forth in Table 20; performing with the computer a classification of each of the biomarker values; and indicating a likelihood that the individual has lung cancer based upon a plurality of classifications.

In another aspect, a computer-implemented method is provided for classifying an individual as either having or not having lung cancer. The method comprises: retrieving on a computer biomarker information for an individual, wherein the biomarker information comprises biomarker values that each correspond to one of at least N biomarkers selected from the group of biomarkers provided in Table 20; performing with the computer a classification of each of the biomarker values; and indicating whether the individual has lung cancer based upon a plurality of classifications.

In another aspect, a computer program product is provided for indicating a likelihood of lung cancer. The computer program product includes a computer readable medium embodying program code executable by a processor of a computing device or system, the program code comprising: code that retrieves data attributed to a biological sample from an individual, wherein the data comprises biomarker values that each correspond to one of at least N biomarkers, wherein N is as defined above, in the biological sample selected from the group of biomarkers set forth in Table 20; and code that executes a classification method that indicates a likelihood that the individual has lung cancer as a function of the biomarker values.

In another aspect, a computer program product is provided for indicating a lung cancer status of an individual. The computer program product includes a computer readable medium embodying program code executable by a processor of a computing device or system, the program code comprising: code that retrieves data attributed to a biological sample from an individual, wherein the data comprises biomarker values that each correspond to one of at least N biomarkers in the biological sample selected from the group of biomarkers provided in Table 20; and code that executes a classification method that indicates a lung cancer status of the individual as a function of the biomarker values.

In another aspect, a computer-implemented method is provided for indicating a likelihood of lung cancer. The method comprises retrieving on a computer biomarker information for an individual, wherein the biomarker information comprises a biomarker value corresponding to a biomarker selected from the group of biomarkers set forth in Table 20; performing with the computer a classification of the biomarker value; and indicating a likelihood that the individual has lung cancer based upon the classification.

In another aspect, a computer-implemented method is provided for classifying an individual as either having or not having lung cancer. The method comprises retrieving from a computer biomarker information for an individual, wherein the biomarker information comprises a biomarker value corresponding to a biomarker selected from the group of biomarkers provided in Table 20; performing with the computer a classification of the biomarker value; and indicating whether the individual has lung cancer based upon the classification.

In still another aspect, a computer program product is provided for indicating a likelihood of lung cancer. The computer program product includes a computer readable medium embodying program code executable by a processor of a computing device or system, the program code comprising: code that retrieves data attributed to a biological sample from an individual, wherein the data comprises a biomarker value corresponding to a biomarker in the biological sample selected from the group of biomarkers set forth in Table 20; and code that executes a classification method that indicates a likelihood that the individual has lung cancer as a function of the biomarker value.

In still another aspect, a computer program product is provided for indicating a lung cancer status of an individual. The computer program product includes a computer readable medium embodying program code executable by a processor of a computing device or system, the program code comprising: code that retrieves data attributed to a biological sample from an individual, wherein the data comprises a biomarker value corresponding to a biomarker in the biological sample selected from the group of biomarkers provided in Table 20; and code that executes a classification method that indicates a lung cancer status of the individual as a function of the biomarker value.

In another embodiment of the instant application, exemplary embodiments include the biomarkers provided in Table 21, which were identified using a multiplex aptamer-based assay, as described generally in Example 1 and more specifically in Examples 2 and 6. The markers provided in Table 21 are useful in distinguishing benign nodules from cancerous nodules. The markers provided in Table 21 are also useful in distinguishing asymptomatic smokers from smokers having lung cancer. With reference to Table 21, N is selected to be any number from 2-86 biomarkers. All of the biomarkers included in Table 21 are useful in providing the information being sought in both tissue and serum samples.

In yet other embodiments, N is selected to be any number from 2-7, 2-10, 2-15, 2-20, 2-25, 2-30, 2-35, 2-40, 2-45, 2-50, 2-55, 2-60, 2-65, 2-70, 2-75, 2-80, or 2-86. In other embodiments, N is selected to be any number from 3-7, 3-10, 3-15, 3-20, 3-25, 3-30, 3-35, 3-40, 3-45, 3-50, 3-55, 3-60, 3-65, 3-70, 3-75, 3-80, or 3-86. In other embodiments, N is selected to be any number from 4-7, 4-10, 4-15, 4-20, 4-25, 4-30, 4-35, 4-40, 4-45, 4-50, 4-55, 4-60, 4-65, 4-70, 4-75, 4-80, or 4-86. In other embodiments, N is selected to be any number from 5-7, 5-10, 5-15, 5-20, 5-25, 5-30, 5-35, 5-40, 5-45, 5-50, 5-55, 5-60, 5-65, 5-70, 5-75, 5-80, or 5-86. In other embodiments, N is selected to be any number from 6-10, 6-15, 6-20, 6-25, 6-30, 6-35, 6-40, 6-45, 6-50, 6-55, 6-60, 6-65, 6-70, 6-75, 6-80, or 6-86. In other embodiments, N is selected to be any number from 7-10, 7-15, 7-20, 7-25, 7-30, 7-35, 7-40, 7-45, 7-50, 7-55, 7-60, 7-65, 7-70, 7-75, 7-80, or 7-86. In other embodiments, N is selected to be any number from 8-10, 8-15, 8-20, 8-25, 8-30, 8-35, 8-40, 8-45, 8-50, 8-55, 8-60, 8-65, 8-70, 8-75, 8-80, or 8-86. In other embodiments, N is selected to be any number from 9-15, 9-20, 9-25, 9-30, 9-35, 9-40, 9-45, 9-50, 9-55, 9-60, 9-65, 9-70, 9-75, 9-80, or 9-86. In other embodiments, N is selected to be any number from 10-15, 10-20, 10-25, 10-30, 10-35, 10-40, 10-45, 10-50, 10-55, 10-60, 10-65, 10-70, 10-75, 10-80, or 10-86. It will be appreciated that N can be selected to encompass similar, but higher order, ranges.

In another aspect, a method is provided for diagnosing lung cancer in an individual, the method including detecting, in a biological sample from an individual, at least one biomarker value corresponding to at least one biomarker selected from the group of biomarkers provided in Table 21, wherein the individual is classified as having lung cancer based on the at least one biomarker value.

In another aspect, a method is provided for diagnosing lung cancer in an individual, the method including detecting, in a biological sample from an individual, biomarker values that each correspond to one of at least N biomarkers selected from the group of biomarkers set forth in Table 21, wherein the likelihood of the individual having lung cancer is determined based on the biomarker values.

In another aspect, a method is provided for diagnosing lung cancer in an individual, the method including detecting, in a biological sample from an individual, biomarker values that each correspond to one of at least N biomarkers selected from the group of biomarkers set forth in Table 21, wherein the individual is classified as having lung cancer based on the biomarker values, and wherein N=2-10.

In another aspect, a method is provided for diagnosing lung cancer in an individual, the method including detecting, in a biological sample from an individual, biomarker values that each correspond to one of at least N biomarkers selected from the group of biomarkers set forth in Table 21, wherein the likelihood of the individual having lung cancer is determined based on the biomarker values, and wherein N=2-10.

In another aspect, a method is provided for screening smokers for lung cancer, the method including detecting, in a biological sample from an individual who is a smoker, at least one biomarker value corresponding to at least one biomarker selected from the group of biomarkers set forth in Table 21, wherein the individual is classified as having lung cancer, or the likelihood of the individual having lung cancer is determined, based on the at least one biomarker value.

In another aspect, a method is provided for screening smokers for lung cancer, the method including detecting, in a biological sample from an individual who is a smoker, biomarker values that each correspond to one of at least N biomarkers selected from the group of biomarkers set forth in Table 21, wherein the individual is classified as having lung cancer, or the likelihood of the individual having lung cancer is determined, based on said biomarker values, wherein N=2-10.

In another aspect, a method is provided for diagnosing that an individual does not have lung cancer, the method including detecting, in a biological sample from an individual, at least one biomarker value corresponding to at least one biomarker selected from the group of biomarkers set forth in Table 21, wherein the individual is classified as not having lung cancer based on the at least one biomarker value.

In another aspect, a method is provided for diagnosing that an individual does not have lung cancer, the method including detecting, in a biological sample from an individual, biomarker values that each corresponding to one of at least N biomarkers selected from the group of biomarkers set forth in Table 21, wherein the individual is classified as not having lung cancer based on the biomarker values, and wherein N=2-10.

In another aspect, a method is provided for diagnosing lung cancer, the method including detecting, in a biological sample from an individual, biomarker values that each correspond to a biomarker on a panel of N biomarkers, wherein the biomarkers are selected from the group of biomarkers set forth in Table 21, wherein a classification of the biomarker values indicates that the individual has lung cancer, and wherein N=3-10.

In another aspect, a method is provided for diagnosing lung cancer, the method including detecting, in a biological sample from an individual, biomarker values that each correspond to a biomarker on a panel of N biomarkers, wherein the biomarkers are selected from the group of biomarkers set forth in Table 21, wherein a classification of the biomarker values indicates that the individual has lung cancer, and wherein N=3-15.

In another aspect, a method is provided for screening smokers for lung cancer, the method including detecting, in a biological sample from an individual who is a smoker, biomarker values that each correspond to a biomarker on a panel of N biomarkers, wherein the biomarkers are selected from the group of biomarkers set forth in Table 21, wherein the individual is classified as having lung cancer, or the likelihood of the individual having lung cancer is determined, based on the biomarker values, and wherein N=3-10.

In another aspect, a method is provided for screening smokers for lung cancer, the method including detecting, in a biological sample from an individual who is a smoker, biomarker values that each correspond to a biomarker on a panel of N biomarkers, wherein the biomarkers are selected from the group of biomarkers set forth in Table 21, wherein the individual is classified as having lung cancer, or the likelihood of the individual having lung cancer is determined, based on the biomarker values, wherein N=3-15.

In another aspect, a method is provided for diagnosing an absence of lung cancer, the method including detecting, in a biological sample from an individual, biomarker values that each correspond to a biomarker on a panel of N biomarkers, wherein the biomarkers are selected from the group of biomarkers set forth in Table 21, wherein a classification of the biomarker values indicates an absence of lung cancer in the individual, and wherein N=3-10.

In another aspect, a method is provided for diagnosing an absence of lung cancer, the method including detecting, in a biological sample from an individual, biomarker values that each correspond to a biomarker on a panel of N biomarkers, wherein the biomarkers are selected from the group of biomarkers set forth in Table 21, wherein a classification of the biomarker values indicates an absence of lung cancer in the individual, and wherein N=3-15.

In another aspect, a method is provided for diagnosing lung cancer in an individual, the method including detecting, in a biological sample from an individual, biomarker values that correspond to one of at least N biomarkers selected from the group of biomarkers set forth in Table 21, wherein the individual is classified as having lung cancer based on a classification score that deviates from a predetermined threshold, and wherein N=2-10.

In another aspect, a method is provided for screening smokers for lung cancer, the method including detecting, in a biological sample from an individual who is a smoker, biomarker values that each correspond to a biomarker on a panel of N biomarkers, wherein the biomarkers are selected from the group of biomarkers set forth in Table 21, wherein the individual is classified as having lung cancer, or the likelihood of the individual having lung cancer is determined, based on a classification score that deviates from a predetermined threshold, wherein N=3-10.

In another aspect, a method is provided for screening smokers for lung cancer, the method including detecting, in a biological sample from an individual who is a smoker, biomarker values that each correspond to a biomarker on a panel of N biomarkers, wherein the biomarkers are selected from the group of biomarkers set forth in Table 21, wherein the individual is classified as having lung cancer, or the likelihood of the individual having lung cancer is determined, based on a classification score that deviates from a predetermined threshold, wherein N=3-15.

In another aspect, a method is provided for diagnosing an absence of lung cancer in an individual, the method including detecting, in a biological sample from an individual, biomarker values that correspond to one of at least N biomarkers selected from the group of biomarkers set forth in Table 21, wherein said individual is classified as not having lung cancer based on a classification score that deviates from a predetermined threshold, and wherein N=2-10.

In another aspect, a computer-implemented method is provided for indicating a likelihood of lung cancer. The method comprises: retrieving on a computer biomarker information for an individual, wherein the biomarker information comprises biomarker values that each correspond to one of at least N biomarkers, wherein N is as defined above, selected from the group of biomarkers set forth in Table 21; performing with the computer a classification of each of the biomarker values; and indicating a likelihood that the individual has lung cancer based upon a plurality of classifications.

In another aspect, a computer-implemented method is provided for classifying an individual as either having or not having lung cancer. The method comprises: retrieving on a computer biomarker information for an individual, wherein the biomarker information comprises biomarker values that each correspond to one of at least N biomarkers selected from the group of biomarkers provided in Table 21; performing with the computer a classification of each of the biomarker values; and indicating whether the individual has lung cancer based upon a plurality of classifications.

In another aspect, a computer program product is provided for indicating a likelihood of lung cancer. The computer program product includes a computer readable medium embodying program code executable by a processor of a computing device or system, the program code comprising: code that retrieves data attributed to a biological sample from an individual, wherein the data comprises biomarker values that each correspond to one of at least N biomarkers, wherein N is as defined above, in the biological sample selected from the group of biomarkers set forth in Table 21; and code that executes a classification method that indicates a likelihood that the individual has lung cancer as a function of the biomarker values.

In another aspect, a computer program product is provided for indicating a lung cancer status of an individual. The computer program product includes a computer readable medium embodying program code executable by a processor of a computing device or system, the program code comprising: code that retrieves data attributed to a biological sample from an individual, wherein the data comprises biomarker values that each correspond to one of at least N biomarkers in the biological sample selected from the group of biomarkers provided in Table 21; and code that executes a classification method that indicates a lung cancer status of the individual as a function of the biomarker values.

In another aspect, a computer-implemented method is provided for indicating a likelihood of lung cancer. The method comprises retrieving on a computer biomarker information for an individual, wherein the biomarker information comprises a biomarker value corresponding to a biomarker selected from the group of biomarkers set forth in Table 21; performing with the computer a classification of the biomarker value; and indicating a likelihood that the individual has lung cancer based upon the classification.

In another aspect, a computer-implemented method is provided for classifying an individual as either having or not having lung cancer. The method comprises retrieving from a computer biomarker information for an individual, wherein the biomarker information comprises a biomarker value corresponding to a biomarker selected from the group of biomarkers provided in Table 21; performing with the computer a classification of the biomarker value; and indicating whether the individual has lung cancer based upon the classification.

In still another aspect, a computer program product is provided for indicating a likelihood of lung cancer. The computer program product includes a computer readable medium embodying program code executable by a processor of a computing device or system, the program code comprising: code that retrieves data attributed to a biological sample from an individual, wherein the data comprises a biomarker value corresponding to a biomarker in the biological sample selected from the group of biomarkers set forth in Table 21; and code that executes a classification method that indicates a likelihood that the individual has lung cancer as a function of the biomarker value.

In still another aspect, a computer program product is provided for indicating a lung cancer status of an individual. The computer program product includes a computer readable medium embodying program code executable by a processor of a computing device or system, the program code comprising: code that retrieves data attributed to a biological sample from an individual, wherein the data comprises a biomarker value corresponding to a biomarker in the biological sample selected from the group of biomarkers provided in Table 21; and code that executes a classification method that indicates a lung cancer status of the individual as a function of the biomarker value.

In one aspect of the application at least one of said N biomarkers selected from Table 21 in each of the above methods is a biomarker selected from the Table 20. In yet another embodiment said biomarker selected from Table 20 is MMP-12.

In another aspect, a method is provided for diagnosing lung cancer, the method including detecting, in a biological sample from an individual, biomarker values that each correspond to a biomarker on a panel of biomarkers selected from the group of panels set forth in Tables 22-25 wherein a classification of the biomarker values indicates that the individual has lung cancer.

In another aspect, a method is provided for diagnosing an absence of lung cancer, the method including detecting, in a biological sample from an individual, biomarker values that each correspond to a biomarker on a panel of biomarkers selected from the group of panels provided in Tables 22-25, wherein a classification of the biomarker values indicates an absence of lung cancer in the individual.

BRIEF DESCRIPTION OF THE DRAWINGS

FIG. 7 is a flowchart for a method of indicating the likelihood that an individual has lung cancer in accordance with one embodiment.

DETAILED DESCRIPTION

Figure 1A:
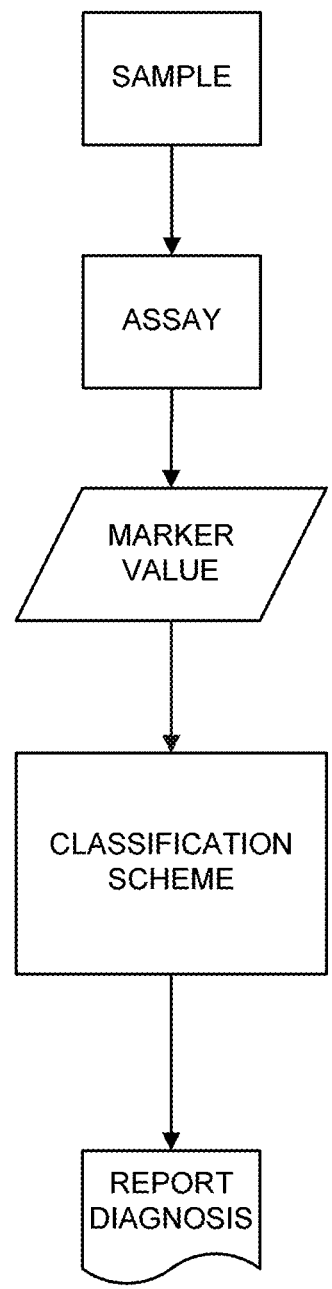
FIG. 1A is a flowchart for an exemplary method for detecting lung cancer in a biological sample.

The practice of the invention disclosed herein employs, unless otherwise indicated, conventional methods of chemistry, microbiology, molecular biology, and recombinant DNA techniques within the level of skill in the art. Such techniques are explained fully in the literature. See, e.g., Sambrook, et al. Molecular Cloning: A Laboratory Manual (Current Edition); DNA Cloning: A Practical Approach, vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition; Histology for Pathologists (S. E. Mills, Current Edition). All publications, published patent documents, and patent applications cited in this specification are indicative of the level of skill in the art(s) to which the invention pertains. All publications, published patent documents, and patent applications cited herein are hereby incorporated by reference to the same extent as though each individual publication, published patent document, or patent application was specifically and individually indicated as being incorporated by reference.

Reference will now be made in detail to representative embodiments of the invention. While the invention will be described in conjunction with the enumerated embodiments, it will be understood that the invention is not intended to be limited to those embodiments. On the contrary, the invention is intended to cover all alternatives, modifications, and equivalents that may be included within the scope of the present invention as defined by the claims.

Unless defined otherwise, technical and scientific terms used herein have the same meaning as commonly understood by one of ordinary skill in the art to which this invention belongs. Although any methods, devices, and materials similar or equivalent to those described herein can be used in the practice or testing of the invention, the preferred methods, devices and materials are now described.

As used in this application, including the appended claims, the singular forms "a," "an," and "the" include plural references, unless the content clearly dictates otherwise, and are used interchangeably with "at least one" and "one or more." Thus, reference to "an aptamer" includes mixtures of aptamers, reference to "a probe" includes mixtures of probes, and the like.

As used herein, the term "about" represents an insignificant modification or variation of the numerical value such that the basic function of the item to which the numerical value relates is unchanged.

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but may include other elements not expressly listed or inherent to such process, method, product-by-process, or composition of matter.

The present application includes biomarkers, methods, devices, reagents, systems, and kits for the detection and diagnosis of lung cancer.

In one aspect, one or more biomarkers are provided for use either alone or in various combinations to diagnose lung cancer, permit the differential diagnosis of pulmonary nodules as benign or malignant, monitor lung cancer recurrence, or address other clinical indications. In other aspects said biomarker(s) can be used in determining information about lung cancer in an individual such as, prognosis, cancer classification, prediction of disease risk or selection of treatment. As described in detail below, exemplary embodiments include the biomarkers provided in Tables 18, 20 and 21, which were identified using a multiplex aptamer-based assay that is described generally in Example 1 and more specifically in Examples 2 and 6. Each of the biomarkers is useful in assaying any type of sample as defined below.

Table 1, Col. 2 sets forth the findings obtained from analyzing hundreds of individual blood samples from NSCLC cancer cases, and hundreds of equivalent individual blood samples from smokers and from individuals diagnosed with benign lung nodules. The smoker and benign nodule groups were designed to match the populations with which a lung cancer diagnostic test can have the most benefit. (These cases and controls were obtained from multiple clinical sites to mimic the range of real world conditions under which such a test can be applied). The potential biomarkers were measured in individual samples rather than pooling the disease and control blood; this allowed a better understanding of the individual and group variations in the phenotypes associated with the presence and absence of disease (in this case lung cancer). Since over 800 protein measurements were made on each sample, and several hundred samples from each of the disease and the control populations were individually measured, Table 1, Col. 2 resulted from an analysis of an uncommonly large set of data. The measurements were analyzed using the methods described in the section, "Classification of Biomarkers and Calculation of Disease Scores" herein.

Table 1, Col. 2 lists the biomarkers found to be useful in distinguishing samples obtained from individuals with NSCLC from "control" samples obtained from smokers and individuals with benign lung nodules. Using a multiplex aptamer assay as described herein, thirty-eight biomarkers were discovered that distinguished the samples obtained from individuals who had lung cancer from the samples obtained from individuals in the smoker control group (see Table 1, Col. 6). Similarly, using a multiplex aptamer assay, forty biomarkers were discovered that distinguished samples obtained from individuals with NSCLC from samples obtained from people who had benign lung nodules (see Table 1, Col. 5). Together, the two lists of 38 and 40 biomarkers are comprised of 61 unique biomarkers, because there is considerable overlap between the list of biomarkers for distinguishing NSCLC from benign nodules and the list for distinguishing NSCLC from smokers who do not have lung cancer.

Table 18 sets forth the findings obtained from analyzing eight individual tissue samples of smokers diagnosed with NSCLC as described in Example 6. All of the patients were smokers ranging from 47 to 75 years old and covering NSCLC stages 1A through 3B. Three samples were obtained from each individual: tumor tissue, adjacent healthy tissue (within 1 cm of the tumor) and distant uninvolved lung tissue. The samples were chosen to match the populations with which a lung cancer diagnostic test can have the most benefit. The potential biomarkers were measured in individual samples rather than pooling the disease and control tissue; this allowed a better understanding of the individual and group variations in the phenotypes associated with the presence and absence of disease (in this case lung cancer). The measurements were analyzed using the Mann-Whitney test.

Table 18 lists the biomarkers found to be useful in distinguishing samples obtained from individuals with NSCLC from "control" samples obtained from adjacent and distal uninvolved lung tissue obtained from the same individuals. Using a multiplex aptamer assay as described herein, thirty-six biomarkers were discovered that distinguished the tumor tissue samples from samples obtained from adjacent and distal lung tissue in individuals who had been diagnosed with NSCLC. With reference to Table 1, col. 2, it can be seen that eleven of the biomarkers overlap those identified in serum samples as described in Example 2. An additional marker which was not measured in the original serum profiling, MMP-12, has since been found to be a useful biomarker in both serum and in tissue. Table 21 provides a list of the total number of biomarkers (eighty-six) identified in both the serum and tumor tissue samples combined. Table 20 provides a list of the biomarkers identified which were unique to the tumor tissue samples (twenty-five).

While certain of the described lung cancer biomarkers are useful alone for detecting and diagnosing lung cancer, methods are also described herein for the grouping of multiple subsets of the lung cancer biomarkers, where each grouping or subset selection is useful as a panel of three or more biomarkers, interchangeably referred to herein as a "biomarker panel" and a panel. Thus, various embodiments of the instant application provide combinations comprising N biomarkers, wherein N is at least two biomarkers. In other embodiments, N is selected from 2-86 biomarkers (Table 21); 2-36 biomarkers (Table 18) or 2-25 biomarkers (Table 20). In other embodiments, N is selected from 2-86 (Table 21) and at least one of said N biomarkers is MMP-12. In other embodiments, N is selected from 2-25 (Table 20) and at least one of said N biomarkers is MMP-12. Representative panels of 2-5 biomarkers including MMP-12 as one of the markers are set forth in Tables 22-25.

In yet other embodiments, the biomarkers are selected from those listed in Table 18 and N is selected to be any number from 2-7, 2-10, 2-15, 2-20, 2-25, 2-30, 2-36. In other embodiments, N is selected to be any number from 3-7, 3-10, 3-15, 3-20, 3-25, 3-30, 3-36. In other embodiments, N is selected to be any number from 4-7, 4-10, 4-15, 4-20, 4-25, 4-30, 4-36. In other embodiments, N is selected to be any number from 5-7, 5-10, 5-15, 5-20, 5-25, 5-30, 5-36. In other embodiments, N is selected to be any number from 6-10, 6-15, 6-20, 6-25, 6-30, 6-36. In other embodiments, N is selected to be any number from 7-10, 7-15, 7-20, 7-25, 7-30, 7-36. In other embodiments, N is selected to be any number from 8-10, 8-15, 8-20, 8-25, 8-30, 8-36. In other embodiments, N is selected to be any number from 9-15, 9-20, 9-25, 9-30, 9-36. In other embodiments, N is selected to be any number from 10-15, 10-20, 10-25, 10-30, 10-36. It will be appreciated that N can be selected to encompass similar, but higher order, ranges.

In yet other embodiments the biomarkers are selected from those listed in Table 20 and N is selected to be any number from 2-7, 2-10, 2-15, 2-20, 2-25. In other embodiments, N is selected to be any number from 3-7, 3-10, 3-15, 3-20, 3-25. In other embodiments, N is selected to be any number from 4-7, 4-10, 4-15, 4-20, 4-25. In other embodiments, N is selected to be any number from 5-7, 5-10, 5-15, 5-20, 5-25. In other embodiments, N is selected to be any number from 6-10, 6-15, 6-20, 6-25. In other embodiments, N is selected to be any number from 7-10, 7-15, 7-20, 7-25. In other embodiments, N is selected to be any number from 8-10, 8-15, 8-20, 8-25. In other embodiments, N is selected to be any number from 9-15, 9-20, 9-25. In other embodiments, N is selected to be any number from 10-15, 10-20, 10-25. In other embodiments, N is selected to be any number from 9-15, 9-20, 9-25. In other embodiments, N is selected to be any number from 10-15, 10-20, 10-25. It will be appreciated that N can be selected to encompass similar, but higher order, ranges.

In yet other embodiments the biomarkers are selected from those listed in Table 21 and N is selected to be any number from 2-7, 2-10, 2-15, 2-20, 2-25, 2-30, 2-35, 2-40, 2-45, 2-50, 2-55, 2-60, 2-65, 2-70, 2-75, 2-80, or 2-86. In other embodiments, N is selected to be any number from 3-7, 3-10, 3-15, 3-20, 3-25, 3-30, 3-35, 3-40, 3-45, 3-50, 3-55, 3-60, 3-65, 3-70, 3-75, 3-80, or 3-86. In other embodiments, N is selected to be any number from 4-7, 4-10, 4-15, 4-20, 4-25, 4-30, 4-35, 4-40, 4-45, 4-50, 4-55, 4-60, 4-65, 4-70, 4-75, 4-80, or 4-86. In other embodiments, N is selected to be any number from 5-7, 5-10, 5-15, 5-20, 5-25, 5-30, 5-35, 5-40, 5-45, 5-50, 5-55, 5-60, 5-65, 5-70, 5-75, 5-80, or 5-86. In other embodiments, N is selected to be any number from 6-10, 6-15, 6-20, 6-25, 6-30, 6-35, 6-40, 6-45, 6-50, 6-55, 6-60, 6-65, 6-70, 6-75, 6-80, or 6-86. In other embodiments, N is selected to be any number from 7-10, 7-15, 7-20, 7-25, 7-30, 7-35, 7-40, 7-45, 7-50, 7-55, 7-60, 7-65, 7-70, 7-75, 7-80, or 7-86. In other embodiments, N is selected to be any number from 8-10, 8-15, 8-20, 8-25, 8-30, 8-35, 8-40, 8-45, 8-50, 8-55, 8-60, 8-65, 8-70, 8-75, 8-80, or 8-86. In other embodiments, N is selected to be any number from 9-15, 9-20, 9-25, 9-30, 9-35, 9-40, 9-45, 9-50, 9-55, 9-60, 9-65, 9-70, 9-75, 9-80, or 9-86. In other embodiments, N is selected to be any number from 10-15, 10-20, 10-25, 10-30, 10-35, 10-40, 10-45, 10-50, 10-55, 10-60, 10-65, 10-70, 10-75, 10-80, or 10-86. It will be appreciated that N can be selected to encompass similar, but higher order, ranges.

In one embodiment, the number of biomarkers useful for a biomarker subset or panel is based on the sensitivity and specificity value for the particular combination of biomarker values. The terms "sensitivity" and "specificity" are used herein with respect to the ability to correctly classify an individual, based on one or more biomarker values detected in their biological sample, as having lung cancer or not having lung cancer. "Sensitivity" indicates the performance of the biomarker(s) with respect to correctly classifying individuals that have lung cancer. "Specificity" indicates the performance of the biomarker(s) with respect to correctly classifying individuals who do not have lung cancer. For example, 85% specificity and 90% sensitivity for a panel of markers used to test a set of control samples and lung cancer samples indicates that 85% of the control samples were correctly classified as control samples by the panel, and 90% of the lung cancer samples were correctly classified as lung cancer samples by the panel. The desired or preferred minimum value can be determined as described in Example 3.

In one aspect, lung cancer is detected or diagnosed in an individual by conducting an assay on a biological sample from the individual and detecting biomarker values that each correspond to at least one of the biomarkers MMP-7, MMP-12, or IGFBP-2 and at least N additional biomarkers selected from the list of biomarkers in Table 21, wherein N equals 2, 3, 4, 5, 6, 7, 8, 9, 10, 11, 12, 13, 14 or 15. In a further aspect, lung cancer is detected or diagnosed in an individual by conducting an assay on a biological sample from the individual and detecting biomarker values that each correspond to the biomarkers MMP-7, MMP-12, or IGFBP-2 and one of at least N additional biomarkers selected from the list of biomarkers in Table 21, wherein N equals 1, 2, 3, 4, 5, 6, 7, 8, 9, 10, 11, 12 or 13. In a further aspect, lung cancer is detected or diagnosed in an individual by conducting an assay on a biological sample from the individual and detecting biomarker values that each correspond to the biomarker MMP-7 and one of at least N additional biomarkers selected from the list of biomarkers in Table 21, wherein N equals 2, 3, 4, 5, 6, 7, 8, 9, 10, 11, 12, 13, 14 or 15. In a further aspect, lung cancer is detected or diagnosed in an individual by conducting an assay on a biological sample from the individual and detecting biomarker values that each correspond to the biomarker MMP-12 and one of at least N additional biomarkers selected from the list of biomarkers in Table 21, wherein N equals 2, 3, 4, 5, 6, 7, 8, 9, 10, 11, 12, 13, 14 or 15. In a further aspect, lung cancer is detected or diagnosed in an individual by conducting an assay on a biological sample from the individual and detecting biomarker values that each correspond to the biomarker IGFBP-2 and one of at least N additional biomarkers selected from the list of biomarkers in Table 21, wherein N equals 2, 3, 4, 5, 6, 7, 8, 9, 10, 11, 12, 13, 14 or 15.

The lung cancer biomarkers identified herein represent a relatively large number of choices for subsets or panels of biomarkers that can be used to effectively detect or diagnose lung cancer. Selection of the desired number of such biomarkers depends on the specific combination of biomarkers chosen. It is important to remember that panels of biomarkers for detecting or diagnosing lung cancer may also include biomarkers not found in Tables 18, 20 or 21, and that the inclusion of additional biomarkers not found in Tables 18, 20 or 21 may reduce the number of biomarkers in the particular subset or panel that is selected from Tables 18, 20 or 21. The number of biomarkers from Tables 18, 20 or 21 used in a subset or panel may also be reduced if additional biomedical information is used in conjunction with the biomarker values to establish acceptable sensitivity and specificity values for a given assay.

Another factor that can affect the number of biomarkers to be used in a subset or panel of biomarkers is the procedures used to obtain biological samples from individuals who are being diagnosed for lung cancer. In a carefully controlled sample procurement environment, the number of biomarkers necessary to meet desired sensitivity and specificity values will be lower than in a situation where there can be more variation in sample collection, handling and storage. In developing the list of biomarkers set forth in Tables 18, 20 or 21, multiple sample collection sites were utilized to collect data for classifier training. This provides for more robust biomarkers that are less sensitive to variations in sample collection, handling and storage, but can also require that the number of biomarkers in a subset or panel be larger than if the training data were all obtained under very similar conditions.

Figure 1B:
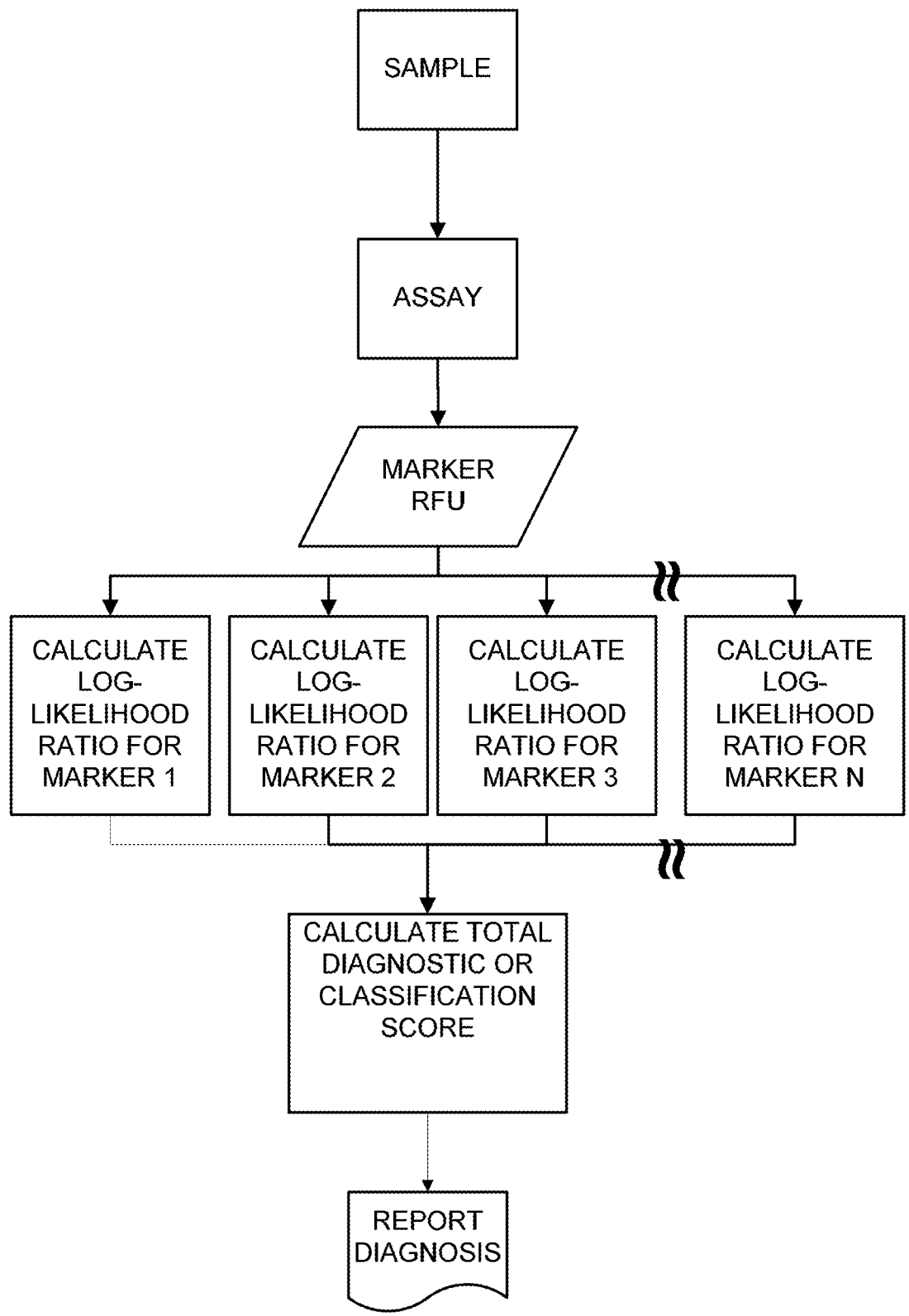
FIG. 1B is a flowchart for an exemplary method for detecting lung cancer in a biological sample using a naïve Bayes classification method.

One aspect of the instant application can be described generally with reference to FIGS. 1A and B. A biological sample is obtained from an individual or individuals of interest. The biological sample is then assayed to detect the presence of one or more (N) biomarkers of interest and to determine a biomarker value for each of said N biomarkers (referred to in FIG. 1B as marker RFU). Once a biomarker has been detected and a biomarker value assigned each marker is scored or classified as described in detail herein. The marker scores are then combined to provide a total diagnostic score, which indicates the likelihood that the individual from whom the sample was obtained has lung cancer.

As used herein, "lung" may be interchangeably referred to as "pulmonary".

As used herein, "smoker" refers to an individual who has a history of tobacco smoke inhalation.

"Biological sample", "sample", and "test sample" are used interchangeably herein to refer to any material, biological fluid, tissue, or cell obtained or otherwise derived from an individual. This includes blood (including whole blood, leukocytes, peripheral blood mononuclear cells, buffy coat, plasma, and serum), sputum, tears, mucus, nasal washes, nasal aspirate, breath, urine, semen, saliva, meningeal fluid, amniotic fluid, glandular fluid, lymph fluid, nipple aspirate, bronchial aspirate, synovial fluid, joint aspirate, cells, a cellular extract, and cerebrospinal fluid. This also includes experimentally separated fractions of all of the preceding. For example, a blood sample can be fractionated into serum or into fractions containing particular types of blood cells, such as red blood cells or white blood cells (leukocytes). If desired, a sample can be a combination of samples from an individual, such as a combination of a tissue and fluid sample. The term "biological sample" also includes materials containing homogenized solid material, such as from a stool sample, a tissue sample, or a tissue biopsy, for example. The term "biological sample" also includes materials derived from a tissue culture or a cell culture. Any suitable methods for obtaining a biological sample can be employed; exemplary methods include, e.g., phlebotomy, swab (e.g., buccal swab), and a fine needle aspirate biopsy procedure. Exemplary tissues susceptible to fine needle aspiration include lymph node, lung, lung washes, BAL (bronchoalveolar lavage), thyroid, breast, and liver. Samples can also be collected, e.g., by micro dissection (e.g., laser capture micro dissection (LCM) or laser micro dissection (LMD)), bladder wash, smear (e.g., a PAP smear), or ductal lavage. A "biological sample" obtained or derived from an individual includes any such sample that has been processed in any suitable manner after being obtained from the individual.

A "Tissue sample" or "Tissue" refers to a certain subset of the biological samples described above. According to this definition, tissues are collections of macromolecules in a heterogeneous environment. As used herein, tissue refers to a single cell type, a collection of cell types, an aggregate of cells, or an aggregate of macromolecules. Tissues are generally a physical array of macromolecules that can be either fluid or rigid, both in terms of structure and composition. Extracellular matrix is an example of a more rigid tissue, both structurally and compositionally, while a membrane bilayer is more fluid in structure and composition. Tissue includes, but is not limited to, an aggregate of cells usually of a particular kind together with their intercellular substance that form one of the structural materials commonly used to denote the general cellular fabric of a given organ, e.g., kidney tissue, brain tissue, lung tissue. The four general classes of tissues are epithelial tissue, connective tissue, nerve tissue, and muscle tissue. Methods for identifying slow off-rate aptamers to tissue targets are described in International Application Pub. No. WO 2011/006075, published Jan. 13, 2011, which is incorporated herein by reference in its entirety.

Examples of tissues which fall within this definition include, but are not limited to, heterogeneous aggregates of macromolecules such as fibrin clots which are acellular; homogeneous or heterogeneous aggregates of cells; higher ordered structures containing cells which have a specific function, such as organs, tumors, lymph nodes, arteries, etc.; and individual cells. Tissues or cells can be in their natural environment, isolated, or in tissue culture. The tissue can be intact or modified. The modification can include numerous changes such as transformation, transfection, activation, and substructure isolation, e.g., cell membranes, cell nuclei, cell organelles, etc.

Sources of the tissue, cell or subcellular structures can be obtained from prokaryotes as well as eukaryotes. This includes human, animal, plant, bacterial, fungal and viral structures.

Further, it should be realized that a biological sample can be derived by taking biological samples from a number of individuals and pooling them or pooling an aliquot of each individual's biological sample. The pooled sample can be treated as a sample from a single individual and if the presence of cancer is established in the pooled sample, then each individual biological sample can be re-tested to determine which individual/s have lung cancer.

For purposes of this specification, the phrase "data attributed to a biological sample from an individual" is intended to mean that the data in some form derived from, or were generated using, the biological sample of the individual. The data may have been reformatted, revised, or mathematically altered to some degree after having been generated, such as by conversion from units in one measurement system to units in another measurement system; but, the data are understood to have been derived from, or were generated using, the biological sample.

"Target", "target molecule", and "analyte" are used interchangeably herein to refer to any molecule of interest that may be present in a biological sample. A "molecule of interest" includes any minor variation of a particular molecule, such as, in the case of a protein, for example, minor variations in amino acid sequence, disulfide bond formation, glycosylation, lipidation, acetylation, phosphorylation, or any other manipulation or modification, such as conjugation with a labeling component, which does not substantially alter the identity of the molecule. A "target molecule", "target", or "analyte" is a set of copies of one type or species of molecule or multi-molecular structure. "Target molecules", "targets", and "analytes" refer to more than one such set of molecules. Exemplary target molecules include proteins, polypeptides, nucleic acids, carbohydrates, lipids, polysaccharides, glycoproteins, hormones, receptors, antigens, antibodies, affybodies, antibody mimics, viruses, pathogens, toxic substances, substrates, metabolites, transition state analogs, cofactors, inhibitors, drugs, dyes, nutrients, growth factors, cells, tissues, and any fragment or portion of any of the foregoing.

As used herein, "polypeptide," "peptide," and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. Polypeptides can be single chains or associated chains. Also included within the definition are preproteins and intact mature proteins; peptides or polypeptides derived from a mature protein; fragments of a protein; splice variants; recombinant forms of a protein; protein variants with amino acid modifications, deletions, or substitutions; digests; and post-translational modifications, such as glycosylation, acetylation, phosphorylation, and the like.

As used herein, "marker" and "biomarker" are used interchangeably to refer to a target molecule that indicates or is a sign of a normal or abnormal process in an individual or of a disease or other condition in an individual. More specifically, a "marker" or "biomarker" is an anatomic, physiologic, biochemical, or molecular parameter associated with the presence of a specific physiological state or process, whether normal or abnormal, and, if abnormal, whether chronic or acute. Biomarkers are detectable and measurable by a variety of methods including laboratory assays and medical imaging. When a biomarker is a protein, it is also possible to use the expression of the corresponding gene as a surrogate measure of the amount or presence or absence of the corresponding protein biomarker in a biological sample or methylation state of the gene encoding the biomarker or proteins that control expression of the biomarker.

As used herein, "biomarker value", "value", "biomarker level", and "level" are used interchangeably to refer to a measurement that is made using any analytical method for detecting the biomarker in a biological sample and that indicates the presence, absence, absolute amount or concentration, relative amount or concentration, titer, a level, an expression level, a ratio of measured levels, or the like, of, for, or corresponding to the biomarker in the biological sample. The exact nature of the "value" or "level" depends on the specific design and components of the particular analytical method employed to detect the biomarker.

When a biomarker indicates or is a sign of an abnormal process or a disease or other condition in an individual, that biomarker is generally described as being either over-expressed or under-expressed as compared to an expression level or value of the biomarker that indicates or is a sign of a normal process or an absence of a disease or other condition in an individual.

"Up-regulation", "up-regulated", "over-expression", "over-expressed", and any variations thereof are used interchangeably to refer to a value or level of a biomarker in a biological sample that is greater than a value or level (or range of values or levels) of the biomarker that is typically detected in similar biological samples from healthy or normal individuals. The terms may also refer to a value or level of a biomarker in a biological sample that is greater than a value or level (or range of values or levels) of the biomarker that may be detected at a different stage of a particular disease.

"Down-regulation", "down-regulated", "under-expression", "under-expressed", and any variations thereof are used interchangeably to refer to a value or level of a biomarker in a biological sample that is less than a value or level (or range of values or levels) of the biomarker that is typically detected in similar biological samples from healthy or normal individuals. The terms may also refer to a value or level of a biomarker in a biological sample that is less than a value or level (or range of values or levels) of the biomarker that may be detected at a different stage of a particular disease.

Further, a biomarker that is either over-expressed or under-expressed can also be referred to as being "differentially expressed" or as having a "differential level" or "differential value" as compared to a "normal" expression level or value of the biomarker that indicates or is a sign of a normal process or an absence of a disease or other condition in an individual. Thus, "differential expression" of a biomarker can also be referred to as a variation from a "normal" expression level of the biomarker.

The term "differential gene expression" and "differential expression" are used interchangeably to refer to a gene (or its corresponding protein expression product) whose expression is activated to a higher or lower level in a subject suffering from a specific disease, relative to its expression in a normal or control subject. The terms also include genes (or the corresponding protein expression products) whose expression is activated to a higher or lower level at different stages of the same disease. It is also understood that a differentially expressed gene may be either activated or inhibited at the nucleic acid level or protein level, or may be subject to alternative splicing to result in a different polypeptide product. Such differences may be evidenced by a variety of changes including mRNA levels, surface expression, secretion or other partitioning of a polypeptide. Differential gene expression may include a comparison of expression between two or more genes or their gene products; or a comparison of the ratios of the expression between two or more genes or their gene products; or even a comparison of two differently processed products of the same gene, which differ between normal subjects and subjects suffering from a disease; or between various stages of the same disease. Differential expression includes both quantitative, as well as qualitative, differences in the temporal or cellular expression pattern in a gene or its expression products among, for example, normal and diseased cells, or among cells which have undergone different disease events or disease stages.

As used herein, "individual" refers to a test subject or patient. The individual can be a mammal or a non-mammal. In various embodiments, the individual is a mammal. A mammalian individual can be a human or non-human. In various embodiments, the individual is a human. A healthy or normal individual is an individual in which the disease or condition of interest (including, for example, lung diseases, lung-associated diseases, or other lung conditions) is not detectable by conventional diagnostic methods.

"Diagnose", "diagnosing", "diagnosis", and variations thereof refer to the detection, determination, or recognition of a health status or condition of an individual on the basis of one or more signs, symptoms, data, or other information pertaining to that individual. The health status of an individual can be diagnosed as healthy/normal (i.e., a diagnosis of the absence of a disease or condition) or diagnosed as ill/abnormal (i.e., a diagnosis of the presence, or an assessment of the characteristics, of a disease or condition). The terms "diagnose", "diagnosing", "diagnosis", etc., encompass, with respect to a particular disease or condition, the initial detection of the disease; the characterization or classification of the disease; the detection of the progression, remission, or recurrence of the disease; and the detection of disease response after the administration of a treatment or therapy to the individual. The diagnosis of lung cancer includes distinguishing individuals, including smokers and nonsmokers, who have cancer from individuals who do not. It further includes distinguishing benign pulmonary nodules from cancerous pulmonary nodules.

"Prognose", "prognosing", "prognosis", and variations thereof refer to the prediction of a future course of a disease or condition in an individual who has the disease or condition (e.g., predicting patient survival), and such terms encompass the evaluation of disease response after the administration of a treatment or therapy to the individual.

"Evaluate", "evaluating", "evaluation", and variations thereof encompass both "diagnose" and "prognose" and also encompass determinations or predictions about the future course of a disease or condition in an individual who does not have the disease as well as determinations or predictions regarding the likelihood that a disease or condition will recur in an individual who apparently has been cured of the disease. The term "evaluate" also encompasses assessing an individual's response to a therapy, such as, for example, predicting whether an individual is likely to respond favorably to a therapeutic agent or is unlikely to respond to a therapeutic agent (or will experience toxic or other undesirable side effects, for example), selecting a therapeutic agent for administration to an individual, or monitoring or determining an individual's response to a therapy that has been administered to the individual. Thus, "evaluating" lung cancer can include, for example, any of the following: prognosing the future course of lung cancer in an individual; predicting the recurrence of lung cancer in an individual who apparently has been cured of lung cancer; or determining or predicting an individual's response to a lung cancer treatment or selecting a lung cancer treatment to administer to an individual based upon a determination of the biomarker values derived from the individual's biological sample.

Any of the following examples may be referred to as either "diagnosing" or "evaluating" lung cancer: initially detecting the presence or absence of lung cancer; determining a specific stage, type or sub-type, or other classification or characteristic of lung cancer; determining whether a pulmonary nodule is a benign lesion or a malignant lung tumor; or detecting/monitoring lung cancer progression (e.g., monitoring lung tumor growth or metastatic spread), remission, or recurrence.

As used herein, "additional biomedical information" refers to one or more evaluations of an individual, other than using any of the biomarkers described herein, that are associated with lung cancer risk. "Additional biomedical information" includes any of the following: physical descriptors of an individual, physical descriptors of a pulmonary nodule observed by CT imaging, the height and/or weight of an individual, the gender of an individual, the ethnicity of an individual, smoking history, occupational history, exposure to known carcinogens (e.g., exposure to any of asbestos, radon gas, chemicals, smoke from fires, and air pollution, which can include emissions from stationary or mobile sources such as industrial/factory or auto/marine/aircraft emissions), exposure to second-hand smoke, family history of lung cancer (or other cancer), the presence of pulmonary nodules, size of nodules, location of nodules, morphology of nodules (e.g., as observed through CT imaging, ground glass opacity (GGO), solid, non-solid), edge characteristics of the nodule (e.g., smooth, lobulated, sharp and smooth, spiculated, infiltrating), and the like. Smoking history is usually quantified in terms of "pack years", which refers to the number of years a person has smoked multiplied by the average number of packs smoked per day. For example, a person who has smoked, on average, one pack of cigarettes per day for 35 years is referred to as having 35 pack years of smoking history. Additional biomedical information can be obtained from an individual using routine techniques known in the art, such as from the individual themselves by use of a routine patient questionnaire or health history questionnaire, etc., or from a medical practitioner, etc. Alternately, additional biomedical information can be obtained from routine imaging techniques, including CT imaging (e.g., low-dose CT imaging) and X-ray. Testing of biomarker levels in combination with an evaluation of any additional biomedical information may, for example, improve sensitivity, specificity, and/or AUC for detecting lung cancer (or other lung cancer-related uses) as compared to biomarker testing alone or evaluating any particular item of additional biomedical information alone (e.g., CT imaging alone).

The term "area under the curve" or "AUC" refers to the area under the curve of a receiver operating characteristic (ROC) curve, both of which are well known in the art. AUC measures are useful for comparing the accuracy of a classifier across the complete data range. Classifiers with a greater AUC have a greater capacity to classify unknowns correctly between two groups of interest (e.g., lung cancer samples and normal or control samples). ROC curves are useful for plotting the performance of a particular feature (e.g., any of the biomarkers described herein and/or any item of additional biomedical information) in distinguishing between two populations (e.g., cases having lung cancer and controls without lung cancer). Typically, the feature data across the entire population (e.g., the cases and controls) are sorted in ascending order based on the value of a single feature. Then, for each value for that feature, the true positive and false positive rates for the data are calculated. The true positive rate is determined by counting the number of cases above the value for that feature and then dividing by the total number of cases. The false positive rate is determined by counting the number of controls above the value for that feature and then dividing by the total number of controls. Although this definition refers to scenarios in which a feature is elevated in cases compared to controls, this definition also applies to scenarios in which a feature is lower in cases compared to the controls (in such a scenario, samples below the value for that feature would be counted). ROC curves can be generated for a single feature as well as for other single outputs, for example, a combination of two or more features can be mathematically combined (e.g., added, subtracted, multiplied, etc.) to provide a single sum value, and this single sum value can be plotted in a ROC curve. Additionally, any combination of multiple features, in which the combination derives a single output value, can be plotted in a ROC curve. These combinations of features may comprise a test. The ROC curve is the plot of the true positive rate (sensitivity) of a test against the false positive rate (1-specificity) of the test.

As used herein, "detecting" or "determining" with respect to a biomarker value includes the use of both the instrument required to observe and record a signal corresponding to a biomarker value and the material/s required to generate that signal. In various embodiments, the biomarker value is detected using any suitable method, including fluorescence, chemiluminescence, surface plasmon resonance, surface acoustic waves, mass spectrometry, infrared spectroscopy, Raman spectroscopy, atomic force microscopy, scanning tunneling microscopy, electrochemical detection methods, nuclear magnetic resonance, quantum dots, and the like.

"Solid support" refers herein to any substrate having a surface to which molecules may be attached, directly or indirectly, through either covalent or non-covalent bonds. A "solid support" can have a variety of physical formats, which can include, for example, a membrane; a chip (e.g., a protein chip); a slide (e.g., a glass slide or coverslip); a column; a hollow, solid, semi-solid, pore- or cavity-containing particle, such as, for example, a bead; a gel; a fiber, including a fiber optic material; a matrix; and a sample receptacle. Exemplary sample receptacles include sample wells, tubes, capillaries, vials, and any other vessel, groove or indentation capable of holding a sample. A sample receptacle can be contained on a multi-sample platform, such as a microtiter plate, slide, microfluidics device, and the like. A support can be composed of a natural or synthetic material, an organic or inorganic material. The composition of the solid support on which capture reagents are attached generally depends on the method of attachment (e.g., covalent attachment). Other exemplary receptacles include microdroplets and microfluidic controlled or bulk oil/aqueous emulsions within which assays and related manipulations can occur. Suitable solid supports include, for example, plastics, resins, polysaccharides, silica or silica-based materials, functionalized glass, modified silicon, carbon, metals, inorganic glasses, membranes, nylon, natural fibers (such as, for example, silk, wool and cotton), polymers, and the like. The material composing the solid support can include reactive groups such as, for example, carboxy, amino, or hydroxyl groups, which are used for attachment of the capture reagents. Polymeric solid supports can include, e.g., polystyrene, polyethylene glycol tetraphthalate, polyvinyl acetate, polyvinyl chloride, polyvinyl pyrrolidone, polyacrylonitrile, polymethyl methacrylate, polytetrafluoroethylene, butyl rubber, styrenebutadiene rubber, natural rubber, polyethylene, polypropylene, (poly)tetrafluoroethylene, (poly) vinylidenefluoride, polycarbonate, and polymethylpentene. Suitable solid support particles that can be used include, e.g., encoded particles, such as Luminex-type encoded particles, magnetic particles, and glass particles.

Exemplary Uses of Biomarkers

In various exemplary embodiments, methods are provided for diagnosing lung cancer in an individual by detecting one or more biomarker values corresponding to one or more biomarkers that are present in the lung tissue of an individual by any number of analytical methods, including any of the analytical methods described herein. These biomarkers are, for example, differentially expressed in individuals with lung cancer as compared to individuals without lung cancer, particularly NSCLC. Detection of the differential expression of a biomarker in an individual can be used, for example, to permit the early diagnosis of lung cancer, to distinguish between a benign and malignant pulmonary nodule (such as, for example, a nodule observed on a computed tomography (CT) scan), to monitor lung cancer recurrence, or for other clinical indications, including determination of prognosis and methods of treatment.

Any of the biomarkers described herein may be used in a variety of clinical indications for lung cancer, including any of the following: detection of lung cancer (such as in a high-risk individual or population); characterizing lung cancer (e.g., determining lung cancer type, sub-type, or stage), such as by distinguishing between non-small cell lung cancer (NSCLC) and small cell lung cancer (SCLC) and/or between adenocarcinoma and squamous cell carcinoma (or otherwise facilitating histopathology); determining whether a lung nodule is a benign nodule or a malignant lung tumor; determining lung cancer prognosis; monitoring lung cancer progression or remission; monitoring for lung cancer recurrence; monitoring metastasis; treatment selection; monitoring response to a therapeutic agent or other treatment; stratification of individuals for computed tomography (CT) screening (e.g., identifying those individuals at greater risk of lung cancer and thereby most likely to benefit from spiral-CT screening, thus increasing the positive predictive value of CT); combining biomarker testing with additional biomedical information, such as smoking history, etc., or with nodule size, morphology, etc. (such as to provide an assay with increased diagnostic performance compared to CT testing or biomarker testing alone); facilitating the diagnosis of a pulmonary nodule as malignant or benign; facilitating clinical decision making once a pulmonary nodule is observed on CT (e.g., ordering repeat CT scans if the nodule is deemed to be low risk, such as if a biomarker-based test is negative, with or without categorization of nodule size, or considering biopsy if the nodule is deemed medium to high risk, such as if a biomarker-based test is positive, with or without categorization of nodule size); and facilitating decisions regarding clinical follow-up (e.g., whether to implement repeat CT scans, fine needle biopsy, or thoracotomy after observing a non-calcified nodule on CT). Biomarker testing may improve positive predictive value (PPV) over CT screening alone. In addition to their utilities in conjunction with CT screening, the biomarkers described herein can also be used in conjunction with any other imaging modalities used for lung cancer, such as chest X-ray. Furthermore, the described biomarkers may also be useful in permitting certain of these uses before indications of lung cancer are detected by imaging modalities or other clinical correlates, or before symptoms appear.

As an example of the manner in which any of the biomarkers described herein can be used to diagnose lung cancer, differential expression of one or more of the described biomarkers in an individual who is not known to have lung cancer may indicate that the individual has lung cancer, thereby enabling detection of lung cancer at an early stage of the disease when treatment is most effective, perhaps before the lung cancer is detected by other means or before symptoms appear. Over-expression of one or more of the biomarkers during the course of lung cancer may be indicative of lung cancer progression, e.g., a lung tumor is growing and/or metastasizing (and thus indicate a poor prognosis), whereas a decrease in the degree to which one or more of the biomarkers is differentially expressed (i.e., in subsequent biomarker tests, the expression level in the individual is moving toward or approaching a "normal" expression level) may be indicative of lung cancer remission, e.g., a lung tumor is shrinking (and thus indicate a good or better prognosis). Similarly, an increase in the degree to which one or more of the biomarkers is differentially expressed (i.e., in subsequent biomarker tests, the expression level in the individual is moving further away from a "normal" expression level) during the course of lung cancer treatment may indicate that the lung cancer is progressing and therefore indicate that the treatment is ineffective, whereas a decrease in differential expression of one or more of the biomarkers during the course of lung cancer treatment may be indicative of lung cancer remission and therefore indicate that the treatment is working successfully. Additionally, an increase or decrease in the differential expression of one or more of the biomarkers after an individual has apparently been cured of lung cancer may be indicative of lung cancer recurrence. In a situation such as this, for example, the individual can be re-started on therapy (or the therapeutic regimen modified such as to increase dosage amount and/or frequency, if the individual has maintained therapy) at an earlier stage than if the recurrence of lung cancer was not detected until later. Furthermore, a differential expression level of one or more of the biomarkers in an individual may be predictive of the individual's response to a particular therapeutic agent. In monitoring for lung cancer recurrence or progression, changes in the biomarker expression levels may indicate the need for repeat imaging (e.g., repeat CT scanning), such as to determine lung cancer activity or to determine the need for changes in treatment.

Detection of any of the biomarkers described herein may be particularly useful following, or in conjunction with, lung cancer treatment, such as to evaluate the success of the treatment or to monitor lung cancer remission, recurrence, and/or progression (including metastasis) following treatment. Lung cancer treatment may include, for example, administration of a therapeutic agent to the individual, performance of surgery (e.g., surgical resection of at least a portion of a lung tumor), administration of radiation therapy, or any other type of lung cancer treatment used in the art, and any combination of these treatments. For example, any of the biomarkers may be detected at least once after treatment or may be detected multiple times after treatment (such as at periodic intervals), or may be detected both before and after treatment. Differential expression levels of any of the biomarkers in an individual over time may be indicative of lung cancer progression, remission, or recurrence, examples of which include any of the following: an increase or decrease in the expression level of the biomarkers after treatment compared with the expression level of the biomarker before treatment; an increase or decrease in the expression level of the biomarker at a later time point after treatment compared with the expression level of the biomarker at an earlier time point after treatment; and a differential expression level of the biomarker at a single time point after treatment compared with normal levels of the biomarker.

As a specific example, the biomarker levels for any of the biomarkers described herein can be determined in pre-surgery and post-surgery (e.g., 2-4 weeks after surgery) serum samples. An increase in the biomarker expression level(s) in the post-surgery sample compared with the pre-surgery sample can indicate progression of lung cancer (e.g., unsuccessful surgery), whereas a decrease in the biomarker expression level(s) in the post-surgery sample compared with the pre-surgery sample can indicate regression of lung cancer (e.g., the surgery successfully removed the lung tumor). Similar analyses of the biomarker levels can be carried out before and after other forms of treatment, such as before and after radiation therapy or administration of a therapeutic agent or cancer vaccine.

In addition to testing biomarker levels as a stand-alone diagnostic test, biomarker levels can also be done in conjunction with determination of SNPs or other genetic lesions or variability that are indicative of increased risk of susceptibility of disease. (See, e.g., Amos et al., Nature Genetics 40, 616-622 (2009)).

In addition to testing biomarker levels as a stand-alone diagnostic test, biomarker levels can also be done in conjunction with CT screening. For example, the biomarkers may facilitate the medical and economic justification for implementing CT screening, such as for screening large asymptomatic populations at risk for lung cancer (e.g., smokers). For example, a "pre-CT" test of biomarker levels could be used to stratify high-risk individuals for CT screening, such as for identifying those who are at highest risk for lung cancer based on their biomarker levels and who should be prioritized for CT screening. If a CT test is implemented, biomarker levels (e.g., as determined by an aptamer assay of serum or plasma samples) of one or more biomarkers can be measured and the diagnostic score could be evaluated in conjunction with additional biomedical information (e.g., tumor parameters determined by CT testing) to enhance positive predictive value (PPV) over CT or biomarker testing alone. A "post-CT" aptamer panel for determining biomarker levels can be used to determine the likelihood that a pulmonary nodule observed by CT (or other imaging modality) is malignant or benign.

Detection of any of the biomarkers described herein may be useful for post-CT testing. For example, biomarker testing may eliminate or reduce a significant number of false positive tests over CT alone. Further, biomarker testing may facilitate treatment of patients. By way of example, if a lung nodule is less than 5 mm in size, results of biomarker testing may advance patients from "watch and wait" to biopsy at an earlier time; if a lung nodule is 5-9 mm, biomarker testing may eliminate the use of a biopsy or thoracotomy on false positive scans; and if a lung nodule is larger than 10 mm, biomarker testing may eliminate surgery for a sub-population of these patients with benign nodules Eliminating the need for biopsy in some patients based on biomarker testing would be beneficial because there is significant morbidity associated with nodule biopsy and difficulty in obtaining nodule tissue depending on the location of nodule. Similarly, eliminating the need for surgery in some patients, such as those whose nodules are actually benign, would avoid unnecessary risks and costs associated with surgery.

In addition to testing biomarker levels in conjunction with CT screening (e.g., assessing biomarker levels in conjunction with size or other characteristics of a lung nodule observed on a CT scan), information regarding the biomarkers can also be evaluated in conjunction with other types of data, particularly data that indicates an individual's risk for lung cancer (e.g., patient clinical history, symptoms, family history of cancer, risk factors such as whether or not the individual is a smoker, and/or status of other biomarkers, etc.). These various data can be assessed by automated methods, such as a computer program/software, which can be embodied in a computer or other apparatus/device.

Any of the described biomarkers may also be used in imaging tests. For example, an imaging agent can be coupled to any of the described biomarkers, which can be used to aid in lung cancer diagnosis, to monitor disease progression/remission or metastasis, to monitor for disease recurrence, or to monitor response to therapy, among other uses.

Detection and Determination of Biomarkers and Biomarker Values

A biomarker value for the biomarkers described herein can be detected using any of a variety of known analytical methods. In one embodiment, a biomarker value is detected using a capture reagent. As used herein, a "capture agent" or "capture reagent" refers to a molecule that is capable of binding specifically to a biomarker. In various embodiments, the capture reagent can be exposed to the biomarker in solution or can be exposed to the biomarker while the capture reagent is immobilized on a solid support. In other embodiments, the capture reagent contains a feature that is reactive with a secondary feature on a solid support. In these embodiments, the capture reagent can be exposed to the biomarker in solution, and then the feature on the capture reagent can be used in conjunction with the secondary feature on the solid support to immobilize the biomarker on the solid support. The capture reagent is selected based on the type of analysis to be conducted. Capture reagents include but are not limited to aptamers, antibodies, adnectins, ankyrins, other antibody mimetics and other protein scaffolds, autoantibodies, chimeras, small molecules, an $F(ab')_2$ fragment, a single chain antibody fragment, an Fv fragment, a single chain Fv fragment, a nucleic acid, a lectin, a ligand-binding receptor, affybodies, nanobodies, imprinted polymers, avimers, peptidomimetics, a hormone receptor, a cytokine receptor, and synthetic receptors, and modifications and fragments of these.

In some embodiments, a biomarker value is detected using a biomarker/capture reagent complex.

In other embodiments, the biomarker value is derived from the biomarker/capture reagent complex and is detected indirectly, such as, for example, as a result of a reaction that is subsequent to the biomarker/capture reagent interaction, but is dependent on the formation of the biomarker/capture reagent complex.

In some embodiments, the biomarker value is detected directly from the biomarker in a biological sample.

In one embodiment, the biomarkers are detected using a multiplexed format that allows for the simultaneous detection of two or more biomarkers in a biological sample. In one embodiment of the multiplexed format, capture reagents are immobilized, directly or indirectly, covalently or non-covalently, in discrete locations on a solid support. In another embodiment, a multiplexed format uses discrete solid supports where each solid support has a unique capture reagent associated with that solid support, such as, for example quantum dots. In another embodiment, an individual device is used for the detection of each one of multiple biomarkers to be detected in a biological sample. Individual devices can be configured to permit each biomarker in the biological sample to be processed simultaneously. For example, a microtiter plate can be used such that each well in the plate is used to uniquely analyze one of multiple biomarkers to be detected in a biological sample.

In one or more of the foregoing embodiments, a fluorescent tag can be used to label a component of the biomarker/capture complex to enable the detection of the biomarker value. In various embodiments, the fluorescent label can be conjugated to a capture reagent specific to any of the biomarkers described herein using known techniques, and the fluorescent label can then be used to detect the corresponding biomarker value. Suitable fluorescent labels include rare earth chelates, fluorescein and its derivatives, rhodamine and its derivatives, dansyl, allophycocyanin, PBXL-3, Qdot 605, Lissamine, phycoerythrin, Texas Red, and other such compounds.

In one embodiment, the fluorescent label is a fluorescent dye molecule. In some embodiments, the fluorescent dye molecule includes at least one substituted indolium ring system in which the substituent on the 3-carbon of the indolium ring contains a chemically reactive group or a conjugated substance. In some embodiments, the dye molecule includes an AlexFluor molecule, such as, for example, AlexaFluor 488, AlexaFluor 532, AlexaFluor 647, AlexaFluor 680, or AlexaFluor 700. In other embodiments, the dye molecule includes a first type and a second type of dye molecule, such as, e.g., two different AlexaFluor molecules. In other embodiments, the dye molecule includes a first type and a second type of dye molecule, and the two dye molecules have different emission spectra.

Fluorescence can be measured with a variety of instrumentation compatible with a wide range of assay formats. For example, spectrofluorimeters have been designed to analyze microtiter plates, microscope slides, printed arrays, cuvettes, etc. See Principles of Fluorescence Spectroscopy, by J. R. Lakowicz, Springer Science+Business Media, Inc., 2004; Bioluminescence & Chemiluminescence: Progress & Current Applications; Philip E. Stanley and Larry J. Kricka editors, World Scientific Publishing Company, January 2002.

In one or more of the foregoing embodiments, a chemiluminescence tag can optionally be used to label a component of the biomarker/capture complex to enable the detection of a biomarker value. Suitable chemiluminescent materials include any of oxalyl chloride, Rodamin 6G, Ru(bipy)$_3^{2+}$, TMAE (tetrakis(dimethylamino)ethylene), pyrogallol (1,2,3-trihydroxibenzene), Lucigenin, peroxyoxalates, aryl oxalates, acridinium esters, dioxetanes, and others.

In yet other embodiments, the detection method includes an enzyme/substrate combination that generates a detectable signal that corresponds to the biomarker value. Generally, the enzyme catalyzes a chemical alteration of the chromogenic substrate which can be measured using various techniques, including spectrophotometry, fluorescence, and chemiluminescence. Suitable enzymes include, for example, luciferases, luciferin, malate dehydrogenase, urease, horseradish peroxidase (HRPO), alkaline phosphatase, beta-galactosidase, glucoamylase, lysozyme, glucose oxidase, galactose oxidase, and glucose-6-phosphate dehydrogenase, uricase, xanthine oxidase, lactoperoxidase, microperoxidase, and the like.

In yet other embodiments, the detection method can be a combination of fluorescence, chemiluminescence, radionuclide or enzyme/substrate combinations that generate a measurable signal. Multimodal signaling could have unique and advantageous characteristics in biomarker assay formats.

More specifically, the biomarker values for the biomarkers described herein can be detected using known analytical methods including, singleplex aptamer assays, multiplexed aptamer assays, singleplex or multiplexed immunoassays, mRNA expression profiling, miRNA expression profiling, mass spectrometric analysis, histological/cytological methods, etc. as detailed below.

Determination of Biomarker Values Using Aptamer-Based Assays

Assays directed to the detection and quantification of physiologically significant molecules in biological samples and other samples are important tools in scientific research and in the health care field. One class of such assays involves the use of a microarray that includes one or more aptamers immobilized on a solid support. The aptamers are each capable of binding to a target molecule in a highly specific manner and with very high affinity. See, e.g., U.S. Pat. No. 5,475,096 entitled "Nucleic Acid Ligands," see also, e.g., U.S. Pat. Nos. 6,242,246, 6,458,543, and 6,503,715, each of which is entitled "Nucleic Acid Ligand Diagnostic Biochip". Once the microarray is contacted with a sample, the aptamers bind to their respective target molecules present in the sample and thereby enable a determination of a biomarker value corresponding to a biomarker.

As used herein, an "aptamer" refers to a nucleic acid that has a specific binding affinity for a target molecule. It is recognized that affinity interactions are a matter of degree; however, in this context, the "specific binding affinity" of an aptamer for its target means that the aptamer binds to its target generally with a much higher degree of affinity than it binds to other components in a test sample. An "aptamer" is a set of copies of one type or species of nucleic acid molecule that has a particular nucleotide sequence. An aptamer can include any suitable number of nucleotides, including any number of chemically modified nucleotides. "Aptamers" refers to more than one such set of molecules. Different aptamers can have either the same or different numbers of nucleotides. Aptamers can be DNA or RNA or chemically modified nucleic acids and can be single stranded, double stranded, or contain double stranded regions, and can include higher ordered structures. An aptamer can also be a photoaptamer, where a photoreactive or chemically reactive functional group is included in the aptamer to allow it to be covalently linked to its corresponding target. Any of the aptamer methods disclosed herein can include the use of two or more aptamers that specifically bind the same target molecule. As further described below, an aptamer may include a tag. If an aptamer includes a tag, all copies of the aptamer need not have the same tag. Moreover, if different aptamers each include a tag, these different aptamers can have either the same tag or a different tag.

An aptamer can be identified using any known method, including the SELEX process. Once identified, an aptamer can be prepared or synthesized in accordance with any known method, including chemical synthetic methods and enzymatic synthetic methods.

The terms "SELEX" and "SELEX process" are used interchangeably herein to refer generally to a combination of (1) the selection of aptamers that interact with a target molecule in a desirable manner, for example binding with high affinity to a protein, with (2) the amplification of those selected nucleic acids. The SELEX process can be used to identify aptamers with high affinity to a specific target or biomarker.

SELEX generally includes preparing a candidate mixture of nucleic acids, binding of the candidate mixture to the desired target molecule to form an affinity complex, separating the affinity complexes from the unbound candidate nucleic acids, separating and isolating the nucleic acid from the affinity complex, purifying the nucleic acid, and identifying a specific aptamer sequence. The process may include multiple rounds to further refine the affinity of the selected aptamer. The process can include amplification steps at one or more points in the process. See, e.g., U.S. Pat. No. 5,475,096, entitled "Nucleic Acid Ligands." The SELEX process can be used to generate an aptamer that covalently binds its target as well as an aptamer that non-covalently binds its target. See, e.g., U.S. Pat. No. 5,705,337 entitled "Systematic Evolution of Nucleic Acid Ligands by Exponential Enrichment: Chemi-SELEX."

The SELEX process can be used to identify high-affinity aptamers containing modified nucleotides that confer improved characteristics on the aptamer, such as, for example, improved in vivo stability or improved delivery characteristics. Examples of such modifications include chemical substitutions at the ribose and/or phosphate and/or base positions. SELEX process-identified aptamers containing modified nucleotides are described in U.S. Pat. No. 5,660,985, entitled "High Affinity Nucleic Acid Ligands Containing Modified Nucleotides," which describes oligonucleotides containing nucleotide derivatives chemically modified at the 5'- and 2'-positions of pyrimidines. U.S. Pat. No. 5,580,737, see supra, describes highly specific aptamers containing one or more nucleotides modified with 2'-amino (2'-$NH_2$), 2'-fluoro (2'-F), and/or 2'-O-methyl (2'-OMe). See also, U.S. Patent Application Publication 20090098549, entitled "SELEX and PHOTOSELEX," which describes nucleic acid libraries having expanded physical and chemical properties and their use in SELEX and photoSELEX.

SELEX can also be used to identify aptamers that have desirable off-rate characteristics. See U.S. Patent Application Publication 20090004667, entitled "Method for Generating Aptamers with Improved Off-Rates," which describes improved SELEX methods for generating aptamers that can bind to target molecules. Methods for producing aptamers and photoaptamers having slower rates of dissociation from their respective target molecules are described. The methods involve contacting the candidate mixture with the target molecule, allowing the formation of nucleic acid-target complexes to occur, and performing a slow off-rate enrichment process wherein nucleic acid-target complexes with fast dissociation rates will dissociate and not reform, while complexes with slow dissociation rates will remain intact. Additionally, the methods include the use of modified nucleotides in the production of candidate nucleic acid mixtures to generate aptamers with improved off-rate performance.

A variation of this assay employs aptamers that include photoreactive functional groups that enable the aptamers to covalently bind or "photocrosslink" their target molecules. See, e.g., U.S. Pat. No. 6,544,776 entitled "Nucleic Acid Ligand Diagnostic Biochip." These photoreactive aptamers are also referred to as photoaptamers. See, e.g., U.S. Pat. Nos. 5,763,177, 6,001,577, and 6,291,184, each of which is entitled "Systematic Evolution of Nucleic Acid Ligands by Exponential Enrichment: Photoselection of Nucleic Acid Ligands and Solution SELEX," see also, e.g., U.S. Pat. No. 6,458,539, entitled "Photoselection of Nucleic Acid Ligands." After the microarray is contacted with the sample and the photoaptamers have had an opportunity to bind to their target molecules, the photoaptamers are photoactivated, and the solid support is washed to remove any non-specifically bound molecules. Harsh wash conditions may be used, since target molecules that are bound to the photoaptamers are generally not removed, due to the covalent bonds created by the photoactivated functional group(s) on the photoaptamers. In this manner, the assay enables the detection of a biomarker value corresponding to a biomarker in the test sample.

In both of these assay formats, the aptamers are immobilized on the solid support prior to being contacted with the sample. Under certain circumstances, however, immobilization of the aptamers prior to contact with the sample may not provide an optimal assay. For example, pre-immobilization of the aptamers may result in inefficient mixing of the aptamers with the target molecules on the surface of the solid support, perhaps leading to lengthy reaction times and, therefore, extended incubation periods to permit efficient binding of the aptamers to their target molecules. Further, when photoaptamers are employed in the assay and depending upon the material utilized as a solid support, the solid support may tend to scatter or absorb the light used to effect the formation of covalent bonds between the photoaptamers and their target molecules. Moreover, depending upon the method employed, detection of target molecules bound to their aptamers can be subject to imprecision, since the surface of the solid support may also be exposed to and affected by any labeling agents that are used. Finally, immobilization of the aptamers on the solid support generally involves an aptamer-preparation step (i.e., the immobilization) prior to exposure of the aptamers to the sample, and this preparation step may affect the activity or functionality of the aptamers.

Aptamer assays that permit an aptamer to capture its target in solution and then employ separation steps that are designed to remove specific components of the aptamer-target mixture prior to detection have also been described (see U.S. Patent Application Publication 20090042206, entitled "Multiplexed Analyses of Test Samples"). The described aptamer assay methods enable the detection and quantification of a non-nucleic acid target (e.g., a protein target) in a test sample by detecting and quantifying a nucleic acid (i.e., an aptamer). The described methods create a nucleic acid surrogate (i.e, the aptamer) for detecting and quantifying a non-nucleic acid target, thus allowing the wide variety of nucleic acid technologies, including amplification, to be applied to a broader range of desired targets, including protein targets.

Aptamers can be constructed to facilitate the separation of the assay components from an aptamer biomarker complex (or photoaptamer biomarker covalent complex) and permit isolation of the aptamer for detection and/or quantification. In one embodiment, these constructs can include a cleavable or releasable element within the aptamer sequence. In other embodiments, additional functionality can be introduced into the aptamer, for example, a labeled or detectable component, a spacer component, or a specific binding tag or immobilization element. For example, the aptamer can include a tag connected to the aptamer via a cleavable moiety, a label, a spacer component separating the label, and the cleavable moiety. In one embodiment, a cleavable element is a photocleavable linker. The photocleavable linker can be attached to a biotin moiety and a spacer section, can include an NHS group for derivatization of amines, and can be used to introduce a biotin group to an aptamer, thereby allowing for the release of the aptamer later in an assay method.

Homogenous assays, done with all assay components in solution, do not require separation of sample and reagents prior to the detection of signal. These methods are rapid and easy to use. These methods generate signal based on a molecular capture or binding reagent that reacts with its specific target. For lung cancer, the molecular capture reagents would be an aptamer or an antibody or the like and the specific target would be a lung cancer biomarker of Table 20.

In one embodiment, a method for signal generation takes advantage of anisotropy signal change due to the interaction of a fluorophore-labeled capture reagent with its specific biomarker target. When the labeled capture reacts with its target, the increased molecular weight causes the rotational motion of the fluorophore attached to the complex to become much slower changing the anisotropy value. By monitoring the anisotropy change, binding events may be used to quantitatively measure the biomarkers in solutions. Other methods include fluorescence polarization assays, molecular beacon methods, time resolved fluorescence quenching, chemiluminescence, fluorescence resonance energy transfer, and the like.

An exemplary solution-based aptamer assay that can be used to detect a biomarker value corresponding to a biomarker in a biological sample includes the following: (a) preparing a mixture by contacting the biological sample with an aptamer that includes a first tag and has a specific affinity for the biomarker, wherein an aptamer affinity complex is formed when the biomarker is present in the sample; (b) exposing the mixture to a first solid support including a first capture element, and allowing the first tag to associate with the first capture element; (c) removing any components of the mixture not associated with the first solid support; (d) attaching a second tag to the biomarker component of the aptamer affinity complex; (e) releasing the aptamer affinity complex from the first solid support; (f) exposing the released aptamer affinity complex to a second solid support that includes a second capture element and allowing the second tag to associate with the second capture element; (g) removing any non-complexed aptamer from the mixture by partitioning the non-complexed aptamer from the aptamer affinity complex; (h) eluting the aptamer from the solid support; and (i) detecting the biomarker by detecting the aptamer component of the aptamer affinity complex.

Determination of Biomarker Values using Immunoassays

Immunoassay methods are based on the reaction of an antibody to its corresponding target or analyte and can detect the analyte in a sample depending on the specific assay format. To improve specificity and sensitivity of an assay method based on immuno-reactivity, monoclonal antibodies are often used because of their specific epitope recognition. Polyclonal antibodies have also been successfully used in various immunoassays because of their increased affinity for the target as compared to monoclonal antibodies Immunoassays have been designed for use with a wide range of biological sample matrices Immunoassay formats have been designed to provide qualitative, semi-quantitative, and quantitative results.

Quantitative results are generated through the use of a standard curve created with known concentrations of the specific analyte to be detected. The response or signal from an unknown sample is plotted onto the standard curve, and a quantity or value corresponding to the target in the unknown sample is established.

Numerous immunoassay formats have been designed. ELISA or EIA can be quantitative for the detection of an analyte. This method relies on attachment of a label to either the analyte or the antibody and the label component includes, either directly or indirectly, an enzyme. ELISA tests may be formatted for direct, indirect, competitive, or sandwich detection of the analyte. Other methods rely on labels such as, for example, radioisotopes ($I^{125}$) or fluorescence. Additional techniques include, for example, agglutination, nephelometry, turbidimetry, Western blot, immunoprecipitation, immunocytochemistry, immunohistochemistry, flow cytometry, Luminex assay, and others (see ImmunoAssay: A Practical Guide, edited by Brian Law, published by Taylor & Francis, Ltd., 2005 edition).

Exemplary assay formats include enzyme-linked immunosorbent assay (ELISA), radioimmunoassay, fluorescent, chemiluminescence, and fluorescence resonance energy transfer (FRET) or time resolved-FRET (TR-FRET) immunoassays. Examples of procedures for detecting biomarkers include biomarker immunoprecipitation followed by quantitative methods that allow size and peptide level discrimination, such as gel electrophoresis, capillary electrophoresis, planar electrochromatography, and the like.

Methods of detecting and/or quantifying a detectable label or signal generating material depend on the nature of the label. The products of reactions catalyzed by appropriate enzymes (where the detectable label is an enzyme; see above) can be, without limitation, fluorescent, luminescent, or radioactive or they may absorb visible or ultraviolet light. Examples of detectors suitable for detecting such detectable labels include, without limitation, x-ray film, radioactivity counters, scintillation counters, spectrophotometers, colorimeters, fluorometers, luminometers, and densitometers.

Any of the methods for detection can be performed in any format that allows for any suitable preparation, processing, and analysis of the reactions. This can be, for example, in multi-well assay plates (e.g., 96 wells or 384 wells) or using any suitable array or microarray. Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting a detectable label.

Determination of Biomarker Values Using Gene Expression Profiling

Measuring mRNA in a biological sample may be used as a surrogate for detection of the level of the corresponding protein in the biological sample. Thus, any of the biomarkers or biomarker panels described herein can also be detected by detecting the appropriate RNA.

mRNA expression levels are measured by reverse transcription quantitative polymerase chain reaction (RT-PCR followed with qPCR). RT-PCR is used to create a cDNA from the mRNA. The cDNA may be used in a qPCR assay to produce fluorescence as the DNA amplification process progresses. By comparison to a standard curve, qPCR can produce an absolute measurement such as number of copies of mRNA per cell. Northern blots, microarrays, Invader assays, and RT-PCR combined with capillary electrophoresis have all been used to measure expression levels of mRNA in a sample (see Gene Expression Profiling: Methods and Protocols, Richard A. Shimkets, editor, Humana Press, 2004).

miRNA molecules are small RNAs that are non-coding but may regulate gene expression. Any of the methods suited to the measurement of mRNA expression levels can also be used for the corresponding miRNA. Recently many laboratories have investigated the use of miRNAs as biomarkers for disease. Many diseases involve wide-spread transcriptional regulation, and it is not surprising that miRNAs might find a role as biomarkers. The connection between miRNA concentrations and disease is often even less clear than the connections between protein levels and disease, yet the value of miRNA biomarkers might be substantial. Of course, as with any RNA expressed differentially during disease, the problems facing the development of an in vitro diagnostic product will include the requirement that the miRNAs survive in the diseased cell and are easily extracted for analysis, or that the miRNAs are released into blood or other matrices where they must survive long enough to be measured. Protein biomarkers have similar requirements, although many potential protein biomarkers are secreted intentionally at the site of pathology and function, during disease, in a paracrine fashion. Many potential protein biomarkers are designed to function outside the cells within which those proteins are synthesized.

Detection of Biomarkers Using In Vivo Molecular Imaging Technologies

Any of the described biomarkers (see Table 20) may also be used in molecular imaging tests. For example, an imaging agent can be coupled to any of the described biomarkers, which can be used to aid in lung cancer diagnosis, to monitor disease progression/remission or metastasis, to monitor for disease recurrence, or to monitor response to therapy, among other uses.

In vivo imaging technologies provide non-invasive methods for determining the state of a particular disease in the body of an individual. For example, entire portions of the body, or even the entire body, may be viewed as a three dimensional image, thereby providing valuable information concerning morphology and structures in the body. Such technologies may be combined with the detection of the biomarkers described herein to provide information concerning the cancer status, in particular the lung cancer status, of an individual.

The use of in vivo molecular imaging technologies is expanding due to various advances in technology. These advances include the development of new contrast agents or labels, such as radiolabels and/or fluorescent labels, which can provide strong signals within the body; and the development of powerful new imaging technology, which can detect and analyze these signals from outside the body, with sufficient sensitivity and accuracy to provide useful information. The contrast agent can be visualized in an appropriate imaging system, thereby providing an image of the portion or portions of the body in which the contrast agent is located. The contrast agent may be bound to or associated with a capture reagent, such as an aptamer or an antibody, for example, and/or with a peptide or protein, or an oligonucleotide (for example, for the detection of gene expression), or a complex containing any of these with one or more macromolecules and/or other particulate forms.

The contrast agent may also feature a radioactive atom that is useful in imaging. Suitable radioactive atoms include technetium-99m or iodine-123 for scintigraphic studies. Other readily detectable moieties include, for example, spin labels for magnetic resonance imaging (MRI) such as, for example, iodine-123 again, iodine-131, indium-111, fluorine-19, carbon-13, nitrogen-15, oxygen-17, gadolinium, manganese or iron. Such labels are well known in the art and could easily be selected by one of ordinary skill in the art.

Standard imaging techniques include but are not limited to magnetic resonance imaging, computed tomography scanning, positron emission tomography (PET), single photon emission computed tomography (SPECT), and the like. For diagnostic in vivo imaging, the type of detection instrument available is a major factor in selecting a given contrast agent, such as a given radionuclide and the particular biomarker that it is used to target (protein, mRNA, and the like). The radionuclide chosen typically has a type of decay that is detectable by a given type of instrument. Also, when selecting a radionuclide for in vivo diagnosis, its half-life should be long enough to enable detection at the time of maximum uptake by the target tissue but short enough that deleterious radiation of the host is minimized.

Exemplary imaging techniques include but are not limited to PET and SPECT, which are imaging techniques in which a radionuclide is synthetically or locally administered to an individual. The subsequent uptake of the radiotracer is measured over time and used to obtain information about the targeted tissue and the biomarker. Because of the high-energy (gamma-ray) emissions of the specific isotopes employed and the sensitivity and sophistication of the instruments used to detect them, the two-dimensional distribution of radioactivity may be inferred from outside of the body.

Commonly used positron-emitting nuclides in PET include, for example, carbon-11, nitrogen-13, oxygen-15, and fluorine-18. Isotopes that decay by electron capture and/or gamma-emission are used in SPECT and include, for example iodine-123 and technetium-99m. An exemplary method for labeling amino acids with technetium-99m is the reduction of pertechnetate ion in the presence of a chelating precursor to form the labile technetium-99m-precursor complex, which, in turn, reacts with the metal binding group of a bifunctionally modified chemotactic peptide to form a technetium-99m-chemotactic peptide conjugate.

Antibodies are frequently used for such in vivo imaging diagnostic methods. The preparation and use of antibodies for in vivo diagnosis is well known in the art. Labeled antibodies which specifically bind any of the biomarkers in Table 20 can be injected into an individual suspected of having a certain type of cancer (e.g., lung cancer), detectable according to the particular biomarker used, for the purpose of diagnosing or evaluating the disease status of the individual. The label used will be selected in accordance with the imaging modality to be used, as previously described. Localization of the label permits determination of the spread of the cancer. The amount of label within an organ or tissue also allows determination of the presence or absence of cancer in that organ or tissue.

Similarly, aptamers may be used for such in vivo imaging diagnostic methods. For example, an aptamer that was used to identify a particular biomarker described in Table 20 (and therefore binds specifically to that particular biomarker) may be appropriately labeled and injected into an individual suspected of having lung cancer, detectable according to the particular biomarker, for the purpose of diagnosing or evaluating the lung cancer status of the individual. The label used will be selected in accordance with the imaging modality to be used, as previously described. Localization of the label permits determination of the spread of the cancer. The amount of label within an organ or tissue also allows determination of the presence or absence of cancer in that organ or tissue. Aptamer-directed imaging agents could have unique and advantageous characteristics relating to tissue penetration, tissue distribution, kinetics, elimination, potency, and selectivity as compared to other imaging agents.

Such techniques may also optionally be performed with labeled oligonucleotides, for example, for detection of gene expression through imaging with antisense oligonucleotides. These methods are used for in situ hybridization, for example, with fluorescent molecules or radionuclides as the label. Other methods for detection of gene expression include, for example, detection of the activity of a reporter gene.

Another general type of imaging technology is optical imaging, in which fluorescent signals within the subject are detected by an optical device that is external to the subject. These signals may be due to actual fluorescence and/or to bioluminescence. Improvements in the sensitivity of optical detection devices have increased the usefulness of optical imaging for in vivo diagnostic assays.

The use of in vivo molecular biomarker imaging is increasing, including for clinical trials, for example, to more rapidly measure clinical efficacy in trials for new cancer therapies and/or to avoid prolonged treatment with a placebo for those diseases, such as multiple sclerosis, in which such prolonged treatment may be considered to be ethically questionable.

For a review of other techniques, see N. Blow, Nature Methods, 6, 465-469, 2009.

Determination of Biomarker Values Using Histology/Cytology Methods

For evaluation of lung cancer, a variety of tissue samples may be used in histological or cytological methods. Sample selection depends on the primary tumor location and sites of metastases. For example, endo- and trans-bronchial biopsies, fine needle aspirates, cutting needles, and core biopsies can be used for histology. Bronchial washing and brushing, pleural aspiration, and sputum, can be used for cyotology. While cytological analysis is still used in the diagnosis of lung cancer, histological methods are known to provide better sensitivity for the detection of cancer. Any of the biomarkers identified herein that were shown to be up-regulated (see Table 19) in the individuals with lung cancer can be used to stain a histological specimen as an indication of disease.

In one embodiment, one or more capture reagent(s) specific to the corresponding biomarker(s) are used in a cytological evaluation of a lung cell sample and may include one or more of the following: collecting a cell sample, fixing the cell sample, dehydrating, clearing, immobilizing the cell sample on a microscope slide, permeabilizing the cell sample, treating for analyte retrieval, staining, destaining, washing, blocking, and reacting with one or more capture reagent/s in a buffered solution. In another embodiment, the cell sample is produced from a cell block.

In another embodiment, one or more capture reagent/s specific to the corresponding biomarkers are used in a histological evaluation of a lung tissue sample and may include one or more of the following: collecting a tissue specimen, fixing the tissue sample, dehydrating, clearing, immobilizing the tissue sample on a microscope slide, permeabilizing the tissue sample, treating for analyte retrieval, staining, destaining, washing, blocking, rehydrating, and reacting with capture reagent/s in a buffered solution. In another embodiment, fixing and dehydrating are replaced with freezing.

In another embodiment, the one or more aptamer/s specific to the corresponding biomarker/s are reacted with the histological or cytological sample and can serve as the nucleic acid target in a nucleic acid amplification method. Suitable nucleic acid amplification methods include, for example, PCR, q-beta replicase, rolling circle amplification, strand displacement, helicase dependent amplification, loop mediated isothermal amplification, ligase chain reaction, and restriction and circularization aided rolling circle amplification.

In one embodiment, the one or more capture reagent(s) specific to the corresponding biomarkers for use in the histological or cytological evaluation are mixed in a buffered solution that can include any of the following: blocking materials, competitors, detergents, stabilizers, carrier nucleic acid, polyanionic materials, etc.

A "cytology protocol" generally includes sample collection, sample fixation, sample immobilization, and staining. "Cell preparation" can include several processing steps after sample collection, including the use of one or more slow off-rate aptamers for the staining of the prepared cells.

Sample collection can include directly placing the sample in an untreated transport container, placing the sample in a transport container containing some type of media, or placing the sample directly onto a slide (immobilization) without any treatment or fixation.

Sample immobilization can be improved by applying a portion of the collected specimen to a glass slide that is treated with polylysine, gelatin, or a silane. Slides can be prepared by smearing a thin and even layer of cells across the slide. Care is generally taken to minimize mechanical distortion and drying artifacts. Liquid specimens can be processed in a cell block method. Or, alternatively, liquid specimens can be mixed 1:1 with the fixative solution for about 10 minutes at room temperature.

Cell blocks can be prepared from residual effusions, sputum, urine sediments, gastrointestinal fluids, cell scraping, or fine needle aspirates. Cells are concentrated or packed by centrifugation or membrane filtration. A number of methods for cell block preparation have been developed. Representative procedures include the fixed sediment, bacterial agar, or membrane filtration methods. In the fixed sediment method, the cell sediment is mixed with a fixative like Bouins, picric acid, or buffered formalin and then the mixture is centrifuged to pellet the fixed cells. The supernatant is removed, drying the cell pellet as completely as possible. The pellet is collected and wrapped in lens paper and then placed in a tissue cassette. The tissue cassette is placed in a jar with additional fixative and processed as a tissue sample. Agar method is very similar but the pellet is removed and dried on paper towel and then cut in half. The cut side is placed in a drop of melted agar on a glass slide and then the pellet is covered with agar making sure that no bubbles form in the agar. The agar is allowed to harden and then any excess agar is trimmed away. This is placed in a tissue cassette and the tissue process completed. Alternatively, the pellet may be directly suspended in 2% liquid agar at 65° C. and the sample centrifuged. The agar cell pellet is allowed to solidify for an hour at 4° C. The solid agar may be removed from the centrifuge tube and sliced in half. The agar is wrapped in filter paper and then the tissue cassette. Processing from this point forward is as described above. Centrifugation can be replaced in any these procedures with membrane filtration. Any of these processes may be used to generate a "cell block sample".

Cell blocks can be prepared using specialized resin including Lowicryl resins, LR White, LR Gold, Unicryl, and MonoStep. These resins have low viscosity and can be polymerized at low temperatures and with ultra violet (UV) light. The embedding process relies on progressively cooling the sample during dehydration, transferring the sample to the resin, and polymerizing a block at the final low temperature at the appropriate UV wavelength.

Cell block sections can be stained with hematoxylin-eosin for cytomorphological examination while additional sections are used for examination for specific markers.

Whether the process is cytologoical or histological, the sample may be fixed prior to additional processing to prevent sample degradation. This process is called "fixation" and describes a wide range of materials and procedures that may be used interchangeably. The sample fixation protocol and reagents are best selected empirically based on the targets to be detected and the specific cell/tissue type to be analyzed. Sample fixation relies on reagents such as ethanol, polyethylene glycol, methanol, formalin, or isopropanol. The samples should be fixed as soon after collection and affixation to the slide as possible. However, the fixative selected can introduce structural changes into various molecular targets making their subsequent detection more difficult. The fixation and immobilization processes and their sequence can modify the appearance of the cell and these changes must be anticipated and recognized by the cytotechnologist. Fixatives can cause shrinkage of certain cell types and cause the cytoplasm to appear granular or reticular. Many fixatives function by crosslinking cellular components. This can damage or modify specific epitopes, generate new epitopes, cause molecular associations, and reduce membrane permeability. Formalin fixation is one of the most common cytological/histological approaches. Formalin forms methyl bridges between neighboring proteins or within proteins. Precipitation or coagulation is also used for fixation and ethanol is frequently used in this type of fixation. A combination of crosslinking and precipitation can also be used for fixation. A strong fixation process is best at preserving morphological information while a weaker fixation process is best for the preservation of molecular targets.

A representative fixative is 50% absolute ethanol, 2 mM polyethylene glycol (PEG), 1.85% formaldehyde. Variations on this formulation include ethanol (50% to 95%), methanol (20%-50%), and formalin (formaldehyde) only. Another common fixative is 2% PEG 1500, 50% ethanol, and 3% methanol. Slides are place in the fixative for about 10 to 15 minutes at room temperature and then removed and allowed to dry. Once slides are fixed they can be rinsed with a buffered solution like PBS.

A wide range of dyes can be used to differentially highlight and contrast or "stain" cellular, sub-cellular, and tissue features or morphological structures. Hematoylin is used to stain nuclei a blue or black color. Orange G-6 and Eosin Azure both stain the cell's cytoplasm. Orange G stains keratin and glycogen containing cells yellow. Eosin Y is used to stain nucleoli, cilia, red blood cells, and superficial epithelial squamous cells. Romanowsky stains are used for air dried slides and are useful in enhancing pleomorphism and distinguishing extracellular from intracytoplasmic material.

The staining process can include a treatment to increase the permeability of the cells to the stain. Treatment of the cells with a detergent can be used to increase permeability. To increase cell and tissue permeability, fixed samples can be further treated with solvents, saponins, or non-ionic detergents. Enzymatic digestion can also improve the accessibility of specific targets in a tissue sample.

After staining, the sample is dehydrated using a succession of alcohol rinses with increasing alcohol concentration. The final wash is done with xylene or a xylene substitute, such as a citrus terpene, that has a refractive index close to that of the coverslip to be applied to the slide. This final step is referred to as clearing. Once the sample is dehydrated and cleared, a mounting medium is applied. The mounting medium is selected to have a refractive index close to the glass and is capable of bonding the coverslip to the slide. It will also inhibit the additional drying, shrinking, or fading of the cell sample.

Regardless of the stains or processing used, the final evaluation of the lung cytological specimen is made by some type of microscopy to permit a visual inspection of the morphology and a determination of the marker's presence or absence. Exemplary microscopic methods include brightfield, phase contrast, fluorescence, and differential interference contrast.

If secondary tests are required on the sample after examination, the coverslip may be removed and the slide destained. Destaining involves using the original solvent systems used in staining the slide originally without the added dye and in a reverse order to the original staining procedure. Destaining may also be completed by soaking the slide in an acid alcohol until the cells are colorless. Once colorless the slides are rinsed well in a water bath and the second staining procedure applied.

In addition, specific molecular differentiation may be possible in conjunction with the cellular morphological analysis through the use of specific molecular reagents such as antibodies or nucleic acid probes or aptamers. This improves the accuracy of diagnostic cytology. Micro-dissection can be used to isolate a subset of cells for additional evaluation, in particular, for genetic evaluation of abnormal chromosomes, gene expression, or mutations.

Preparation of a tissue sample for histological evaluation involves fixation, dehydration, infiltration, embedding, and sectioning. The fixation reagents used in histology are very similar or identical to those used in cytology and have the same issues of preserving morphological features at the expense of molecular ones such as individual proteins. Time can be saved if the tissue sample is not fixed and dehydrated but instead is frozen and then sectioned while frozen. This is a more gentle processing procedure and can preserve more individual markers. However, freezing is not acceptable for long term storage of a tissue sample as subcellular information is lost due to the introduction of ice crystals. Ice in the frozen tissue sample also prevents the sectioning process from producing a very thin slice and thus some microscopic resolution and imaging of subcellular structures can be lost. In addition to formalin fixation, osmium tetroxide is used to fix and stain phospholipids (membranes).

Dehydration of tissues is accomplished with successive washes of increasing alcohol concentration. Clearing employs a material that is miscible with alcohol and the embedding material and involves a stepwise process starting at 50:50 alcohol:clearing reagent and then 100% clearing agent (xylene or xylene substitute). Infiltration involves incubating the tissue with a liquid form of the embedding agent (warm wax, nitrocellulose solution) first at 50:50 embedding agent: clearing agent and the 100% embedding agent. Embedding is completed by placing the tissue in a mold or cassette and filling with melted embedding agent such as wax, agar, or gelatin. The embedding agent is allowed to harden. The hardened tissue sample may then be sliced into thin section for staining and subsequent examination.

Prior to staining, the tissue section is dewaxed and rehydrated. Xylene is used to dewax the section, one or more changes of xylene may be used, and the tissue is rehydrated by successive washes in alcohol of decreasing concentration. Prior to dewax, the tissue section may be heat immobilized to a glass slide at about 80° C. for about 20 minutes.

Laser capture micro-dissection allows the isolation of a subset of cells for further analysis from a tissue section.

As in cytology, to enhance the visualization of the microscopic features, the tissue section or slice can be stained with a variety of stains. A large menu of commercially available stains can be used to enhance or identify specific features.

To further increase the interaction of molecular reagents with cytological/histological samples, a number of techniques for "analyte retrieval" have been developed. The first such technique uses high temperature heating of a fixed sample. This method is also referred to as heat-induced epitope retrieval or HIER. A variety of heating techniques have been used, including steam heating, microwaving, autoclaving, water baths, and pressure cooking or a combination of these methods of heating. Analyte retrieval solutions include, for example, water, citrate, and normal saline buffers. The key to analyte retrieval is the time at high temperature but lower temperatures for longer times have also been successfully used. Another key to analyte retrieval is the pH of the heating solution. Low pH has been found to provide the best immunostaining but also gives rise to backgrounds that frequently require the use of a second tissue section as a negative control. The most consistent benefit (increased immunostaining without increase in background) is generally obtained with a high pH solution regardless of the buffer composition. The analyte retrieval process for a specific target is empirically optimized for the target using heat, time, pH, and buffer composition as variables for process optimization. Using the microwave analyte retrieval method allows for sequential staining of different targets with antibody reagents. But the time required to achieve antibody and enzyme complexes between staining steps has also been shown to degrade cell membrane analytes. Microwave heating methods have improved in situ hybridization methods as well.

To initiate the analyte retrieval process, the section is first dewaxed and hydrated. The slide is then placed in 10 mM sodium citrate buffer pH 6.0 in a dish or jar. A representative procedure uses an 1100 W microwave and microwaves the slide at 100% power for 2 minutes followed by microwaving the slides using 20% power for 18 minutes after checking to be sure the slide remains covered in liquid. The slide is then allowed to cool in the uncovered container and then rinsed with distilled water. HIER may be used in combination with an enzymatic digestion to improve the reactivity of the target to immunochemical reagents.

One such enzymatic digestion protocol uses proteinase K. A 20 μg/ml concentration of proteinase K is prepared in 50 mM Tris Base, 1 mM EDTA, 0.5% Triton X-100, pH 8.0 buffer. The process first involves dewaxing sections in 2 changes of xylene, 5 minutes each. Then the sample is hydrated in 2 changes of 100% ethanol for 3 minutes each, 95% and 80% ethanol for 1 minute each, and then rinsed in distilled water. Sections are covered with Proteinase K working solution and incubated 10-20 minutes at 37° C. in humidified chamber (optimal incubation time may vary depending on tissue type and degree of fixation). The sections are cooled at room temperature for 10 minutes and then rinsed in PBS Tween 20 for 2×2 mM If desired, sections can be blocked to eliminate potential interference from endogenous compounds and enzymes. The section is then incubated with primary antibody at appropriate dilution in primary antibody dilution buffer for 1 hour at room temperature or overnight at 4° C. The section is then rinsed with PBS Tween 20 for 2×2 mM Additional blocking can be performed, if required for the specific application, followed by additional rinsing with PBS Tween 20 for 3×2 mM and then finally the immunostaining protocol completed.

A simple treatment with 1% SDS at room temperature has also been demonstrated to improve immunohistochemical staining. Analyte retrieval methods have been applied to slide mounted sections as well as free floating sections. Another treatment option is to place the slide in a jar containing citric acid and 0.1 Nonident P40 at pH 6.0 and heating to 95° C. The slide is then washed with a buffer solution like PBS.

For immunological staining of tissues it may be useful to block non-specific association of the antibody with tissue proteins by soaking the section in a protein solution like serum or non-fat dry milk.

Blocking reactions may include the need to reduce the level of endogenous biotin; eliminate endogenous charge effects; inactivate endogenous nucleases; and/or inactivate endogenous enzymes like peroxidase and alkaline phosphatase. Endogenous nucleases may be inactivated by degradation with proteinase K, by heat treatment, use of a chelating agent such as EDTA or EGTA, the introduction of carrier DNA or RNA, treatment with a chaotrope such as urea, thiourea, guanidine hydrochloride, guanidine thiocyanate, lithium perchlorate, etc, or diethyl pyrocarbonate. Alkaline phosphatase may be inactivated by treated with 0.1N HCl for 5 minutes at room temperature or treatment with 1 mM levamisole. Peroxidase activity may be eliminated by treatment with 0.03% hydrogen peroxide. Endogenous biotin may be blocked by soaking the slide or section in an avidin (streptavidin, neutravidin may be substituted) solution for at least 15 minutes at room temperature. The slide or section is then washed for at least 10 minutes in buffer. This may be repeated at least three times. Then the slide or section is soaked in a biotin solution for 10 minutes. This may be repeated at least three times with a fresh biotin solution each time. The buffer wash procedure is repeated. Blocking protocols should be minimized to prevent damaging either the cell or tissue structure or the target or targets of interest but one or more of these protocols could be combined to "block" a slide or section prior to reaction with one or more slow off-rate aptamers. See Basic Medical Histology: the Biology of Cells, Tissues and Organs, authored by Richard G. Kessel, Oxford University Press, 1998.

Determination of Biomarker Values Using Mass Spectrometry Methods

A variety of configurations of mass spectrometers can be used to detect biomarker values. Several types of mass spectrometers are available or can be produced with various configurations. In general, a mass spectrometer has the following major components: a sample inlet, an ion source, a mass analyzer, a detector, a vacuum system, and instrument-control system, and a data system. Difference in the sample inlet, ion source, and mass analyzer generally define the type of instrument and its capabilities. For example, an inlet can be a capillary-column liquid chromatography source or can be a direct probe or stage such as used in matrix-assisted laser desorption. Common ion sources are, for example, electrospray, including nanospray and microspray or matrix-assisted laser desorption. Common mass analyzers include a quadrupole mass filter, ion trap mass analyzer and time-of-flight mass analyzer. Additional mass spectrometry methods are well known in the art (see Burlingame et al. Anal. Chem. 70:647 R-716R (1998); Kinter and Sherman. Protein sequencing and identification using tandem mass spectrometry. New York: Wiley-Interscience (2000).

Protein biomarkers and biomarker values can be detected and measured by any of the following: electrospray ionization mass spectrometry (ESI-MS), ESI-MS/MS, ESI-MS/(MS)n, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), tandem time-of-flight (TOF/TOF) technology, called ultraflex III TOF/TOF, atmospheric pressure chemical ionization mass spectrometry (APCI-MS), APCI-MS/MS, APCI-(MS)$^N$, atmospheric pressure photoionization mass spectrometry (APPI-MS), APPI-MS/MS, and APPI-(MS)$^N$, quadrupole mass spectrometry, Fourier transform mass spectrometry (FTMS), quantitative mass spectrometry, and ion trap mass spectrometry.

Sample preparation strategies are used to label and enrich samples before mass spectroscopic characterization of protein biomarkers and determination biomarker values. Labeling methods include but are not limited to isobaric tag for relative and absolute quantitation (iTRAQ) and stable isotope labeling with amino acids in cell culture (SILAC). Capture reagents used to selectively enrich samples for candidate biomarker proteins prior to mass spectroscopic analysis include but are not limited to aptamers, antibodies, nucleic acid probes, chimeras, small molecules, an F(ab')$_2$ fragment, a single chain antibody fragment, an Fv fragment, a single chain Fv fragment, a nucleic acid, a lectin, a ligand-binding receptor, affybodies, nanobodies, ankyrins, domain antibodies, alternative antibody scaffolds (e.g. diabodies etc) imprinted polymers, avimers, peptidomimetics, peptoids, peptide nucleic acids, threose nucleic acid, a hormone receptor, a cytokine receptor, and synthetic receptors, and modifications and fragments of these.

The foregoing assays enable the detection of biomarker values that are useful in methods for diagnosing lung cancer, where the methods comprise detecting, in a biological sample from an individual, at least N biomarker values that each correspond to a biomarker selected from the group consisting of the biomarkers provided in Tables 18, 20 or 21, wherein a classification, as described in detail below, using the biomarker values indicates whether the individual has lung cancer. While certain of the described lung cancer biomarkers are useful alone for detecting and diagnosing lung cancer, methods are also described herein for the grouping of multiple subsets of the lung cancer biomarkers that are each useful as a panel of three or more biomarkers. Thus, various embodiments of the instant application provide combinations comprising N biomarkers, wherein N is at least three biomarkers. In other embodiments, N is selected to be any number from 2-86 biomarkers. It will be appreciated that N can be selected to be any number from any of the above described ranges, as well as similar, but higher order, ranges. In accordance with any of the methods described herein, biomarker values can be detected and classified individually or they can be detected and classified collectively, as for example in a multiplex assay format.

In another aspect, methods are provided for detecting an absence of lung cancer, the methods comprising detecting, in a biological sample from an individual, at least N biomarker values that each correspond to a biomarker selected from the group consisting of the biomarkers provided in Tables 18, 20 or 21, wherein a classification, as described in detail below, of the biomarker values indicates an absence of lung cancer in the individual. While certain of the described lung cancer biomarkers are useful alone for detecting and diagnosing the absence of lung cancer, methods are also described herein for the grouping of multiple subsets of the lung cancer biomarkers that are each useful as a panel of three or more biomarkers. Thus, various embodiments of the instant application provide combinations comprising N biomarkers, wherein N is at least three biomarkers. In other embodiments, N is selected to be any number from 2-86 biomarkers. It will be appreciated that N can be selected to be any number from any of the above described ranges, as well as similar, but higher order, ranges. In accordance with any of the methods described herein, biomarker values can be detected and classified individually or they can be detected and classified collectively, as for example in a multiplex assay format.

Classification of Biomarkers and Calculation of Disease Scores

A biomarker "signature" for a given diagnostic test contains a set of markers, each marker having different levels in the populations of interest. Different levels, in this context, may refer to different means of the marker levels for the individuals in two or more groups, or different variances in the two or more groups, or a combination of both. For the simplest form of a diagnostic test, these markers can be used to assign an unknown sample from an individual into one of two groups, either diseased or not diseased. The assignment of a sample into one of two or more groups is known as classification, and the procedure used to accomplish this assignment is known as a classifier or a classification method. Classification methods may also be referred to as scoring methods. There are many classification methods that can be used to construct a diagnostic classifier from a set of biomarker values. In general, classification methods are most easily performed using supervised learning techniques where a data set is collected using samples obtained from individuals within two (or more, for multiple classification states) distinct groups one wishes to distinguish. Since the class (group or population) to which each sample belongs is known in advance for each sample, the classification method can be trained to give the desired classification response. It is also possible to use unsupervised learning techniques to produce a diagnostic classifier.

Common approaches for developing diagnostic classifiers include decision trees; bagging+boosting+forests; rule inference based learning; Parzen Windows; linear models; logistic; neural network methods; unsupervised clustering; K-means; hierarchical ascending/descending; semi-supervised learning; prototype methods; nearest neighbor; kernel density estimation; support vector machines; hidden Markov models; Boltzmann Learning; and classifiers may be combined either simply or in ways which minimize particular objective functions. For a review, see, e.g., Pattern Classification, R. O. Duda, et al., editors, John Wiley & Sons, 2nd edition, 2001; see also, The Elements of Statistical Learning—Data Mining, Inference, and Prediction, T. Hastie, et al., editors, Springer Science+Business Media, LLC, 2nd edition, 2009; each of which is incorporated by reference in its entirety.

To produce a classifier using supervised learning techniques, a set of samples called training data are obtained. In the context of diagnostic tests, training data includes samples from the distinct groups (classes) to which unknown samples will later be assigned. For example, samples collected from individuals in a control population and individuals in a particular disease population can constitute training data to develop a classifier that can classify unknown samples (or, more particularly, the individuals from whom the samples were obtained) as either having the disease or being free from the disease. The development of the classifier from the training data is known as training the classifier. Specific details on classifier training depend on the nature of the supervised learning technique. For purposes of illustration, an example of training a naïve Bayesian classifier will be described below (see, e.g., Pattern Classification, R. O. Duda, et al., editors, John Wiley & Sons, 2nd edition, 2001; see also, The Elements of Statistical Learning—Data Mining, Inference, and Prediction, T. Hastie, et al., editors, Springer Science+Business Media, LLC, 2nd edition, 2009).

Since typically there are many more potential biomarker values than samples in a training set, care must be used to avoid over-fitting. Over-fitting occurs when a statistical model describes random error or noise instead of the underlying relationship. Over-fitting can be avoided in a variety of way, including, for example, by limiting the number of markers used in developing the classifier, by assuming that the marker responses are independent of one another, by limiting the complexity of the underlying statistical model employed, and by ensuring that the underlying statistical model conforms to the data.

An illustrative example of the development of a diagnostic test using a set of biomarkers includes the application of a naïve Bayes classifier, a simple probabilistic classifier based on Bayes theorem with strict independent treatment of the biomarkers. Each biomarker is described by a class-dependent probability density function (pdf) for the measured RFU values or log RFU (relative fluorescence units) values in each class. The joint pdfs for the set of markers in one class is assumed to be the product of the individual class-dependent pdfs for each biomarker. Training a naïve Bayes classifier in this context amounts to assigning parameters ("parameterization") to characterize the class dependent pdfs. Any underlying model for the class-dependent pdfs may be used, but the model should generally conform to the data observed in the training set.

Specifically, the class-dependent probability of measuring a value $x_i$ for biomarker i in the disease class is written as $p(x_i|d)$ and the overall naïve Bayes probability of observing n markers with values $$x = (x_1, x_2, \ldots x_n)$$

is written as $$p(x|d) = \prod_{i=1}^{n} p(x_i|d)$$

where the individual $x_i$ is are the measured biomarker levels in RFU or log RFU. The classification assignment for an unknown is facilitated by calculating the probability of being diseased $$p(d|x)$$

having measured $$x$$

compared to the probability of being disease free (control)

$$p(c|x)$$

for the same measured values. The ratio of these probabilities is computed from the class-dependent pdfs by application of Bayes theorem, i.e., $$\frac{p(c|x)}{p(d|x)} = \frac{p(x|c)(1-P(d))}{p(x|d)P(d)}$$

where P(d) is the prevalence of the disease in the population appropriate to the test. Taking the logarithm of both sides of this ratio and substituting the naïve Bayes class-dependent probabilities from above gives ln $$\frac{p(c|x)}{p(d|x)} = \sum_{i=1}^{n} \ln \frac{p(x_i|c)}{p(x_i|d)} + \ln \frac{(1-P(d))}{P(d)}.$$

This form is known as the log likelihood ratio and simply states that the log likelihood of being free of the particular disease versus having the disease and is primarily composed of the sum of individual log likelihood ratios of the n individual biomarkers. In its simplest form, an unknown sample (or, more particularly, the individual from whom the sample was obtained) is classified as being free of the disease if the above ratio is greater than zero and having the disease if the ratio is less than zero.

In one exemplary embodiment, the class-dependent biomarker pdfs $p(x_i|c)$ and $p(x_i|d)$ are assumed to be normal or log-normal distributions in the measured RFU values $x_i$, i.e. $$p(x_i|c) = \frac{1}{\sqrt{2\pi}\,\sigma_{c,i}} e^{-\frac{(x_i-\mu_{c,i})^2}{2\sigma_{c,i}^2}}$$

with a similar expression for $p(x_i|d)$ with $\mu_{d,i}$ and $\sigma_{d,i}^2$. Parameterization of the model requires estimation of two parameters for each class-dependent pdf, a mean p, and a variance $\sigma^2$, from the training data. This may be accomplished in a number of ways, including, for example, by maximum likelihood estimates, by least-squares, and by any other methods known to one skilled in the art. Substituting the normal distributions for $p(x_i|c)$ and $p(x_i|d)$ into the log-likelihood ratio defined above gives the following expression:

$$\ln\frac{p(c|\underline{x})}{p(d|\underline{x})} = \sum_{i=1}^{n} \ln\frac{\sigma_{d,i}}{\sigma_{c,i}} - \frac{1}{2}\sum_{i=1}^{n}\left[\left(\frac{x_i - \mu_{c,i}}{\sigma_{c,i}}\right)^2 - \left(\frac{x_i - \mu_{d,i}}{\sigma_{d,i}}\right)^2\right] + \ln\frac{(1 - P(d))}{P(d)}.$$

Once a set of μs and σ²s have been defined for each pdf in each class from the training data and the disease prevalence in the population is specified, the Bayes classifier is fully determined and may be used to classify unknown samples with measured values x.

The performance of the naïve Bayes classifier is dependent upon the number and quality of the biomarkers used to construct and train the classifier. A single biomarker will perform in accordance with its KS-distance (Kolmogorov-Smirnov), as defined in Example 3, below. If a classifier performance metric is defined as the sum of the sensitivity (fraction of true positives, $f_{TP}$) and specificity (one minus the fraction of false positives, $1-f_{FP}$), a perfect classifier will have a score of two and a random classifier, on average, will have a score of one. Using the definition of the KS-distance, that value x* which maximizes the difference in the cdf functions can be found by solving $$\frac{\partial KS}{\partial x} = \frac{\partial(cdf_c(x) - cdf_d(x))}{\partial x} = 0$$

for x which leads to p(x*|c)=p(x*|d), i.e, the KS distance occurs where the class-dependent pdfs cross. Substituting this value of x* into the expression for the KS-distance yields the following definition for $$\begin{aligned} KS &= cdf_c(x^*) - cdf_d(x^*) \\ &= \int_{-\infty}^{x^*} p(x|c)dx - \int_{-\infty}^{x^*} p(x|d)dx \\ &= 1 - \int_{x^*}^{\infty} p(x|c)dx - \int_{-\infty}^{x^*} p(x|d)dx \\ &= 1 - f_{FP} - f_{FN}, \end{aligned}$$

the KS distance is one minus the total fraction of errors using a test with a cut-off at x*, essentially a single analyte Bayesian classifier. Since we define a score of sensitivity+specificity=$2-f_{FP}-f_{FN}$, combining the above definition of the KS-distance we see that sensitivity+specificity=1+KS. We select biomarkers with a statistic that is inherently suited for building naïve Bayes classifiers.

The addition of subsequent markers with good KS distances (>0.3, for example) will, in general, improve the classification performance if the subsequently added markers are independent of the first marker. Using the sensitivity plus specificity as a classifier score, it is straightforward to generate many high scoring classifiers with a variation of a greedy algorithm. (A greedy algorithm is any algorithm that follows the problem solving metaheuristic of making the locally optimal choice at each stage with the hope of finding the global optimum.)

The algorithm approach used here is described in detail in Example 4. Briefly, all single analyte classifiers are generated from a table of potential biomarkers and added to a list. Next, all possible additions of a second analyte to each of the stored single analyte classifiers is then performed, saving a predetermined number of the best scoring pairs, say, for example, a thousand, on a new list. All possible three marker classifiers are explored using this new list of the best two-marker classifiers, again saving the best thousand of these. This process continues until the score either plateaus or begins to deteriorate as additional markers are added. Those high scoring classifiers that remain after convergence can be evaluated for the desired performance for an intended use. For example, in one diagnostic application, classifiers with a high sensitivity and modest specificity may be more desirable than modest sensitivity and high specificity. In another diagnostic application, classifiers with a high specificity and a modest sensitivity may be more desirable. The desired level of performance is generally selected based upon a trade-off that must be made between the number of false positives and false negatives that can each be tolerated for the particular diagnostic application. Such trade-offs generally depend on the medical consequences of an error, either false positive or false negative.

Various other techniques are known in the art and may be employed to generate many potential classifiers from a list of biomarkers using a naïve Bayes classifier. In one embodiment, what is referred to as a genetic algorithm can be used to combine different markers using the fitness score as defined above. Genetic algorithms are particularly well suited to exploring a large diverse population of potential classifiers. In another embodiment, so-called ant colony optimization can be used to generate sets of classifiers. Other strategies that are known in the art can also be employed, including, for example, other evolutionary strategies as well as simulated annealing and other stochastic search methods. Metaheuristic methods, such as, for example, harmony search may also be employed.

Figure 2:
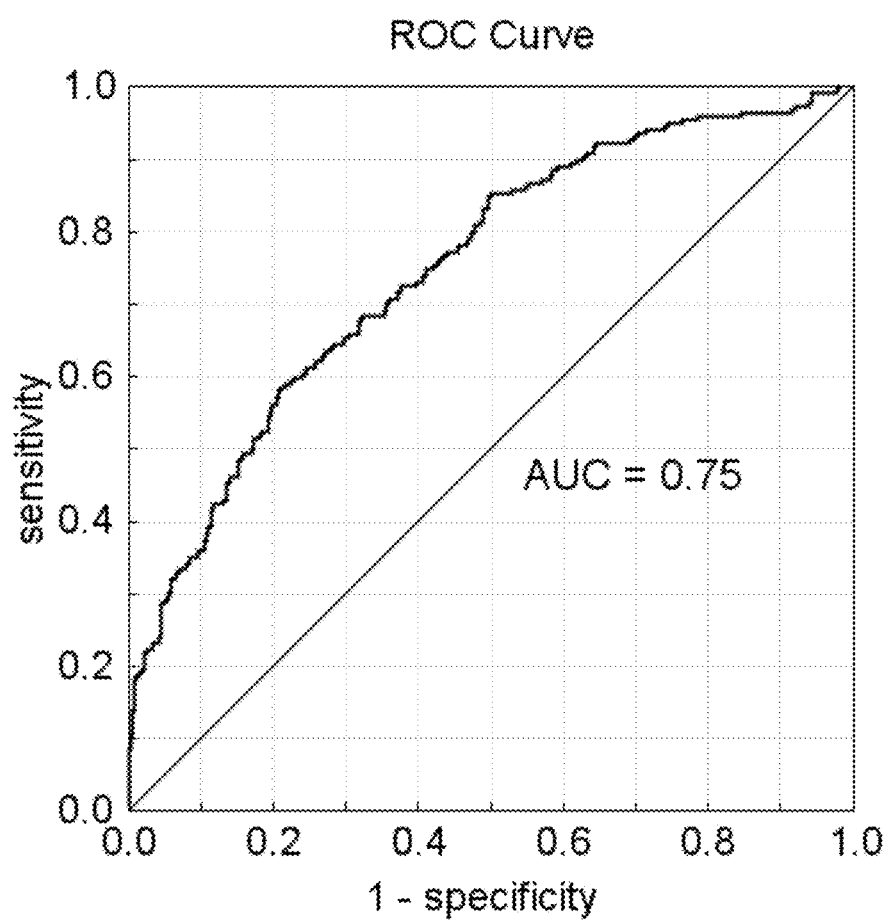
FIG. 2 shows a ROC curve for a single biomarker, SCFsR, using a naïve Bayes classifier for a test that detects lung cancer in asymptomatic smokers.

Exemplary embodiments use any number of the lung cancer biomarkers listed in Tables 18, 20 or 21 in various combinations to produce diagnostic tests for detecting lung cancer (see Examples 2 and 6 for a detailed description of how these biomarkers were identified). In one embodiment, a method for diagnosing lung cancer uses a naïve Bayes classification method in conjunction with any number of the lung cancer biomarkers listed in Tables 18, 20 or 21. In an illustrative example (Example 3), the simplest test for detecting lung cancer from a population of asymptomatic smokers can be constructed using a single biomarker, for example, SCFsR which is down-regulated in lung cancer with a KS-distance of 0.37 (1+KS=1.37). Using the parameters $\mu_{c,i}$, $\sigma_{d,i}$ and $\sigma_{d,i}$ for SCFsR from Table 15 and the equation for the log-likelihood described above, a diagnostic test with a sensitivity of 63% and specificity of 73% (sensitivity+specificity=1.36) can be produced, see Table 14. The ROC curve for this test is displayed in FIG. 2 and has an AUC of 0.75.

Figure 3:
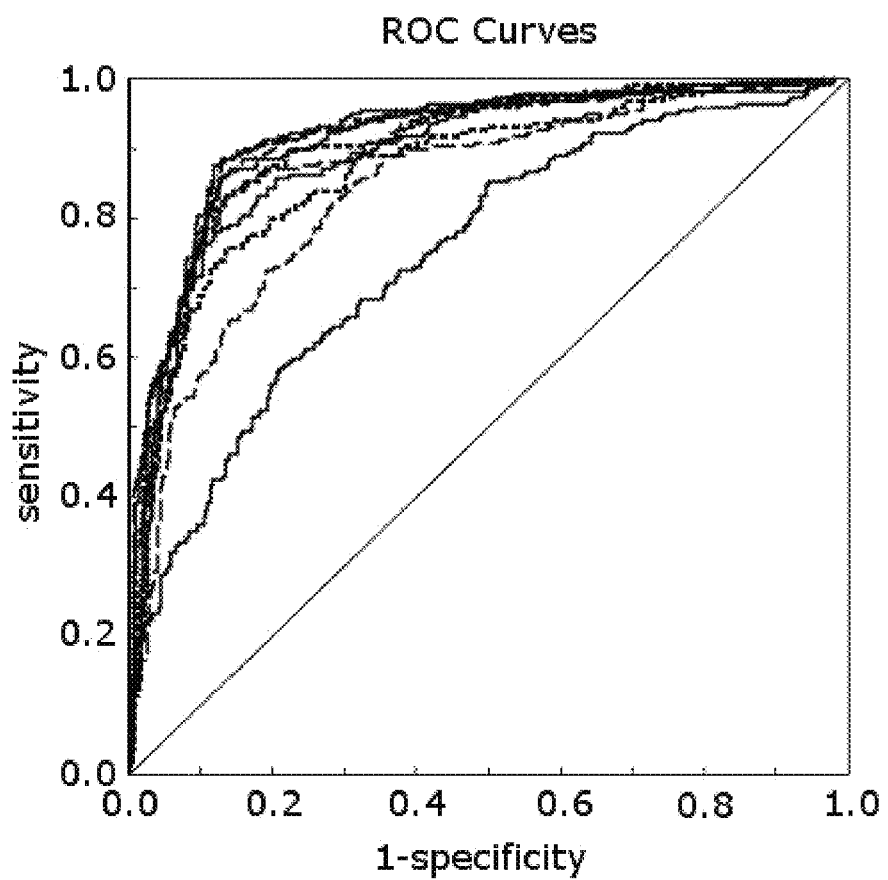
FIG. 3 shows ROC curves for biomarker panels of from one to ten biomarkers using naïve Bayes classifiers for a test that detects lung cancer in asymptomatic smokers.
Figure 4:
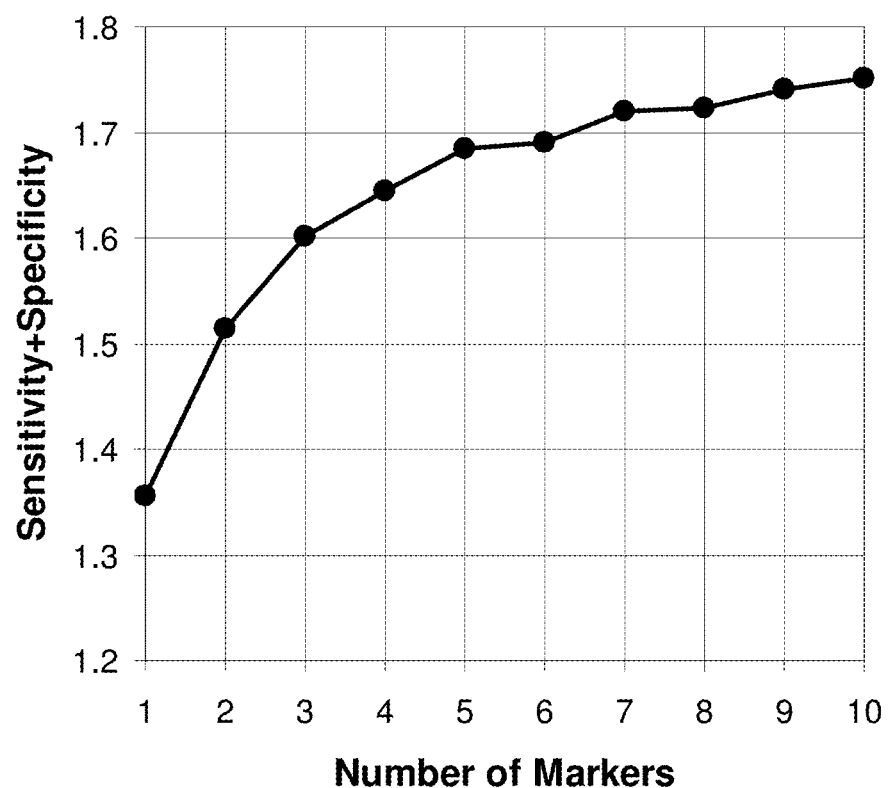
FIG. 4 illustrates the increase in the classification score (specificity+sensitivity) as the number of biomarkers is increased from one to ten using naïve Bayes classification for a benign nodule-lung cancer panel.

Addition of biomarker HSP90a, for example, with a KS-distance of 0.5, significantly improves the classifier performance to a sensitivity of 76% and specificity of 0.75% (sensitivity+specificity=1.51) and an AUC=0.84. Note that the score for a classifier constructed of two biomarkers is not a simple sum of the KS-distances; KS-distances are not additive when combining biomarkers and it takes many more weak markers to achieve the same level of performance as a strong marker. Adding a third marker, ERBB1, for example, boosts the classifier performance to 78% sensitivity and 83% specificity and AUC=0.87. Adding additional biomarkers, such as, for example, PTN, BTK, CD30, Kallikrein 7, LRIG3, LDH-H1, and PARC, produces a series of lung cancer tests summarized in Table 14 and displayed as a series of ROC curves in FIG. 3. The score of the classifiers as a function of the number of analytes used in classifier construction is displayed in FIG. 4. The sensitivity and specificity of this exemplary ten-marker classifier is >87% and the AUC is 0.91.

The markers listed in Tables 18, 20 or 21 can be combined in many ways to produce classifiers for diagnosing lung cancer. In some embodiments, panels of biomarkers are comprised of different numbers of analytes depending on a specific diagnostic performance criterion that is selected. For example, certain combinations of biomarkers will produce tests that are more sensitive (or more specific) than other combinations.

Once a panel is defined to include a particular set of biomarkers from Tables 18, 20 or 21 and a classifier is constructed from a set of training data, the definition of the diagnostic test is complete. In one embodiment, the procedure used to classify an unknown sample is outlined in FIG. 1A. In another embodiment the procedure used to classify an unknown sample is outlined in FIG. 1B. The biological sample is appropriately diluted and then run in one or more assays to produce the relevant quantitative biomarker levels used for classification. The measured biomarker levels are used as input for the classification method that outputs a classification and an optional score for the sample that reflects the confidence of the class assignment.

Table 21 identifies eighty-six biomarkers that are useful for diagnosing lung cancer in both tissue and blood samples. Table 20 identifies twenty-five biomarkers that were identified in tissue samples, but which are useful in serum and plasma samples as well. This is a surprisingly larger number than expected when compared to what is typically found during biomarker discovery efforts and may be attributable to the scale of the described study, which encompassed over 800 proteins measured in hundreds of individual samples, in some cases at concentrations in the low femtomolar range. Presumably, the large number of discovered biomarkers reflects the diverse biochemical pathways implicated in both tumor biology and the body's response to the tumor's presence; each pathway and process involves many proteins. The results show that no single protein of a small group of proteins is uniquely informative about such complex processes; rather, that multiple proteins are involved in relevant processes, such as apoptosis or extracellular matrix repair, for example.

Given the numerous biomarkers identified during the described study, one would expect to be able to derive large numbers of high-performing classifiers that can be used in various diagnostic methods. To test this notion, tens of thousands of classifiers were evaluated using the biomarkers in Table 1. As described in Example 4, many subsets of the biomarkers presented in Table 1 can be combined to generate useful classifiers. By way of example, descriptions are provided for classifiers containing 1, 2, and 3 biomarkers for each of two uses: lung cancer screening of smokers at high risk and diagnosis of individuals that have pulmonary nodules that are detectable by CT. As described in Example 4, all classifiers that were built using the biomarkers in Table 1 perform distinctly better than classifiers that were built using "non-markers".

The performance of classifiers obtained by randomly excluding some of the markers in Table 1, which resulted in smaller subsets from which to build the classifiers, was also tested. As described in Example 4, Part 3, the classifiers that were built from random subsets of the markers in Table 1 performed similarly to optimal classifiers that were built using the full list of markers in Table 1.

The performance of ten-marker classifiers obtained by excluding the "best" individual markers from the ten-marker aggregation was also tested. As described in Example 4, Part 3, classifiers constructed without the "best" markers in Table 1 also performed well. Many subsets of the biomarkers listed in Table 1 performed close to optimally, even after removing the top 15 of the markers listed in the Table. This implies that the performance characteristics of any particular classifier are likely not due to some small core group of biomarkers and that the disease process likely impacts numerous biochemical pathways, which alters the expression level of many proteins.

The results from Example 4 suggest certain possible conclusions: First, the identification of a large number of biomarkers enables their aggregation into a vast number of classifiers that offer similarly high performance Second, classifiers can be constructed such that particular biomarkers may be substituted for other biomarkers in a manner that reflects the redundancies that undoubtedly pervade the complexities of the underlying disease processes. That is to say, the information about the disease contributed by any individual biomarker identified in Table 1 overlaps with the information contributed by other biomarkers, such that it may be that no particular biomarker or small group of biomarkers in Table 1 must be included in any classifier.

Exemplary embodiments use naïve Bayes classifiers constructed from the data in Tables 38 and 39 to classify an unknown sample. The procedure is outlined in FIGS. 1A and B. In one embodiment, the biological sample is optionally diluted and run in a multiplexed aptamer assay. The data from the assay are normalized and calibrated as outlined in Example 3, and the resulting biomarker levels are used as input to a Bayes classification scheme. The log-likelihood ratio is computed for each measured biomarker individually and then summed to produce a final classification score, which is also referred to as a diagnostic score. The resulting assignment as well as the overall classification score can be reported. Optionally, the individual log-likelihood risk factors computed for each biomarker level can be reported as well. The details of the classification score calculation are presented in Example 3.

To demonstrate the utility of aptamer-based proteomic technology described herein for use in discovery of disease-related biomarkers from tissues, homogenized tissues samples from surgical resections obtained from eight non-small cell lung cancer (NSCLC) patients were analyzed, as described in Example 6. All NSCLC patients were smokers, ranging in age from 47 to 75 years old and covering NSCLC stages 1A through 3B (Table 17). Three samples were obtained from each resection: tumor tissue sample, adjacent non-tumor tissue. Total protein concentration was adjusted and normalized in each homogenate for proteomic profiling followed by analysis the DNA microarray platform to measure the concentrations of over 800 human proteins (see Gold et al., "Aptamer-based multiplexed proteomic technology for biomarker discovery," Nature Precedings (2010)).

Figure 21A:
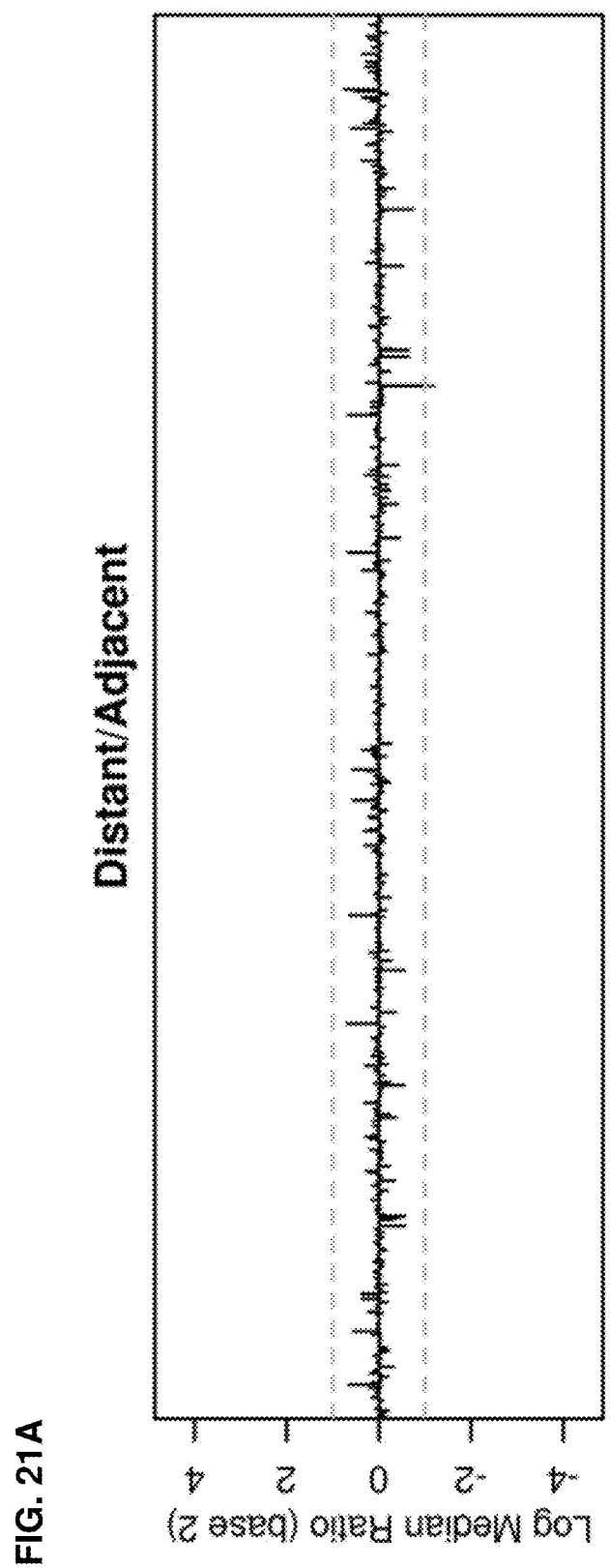
FIGS. 21A-21C show relative changes in protein expression for 813 proteins from eight NSCLC resection samples between adjacent and distant tissue (FIG. 21A), tumor and adjacent tissue (FIG. 21B) and tumor and distant tissue (FIG. 21C) expressed as log 2 median ratios. The dotted line represents a two-fold change (log 2=1).

The protein concentration measurements, expressed as relative fluorescence units (RFU), allow large-scale comparisons of protein signatures among samples (see FIG. 21). With reference to FIG. 21, first the protein expression levels between the control adjacent and distant tissues was compared for each patient sample (FIG. 21A). In this comparison, only one analyte (fibrinogen) exhibited more than a two-fold difference between the samples. Overall, the signals generated by most analytes were similar in adjacent and distant tissue.

Figure 21B:
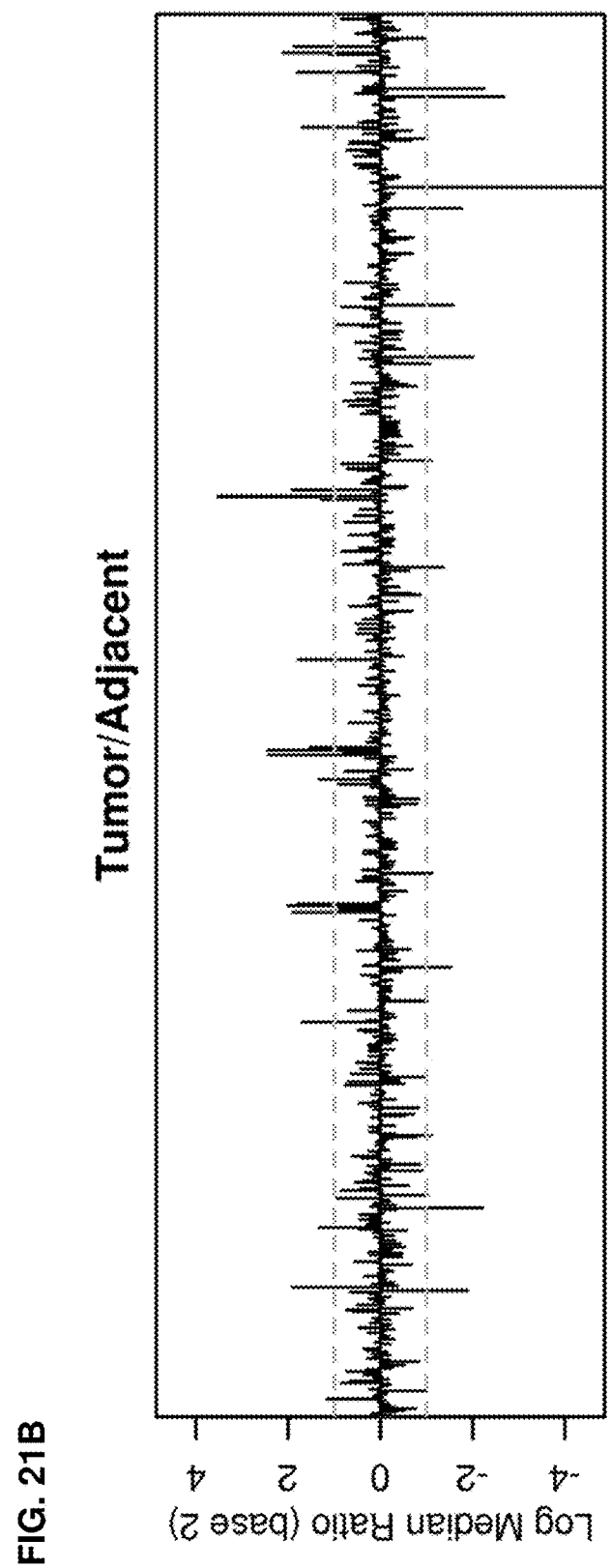
Figure 21C:
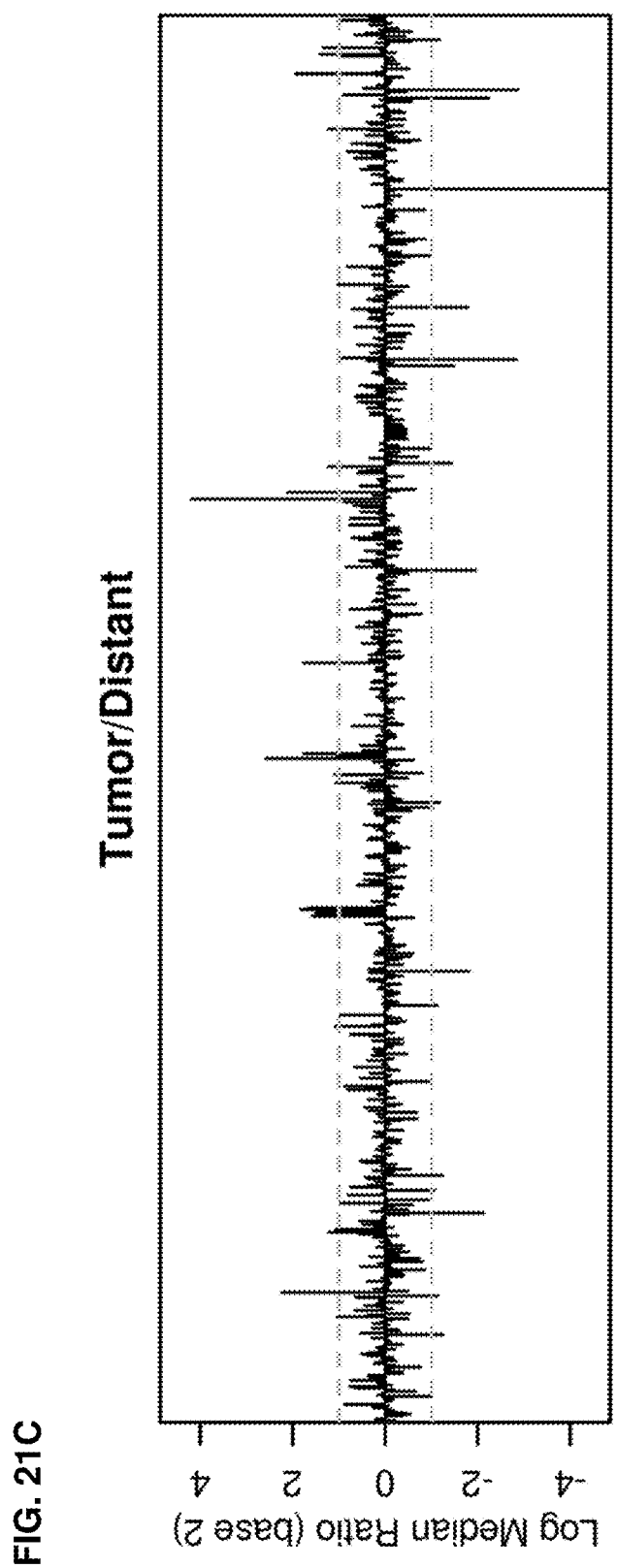
Figure 22:
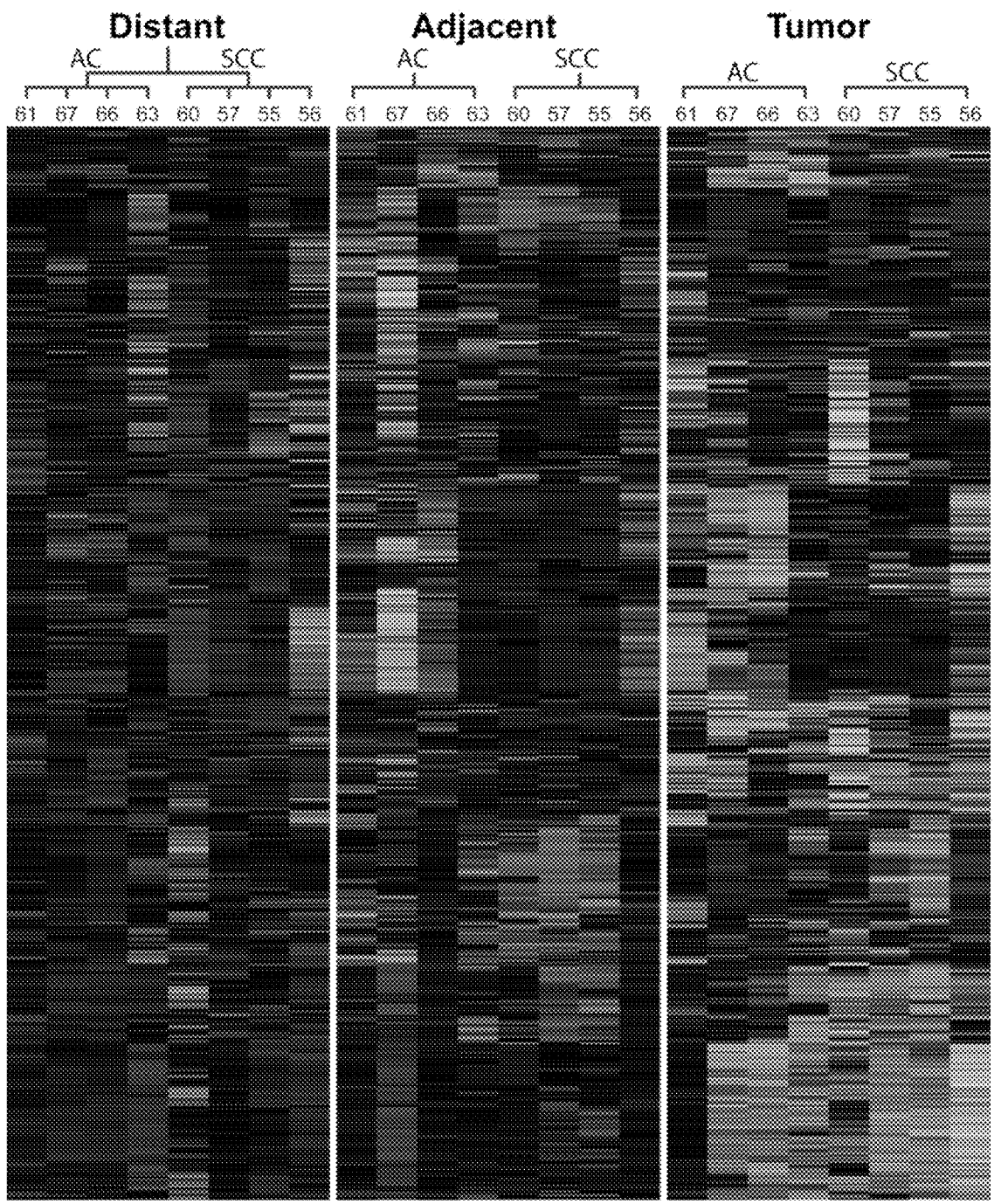
FIG. 22 show a heat map of protein levels in tumor tissue samples. The samples are arranged in columns and are separated into distant, adjacent, and tumor samples. Within each tissue type, the samples are separated into adenocarcinoma (AC) and squamous cell carcinoma (SCC). The numbers above each column correspond to patient codes. The proteins are displayed in rows and were ordered using hierarchial clustering.
Figure 23I:
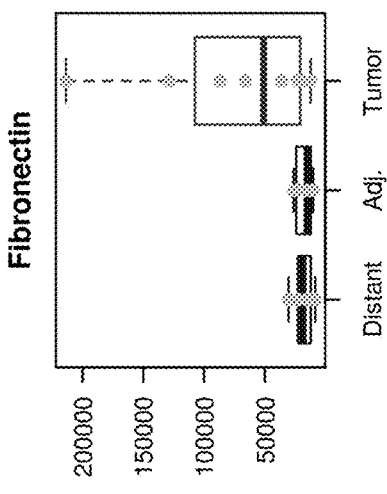
FIGS. 23A-23T) depict proteins with increased levels in tumor tissue compared with adjacent or distal tissue.
Figure 23H:
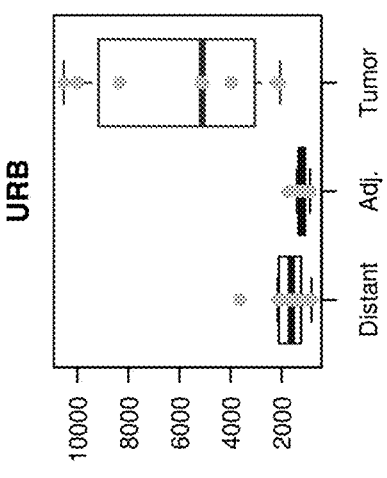
Figure 23G:
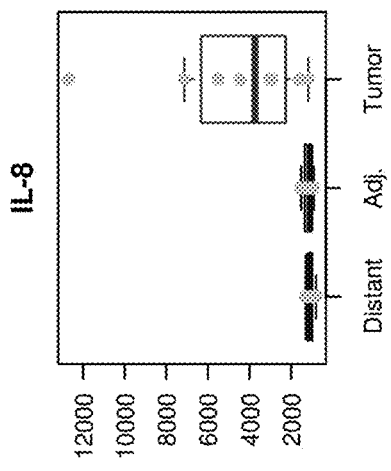
Figure 23L:
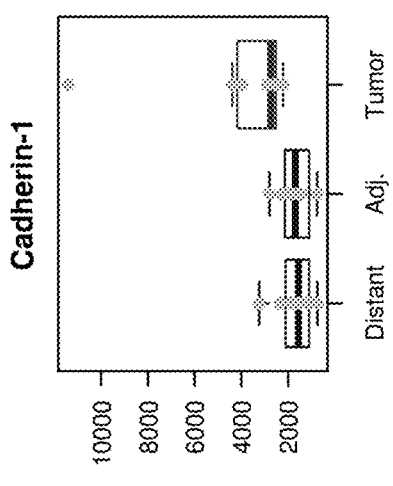
Figure 23K:
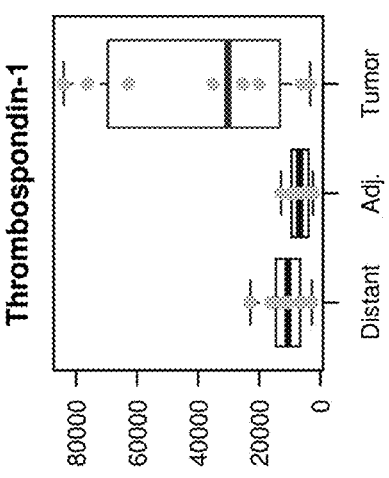
Figure 23J:
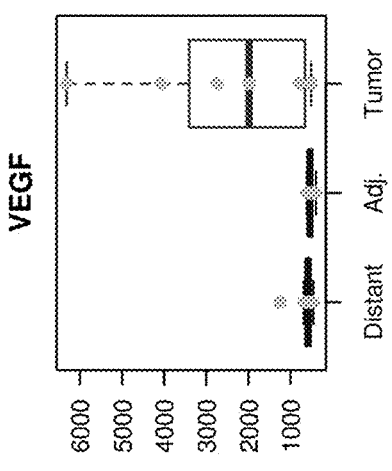
Figure 23M:
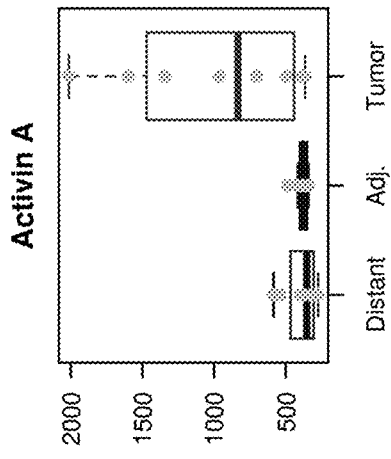
Figure 23N:
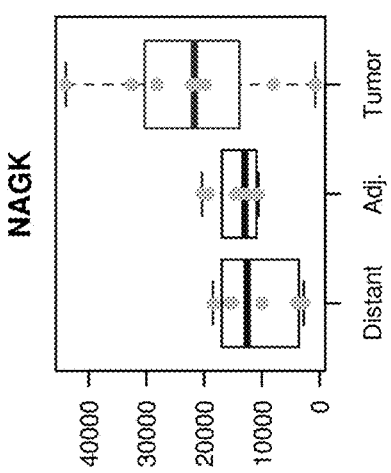
Figure 23O:
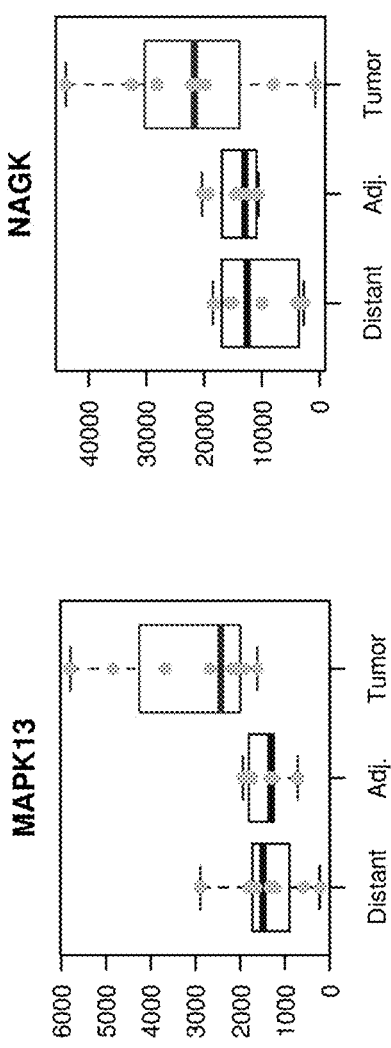
Figure 23P:
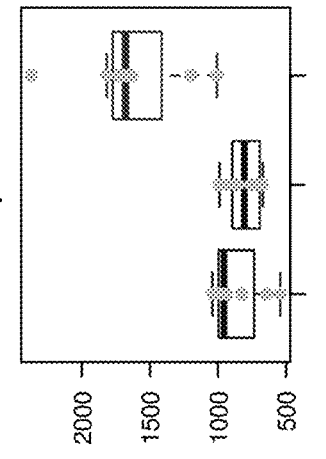
Figure 23Q:
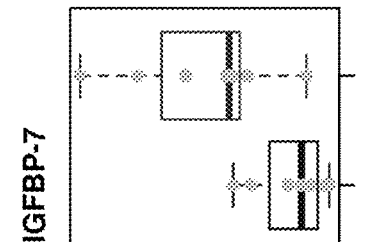
Figure 23R:
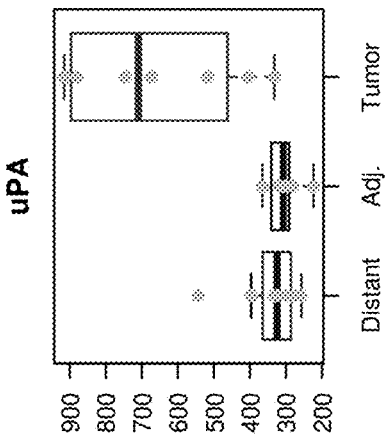
Figures 23S, 23T:
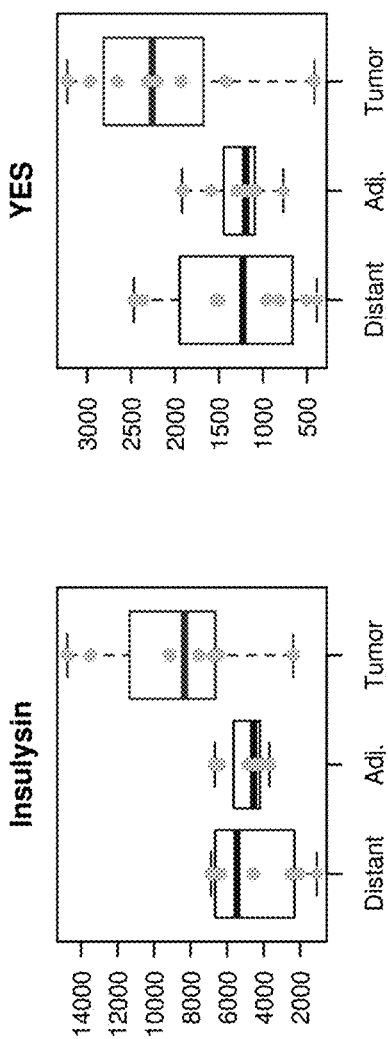
Figure 24G:
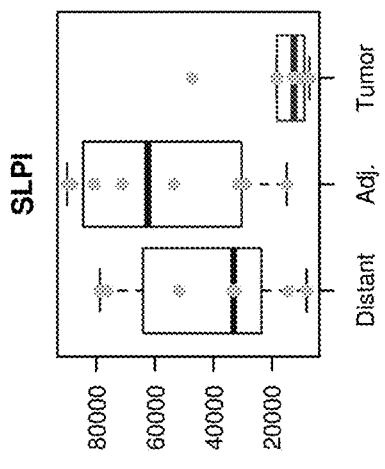
FIGS. 24A-24P depict proteins with decreased levels in tumor tissue compared with adjacent or distal tissue from the eight NSCLC samples used in this study.
Figure 24H:
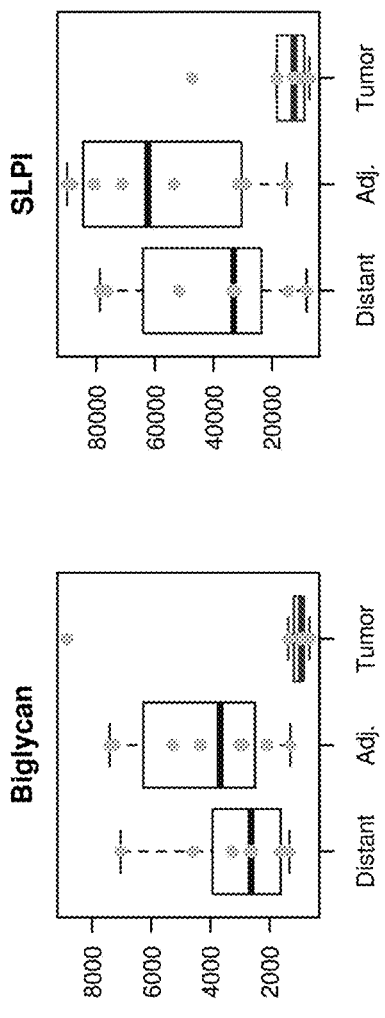
Figure 24I:
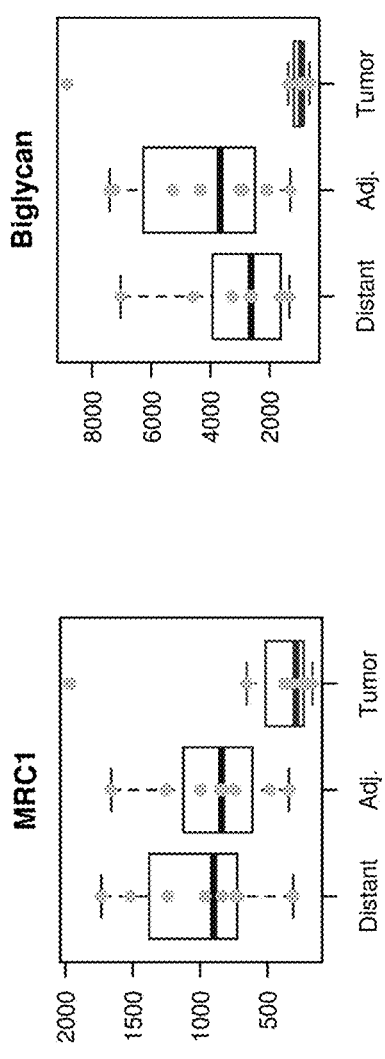
Figure 24J:
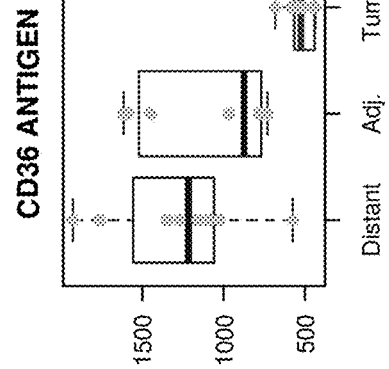
Figure 24K:
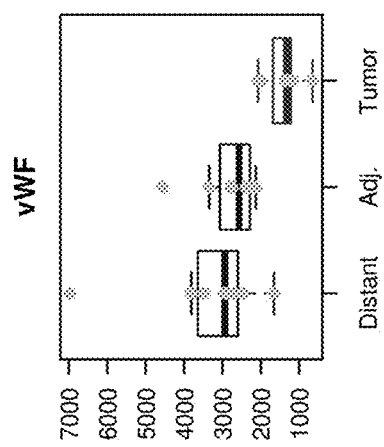
Figure 24L:
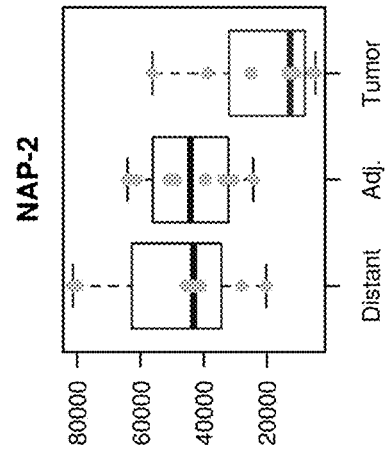

In contrast, comparison of tumor tissues with non-tumor tissue (adjacent or distant) identified 11 (1.3%) proteins with greater than four-fold differences and 53 (6.5%) proteins with greater than two-fold differences (see FIGS. 21B and 21C). The remaining 767 (93.5%) proteins showed relatively smaller differences between tumor and non-tumor tissue. Some proteins were substantially suppressed while others were elevated in tumor tissues compared to adjacent or distant tissues. Differential expression of proteins between adjacent and tumor tissue, or between distal and tumor tissue, was similar overall. Changes in distal tissue were generally larger (FIG. 21), which demonstrates that most protein changes are specific to the local tumor environment.

To identify NSCLC tissue biomarkers, protein expression levels between tumor, adjacent and distant tissue samples were compared using the Mann-Whitney test as described in Ostroff et al., "Unlocking biomarker discovery: Large scale application of aptamer proteomic technology for early detection of lung cancer," Nature Precedings, (2010)). Thirty-six proteins with the greatest fold change and with statistically significant differences between tumor and non-tumor tissue were identified with a false discovery rate cutoff of q<0.05 for significance FIGS. 23 and 24, and Table 18). Twenty of these proteins were up-regulated and 16 were down-regulated in tumor tissue. Although the number of samples used for this study was relatively small, a powerful individual-based study design in which each tumor sample had its own healthy tissue controls was employed. This eliminates the population variance associated with population-based study designs. The availability of appropriately chosen reference samples is increasingly recognized as a critically important component in biomarker discovery research (Bossuyt (2011) J. Am. Med. Assoc. 305:2229-30; Ioannidis and Panagiotou (2011) J. Am. Med. Assoc. 305:2200-10; Diamandis (2010) J. Natl. Cancer Inst. 102:1462-7).

It is believed that approximately one-third (13/36) of the NSCLC tissue biomarkers identified herein are novel. The remaining two-thirds (23/36) have been reported previously as differentially expressed proteins or genes in NSCLC tumor tissue (Table 18).

The biomarkers identified according to the method of Example 6 can be classified broadly into four biological processes associated with important hallmarks of tumor biology (Hanahan & Weinberg (2011) Cell 144:646-74) as shown in Table 19: 1) angiogenesis, 2) growth and metabolism, 3) inflammation and apoptosis, and 4) invasion and metastasis. Admittedly, these are convenient albeit inexact classifications that approximate a highly complex and dynamic system in which these molecules often play multiple and nuanced roles. Therefore, the specific state of a given system ultimately affects the expression and function of any particular molecule. Biological understanding is far from complete in these systems. With the SOMAscan platform, the quantitative expression of large numbers of proteins in various tissues and disease processes is made possible. These data provide new coordinates to help map the dynamics of these systems, which in turn will provide a more complete understanding of the biology of lung cancer as well as other diseases. The results from the current study provide a new perspective on NSCLC tumor biology, with both familiar and new elements.

Angiogenesis

Angiogenesis drives growth of new blood vessels to support tumor growth and metabolism. The regulation of angiogenesis is a complex biological phenomenon controlled by both positive and negative signals (Hanahan & Weinberg, (2011) Cell 144:646-74). Among the NSCLC tissue biomarkers identified in this study were well known positive and negative angiogenesis regulators (FIGS. 23 and 24 and Table 19), all of which have been observed previously in NSCLC tumor tissue (Fontanini et al. (1999) British Journal of Cancer 79(2):363-369; Imoto et al. (1998) J. Thorac. Carciovasc. Surg 115:1007-1011; Ohta et al. (2006) Ann. Thorac. Surg. 82:1180-1184; Iizasa et al. (2004) Clinical Cancer Research 10:5361-5366). These include the prototypic angiogenesis inducer VEGF and inhibitors endostatin and thrombospondin-1 (TSP-1). VEGF is a powerful growth factor that promotes new blood vessel growth and was strongly up-regulated in NSCLC tumor tissue, consistent with previous observations (Imoto et al. (1998) J. Thorac. Carciovasc. Surg 115:1007-1011), and including our study of serum samples from NSCLC patients (Ostroff et al., "Unlocking biomarker discovery: Large scale application of aptamer proteomic technology for early detection of lung cancer," Nature Precedings, (2010)). Endostatin is a proteolytic fragment of Collagen XVIII and a strong inhibitor of endothelial cell proliferation and angiogenesis (Iizasa et al. (August 2004) Clinical Cancer Research 10:5361-5366). TSP-1 and the related thrombospondin-2 (TSP-2) were substantially up-regulated in NSCLC tumor tissue. TSP-1 and TSP-2 are extracellular matrix proteins with complex, context-dependent effects modulated through a variety of interactions with cell-surface receptors, growth factors, cytokines, matrix metalloproteinases, and other molecules. Archetypically in model systems, TSP-1 and TSP-2 inhibit angiogenesis by inhibiting endothelial cell proliferation through the CD47 receptor and inducing endothelial cell apoptosis through the CD36 receptor. There is also evidence for proangiogenic influences for TSP-1 and TSP-2 (Bornstein (2009) J. Cell Commun. Signal. 3(3-4):189-200). Finally, reported TSP-1 and TSP-2 relative and absolute expression levels in NSCLC tissue vary (Chijiwa et al. (2009) Oncology Reports 22:279-283; Chen et al. (2009) J Int Med Res 37:551-556; Oshika 1998, Fontanini et al. (1999) British Journal of Cancer 79(2):363-369), likely due to their complex functions. In this study, it was found that CD36 was down-regulated in NSCLC tumor tissue, which could indicate an adaptation of tumor cells reduce sensitivity to TSP-1 and TSP-2-mediated apoptosis.

Growth and Metabolism

Ten of the NSCLC biomarkers identified are associated with growth and metabolism functions. Half of these biomarkers are involved in the complex hormonal regulation of cellular growth and energy metabolism. Three insulin-like growth factor binding proteins (IGFBPs), which modulate the activity of insulin-like growth factors (IGFs), were up-regulated in NSCLC tumors (IGFBP-2, -5, and -7). Several reports have qualitatively assessed IGFBP-2, -5, and -7 in NSCLC (Table 18) and suggest higher expression in NSCLC tissue than in normal tissue. Insulin and IGFs are hormones that strongly influence cellular growth and metabolism, and cancer cells are often dependent on these molecules for growth and proliferation (Robert et al. (August 1999) Clinical Cancer Research 5:2094-2102; Liu et al. (June 2007) Lung Cancer 56(3):307-317; Singhal et al. (2008) Lung Cancer 60:313-324). These hormones are in turn degraded by insulysin, which we find up-regulated in NSCLC tumor tissue. The hormone adiponectin controls lipid metabolism and insulin sensitivity, and we found adiponectin down-regulated in NSCLC tumors. The remaining five biomarkers, carbonic anhydrase III, NAGK, TrATPase, tryptase β-2, and MAPK13, are enzymes with roles in cellular metabolism (Table 17).

Inflammation and Apoptosis

Inflammation and apoptosis are hallmarks of cancer biology, and a number of potential biomarkers associated with these processes that have been associated previously with NSCLC (Table 19). Caspase-3, which has been associated with metastasis (Chen et al. (2010) Lung Cancer (doi:1016/j.lungcan.2010.10.015), was found to be up-regulated in NSCLC tumor tissue. Another notable example is RAGE, which has been reported to be dramatically down-regulated in NSCLC tissue (Jing et al. (2010) Neoplasma. 57:55-61, Bartling et al. (2005) Carcinogenesis 26:293-301). This finding is consistent with the measurement disclosed herein, in which sRAGE had the largest observed change for proteins that are lower in tumor than in non-malignant tissue. Although not limited by theory, one hypothesis is that RAGE plays a role in epithelial organization, and decreased levels of RAGE in lung tumors may contribute to loss of epithelial tissue structure, potentially leading to malignant transformation (Bartling et al. (2005) Carcinogenesis 26(2): 293-301). Several chemokines, such as BCA-1, CXCL16, IL-8, and NAP-2, are altered (Table 18), consistent with the hypothesis that invasion of tumors with cells from the innate and adaptive arms of the immune system provide bioactive molecules that affect proliferative and angiogenic signals (Hanahan & Weinberg (2011) Cell 144:646-74).

Invasion and Metastasis

The largest group of potential biomarkers contains proteins that function in cell-cell and cell-matrix interactions and are involved in invasion and metastasis. Many have been previously reported to be associated with NSCLC. Most notable are two of the matrix metalloproteases, MMP-7 and MMP-12, which contribute to proteolytic degradation of extracellular matrix components and processing of substrates such as growth factors (see e.g. Su et al. (2004) Chinese Journal of Clinical Oncology 1(2):126-130; Wegmann et al. (1993) Eur. J. Cancer 29A(11):1578-1584). Such processes are well known to play a role in creating tumor microenvironments. It was found that both MMP-7 and MMP-12 were up-regulated in NSCLC tissue (Table 18), which is consistent with similar study that used antibody-based measurements (Shah et al. (2010) The Journal of Thoracic and Cardiovascular Surgery 139(4):984-990). The over-expression of MMP-7 and MMP-12 has been associated with poor prognosis in NSCLC (Shah et al. (2010) The Journal of Thoracic and Cardiovascular Surgery 139(4):984-990). MMP-12 levels have been correlated with local recurrence and metastatic disease (Hofmann et al. (2005) Clin. Cancer Res. 11:1086-92, Hoffman et al. (2006) Oncol. Rep. 16:587-95).). Two of the eight subjects studied had normal levels of MMP-12, whereas the other six had 15-50× elevation of MMP-12 in tumor tissue compared to non-tumor tissue.

Performance of NSCLC Biomarkers as Histochemistry Probes

Figure 25:
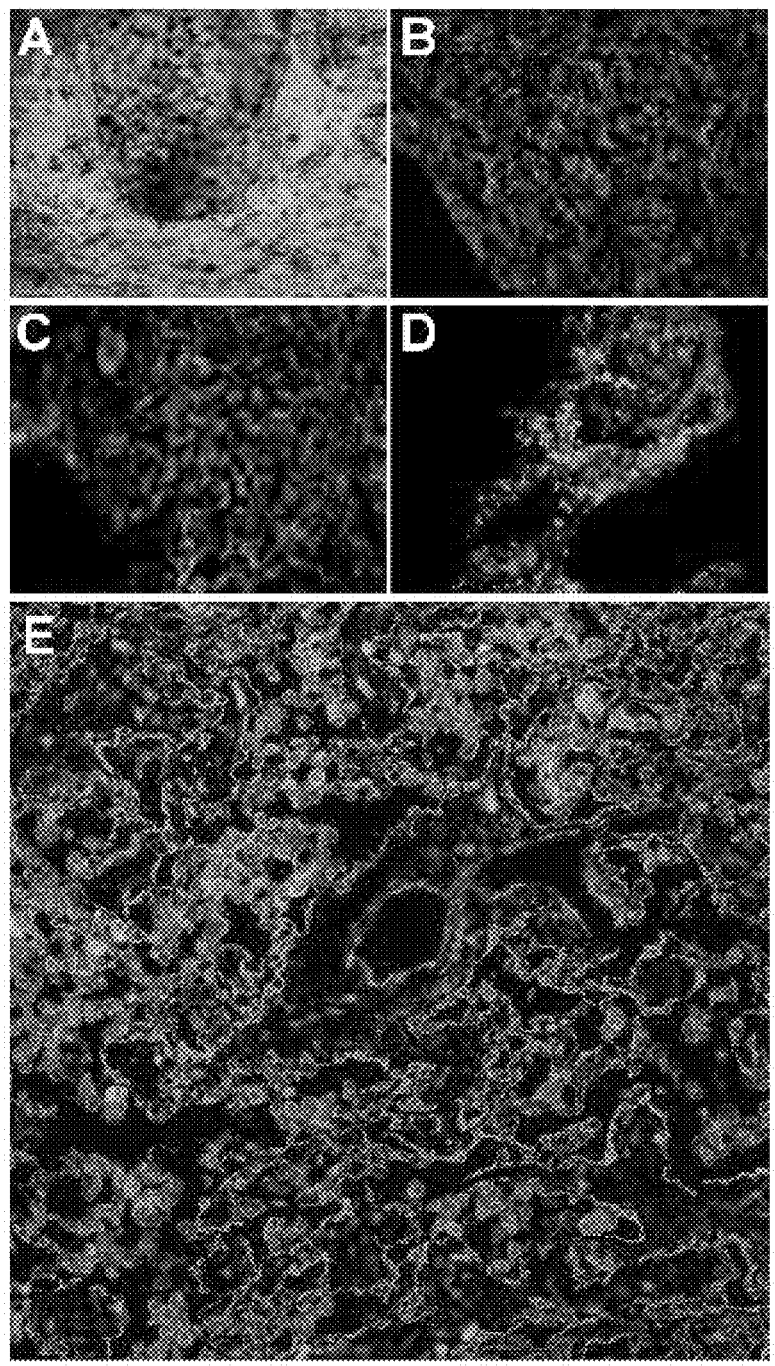
FIG. 25 shows SOMAmer histochemistry on frozen tissue sections for selected biomarkers detected in this study. (A) Thrombospondin-2 (red) staining the fibrocollagenous matrix surrounding a tumor nest. (B) Corresponding normal lung specimen stained with Thrombospondin-2 SOMAmer (red). (C) Macrophage Mannose Receptor SOMAmer (red) staining scattered macrophages in a lung adenocarcinoma. (D) Macrophage Mannose Receptor SOMAmer (red) staining numerous alveolar macrophages in a section of normal lung parenchyma. (E) Multicolor image highlighting the cytomorphologic distribution of Macrophage Mannose Receptor SOMAmer staining: Green=Cytokeratin (AE1/AE3 antibody), Red=CD31 (EP3095 Antibody), and Orange=SOMAmer. All nuclei in this figure are counterstained with DAPI.
Figure 26A:
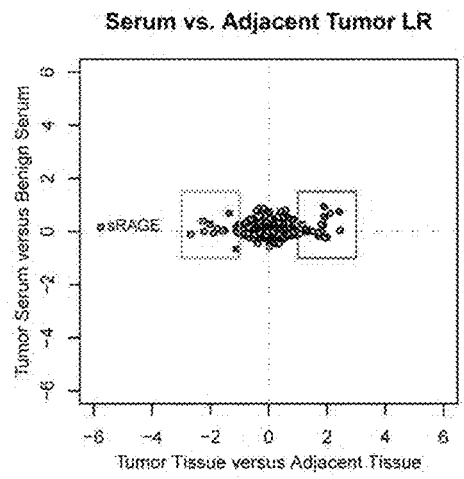
FIGS. 26A-26F show changes in protein expression in NSCLC tissue compared to serum. The top two panels show the log 2 ratio (LR) derived from serum samples versus log ratios derived from adjacent tissue and distant tissue, respectively. The bottom four panels feature zoomed portions of plots above, indicated by the color of the plot (green for decreased and red for increased expression compared to non-tumor tissue). Analytes shown in FIGS. 23 and 24 have been labeled and analytes mentioned in the publication on the serum samples are shown in filled red symbols red.
Figure 26D:
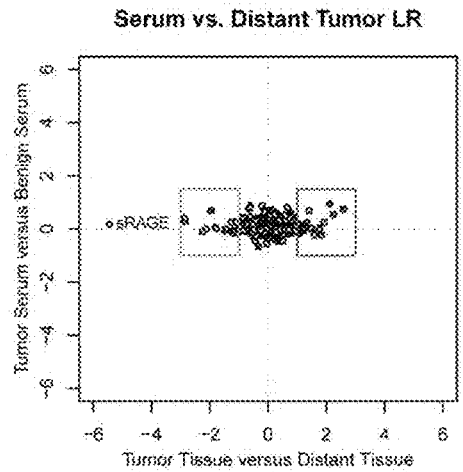
Figure 26B:
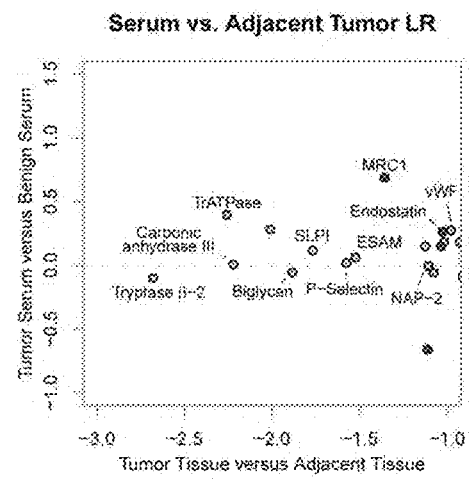
Figure 26E:
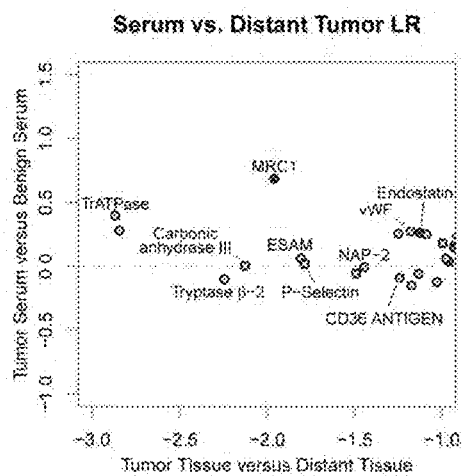
Figure 26C:
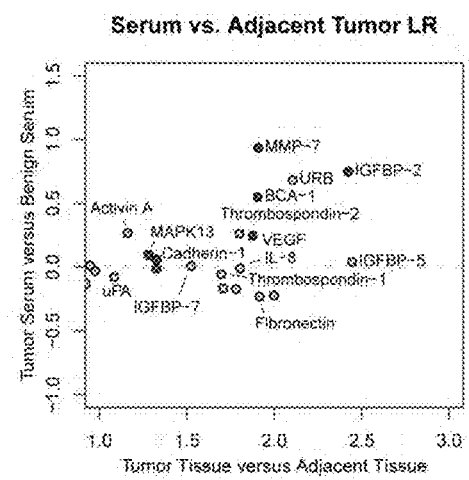
Figure 26F:
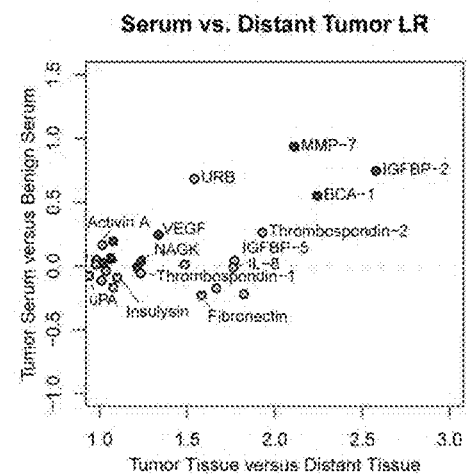
Figure 27:
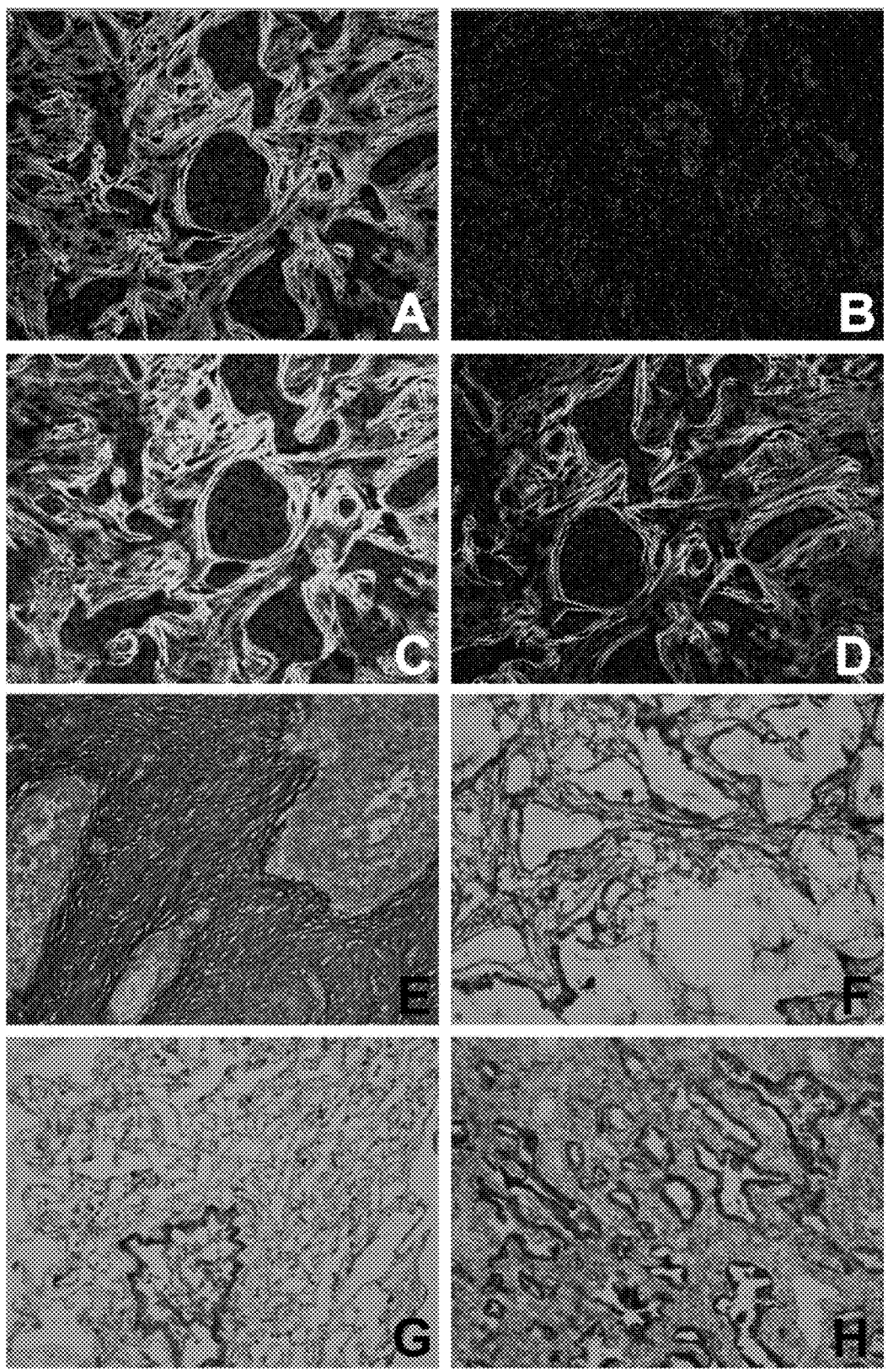
FIG. 27 depicts thrombospondin-2 histochemical identification in tissue samples. Thrombospondin-2 is identified in a serial frozen section of a single lung carcinoma specimen by (A) a home-made rabbit polyclonal thrombospondin-2 polyclonal antibody, (B) the pre-immune serum from rabbits used to make the home-made polyclonal antibody, (C) a commercial (Novus) rabbit polyclonal thrombospondin-2 antibody, and (D) the thrombospondin-2 SOMAmer. The thrombospondin-2 SOMAmer was then used to stain frozen sections of normal and malignant lung tissue, with standard Avidin-Biotin-Peroxidase color development, to demonstrate different morphologic distributions: (E) Strong staining of the fibrotic stroma surrounding tumor nests, with minimal cytosolic staining of carcinoma cells, (F) Strong staining of the fibrotic stroma surrounding tumor nests in a mucinous adenocarcinoma, with no significant staining of the carcinoma cells, (G) normal lung tissue, showing strong cytosolic staining of bronchial epithelium and scattered alveolar macrophages, and (H) strong cytosolic staining of an adenocarcinoma, with no significant staining of the non-fibrotic, predominantly inflammatory stroma.

An understanding of the differences in protein expression between tumor and non-tumor tissues can be used to identify novel histochemistry probes. Such probes can enable more precise molecular characterization of tumors and their effects on the surrounding stroma. FIG. 25 demonstrates the ability of two of the identified SOMAmers to stain fresh frozen tissues obtained from the same tumor resections used for the discovery of these biomarkers. Thrombospondin-2 (TSP2) was found to be increased in tumor tissue homogenates while macrophage mannose receptor (MRC1) was decreased. Tissue staining with these SOMAmers was consistent with the profiling results. Additional examples, as well as antibody confirmation of staining patterns, are shown in FIG. 27.

Comparison of NSCLC Tissue and Serum Biomarkers

Differential expression of proteins in sera of NSCLC patients relative to cancer-free controls compared with that of NSCLC tissue samples yields useful insights (FIG. 26). The most striking observation is that relative changes in protein expression are greater in tissues than in serum. This result could be expected since tumor tissue is the source of the changes in protein expression that is then, even if fully released into circulation, diluted many-fold into total volume of blood. This trend is evident in the elongated distribution of data points along the x-axis in FIG. 26 in which axes are drawn on the same scale to illustrate this point. Twelve of the analytes shown in FIGS. 23 and 24 as altered in tumor tissue are also differentially expressed in sera from NSCLC patients vs. controls (filled red circles in FIG. 26). Most of the directional changes are the same between tissue and sera, but a few are not. Local concentrations of proteins in a tissue homogenate clearly need not correlate with circulating levels of the proteins and inverse correlations may provide clues regarding the redistribution of certain biomarkers in diseased versus normal tissues.

The discovery of novel biomarkers with demonstrable diagnostic or clinical utility has been a considerable challenge in recent years (Diamandis (2010) J. Natl, Cancer Inst. 102:1462-7). The reasons for this include the omnipresence of pre-analytical and analytical artifacts, unavailability of suitable healthy-state controls and unsophisticated study designs, and the difficulty of detecting small changes in protein levels at very low concentrations. This challenge is especially pronounced with cancer biomarkers where the objective is often to identify a tiny malignancy in a relatively large human body at an early stage. With regard to the later point, one way to improve the chances of discovering true cancer biomarkers is to obtain protein expression data from both the source of the disease, such as tumor tissue, as well as from the circulation. The combined results can partially corroborate the validity of potential biomarkers. The instant application demonstrates that this is possible with the disclosed highly multiplexed and sensitive proteomic assay. It has been shown that tissues, like plasma or serum, are also amenable to SOMAscan, and the resulting comparative analysis of protein expression in NSCLC tumor tissues with surrounding healthy lung tissues offers a complement to the existing dataset of potential NSCLC biomarkers identified from serum samples (see U.S. Pub. No. 2010/0070191). In the instant case, one third, or twelve of the thirty-six tissue biomarkers reported herein (BCA-1 (BCL), cadherin-1 (cadherin-E), catalase, endostatin, IGFBP-2, MRC1 (macrophage mannose receptor), MAPK-13 (MK13), MMP-7, MMP-12, NAGK, VEGF and YES have been previously identified in serum. Taken together, these data contribute to further understanding of the complexity of changes accompanying NSCLC and provide additional potential biomarkers for the early detection of this deadly disease.

Kits

Any combination of the biomarkers of Table 20 (as well as additional biomedical information) can be detected using a suitable kit, such as for use in performing the methods disclosed herein. Furthermore, any kit can contain one or more detectable labels as described herein, such as a fluorescent moiety, etc.

In one embodiment, a kit includes (a) one or more capture reagents (such as, for example, at least one aptamer or antibody) for detecting one or more biomarkers in a biological sample, wherein the biomarkers include any of the biomarkers set forth in Tables 18, 20 or 21 and optionally (b) one or more software or computer program products for classifying the individual from whom the biological sample was obtained as either having or not having lung cancer or for determining the likelihood that the individual has lung cancer, as further described herein. Alternatively, rather than one or more computer program products, one or more instructions for manually performing the above steps by a human can be provided.

The combination of a solid support with a corresponding capture reagent and a signal generating material is referred to herein as a "detection device" or "kit". The kit can also include instructions for using the devices and reagents, handling the sample, and analyzing the data. Further the kit may be used with a computer system or software to analyze and report the result of the analysis of the biological sample.

The kits can also contain one or more reagents (e.g., solubilization buffers, detergents, washes, or buffers) for processing a biological sample. Any of the kits described herein can also include, e.g., buffers, blocking agents, mass spectrometry matrix materials, antibody capture agents, positive control samples, negative control samples, software and information such as protocols, guidance and reference data.

In one aspect, the invention provides kits for the analysis of lung cancer status. The kits include PCR primers for one or more biomarkers selected from Tables 18, 20, or 21. The kit may further include instructions for use and correlation of the biomarkers with lung cancer. The kit may also include a DNA array containing the complement of one or more of the biomarkers selected from Table 20, reagents, and/or enzymes for amplifying or isolating sample DNA. The kits may include reagents for real-time PCR, for example, TaqMan probes and/or primers, and enzymes.

For example, a kit can comprise (a) reagents comprising at least capture reagent for quantifying one or more biomarkers in a test sample, wherein said biomarkers comprise the biomarkers set forth in Tables 18, 20, or 21, or any other biomarkers or biomarkers panels described herein, and optionally (b) one or more algorithms or computer programs for performing the steps of comparing the amount of each biomarker quantified in the test sample to one or more predetermined cutoffs and assigning a score for each biomarker quantified based on said comparison, combining the assigned scores for each biomarker quantified to obtain a total score, comparing the total score with a predetermined score, and using said comparison to determine whether an individual has lung cancer. Alternatively, rather than one or more algorithms or computer programs, one or more instructions for manually performing the above steps by a human can be provided.

Computer Methods and Software

Once a biomarker or biomarker panel is selected, a method for diagnosing an individual can comprise the following: 1) collect or otherwise obtain a biological sample; 2) perform an analytical method to detect and measure the biomarker or biomarkers in the panel in the biological sample; 3) perform any data normalization or standardization required for the method used to collect biomarker values; 4) calculate the marker score; 5) combine the marker scores to obtain a total diagnostic score; and 6) report the individual's diagnostic score. In this approach, the diagnostic score may be a single number determined from the sum of all the marker calculations that is compared to a preset threshold value that is an indication of the presence or absence of disease. Or the diagnostic score may be a series of bars that each represent a biomarker value and the pattern of the responses may be compared to a pre-set pattern for determination of the presence or absence of disease.

Figure 6:
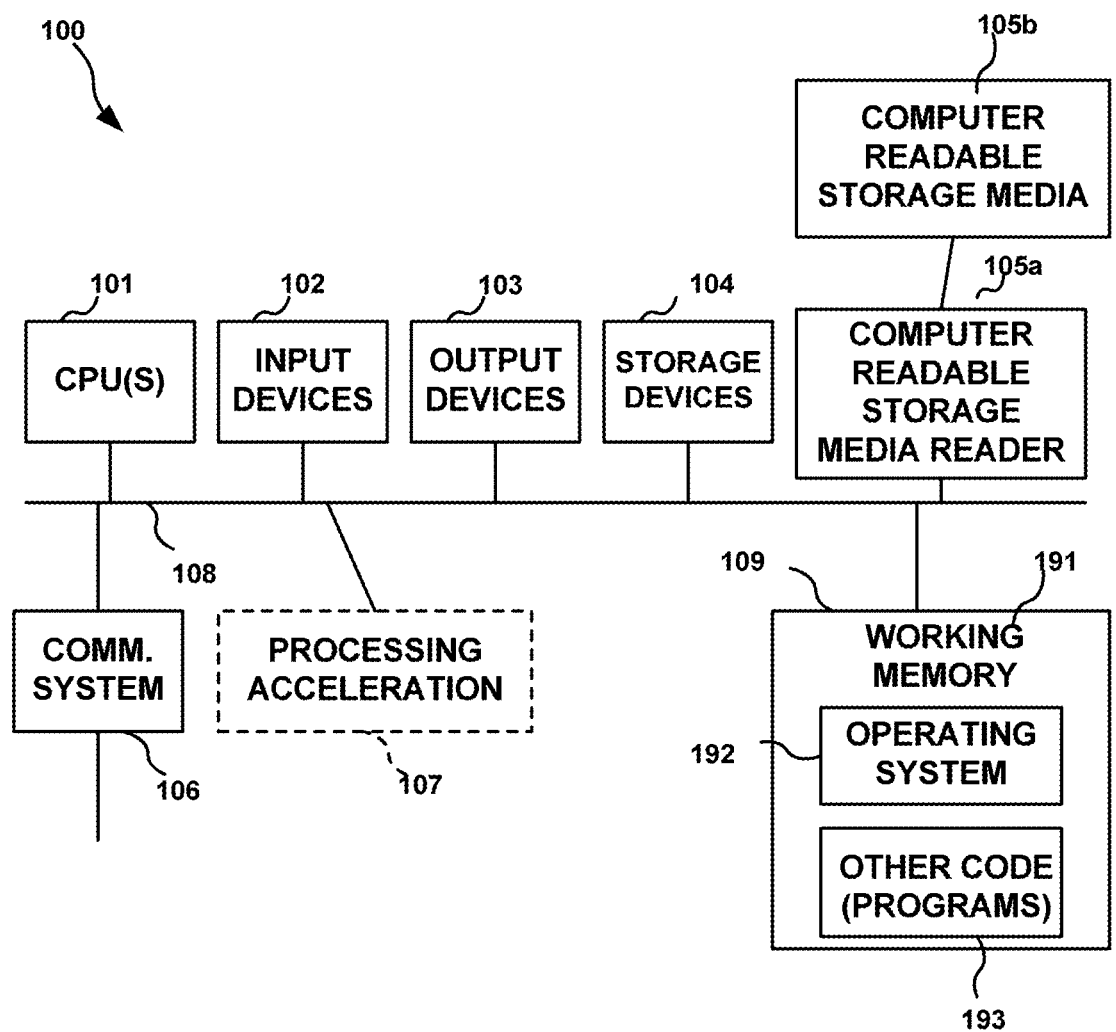
FIG. 6 illustrates an exemplary computer system for use with various computer-implemented methods described herein.

At least some embodiments of the methods described herein can be implemented with the use of a computer. An example of a computer system 100 is shown in FIG. 6. With reference to FIG. 6, system 100 is shown comprised of hardware elements that are electrically coupled via bus 108, including a processor 101, input device 102, output device 103, storage device 104, computer-readable storage media reader 105a, communications system 106 processing acceleration (e.g., DSP or special-purpose processors) 107 and memory 109. Computer-readable storage media reader 105a is further coupled to computer-readable storage media 105b, the combination comprehensively representing remote, local, fixed and/or removable storage devices plus storage media, memory, etc. for temporarily and/or more permanently containing computer-readable information, which can include storage device 104, memory 109 and/or any other such accessible system 100 resource. System 100 also comprises software elements (shown as being currently located within working memory 191) including an operating system 192 and other code 193, such as programs, data and the like.

With respect to FIG. 6, system 100 has extensive flexibility and configurability. Thus, for example, a single architecture might be utilized to implement one or more servers that can be further configured in accordance with currently desirable protocols, protocol variations, extensions, etc. However, it will be apparent to those skilled in the art that embodiments may well be utilized in accordance with more specific application requirements. For example, one or more system elements might be implemented as sub-elements within a system 100 component (e.g., within communications system 106). Customized hardware might also be utilized and/or particular elements might be implemented in hardware, software or both. Further, while connection to other computing devices such as network input/output devices (not shown) may be employed, it is to be understood that wired, wireless, modem, and/or other connection or connections to other computing devices might also be utilized.

In one aspect, the system can comprise a database containing features of biomarkers characteristic of lung cancer. The biomarker data (or biomarker information) can be utilized as an input to the computer for use as part of a computer implemented method. The biomarker data can include the data as described herein.

In one aspect, the system further comprises one or more devices for providing input data to the one or more processors.

The system further comprises a memory for storing a data set of ranked data elements.

In another aspect, the device for providing input data comprises a detector for detecting the characteristic of the data element, e.g., such as a mass spectrometer or gene chip reader.

The system additionally may comprise a database management system. User requests or queries can be formatted in an appropriate language understood by the database management system that processes the query to extract the relevant information from the database of training sets.

The system may be connectable to a network to which a network server and one or more clients are connected. The network may be a local area network (LAN) or a wide area network (WAN), as is known in the art. Preferably, the server includes the hardware necessary for running computer program products (e.g., software) to access database data for processing user requests.

The system may include an operating system (e.g., UNIX or Linux) for executing instructions from a database management system. In one aspect, the operating system can operate on a global communications network, such as the internet, and utilize a global communications network server to connect to such a network.

The system may include one or more devices that comprise a graphical display interface comprising interface elements such as buttons, pull down menus, scroll bars, fields for entering text, and the like as are routinely found in graphical user interfaces known in the art. Requests entered on a user interface can be transmitted to an application program in the system for formatting to search for relevant information in one or more of the system databases. Requests or queries entered by a user may be constructed in any suitable database language.

The graphical user interface may be generated by a graphical user interface code as part of the operating system and can be used to input data and/or to display inputted data. The result of processed data can be displayed in the interface, printed on a printer in communication with the system, saved in a memory device, and/or transmitted over the network or can be provided in the form of the computer readable medium.

The system can be in communication with an input device for providing data regarding data elements to the system (e.g., expression values). In one aspect, the input device can include a gene expression profiling system including, e.g., a mass spectrometer, gene chip or array reader, and the like.

The methods and apparatus for analyzing lung cancer biomarker information according to various embodiments may be implemented in any suitable manner, for example, using a computer program operating on a computer system. A conventional computer system comprising a processor and a random access memory, such as a remotely-accessible application server, network server, personal computer or workstation may be used. Additional computer system components may include memory devices or information storage systems, such as a mass storage system and a user interface, for example a conventional monitor, keyboard and tracking device. The computer system may be a stand-alone system or part of a network of computers including a server and one or more databases.

The lung cancer biomarker analysis system can provide functions and operations to complete data analysis, such as data gathering, processing, analysis, reporting and/or diagnosis. For example, in one embodiment, the computer system can execute the computer program that may receive, store, search, analyze, and report information relating to the lung cancer biomarkers. The computer program may comprise multiple modules performing various functions or operations, such as a processing module for processing raw data and generating supplemental data and an analysis module for analyzing raw data and supplemental data to generate a lung cancer status and/or diagnosis. Diagnosing lung cancer status may comprise generating or collecting any other information, including additional biomedical information, regarding the condition of the individual relative to the disease, identifying whether further tests may be desirable, or otherwise evaluating the health status of the individual.

Referring to FIG. 7, an example of a method of utilizing a computer in accordance with principles of a disclosed embodiment can be seen. In FIG. 7, a flowchart 3000 is shown. In block 3004, biomarker information can be retrieved for an individual. The biomarker information can be retrieved from a computer database, for example, after testing of the individual's biological sample is performed. The biomarker information can comprise biomarker values that each correspond to one of at least N biomarkers selected from a group consisting of the biomarkers provided in Table 18, wherein N=2-36, Table 20, wherein N=2-25 or Table 21, wherein N=2-86. In block 3008, a computer can be utilized to classify each of the biomarker values. And, in block 3012, a determination can be made as to the likelihood that an individual has lung cancer based upon a plurality of classifications. The indication can be output to a display or other indicating device so that it is viewable by a person. Thus, for example, it can be displayed on a display screen of a computer or other output device.

Figure 8:
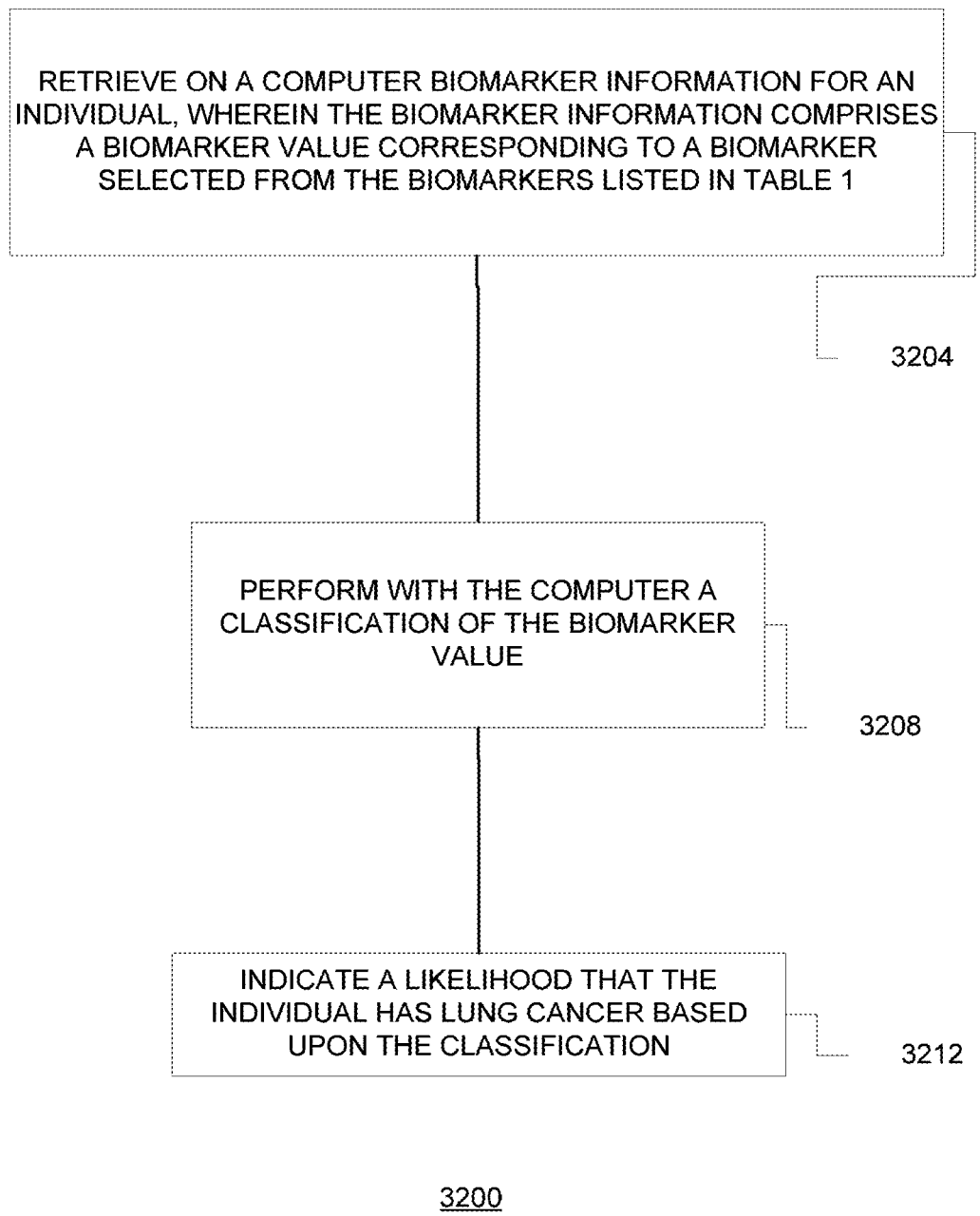
FIG. 8 is a flowchart for a method of indicating the likelihood that an individual has lung cancer in accordance with one embodiment.

Referring to FIG. 8, an alternative method of utilizing a computer in accordance with another embodiment can be illustrated via flowchart 3200. In block 3204, a computer can be utilized to retrieve biomarker information for an individual. The biomarker information comprises a biomarker value corresponding to a biomarker selected from the group of biomarkers provided in Tables 18, 20 or 21. In block 3208, a classification of the biomarker value can be performed with the computer. And, in block 3212, an indication can be made as to the likelihood that the individual has lung cancer based upon the classification. The indication can be output to a display or other indicating device so that it is viewable by a person. Thus, for example, it can be displayed on a display screen of a computer or other output device.

Some embodiments described herein can be implemented so as to include a computer program product. A computer program product may include a computer readable medium having computer readable program code embodied in the medium for causing an application program to execute on a computer with a database.

As used herein, a "computer program product" refers to an organized set of instructions in the form of natural or programming language statements that are contained on a physical media of any nature (e.g., written, electronic, magnetic, optical or otherwise) and that may be used with a computer or other automated data processing system. Such programming language statements, when executed by a computer or data processing system, cause the computer or data processing system to act in accordance with the particular content of the statements. Computer program products include without limitation: programs in source and object code and/or test or data libraries embedded in a computer readable medium. Furthermore, the computer program product that enables a computer system or data processing equipment device to act in pre-selected ways may be provided in a number of forms, including, but not limited to, original source code, assembly code, object code, machine language, encrypted or compressed versions of the foregoing and any and all equivalents.

In one aspect, a computer program product is provided for indicating a likelihood of lung cancer. The computer program product includes a computer readable medium embodying program code executable by a processor of a computing device or system, the program code comprising: code that retrieves data attributed to a biological sample from an individual, wherein the data comprises biomarker values that each correspond to one of at least N biomarkers in the biological sample selected from the group of biomarkers provided in Table 18, wherein N=2-36, Table 20, wherein N=2-25 or Table 21, wherein N=2-86; and code that executes a classification method that indicates a lung disease status of the individual as a function of the biomarker values.

In still another aspect, a computer program product is provided for indicating a likelihood of lung cancer. The computer program product includes a computer readable medium embodying program code executable by a processor of a computing device or system, the program code comprising: code that retrieves data attributed to a biological sample from an individual, wherein the data comprises a biomarker value corresponding to a biomarker in the biological sample selected from the group of biomarkers provided in Table 18, wherein N=2-36, Table 20, wherein N=2-25 or Table 21, wherein N-2-86; and code that executes a classification method that indicates a lung disease status of the individual as a function of the biomarker value.

While various embodiments have been described as methods or apparatuses, it should be understood that embodiments can be implemented through code coupled with a computer, e.g., code resident on a computer or accessible by the computer. For example, software and databases could be utilized to implement many of the methods discussed above. Thus, in addition to embodiments accomplished by hardware, it is also noted that these embodiments can be accomplished through the use of an article of manufacture comprised of a computer usable medium having a computer readable program code embodied therein, which causes the enablement of the functions disclosed in this description. Therefore, it is desired that embodiments also be considered protected by this patent in their program code means as well. Furthermore, the embodiments may be embodied as code stored in a computer-readable memory of virtually any kind including, without limitation, RAM, ROM, magnetic media, optical media, or magneto-optical media. Even more generally, the embodiments could be implemented in software, or in hardware, or any combination thereof including, but not limited to, software running on a general purpose processor, microcode, PLAs, or ASICs.

It is also envisioned that embodiments could be accomplished as computer signals embodied in a carrier wave, as well as signals (e.g., electrical and optical) propagated through a transmission medium. Thus, the various types of information discussed above could be formatted in a structure, such as a data structure, and transmitted as an electrical signal through a transmission medium or stored on a computer readable medium.

It is also noted that many of the structures, materials, and acts recited herein can be recited as means for performing a function or step for performing a function. Therefore, it should be understood that such language is entitled to cover all such structures, materials, or acts disclosed within this specification and their equivalents, including the matter incorporated by reference.

EXAMPLES

The following examples are provided for illustrative purposes only and are not intended to limit the scope of the application as defined by the appended claims. All examples described herein were carried out using standard techniques, which are well known and routine to those of skill in the art. Routine molecular biology techniques described in the following examples can be carried out as described in standard laboratory manuals, such as Sambrook et al., Molecular Cloning: A Laboratory Manual, 3rd. ed., Cold Spring Harbor Laboratory Press, Cold Spring Harbor, N.Y., (2001).

Figure 9:
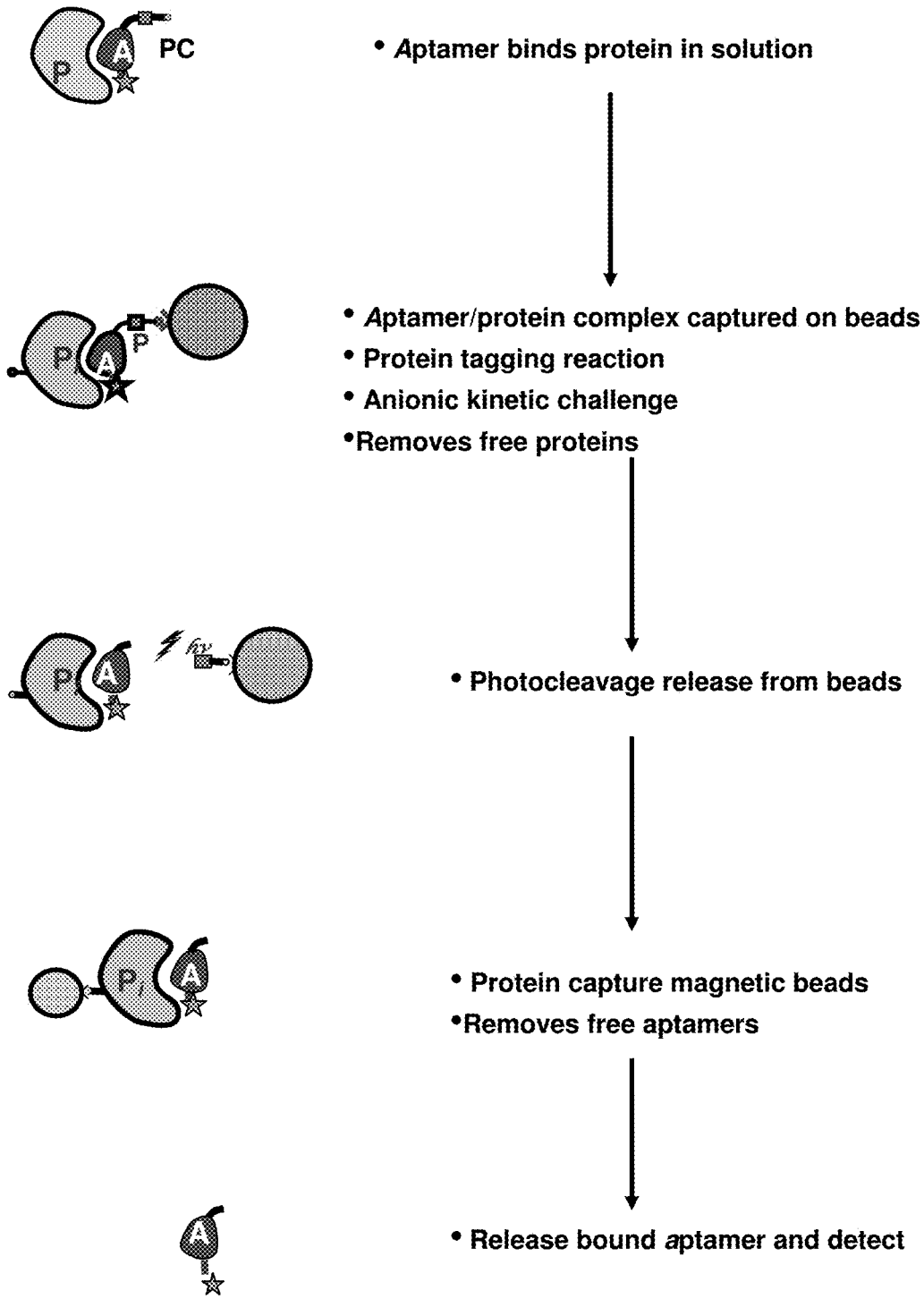
FIG. 9 illustrates an exemplary aptamer assay that can be used to detect one or more lung cancer biomarkers in a biological sample.
Figure 10:
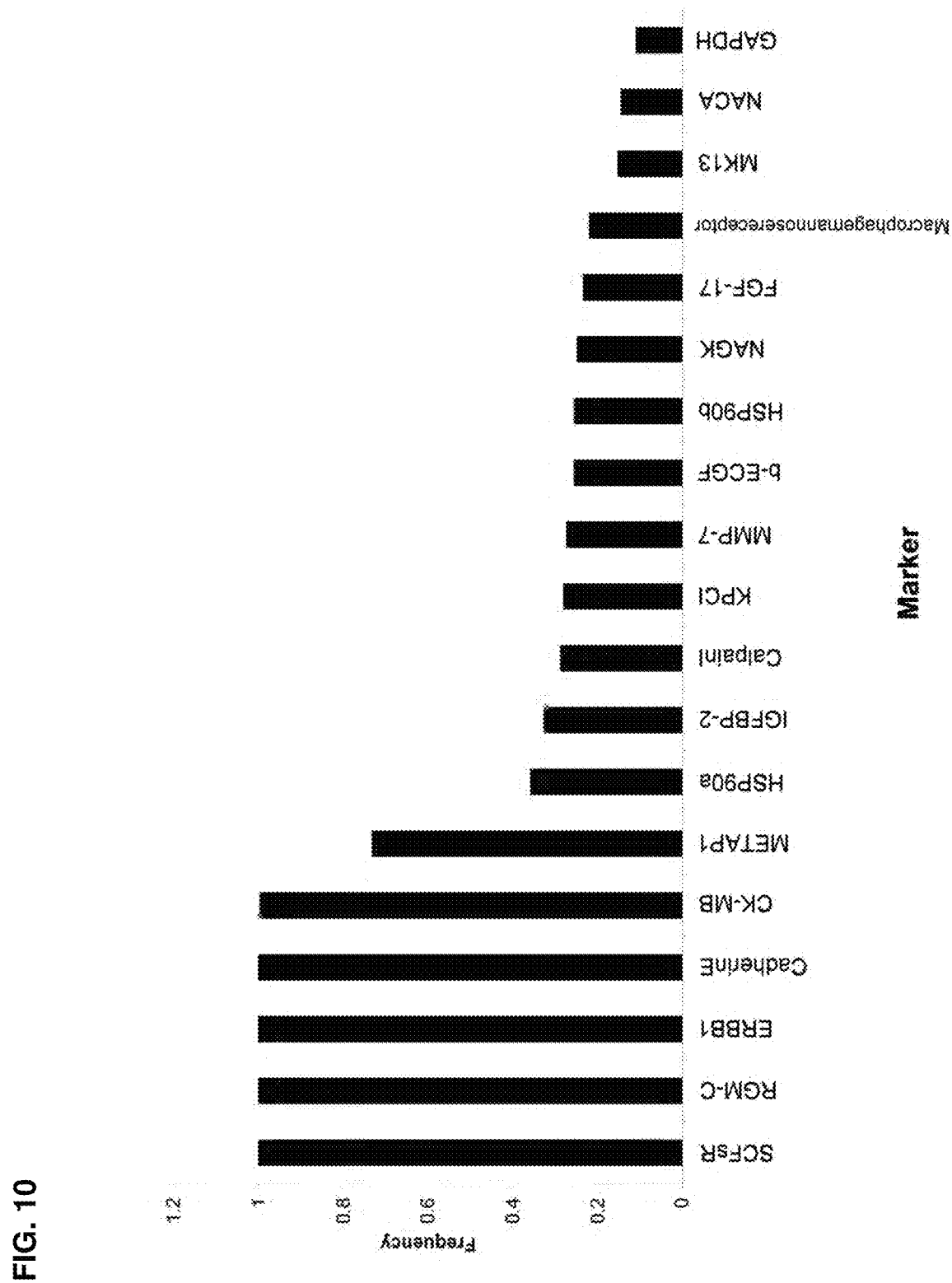
FIG. 10 shows a histogram of frequencies for which biomarkers were used in building classifiers to distinguish between NSCLC and benign nodules from an aggregated set of potential biomarkers.
Figure 11:
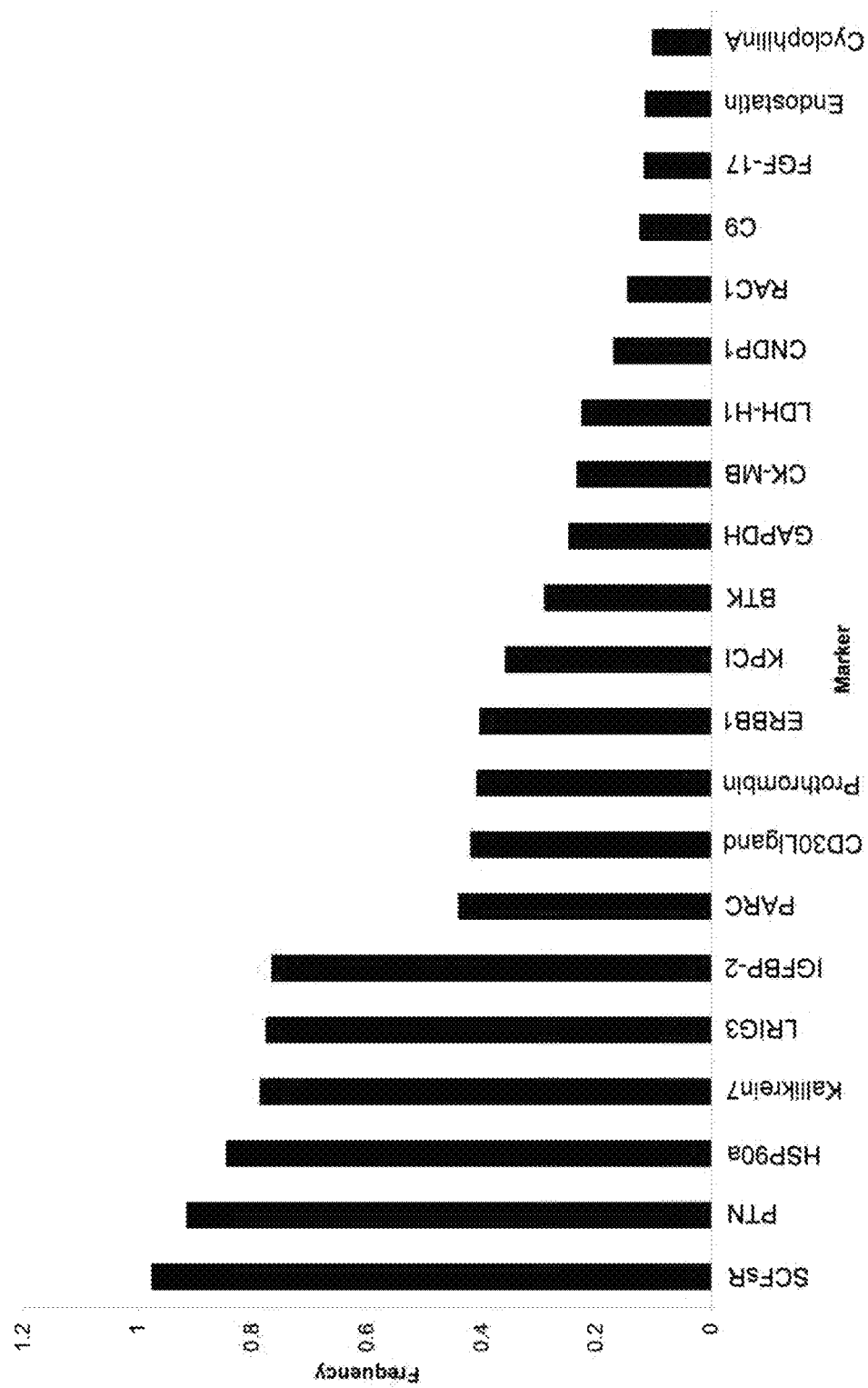
FIG. 11 shows a histogram of frequencies for which biomarkers were used in building classifiers to distinguish between NSCLC and asymptomatic smokers from an aggregated set of potential biomarkers.
Figure 12:
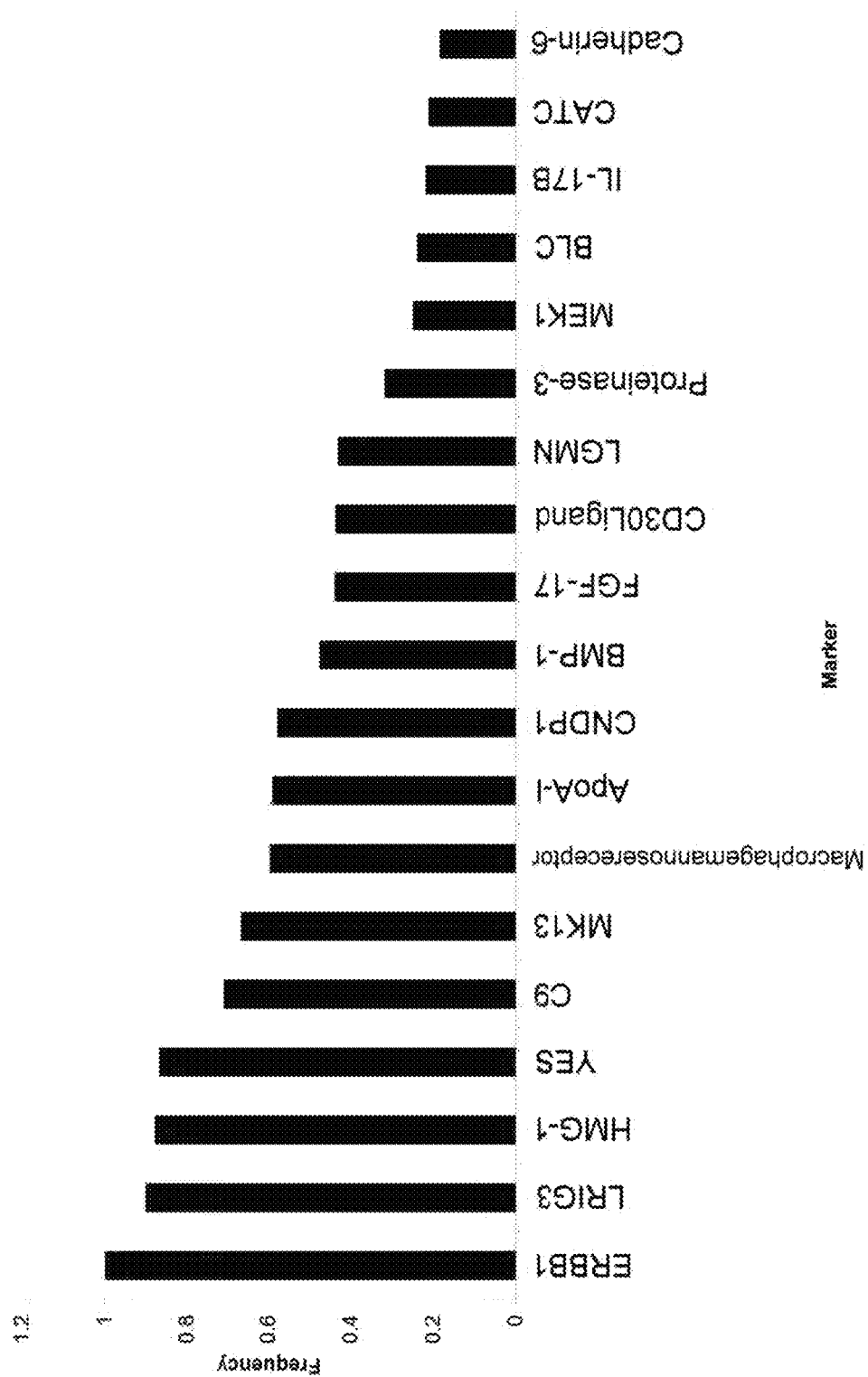
FIG. 12 shows a histogram of frequencies for which biomarkers were used in building classifiers to distinguish between NSCLC and benign nodules from a site-consistent set of potential biomarkers.
Figure 13:
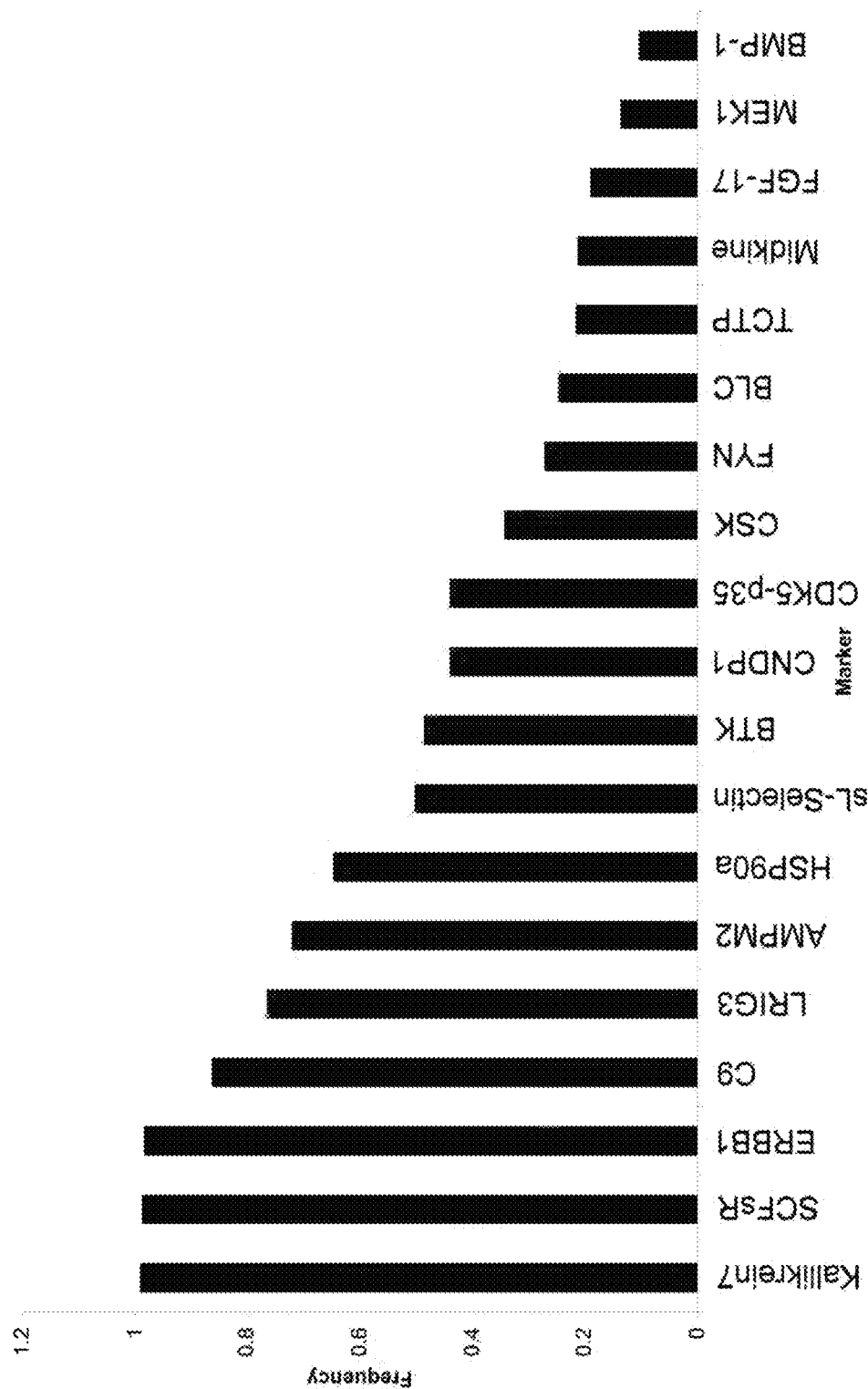
FIG. 13 shows a histogram of frequencies for which biomarkers were used in building classifiers to distinguish between NSCLC and asymptomatic smokers from a site-consistent set of potential biomarkers.
Figure 14:
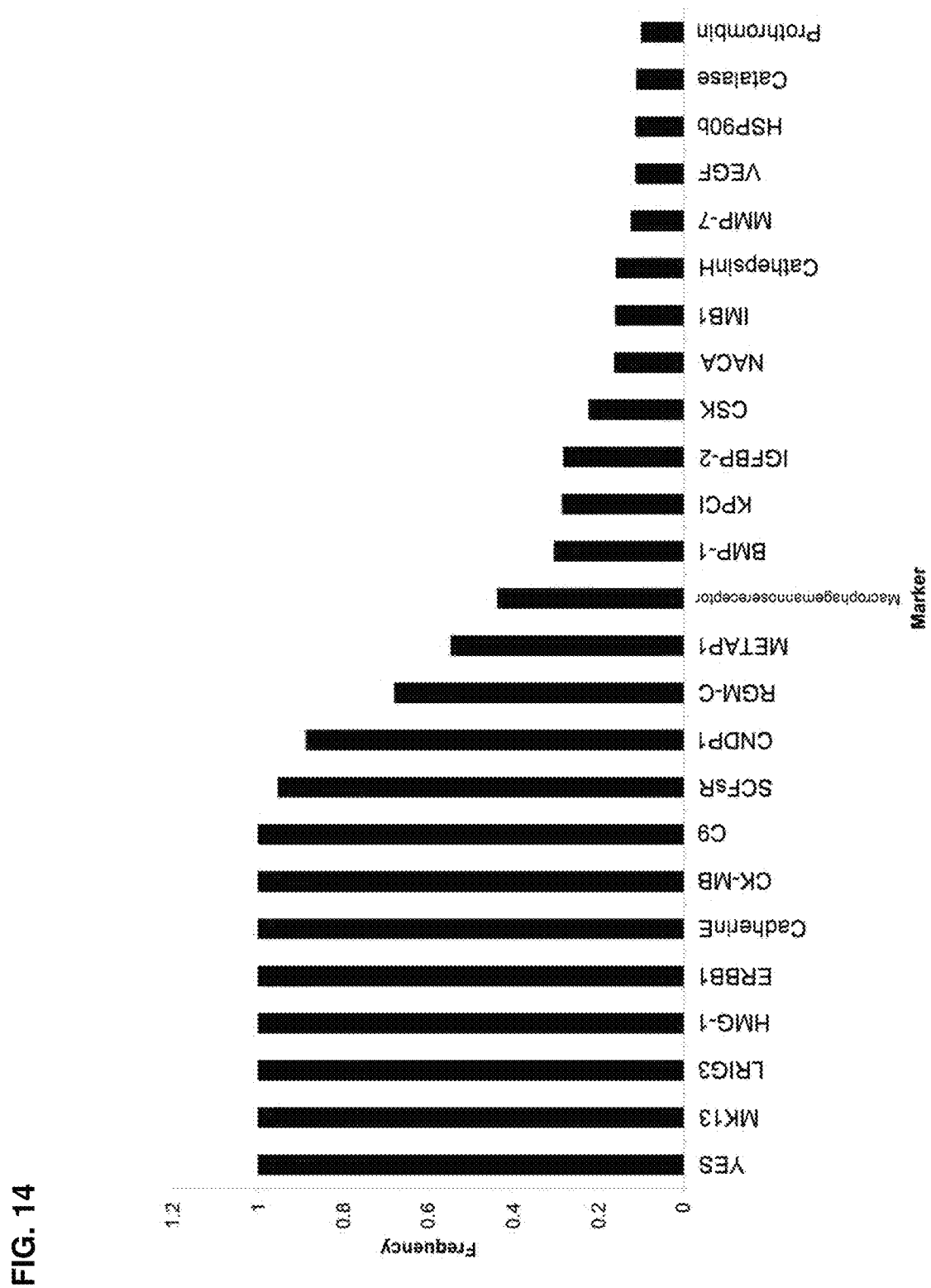
FIG. 14 shows a histogram of frequencies for which biomarkers were used in building classifiers to distinguish between NSCLC and benign nodules from a set of potential biomarkers resulting from a combination of aggregated and site-consistent markers.
Figure 15:
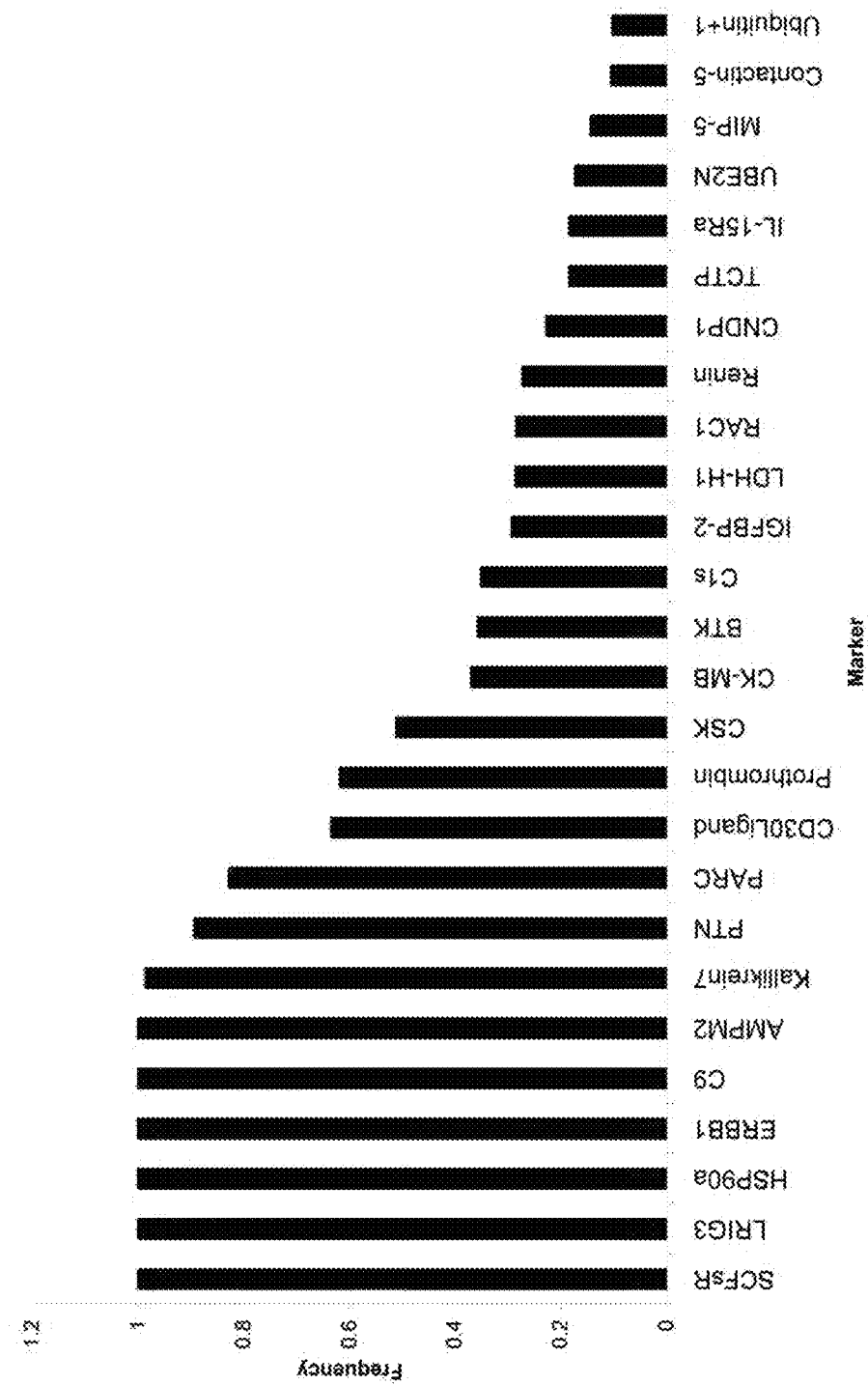
FIG. 15 shows a histogram of frequencies for which biomarkers were used in building classifiers to distinguish between NSCLC and asymptomatic smokers from a set of potential biomarkers resulting from a combination of aggregated and site-consistent markers.

Example 1. Multiplexed Aptamer Analysis of Samples for Lung Cancer Biomarker Selection This example describes the multiplex aptamer assay used to analyze the samples and controls for the identification of the biomarkers set forth in Table 1, Col. 2 (see FIG. 9). In this case, the multiplexed analysis utilized 820 aptamers, each unique to a specific target.

In this method, pipette tips were changed for each solution addition.

Also, unless otherwise indicated, most solution transfers and wash additions used the 96-well head of a Beckman Biomek Fx$^P$. Method steps manually pipetted used a twelve channel P200 Pipetteman (Rainin Instruments, LLC, Oakland, Calif.), unless otherwise indicated. A custom buffer referred to as SB17 was prepared in-house, comprising 40 mM HEPES, 100 mM NaCl, 5 mM KCl, 5 mM MgCl$_2$, 1 mM EDTA at pH7.5. All steps were performed at room temperature unless otherwise indicated.

1. Preparation of Aptamer Stock Solution

For aptamers without a photo-cleavable biotin linker, custom stock aptamer solutions for 10%, 1% and 0.03% serum were prepared at 8× concentration in 1×SB17, 0.05% Tween-20 with appropriate photo-cleavable, biotinylated primers, where the resultant primer concentration was 3 times the relevant aptamer concentration. The primers hybridized to all or part of the corresponding aptamer.

Each of the 3, 8× aptamer solutions were diluted separately 1:4 into 1×SB17, 0.05% Tween-20 (1500 μL of 8× stock into 4500 μL of 1×SB17, 0.05% Tween-20) to achieve a 2× concentration. Each diluted aptamer master mix was then split, 1500 μL each, into 4, 2 mL screw cap tubes and brought to 95° C. for 5 minutes, followed by a 37° C. incubation for 15 minutes. After incubation, the 4, 2 mL tubes corresponding to a particular aptamer master mix were combined into a reagent trough, and 55 μL of a 2× aptamer mix (for all three mixes) was manually pipetted into a 96-well Hybaid plate and the plate foil sealed. The final result was 3, 96-well, foil-sealed Hybaid plates. The individual aptamer concentration ranged from 0.5-4 nM as indicated in Table 2.

2. Assay Sample Preparation

Frozen aliquots of 100% serum, stored at −80° C., were placed in 25° C. water bath for 10 minutes. Thawed samples were placed on ice, gently vortexed (set on 4) for 8 seconds and then replaced on ice.

A 20% sample solution was prepared by transferring 16 μL of sample using a 50 μL 8-channel spanning pipettor into 96-well Hybaid plates, each well containing 64 μL of the appropriate sample diluent at 4° C. (0.8×SB17, 0.05% Tween-20, 2 μM Z-block_2, 0.6 mM MgCl$_2$ for serum). This plate was stored on ice until the next sample dilution steps were initiated.

To commence sample and aptamer equilibration, the 20% sample plate was briefly centrifuged and placed on the Beckman FX where it was mixed by pipetting up and down with the 96-well pipettor. A 2% sample was then prepared by diluting 10 μL of the 20% sample into 90 μL of 1×SB17, 0.05% Tween-20. Next, dilution of 6 μL of the resultant 2% sample into 194 μL of 1×SB17, 0.05% Tween-20 made a 0.06% sample plate. Dilutions were done on the Beckman Biomek Fx$^P$. After each transfer, the solutions were mixed by pipetting up and down. The 3 sample dilution plates were then transferred to their respective aptamer solutions by adding 55 μL of the sample to 55 μL of the appropriate 2× aptamer mix. The sample and aptamer solutions were mixed on the robot by pipetting up and down.

3. Sample Equilibration Binding

The sample/aptamer plates were foil sealed and placed into a 37° C. incubator for 3.5 hours before proceeding to the Catch 1 step.

4. Preparation of Catch 2 bead plate

An 11 mL aliquot of MyOne (Invitrogen Corp., Carlsbad, Calif.) Streptavidin C1 beads was washed 2 times with equal volumes of 20 mM NaOH (5 minute incubation for each wash), 3 times with equal volumes of 1×SB17, 0.05% Tween-20 and resuspended in 11 mL 1×SB17, 0.05% Tween-20. Using a 12-span multichannel pipettor, 50 µL of this solution was manually pipetted into each well of a 96-well Hybaid plate. The plate was then covered with foil and stored at 4° C. for use in the assay.

5. Preparation of Catch 1 bead plates

Three 0.45 µm Millipore HV plates (Durapore membrane, Cat # MAHVN4550) were equilibrated with 100 µL of 1×SB17, 0.05% Tween-20 for at least 10 minutes. The equilibration buffer was then filtered through the plate and 133.3 µL of a 7.5% Streptavidin-agarose bead slurry (in 1×SB17, 0.05% Tween-20) was added into each well. To keep the streptavidin-agarose beads suspended while transferring them into the filter plate, the bead solution was manually mixed with a 200 µL, 12-channel pipettor, 15 times. After the beads were distributed across the 3 filter plates, a vacuum was applied to remove the bead supernatant. Finally, the beads were washed in the filter plates with 200 µL 1×SB17, 0.05% Tween-20 and then resuspended in 200 µL 1×SB17, 0.05% Tween-20. The bottoms of the filter plates were blotted and the plates stored for use in the assay.

6. Loading the Cytomat

The cytomat was loaded with all tips, plates, all reagents in troughs (except NHS-biotin reagent which was prepared fresh right before addition to the plates), 3 prepared catch 1 filter plates and 1 prepared MyOne plate.

7. Catch 1

After a 3.5 hour equilibration time, the sample/aptamer plates were removed from the incubator, centrifuged for about 1 minute, foil removed, and placed on the deck of the Beckman Biomek Fx$^P$. The Beckman Biomek Fx$^P$ program was initiated. All subsequent steps in Catch 1 were performed by the Beckman Biomek Fx$^P$ robot unless otherwise noted. Within the program, the vacuum was applied to the Catch 1 filter plates to remove the bead supernatant. One hundred microlitres of each of the 10%, 1% and 0.03% equilibration binding reactions were added to their respective Catch 1 filtration plates, and each plate was mixed using an on-deck orbital shaker at 800 rpm for 10 minutes.

Unbound solution was removed via vacuum filtration. The catch 1 beads were washed with 190 µL of 100 µM biotin in 1×SB17, 0.05% Tween-20 followed by 190 µL of 1×SB17, 0.05% Tween-20 by dispensing the solution and immediately drawing a vacuum to filter the solution through the plate.

Next, 190 µL 1×SB17, 0.05% Tween-20 was added to the Catch 1 plates. Plates were blotted to remove droplets using an on-deck blot station and then incubated with orbital shakers at 800 rpm for 10 minutes at 25° C.

The robot removed this wash via vacuum filtration and blotted the bottom of the filter plate to remove droplets using the on-deck blot station.

8. Tagging

A NHS-PEO4-biotin aliquot was thawed at 37° C. for 6 minutes and then diluted 1:100 with tagging buffer (SB17 at pH=7.25 0.05% Tween-20). The NHS-PEO4-biotin reagent was dissolved at 100 mM concentration in anhydrous DMSO and had been stored frozen at −20° C. Upon a robot prompt, the diluted NHS-PEO4-biotin reagent was manually added to an on-deck trough and the robot program was manually re-initiated to dispense 100 µL of the NHS-PEO4-biotin into each well of each Catch 1 filter plate. This solution was allowed to incubate with Catch 1 beads shaking at 800 rpm for 5 minutes on the orbital shakers.

9. Kinetic Challenge and Photo-Cleavage

The tagging reaction was quenched by the addition of 150 µL of 20 mM glycine in 1×SB17, 0.05% Tween-20 to the Catch 1 plates while still containing the NHS tag. The plates were then incubated for 1 minute on orbital shakers at 800 rpm. The NHS-tag/glycine solution was removed via vacuum filtration. Next, 190 µL 20 mM glycine (1×SB17, 0.05% Tween-20) was added to each plate and incubated for 1 minute on orbital shakers at 800 rpm before removal by vacuum filtration.

190 µL of 1×SB17, 0.05% Tween-20 was added to each plate and removed by vacuum filtration.

The wells of the Catch 1 plates were subsequently washed three times by adding 190 µL 1×SB17, 0.05% Tween-20, placing the plates on orbital shakers for 1 minute at 800 rpm followed by vacuum filtration. After the last wash the plates were placed on top of a 1 mL deep-well plate and removed from the deck. The Catch 1 plates were centrifuged at 1000 rpm for 1 minute to remove as much extraneous volume from the agarose beads before elution as possible.

The plates were placed back onto the Beckman Biomek Fx$^P$ and 85 µL of 10 mM DxSO4 in 1×SB17, 0.05% Tween-20 was added to each well of the filter plates.

The filter plates were removed from the deck, placed onto a Variomag Thermoshaker (Thermo Fisher Scientific, Inc., Waltham, Mass.) under the BlackRay (Ted Pella, Inc., Redding, Calif.) light sources, and irradiated for 10 minutes while shaking at 800 rpm.

The photocleaved solutions were sequentially eluted from each Catch 1 plate into a common deep well plate by first placing the 10% Catch 1 filter plate on top of a 1 mL deep-well plate and centrifuging at 1000 rpm for 1 minute. The 1% and 0.03% catch 1 plates were then sequentially centrifuged into the same deep well plate.

10. Catch 2 Bead Capture

The 1 mL deep well block containing the combined eluates of catch 1 was placed on the deck of the Beckman Biomek Fx$^P$ for catch 2.

The robot transferred all of the photo-cleaved eluate from the 1 mL deep-well plate onto the Hybaid plate containing the previously prepared catch 2 MyOne magnetic beads (after removal of the MyOne buffer via magnetic separation).

The solution was incubated while shaking at 1350 rpm for 5 minutes at 25° C. on a Variomag Thermoshaker (Thermo Fisher Scientific, Inc., Waltham, Mass.).

The robot transferred the plate to the on deck magnetic separator station. The plate was incubated on the magnet for 90 seconds before removal and discarding of the supernatant.

11. 37° C. 30% Glycerol Washes

The catch 2 plate was moved to the on-deck thermal shaker and 75 µL of 1×SB17, 0.05% Tween-20 was transferred to each well. The plate was mixed for 1 minute at 1350 rpm and 37° C. to resuspend and warm the beads. To each well of the catch 2 plate, 75 µL of 60% glycerol at 37° C. was transferred and the plate continued to mix for another minute at 1350 rpm and 37° C. The robot transferred the plate to the 37° C. magnetic separator where it was incubated on the magnet for 2 minutes and then the robot removed and discarded the supernatant. These washes were repeated two more times.

After removal of the third 30% glycerol wash from the catch 2 beads, 150 µL of 1×SB17, 0.05% Tween-20 was added to each well and incubated at 37° C., shaking at 1350 rpm for 1 minute, before removal by magnetic separation on the 37° C. magnet.

The catch 2 beads were washed a final time using 150 µL 1×SB19, 0.05% Tween-20 with incubation for 1 minute while shaking at 1350 rpm, prior to magnetic separation.

12. Catch 2 Bead Elution and Neutralization

The aptamers were eluted from catch 2 beads by adding 105 µL of 100 mM CAPSO with 1 M NaCl, 0.05% Tween-20 to each well. The beads were incubated with this solution with shaking at 1300 rpm for 5 minutes.

The catch 2 plate was then placed onto the magnetic separator for 90 seconds prior to transferring 90 µL of the eluate to a new 96-well plate containing 10 µL of 500 mM HCl, 500 mM HEPES, 0.05% Tween-20 in each well. After transfer, the solution was mixed robotically by pipetting 90 µL up and down five times.

13. Hybridization

The Beckman Biomek Fx$^P$ transferred 20 µL of the neutralized catch 2 eluate to a fresh Hybaid plate, and 5 µL of 10× Agilent Block, containing a 10× spike of hybridization controls, was added to each well. Next, 25 µL of 2× Agilent Hybridization buffer was manually pipetted to the each well of the plate containing the neutralized samples and blocking buffer and the solution was mixed by manually pipetting 25 µL up and down 15 times slowly to avoid extensive bubble formation. The plate was spun at 1000 rpm for 1 minute.

A gasket slide was placed into an Agilent hybridization chamber and 40 µL of each of the samples containing hybridization and blocking solution was manually pipetted into each gasket. An 8-channel variable spanning pipettor was used in a manner intended to minimize bubble formation. Custom Agilent microarray slides (Agilent Technologies, Inc., Santa Clara, Calif.), with their Number Barcode facing up, were then slowly lowered onto the gasket slides (see Agilent manual for detailed description).

The top of the hybridization chambers were placed onto the slide/backing sandwich and clamping brackets slid over the whole assembly. These assemblies were tightly clamped by turning the screws securely.

Each slide/backing slide sandwich was visually inspected to assure the solution bubble could move freely within the sample. If the bubble did not move freely the hybridization chamber assembly was gently tapped to disengage bubbles lodged near the gasket.

The assembled hybridization chambers were incubated in an Agilent hybridization oven for 19 hours at 60° C. rotating at 20 rpm.

14. Post Hybridization Washing

Approximately 400 mL Agilent Wash Buffer 1 was placed into each of two separate glass staining dishes. One of the staining dishes was placed on a magnetic stir plate and a slide rack and stir bar were placed into the buffer.

A staining dish for Agilent Wash 2 was prepared by placing a stir bar into an empty glass staining dish.

A fourth glass staining dish was set aside for the final acetonitrile wash.

Each of six hybridization chambers was disassembled. One-by-one, the slide/backing sandwich was removed from its hybridization chamber and submerged into the staining dish containing Wash 1. The slide/backing sandwich was pried apart using a pair of tweezers, while still submerging the microarray slide. The slide was quickly transferred into the slide rack in the Wash 1 staining dish on the magnetic stir plate.

The slide rack was gently raised and lowered 5 times. The magnetic stirrer was turned on at a low setting and the slides incubated for 5 minutes.

When one minute was remaining for Wash 1, Wash Buffer 2 pre-warmed to 37° C. in an incubator was added to the second prepared staining dish. The slide rack was quickly transferred to Wash Buffer 2 and any excess buffer on the bottom of the rack was removed by scraping it on the top of the stain dish. The slide rack was gently raised and lowered 5 times. The magnetic stirrer was turned on at a low setting and the slides incubated for 5 minutes.

The slide rack was slowly pulled out of Wash 2, taking approximately 15 seconds to remove the slides from the solution.

With one minute remaining in Wash 2 acetonitrile (ACN) was added to the fourth staining dish. The slide rack was transferred to the acetonitrile stain dish. The slide rack was gently raised and lowered 5 times. The magnetic stirrer was turned on at a low setting and the slides incubated for 5 minutes.

The slide rack was slowly pulled out of the ACN stain dish and placed on an absorbent towel. The bottom edges of the slides were quickly dried and the slide was placed into a clean slide box.

15. Microarray Imaging

The microarray slides were placed into Agilent scanner slide holders and loaded into the Agilent Microarray scanner according to the manufacturer's instructions.

The slides were imaged in the Cy3-channel at 5 µm resolution at the 100% PMT setting and the XRD option enabled at 0.05. The resulting tiff images were processed using Agilent feature extraction software version 10.5.

Example 2. Biomarker Identification

The identification of potential lung cancer biomarkers was performed for three different diagnostic applications, diagnosis of suspicious nodules from a CT scan, screening of asymptomatic smokers for lung cancer, and diagnosing an individual with lung cancer. Serum samples were collected from four different sites in support of these three applications and include 48 NSCLC cases, 218 high risk controls composed of heavy smokers and patients with benign nodules. The multiplexed aptamer affinity assay as described in Example 1 was used to measure and report the RFU value for 820 analytes in each of these 264 samples. The KS-test was then applied to each analyte. The KS-distance (Kolmogorov-Smirnov statistic) between values from two sets of samples is a non parametric measurement of the extent to which the empirical distribution of the values from one set (Set A) differs from the distribution of values from the other set (Set B). For any value of a threshold T some proportion of the values from Set A will be less than T, and some proportion of the values from Set B will be less than T. The KS-distance measures the maximum (unsigned) difference between the proportion of the values from the two sets for any choice of T.

Sets of biomarkers can be used to build classifiers that assign samples to either a control or disease group. In fact, many such classifiers were produced from these sets of biomarkers and the frequency with which any biomarker was used in good scoring classifiers determined. Those biomarkers that occurred most frequently among the top scoring classifiers were the most useful for creating a diagnostic test. In this example, Bayesian classifiers were used to explore the classification space but many other supervised learning techniques may be employed for this purpose. The scoring fitness of any individual classifier was gauged using the area under the receiver operating characteristic curve (AUC of ROC) of the classifier at the Bayesian surface assuming a disease prevalence of 0.5. This scoring metric varies from zero to one, with one being an error-free classifier. The details of constructing a Bayesian classifier from biomarker population measurements are described in Example 3.

Example 3. Naïve Bayesian Classification for Lung Cancer

Figure 5:
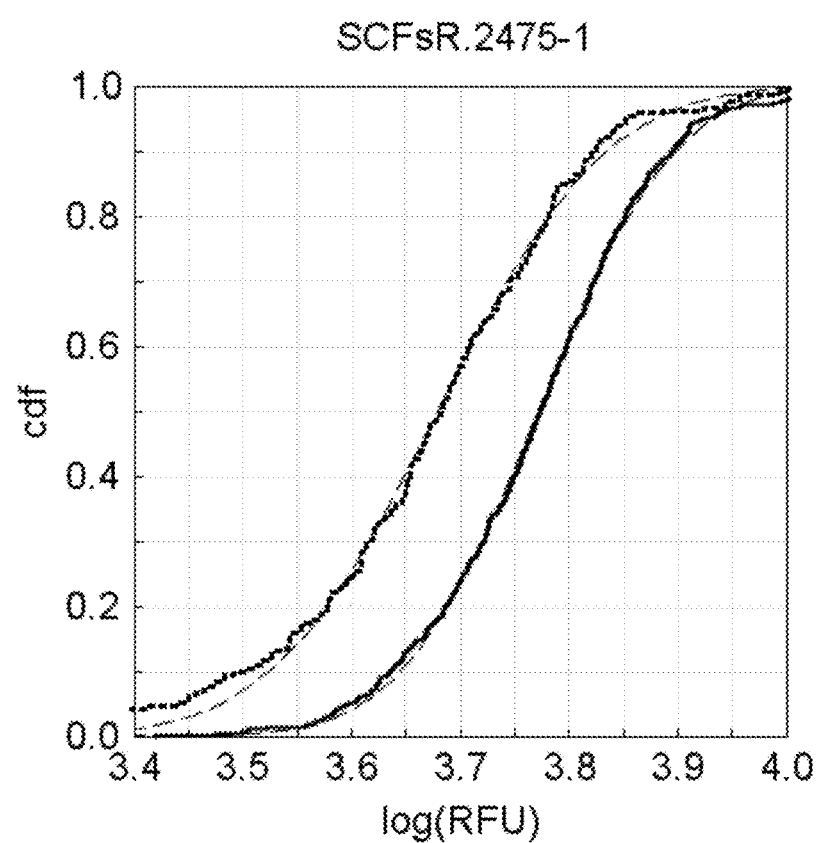
FIG. 5 shows the measured biomarker distributions for SCFsR as a cumulative distribution function (cdf) in log-transformed RFU for the benign nodule control group (solid line) and the lung cancer disease group (dotted line) along with their curve fits to a normal cdf (dashed lines) used to train the naïve Bayes classifiers

From the list of biomarkers identified as useful for discriminating between NSCLC and the high risk control group, a panel of five biomarkers was selected and a naïve Bayes classifier was constructed, see Table 14. The class-dependent probability density functions (pdfs), $p(x_i|c)$ and $p(x_i|d)$, where $x_i$ is the log of the measured RFU value for biomarker i, and c and d refer to the control and disease populations, were modeled as normal distribution functions characterized by a mean $\mu$ and variance $\sigma^2$. The parameters for pdfs of the five biomarkers are listed in Table 15 and an example of the raw data along with the model fit to a normal pdf is displayed in FIG. 5. The underlying assumption appears to fit the data quite well as evidenced by FIG. 5.

The naïve Bayes classification for such a model is given by the following equation, where P(d) is the prevalence of the disease in the population $$\ln\frac{p(c|\underline{x})}{p(d|\underline{x})} = \sum_{i=1}^{n}\left(\ln\frac{\sigma_{d,i}}{\sigma_{c,i}} - \frac{1}{2}\left[\left(\frac{x_i - \mu_{c,i}}{\sigma_{c,i}}\right)^2 - \left(\frac{x_i - \mu_{d,i}}{\sigma_{d,i}}\right)^2\right]\right) + \ln\frac{(1-P(d))}{P(d)}$$

appropriate to the test and n=5 here. Each of the terms in the summation is a log-likelihood ratio for an individual marker and the total log-likelihood ratio of a sample $\underline{x}$ being free from the disease of interest (i.e. in this case, NSCLC) versus having the disease is simply the sum of these individual terms plus a term that accounts for the prevalence of the disease. For simplicity, we assume P(d)=0.5 so that $$\ln\frac{(1-P(d))}{P(d)} = 0.$$

Given an unknown sample measurement in log(RFU) for each of the ten biomarkers of. The individual components comprising the log likelihood ratio for control versus disease class are tabulated and can be computed from the parameters in Table 15 and the values of $\underline{x}$. The sum of the individual log likelihood ratios is 3.47, or a likelihood of being free from the disease versus having the disease of 32:1, where likelihood=$e^{3.47}$=32. All five biomarkers are all consistently found to favor the control group. Multiplying the likelihoods together gives the same results as that shown above; a likelihood of 32:1 that the unknown sample is free from the disease. In fact, this sample came from the control population in the training set. Although this example demonstrates the classification of serum samples using the biomarkers in Table 15, the same approach can be used in any tissue type with any set of biomarkers from Table 21.

Example 4. Greedy Algorithm for Selecting Biomarker Panels for Classifiers Part 1

This example describes the selection of biomarkers from Table 21 to form panels that can be used as classifiers in any of the methods described herein. Panels of biomarkers containing MMP-12 and Subsets of the biomarkers in Table 21 were selected to construct classifiers with good performance. This method was also used to determine which potential markers were included as biomarkers in Example 2.

The measure of classifier performance used here is the area under the ROC curve (AUC); a performance of 0.5 is the baseline expectation for a random (coin toss) classifier, a classifier worse than random would score between 0.0 and 0.5, a classifier with better than random performance would score between 0.5 and 1.0. A perfect classifier with no errors would have a sensitivity of 1.0, a specificity of 1.0 and an AUC of 1.0. One can apply the methods described in Example 4 to other common measures of performance such as the F-measure, the sum of sensitivity and specificity, or the product of sensitivity and specificity. Specifically one might want to treat specificity and specificity with differing weight, so as to select those classifiers which perform with higher specificity at the expense of some sensitivity, or to select those classifiers which perform with higher sensitivity at the expense of some specificity. Since the method described here only involves a measure of "performance", any weighting scheme which results in a single performance measure can be used. Different applications will have different benefits for true positive and true negative findings, and also different costs associated with false positive findings from false negative findings. For example, screening asymptomatic smokers and the differential diagnosis of benign nodules found on CT will not in general have the same optimal trade-off between specificity and sensitivity. The different demands of the two tests will in general require setting different weighting to positive and negative misclassifications, reflected in the performance measure. Changing the performance measure will in general change the exact subset of markers selected from Table 21 for a given set of data.

For the Bayesian approach to the discrimination of lung cancer samples from control samples described in Example 3, the classifier was completely parameterized by the distributions of biomarkers in the disease and benign training samples, and the list of biomarkers was chosen from Table 21; that is to say, the subset of markers chosen for inclusion determined a classifier in a one-to-one manner given a set of training data.

The greedy method employed here was used to search for the optimal subset of markers from Table 21. For small numbers of markers or classifiers with relatively few markers, every possible subset of markers was enumerated and evaluated in terms of the performance of the classifier constructed with that particular set of markers (see Example 4, Part 2). (This approach is well known in the field of statistics as "best subset selection"; see, e.g., The Elements of Statistical Learning-Data Mining, Inference, and Prediction, T. Hastie, et al., editors, Springer Science+Business Media, LLC, 2nd edition, 2009). However, for the classifiers described herein, the number of combinations of multiple markers can be very large, and it was not feasible to evaluate every possible set of five markers, for example, from the list of 86 markers (Table 21) (i.e., 34,826,302 combinations). Because of the impracticality of searching through every subset of markers, the single optimal subset may not be found; however, by using this approach, many excellent subsets were found, and, in many cases, any of these subsets may represent an optimal one.

Instead of evaluating every possible set of markers, a "greedy" forward stepwise approach may be followed (see, e.g., Dabney A R, Storey J D (2007) Optimality Driven Nearest Centroid Classification from Genomic Data. PLoS ONE 2(10): e1002. doi:10.1371/journal.pone.0001002). Using this method, a classifier is started with the best single marker (based on KS-distance for the individual markers) and is grown at each step by trying, in turn, each member of a marker list that is not currently a member of the set of markers in the classifier. The one marker which scores best in combination with the existing classifier is added to the classifier. This is repeated until no further improvement in performance is achieved. Unfortunately, this approach may miss valuable combinations of markers for which some of the individual markers are not all chosen before the process stops.

The greedy procedure used here was an elaboration of the preceding forward stepwise approach, in that, to broaden the search, rather than keeping just a single candidate classifier (marker subset) at each step, a list of candidate classifiers was kept. The list was seeded with every single marker subset (using every marker in the table on its own). The list was expanded in steps by deriving new classifiers (marker subsets) from the ones currently on the list and adding them to the list. Each marker subset currently on the list was extended by adding any marker from Table 1 not already part of that classifier, and which would not, on its addition to the subset, duplicate an existing subset (these are termed "permissible markers"). Every existing marker subset was extended by every permissible marker from the list. Clearly, such a process would eventually generate every possible subset, and the list would run out of space. Therefore, all the generated classifiers were kept only while the list was less than some predetermined size (often enough to hold all three marker subsets). Once the list reached the predetermined size limit, it became elitist; that is, only those classifiers which showed a certain level of performance were kept on the list, and the others fell off the end of the list and were lost. This was achieved by keeping the list sorted in order of classifier performance; new classifiers which were at least as good as the worst classifier currently on the list were inserted, forcing the expulsion of the current bottom underachiever. One further implementation detail is that the list was completely replaced on each generational step; therefore, every classifier on the list had the same number of markers, and at each step the number of markers per classifier grew by one.

Since this method produced a list of candidate classifiers using different combinations of markers, one may ask if the classifiers can be combined in order to avoid errors which might be made by the best single classifier, or by minority groups of the best classifiers. Such "ensemble" and "committee of experts" methods are well known in the fields of statistical and machine learning and include, for example, "averaging", "voting", "stacking", "bagging" and "boosting" (see, e.g., The Elements of Statistical Learning—Data Mining, Inference, and Prediction, T. Hastie, et al., editors, Springer Science+Business Media, LLC, 2nd edition, 2009). These combinations of simple classifiers provide a method for reducing the variance in the classifications due to noise in any particular set of markers by including several different classifiers and therefore information from a larger set of the markers from the biomarker table, effectively averaging between the classifiers. An example of the usefulness of this approach is that it can prevent outliers in a single marker from adversely affecting the classification of a single sample. The requirement to measure a larger number of signals may be impractical in conventional "one marker at a time" antibody assays but has no downside for a fully multiplexed aptamer assay. Techniques such as these benefit from a more extensive table of biomarkers and use the multiple sources of information concerning the disease processes to provide a more robust classification.

Part 2

The biomarkers selected in Table 1 gave rise to classifiers which perform better than classifiers built with "non-markers" (i.e., proteins having signals that did not meet the criteria for inclusion in Table 1 (as described in Example 2)).

For classifiers containing only one, two, and three markers, all possible classifiers obtained using the biomarkers in Table 1 were enumerated and examined for the distribution of performance compared to classifiers built from a similar table of randomly selected non-markers signals.

In FIG. 17 and FIG. 18, the sum of the sensitivity and specificity was used as the measure of performance; a performance of 1.0 is the baseline expectation for a random (coin toss) classifier. The histogram of classifier performance was compared with the histogram of performance from a similar exhaustive enumeration of classifiers built from a "non-marker" table of 40 non-marker signals; the 40 signals were randomly chosen from 400 aptamers that did not demonstrate differential signaling between control and disease populations (KS-distance <1.4).

Figure 17A:
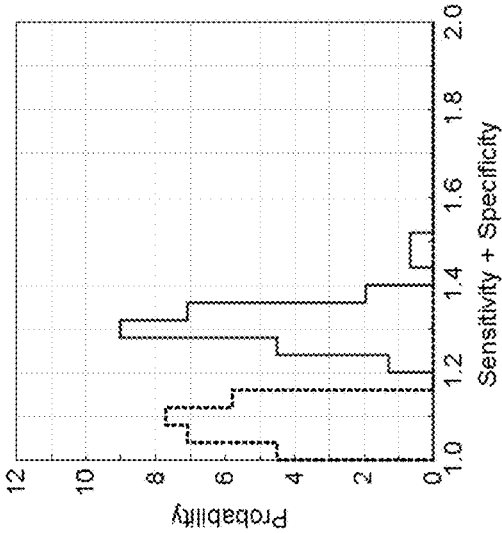
FIG. 17A shows a pair of histograms summarizing all possible single protein naïve Bayes classifier scores (sensitivity+specificity) using the biomarkers set forth in Table 1, Col 5 (solid) and a set of random markers (dotted).
Figure 17B:
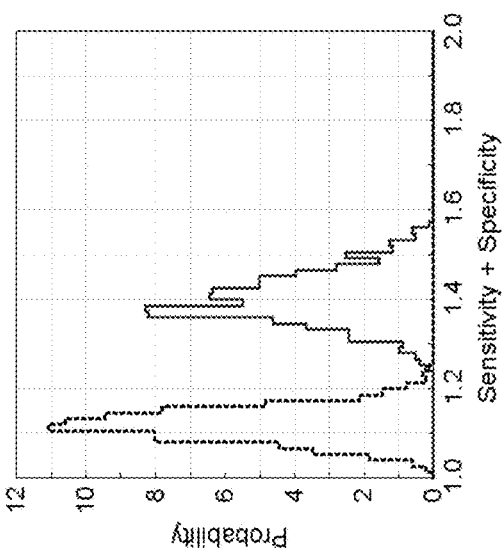
FIG. 17B shows a pair of histograms summarizing all possible two-protein protein naïve Bayes classifier scores (sensitivity+specificity) using the biomarkers set forth in Table 1, Col 5 (solid) and a set of random markers (dotted).
Figure 17C:
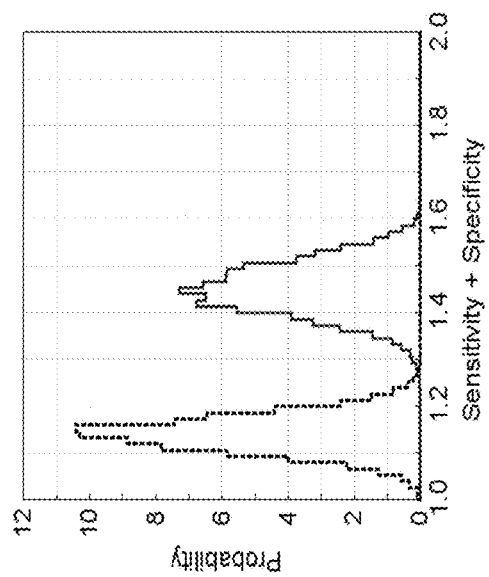
FIG. 17C shows a pair of histograms summarizing all possible three-protein naïve Bayes classifier scores (sensitivity+specificity) using the biomarkers set forth in Table 1, Col 5 (solid) and a set of random markers (dotted).

FIG. 17 shows histograms of the performance of all possible one, two, and three-marker classifiers built from the biomarker parameters in Table 13 for biomarkers that can discriminate between benign nodules and NSCLC and compares these classifiers with all possible one, two, and three-marker classifiers built using the 40 "non-marker" aptamer RFU signals. FIG. 17A shows the histograms of single marker classifier performance, FIG. 17B shows the histogram of two marker classifier performance, and FIG. 17C shows the histogram of three marker classifier performance.

In FIG. 17, the solid lines represent the histograms of the classifier performance of all one, two, and three-marker classifiers using the biomarker data for benign nodules and NSCLC in Table 13. The dotted lines are the histograms of the classifier performance of all one, two, and three-marker classifiers using the data for benign nodules and NSCLC but using the set of random non-marker signals.

Figure 18A:
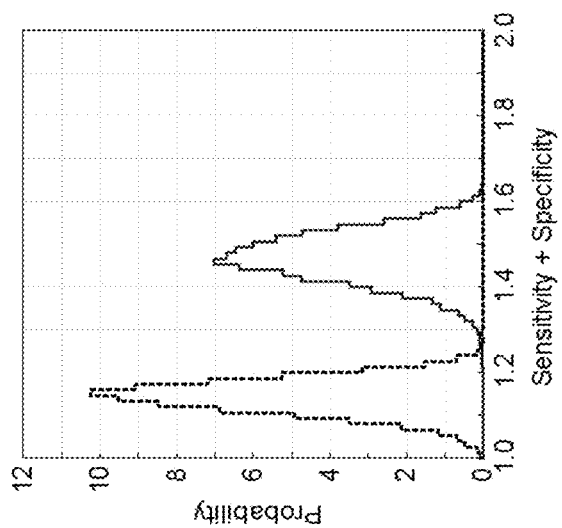
FIG. 18A shows a pair of histograms summarizing all possible single protein naïve Bayes classifier scores (sensitivity+specificity) using the biomarkers set forth in Table 1, Col 6 (solid) and a set of random markers (dotted).
Figure 18B:
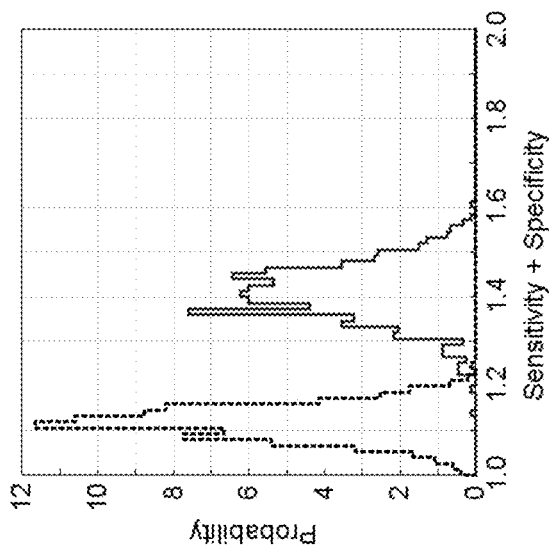
FIG. 18B shows a pair of histograms summarizing all possible two-protein protein naïve Bayes classifier scores (sensitivity+specificity) using the biomarkers set forth in Table 1, Col 6 (solid) and a set of random markers (dotted).
Figure 18C:
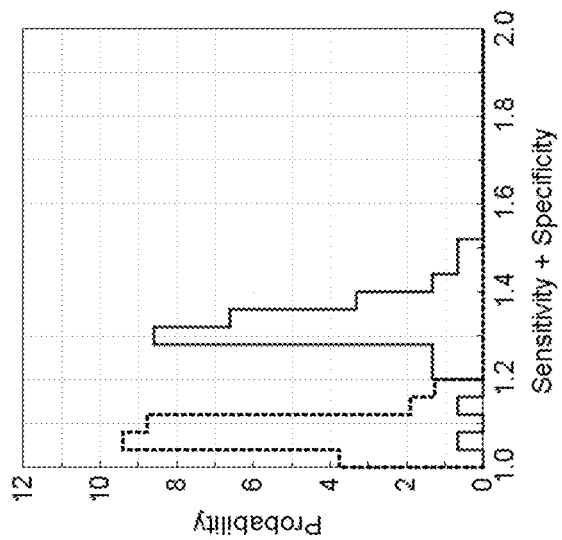
FIG. 18C shows a pair of histograms summarizing all possible three-protein naïve Bayes classifier scores (sensitivity+specificity) using the biomarkers set forth in Table 1, Col 6 (solid) and a set of random markers (dotted).

FIG. 18 shows histograms of the performance of all possible one, two, and three-marker classifiers built from the biomarker parameters in Table 12 for biomarkers that can discriminate between asymptomatic smokers and NSCLC and compares these with all possible one, two, and three-marker classifiers built using 40 "non-marker" aptamer RFU signals. FIG. 18A shows the histograms of single marker classifier performance, FIG. 18B shows the histogram of two marker classifier performance, and FIG. 18C shows the histogram of three marker classifier performance.

In FIG. 18, the solid lines represent the histograms of the classifier performance of all one, two, and three-marker classifiers using the biomarker parameters for asymptomatic smokers and NSCLC in Table 12. The dotted lines are the histograms of the classifier performance of all one, two, and three-marker classifiers using the data for asymptomatic smokers and NSCLC but using the set of random non-marker signals.

The classifiers built from the markers listed in Table 1 form a distinct histogram, well separated from the classifiers built with signals from the "non-markers" for all one-marker, two-marker, and three-marker comparisons. The performance and AUC score of the classifiers built from the biomarkers in Table 1 also increase faster with the number of markers than do the classifiers built from the non-markers, the separation increases between the marker and non-marker classifiers as the number of markers per classifier increases. All classifiers built using the biomarkers listed in Tables 38 and 39 perform distinctly better than classifiers built using the "non-markers".

Part 3

To test whether a core subset of markers accounted for the good performance of the classifiers, half of the markers were randomly dropped from the lists of biomarkers in Tables 38 and 39. The performance, as measured by sensitivity plus specificity, of classifiers for distinguishing benign nodules from malignant nodules dropped slightly by 0.07 (from 1.74 to 1.67), and the performance of classifiers for distinguishing smokers who had cancer from those who did not also dropped slightly by 0.06 (from 1.76 to 1.70). The implication of the performance characteristics of subsets of the biomarker table is that multiple subsets of the listed biomarkers are effective in building a diagnostic test, and no particular core subset of markers dictates classifier performance.

In the light of these results, classifiers that excluded the best markers from Tables 12 and 13 were tested. FIG. 19 compares the performance of classifiers built with the full list of biomarkers in Tables 12 and 13 with the performance of classifiers built with a set of biomarkers from Tables 38 and 39 excluding top ranked markers.

FIG. 19 demonstrates that classifiers constructed without the best markers perform well, implying that the performance of the classifiers was not due to some small core group of markers and that the changes in the underlying processes associated with disease are reflected in the activities of many proteins. Many subsets of the biomarkers in Table 1 performed close to optimally, even after removing the top 15 of the 40 markers from Table 1.

Figure 19A:
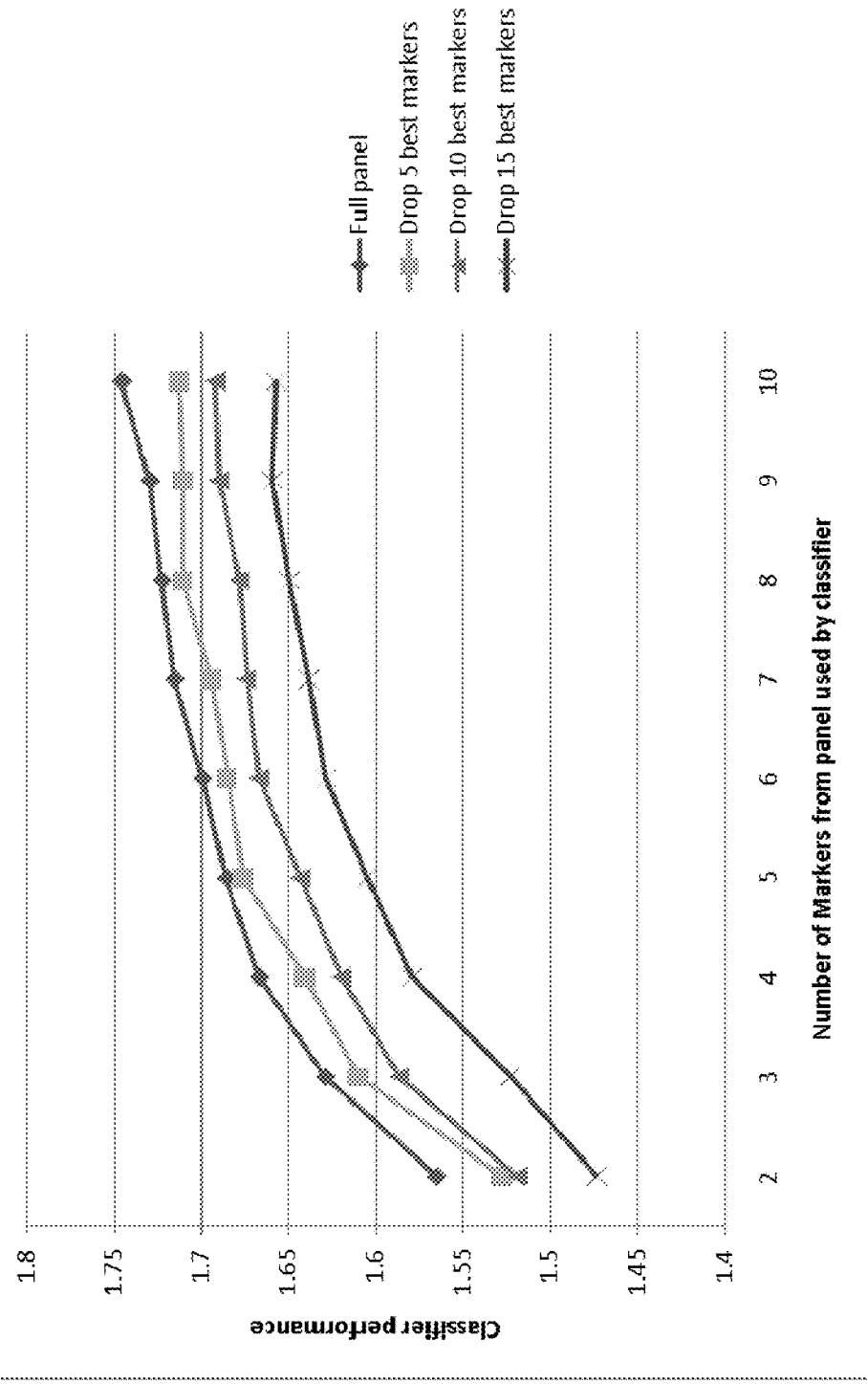
FIG. 19A shows the sensitivity+specificity score for naïve Bayes classifiers using from 2-10 markers selected from the full panel (♦) and the scores obtained by dropping the best 5 (■), 10 (▲) and 15 (x) markers during classifier generation for the benign nodule control group.

FIG. 19A shows the effect on classifiers for discriminating benign nodules from NSCLC built with 2 to 10 markers. Even after dropping the 15 top-ranked markers (ranked by KS-distance) from Table 13, the benign nodule vs. NSCLC performance increased with the number of markers selected from the table to reach over 1.65 (Sensitivity+Specificity).

Figure 19B:
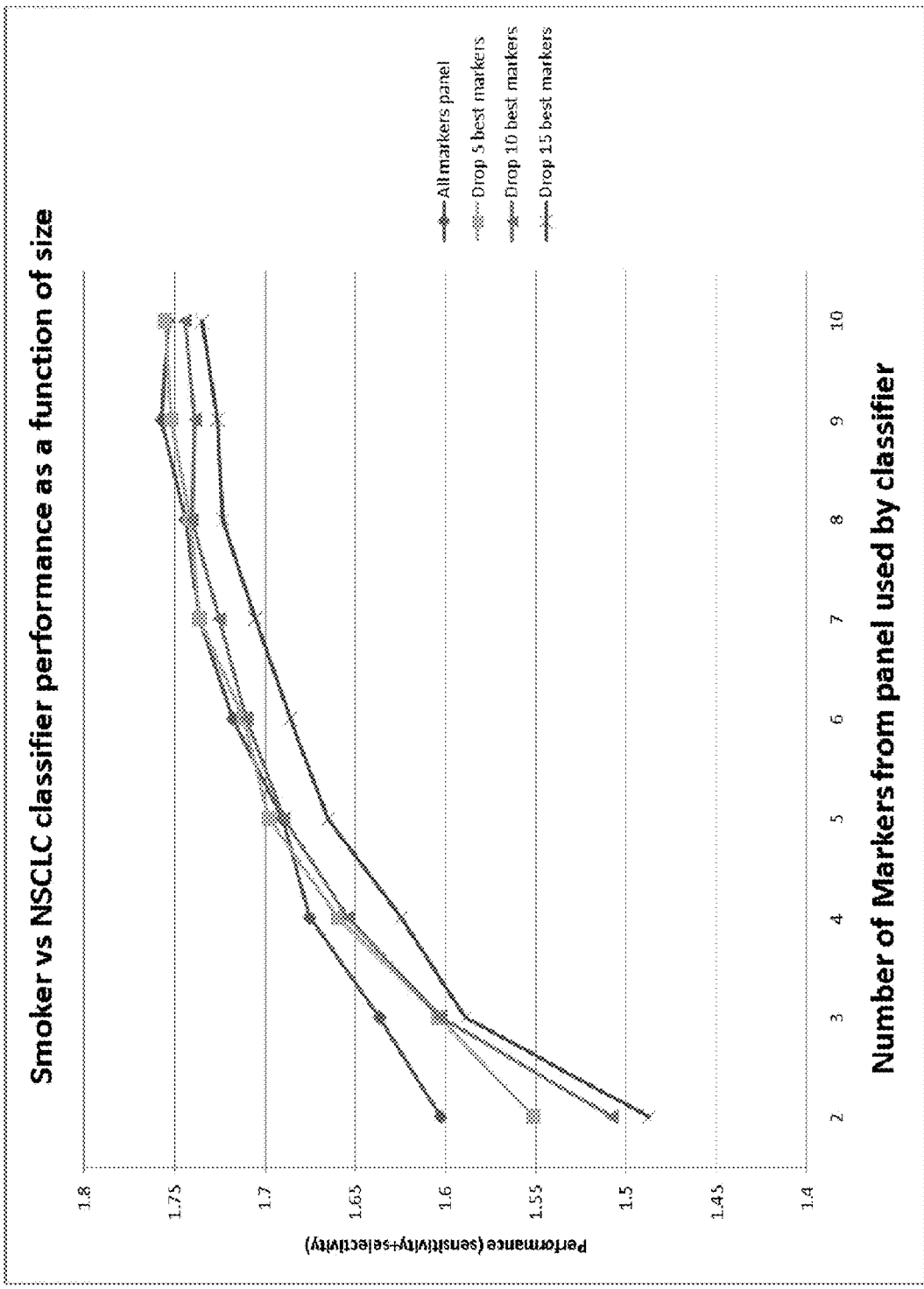
FIG. 19B shows the sensitivity+specificity score for naïve Bayes classifiers using from 2-10 markers selected from the full panel (♦) and the scores obtained by dropping the best 5 (■), 10 (▲) and 15 (x) markers during classifier generation for the smoker control group.

FIG. 19B shows the effect on classifiers for discriminating asymptomatic smokers from NSCLC built with 2 to 10 markers. Even after dropping the 15 top-ranked markers (ranked by KS-distance) from Table 12, the asymptomatic smokers vs. NSCLC performance increased with the number of markers selected from the table to reach over 1.7 (Sensitivity+Specificity), and closely approached the performance of the best classifier selected from the full list of biomarkers in Table 12.

Figure 20B:
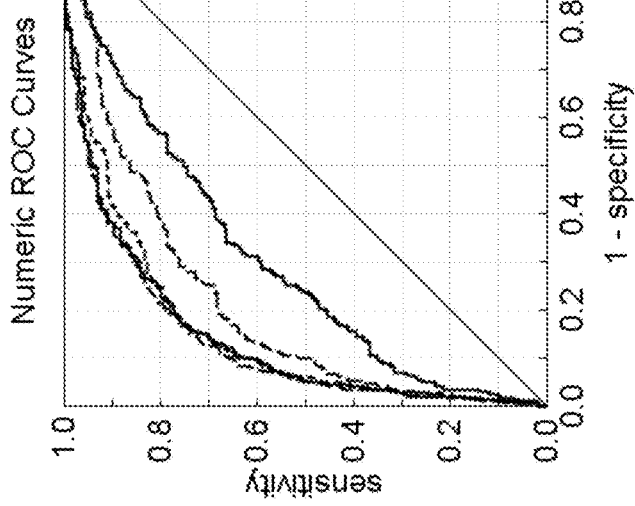
FIG. 20B shows a set of ROC curves computed from the training data for panels of from one to five markers as in FIG. 19A.
Figure 20A:
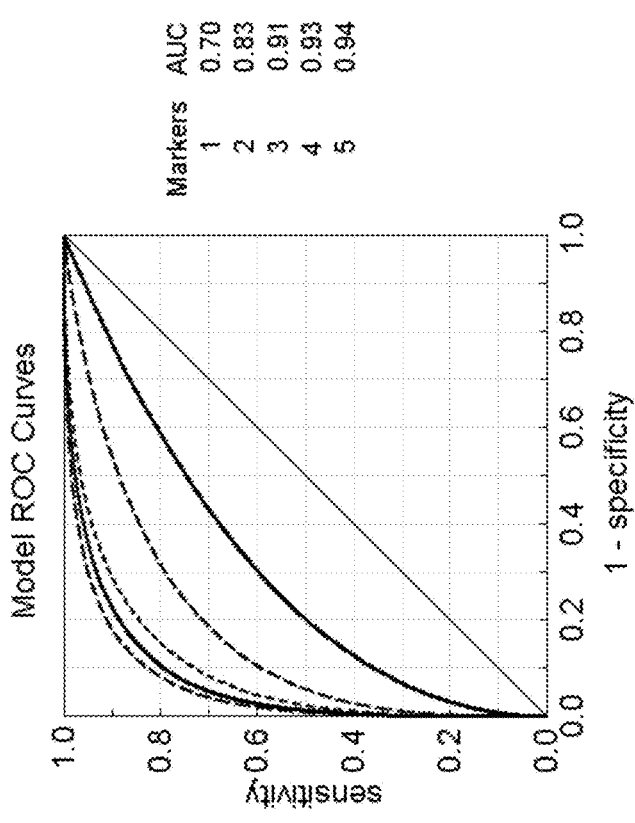
FIG. 20A shows a set of ROC curves modeled from the data in Tables 38 and 39 for panels of from one to five markers.

Finally, FIG. 20 shows how the ROC performance of typical classifiers constructed from the list of parameters in Tables 12 and 13 according to Example 3. FIG. 20A shows the model performance from assuming the independence of markers as in Example 3, and FIG. 20B shows the actual ROC curves using the assay data set used to generate the parameters in Tables 12 and 13. It can be seen that the performance for a given number of selected markers was qualitatively in agreement, and that quantitative agreement degraded as the number of markers increases. (This is consistent with the notion that the information contributed by any particular biomarker concerning the disease processes is redundant with the information contributed by other biomarkers provided in Tables 12 and 13). FIG. 20 thus demonstrates that Tables 12 and 13 in combination with the methods described in Example 3 enable the construction and evaluation of a great many classifiers useful for the discrimination of NSCLC from benign nodules and the discrimination of asymptomatic smokers who have NSCLC from those who do not have NSCLC.

Example 5. Aptamer Specificity Demonstration in a Pull-Down Assay

The final readout on the multiplex assay is based on the amount of aptamer recovered after the successive capture steps in the assay. The multiplex assay is based on the premise that the amount of aptamer recovered at the end of the assay is proportional to the amount of protein in the original complex mixture (e.g., plasma). In order to demonstrate that this signal is indeed derived from the intended analyte rather than from non-specifically bound proteins in plasma, we developed a gel-based pull-down assay in plasma. This assay can be used to visually demonstrate that a desired protein is in fact pulled out from plasma after equilibration with an aptamer as well as to demonstrate that aptamers bound to their intended protein targets can survive as a complex through the kinetic challenge steps in the assay. In the experiments described in this example, recovery of protein at the end of this pull-down assay requires that the protein remain non-covalently bound to the aptamer for nearly two hours after equilibration. Importantly, in this example we also provide evidence that non-specifically bound proteins dissociate during these steps and do not contribute significantly to the final signal. It should be noted that the pull-down procedure described in this example includes all of the key steps in the multiplex assay described above.

Plasma Pull-down Assay

Plasma samples were prepared by diluting 50 µL EDTA-plasma to 100 µL in SB18 with 0.05% Tween-20 (SB18T) and 2 µM Z-Block. The plasma solution was equilibrated with 10 pmoles of a PBDC-aptamer in a final volume of 150 µL for 2 hours at 37° C. After equilibration, complexes and unbound aptamer were captured with 133 µL of a 7.5% Streptavidin-agarose bead slurry by incubating with shaking for 5 minutes at RT in a Durapore filter plate. The samples bound to beads were washed with biotin and with buffer under vacuum as described in Example 1. After washing, bound proteins were labeled with 0.5 mM NHS-S-S-biotin, 0.25 mM NHS-Alexa647 in the biotin diluent for 5 minutes with shaking at RT. This staining step allows biotinylation for capture of protein on streptavidin beads as well as highly sensitive staining for detection on a gel. The samples were washed with glycine and with buffer as described in Example 1. Aptamers were released from the beads by photocleavage using a Black Ray light source for 10 minutes with shaking at RT. At this point, the biotinylated proteins were captured on 0.5 mg MyOne Streptavidin beads by shaking for 5 minutes at RT. This step will capture proteins bound to aptamers as well as proteins that may have dissociated from aptamers since the initial equilibration. The beads were washed as described in Example 1. Proteins were eluted from the MyOne Streptavidin beads by incubating with 50 mM DTT in SB17T for 25 minutes at 37° C. with shaking. The eluate was then transferred to MyOne beads coated with a sequence complimentary to the 3' fixed region of the aptamer and incubated for 25 minutes at 37° C. with shaking. This step captures all of the remaining aptamer. The beads were washed 2× with 100 µL SB17T for 1 minute and 1× with 100 µL SB19T for 1 minute. Aptamer was eluted from these final beads by incubating with 45 µL 20 mM NaOH for 2 minutes with shaking to disrupt the hybridized strands. 40 µL of this eluate was neutralized with 10 µL 80 mM HCl containing 0.05% Tween-20. Aliquots representing 5% of the eluate from the first set of beads (representing all plasma proteins bound to the aptamer) and 20% of the eluate from the final set of beads (representing all plasma proteins remaining bound at the end of our clinical assay) were run on a NuPAGE 4-12% Bis-Tris gel (Invitrogen) under reducing and denaturing conditions. Gels were imaged on an Alpha Innotech FluorChem Q scanner in the Cy5 channel to image the proteins.

Figure 16:
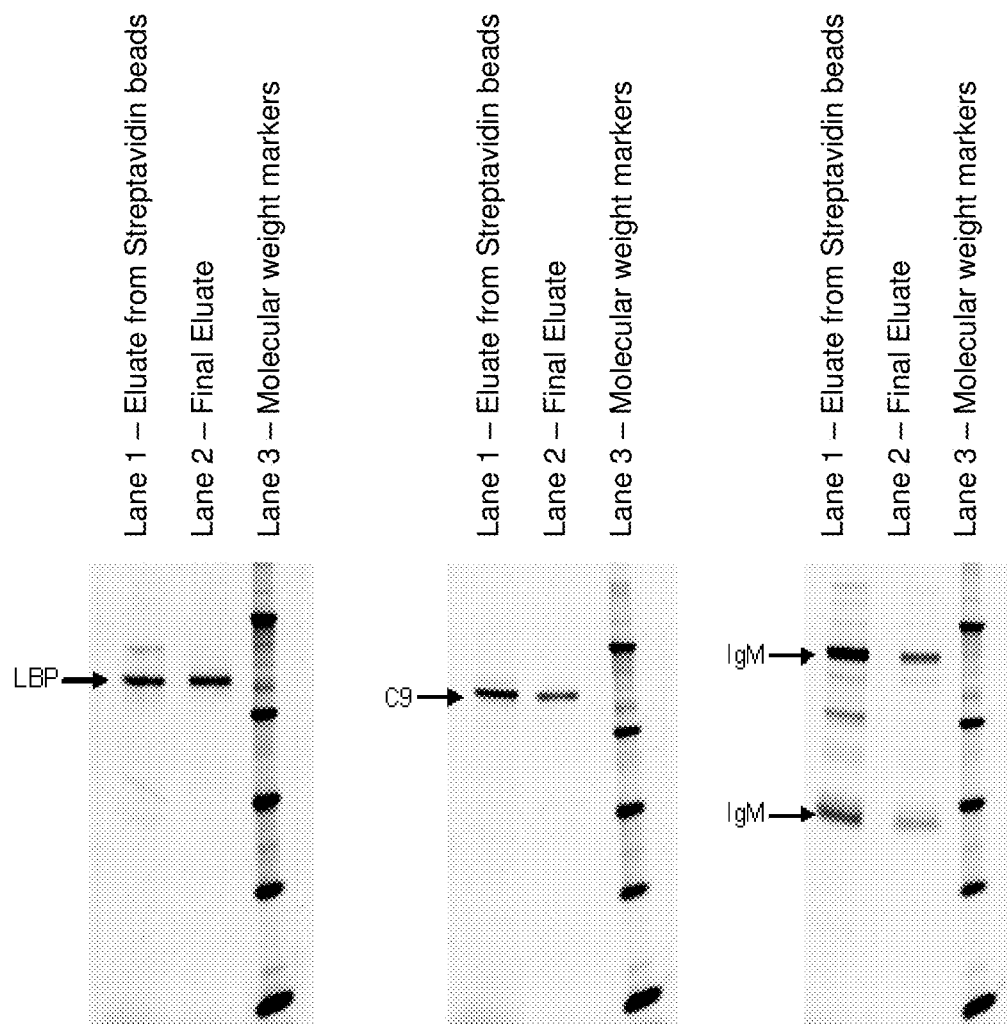
FIG. 16 shows gel images resulting from pull-down experiments that illustrate the specificity of aptamers as capture reagents for the proteins LBP, C9 and IgM. For each gel, lane 1 is the eluate from the Streptavidin-agarose beads, lane 2 is the final eluate, and lane is a MW marker lane (major bands are at 110, 50, 30, 15, and 3.5 kDa from top to bottom).

Pull-down gels for aptamers were selected against LBP ($\sim 1 \times 10^{-7}$ M in plasma, polypeptide MW ~60 kDa), C9 ($\sim 1 \times 10^{-6}$ M in plasma, polypeptide MW ~60 kDa), and IgM ($\sim 9 \times 10^{-6}$ M in plasma, MW ~70 kDa and 23 kDa), respectively. (See FIG. 16).

For each gel, lane 1 is the eluate from the Streptavidin-agarose beads, lane 2 is the final eluate, and lane 3 is a MW marker lane (major bands are at 110, 50, 30, 15, and 3.5 kDa from top to bottom). It is evident from these gels that there is a small amount non-specific binding of plasma proteins in the initial equilibration, but only the target remains after performing the capture steps of the assay. It is clear that the single aptamer reagent is sufficient to capture its intended analyte with no up-front depletion or fractionation of the plasma. The amount of remaining aptamer after these steps is then proportional to the amount of the analyte in the initial sample.

Example 6. Analysis of NSCLC Surgical Resections

To demonstrate the utility of the platform based technology described herein to identify disease-related biomarkers from tissues, homogenized tissues samples from surgical resections obtained from eight NSCLC patients were analyzed. All NSCLC patients were smokers, ranging in age from 47 to 75 years old and covering NSCLC stages 1A through 3B (Table 17). All tissue samples were obtained by freezing the tissue within 5-10 minutes of excision during surgery and after placing the tissues in OCT medium (10.24% polyvinyl alcohol, 4.26% polyethylene glycol, and 85.5% non-reactive ingredients). Three samples were obtained from each resection: tumor tissue sample, adjacent healthy tissue (within 1 cm of the tumor) and distant uninvolved lung tissue. While keeping the samples constantly frozen, five 10 inn thick sections were cut, trimmed of excess OCT from around the tissue, and placed into frozen 1.5 mL microfuge tubes. Following the addition of 200 µL homogenization buffer (SB18 buffer plus PI cocktail (Pierce HALT protease inhibitor cocktail without magnesium), the samples were homogenized in the microfuge tubes on ice with rotary pestle for 30 seconds, until no tissue fragments were visible. The samples were then spun in a centrifuge at 21,000 g for 10 minutes and filtered through a 0.2 µm multiwell plate filter into a sterile multiwell plate. Five µL aliquots were taken for BCA protein assay and the rest of the sample was stored frozen and sealed in 96 well plates at −70° C.

Sample total protein was adjusted to 16 µg/mL in SB17T buffer (SB17 buffer containing 0.05% tween 20) for proteomic profiling. Samples prepared in this manner were run on the multiplex aptamer assay which, as noted above, measures over 800 proteins as described previously (Ostroff et al., "Unlocking biomarker discovery: Large scale application of aptamer proteomic technology for early detection of lung cancer," Nature Precedings, (2010)). Among the measured analytes, most were unchanged between tumor, adjacent tissue and distal tissue. However, some proteins were clearly suppressed (FIG. 24) while others were elevated substantially in tumor tissues (FIG. 23) compared to adjacent and distal tissues.

The foregoing embodiments and examples are intended only as examples. No particular embodiment, example, or element of a particular embodiment or example is to be construed as a critical, required, or essential element or feature of any of the claims. Further, no element described herein is required for the practice of the appended claims unless expressly described as "essential" or "critical." Various alterations, modifications, substitutions, and other variations can be made to the disclosed embodiments without departing from the scope of the present application, which is defined by the appended claims. The specification, including the figures and examples, is to be regarded in an illustrative manner, rather than a restrictive one, and all such modifications and substitutions are intended to be included within the scope of the application. Accordingly, the scope of the application should be determined by the appended claims and their legal equivalents, rather than by the examples given above. For example, steps recited in any of the method or process claims may be executed in any feasible order and are not limited to an order presented in any of the embodiments, the examples, or the claims. Further, in any of the aforementioned methods, one or more biomarkers of Table 18, Table 20, or Table 21 can be specifically excluded either as an individual biomarker or as a biomarker from any panel.

TABLE 1

| | | | Lung Cancer Biomarkers | | |
|---|---|---|---|---|---|
| Column #1 Biomarker # | Column #2 Biomarker Designation | Column #3 Alternate Protein Names | Column #4 Gene Designation (Entrez Gene Link) | Column #5 Benign Nodule versus NSCLC | Column #6 Smokers versus NSCLC |
| 1 | AMPM2 | Methionine aminopeptidase 2 p67eIF2 p67 Initiation factor 2-associated 67 kDa glycoprotein Peptidase M 2 MetAP 2 MAP 2 | METAP2 | | X |
| 2 | Apo A-I | apolipoprotein A-I Apolipoprotein A-1 | APOA1 | X | |

TABLE 1-continued

Lung Cancer Biomarkers

| Column #1 Biomarker # | Column #2 Biomarker Designation | Column #3 Alternate Protein Names | Column #4 Gene Designation (Entrez Gene Link) | Column #5 Benign Nodule versus NSCLC | Column #6 Smokers versus NSCLC |
|---|---|---|---|---|---|
| 3 | b-ECGF | FGF acidic<br>FGF1<br>beta-ECGF<br>Beta-endothelial cell growth factor | FGF1 | X | |
| 4 | BLC | BLC B lymphocyte chemoattractant<br>Small inducible cytokine B13<br>CXCL13<br>BCA-1 | CXCL13 | X | X |
| 5 | BMP-1 | Bone morphogenetic protein 1<br>Procollagen C-proteinase<br>PCP<br>Mammalian tolloid protein<br>mTld | BMP1 | X | X |
| 6 | BTK | Tyrosine-protein kinase BTK<br>Bruton tyrosine kinase<br>Agammaglobulinaemia tyrosine kinase<br>ATK<br>B-cell progenitor kinase | BTK | | X |
| 7 | C1s | Complement C1s subcomponent<br>C1s, Activated, Two-Chain Form | C1S | | X |
| 8 | C9 | Complement component C9 | C9 | X | X |
| 9 | Cadherin E | Cadherin-1<br>Epithelial cadherin<br>E-cadherin<br>Uvomorulin<br>CAM 120/80<br>CD_antigen = CD324 | CDH1 | X | |
| 10 | Cadherin-6 | Kidney-cadherin<br>K-cadherin | CDH6 | X | |
| 11 | Calpain I | Calpain I (dimer of Calpain-1 catalytic subunit and Calpain small subunit 1)<br>synonyms of the catalytic subunit include Calpain-1 large subunit:<br>Calcium-activated neutral proteinase 1<br>Micromolar-calpain<br>Cell proliferation-inducing gene 30 protein<br>synonyms of the small subunit include:<br>Calcium-dependent protease small subunit 1<br>Calcium-activated neutral proteinase small subunit CANP small subunit | CAPN1<br>CAPNS1 | X | |
| 12 | Catalase | Catalase | CAT | X | |
| 13 | CATC | Dipeptidyl-peptidase 1 precursor<br>Dipeptidyl-peptidase I<br>DPP-I<br>DPPI<br>Cathepsin C<br>Cathepsin J<br>Dipeptidyl transferase | CTSC | X | |
| 14 | Cathepsin H | Cathepsin H | CTSH | X | |
| 15 | CD30 Ligand | Tumor necrosis factor ligand superfamily member 8<br>CD30-L<br>CD153 antigen | TNFSF8 | X | X |
| 16 | CDK5-p35 | CDK5/p35 is a dimer of Cell division protein kinase 5, and the p35 chain of Cyclin-dependent kinase 5 activator 1<br>Cell division protein kinase 5 is also known as:<br>Cyclin-dependent kinase 5<br>Tau protein kinase II catalytic subunit<br>Serine/threonine-protein kinase<br>PSSALRE<br>p35 chain of Cyclin-dependent kinase 5 activator 1 is also known as: | CDK5<br>CDK5R1 | | X |

TABLE 1-continued

Lung Cancer Biomarkers

| Column #1 Biomarker # | Column #2 Biomarker Designation | Column #3 Alternate Protein Names | Column #4 Gene Designation (Entrez Gene Link) | Column #5 Benign Nodule versus NSCLC | Column #6 Smokers versus NSCLC |
|---|---|---|---|---|---|
| | | Cyclin-dependent kinase 5 regulatory subunit 1 CDK5 activator 1 Cyclin-dependent kinase 5 regulatory subunit 1 Tau protein kinase II regulatory subunit. | | | |
| 17 | CK-MB | Creatine Phosphokinase-MB Isoenzyme, which is a dimer of Creatine kinase M-type and B-type Creatine kinase M and B chains M-CK and B-CK CKM and CKB | CKB CKM | X | X |
| 18 | CNDP1 | Beta-Ala-His dipeptidase Carnosine dipeptidase 1 CNDP dipeptidase 1 Serum carnosinase Glutamate carboxypeptidase-like protein 2 | CNDP1 | X | X |
| 19 | Contactin-5 | Neural recognition molecule NB-2 hNB-2 | CNTN5 | | X |
| 20 | CSK | Tyrosine-protein kinase CSK C-SRC kinase Protein-tyrosine kinase CYL | CSK | X | X |
| 21 | Cyclophilin A | Cyclophilin A Peptidyl-prolyl cis-trans isomerase A PPIase Peptidylprolyl isomerase Cyclosporin A-binding protein Rotamase A PPIase A | PPIA | | X |
| 22 | Endostatin | Endostatin, which is cleaved from Collagen alpha-1(XVIII) chain | COL18A1 | | X |
| 23 | ERBB1 | Epidermal growth factor receptor Receptor tyrosine-protein kinase ErbB-1 EGFR HER1 | EGFR | X | X |
| 24 | FGF-17 | Fibroblast Growth Factor-17 | FGF17 | X | X |
| 25 | FYN | Proto-oncogene tyrosine-protein kinase Fyn Protooncogene Syn p59-Fyn | FYN | | X |
| 26 | GAPDH, liver | Glyceraldehyde 3-phosphate dehydrogenase | GAPDH | X | X |
| 27 | HMG-1 | High mobility group protein B1 amphoterin Neurite growth-promoting protein | HMGB1 | X | |
| 28 | HSP 90a | Heat shock protein HSP 90-alpha HSP 86 Renal carcinoma antigen NY-REN-38 | HSP90AA1 | X | X |
| 29 | HSP 90b | Heat shock protein HSP 90-beta HSP 90 HSP 84 | HSP90AB1 | X | |
| 30 | IGFBP-2 | Insulin-like growth factor-binding protein 2 (IGF-binding protein 2; IGFBP-2; IBP-2; BP2) | IGFBP2 | X | X |
| 31 | IL-15 Ra | Interleukin-15 receptor subunit alpha | IL15RA | | X |
| 32 | IL-17B | Interleukin-17B Neuronal interleukin-17 related factor Interleukin-20 Cytokine-like protein ZCYTO7 | IL17B | X | |
| 33 | IMB1 | Importin subunit beta-1 Karyopherin subunit beta-1 Nuclear factor P97 Importin-90 | KPNB1 | X | |
| 34 | Kallikrein 7 | Kallikrein-7 hK7 Stratum corneum chymotryptic | KLK7 | | X |

TABLE 1-continued

Lung Cancer Biomarkers

| Column #1 Biomarker # | Column #2 Biomarker Designation | Column #3 Alternate Protein Names | Column #4 Gene Designation (Entrez Gene Link) | Column #5 Benign Nodule versus NSCLC | Column #6 Smokers versus NSCLC |
|---|---|---|---|---|---|
| | | enzyme | | | |
| | | hSCCE | | | |
| | | Serine protease 6 | | | |
| 35 | KPCI | Protein kinase C iota type | PRKCI | X | X |
| | | nPKC-iota | | | |
| | | Atypical protein kinase C-lambda/iota | | | |
| | | aPKC-lambda/iota | | | |
| | | PRKC-lambda/iota | | | |
| 36 | LDH-H 1 | L-lactate dehydrogenase B chain | LDHB | | X |
| | | LDH-B | | | |
| | | LDH heart subunit | | | |
| | | LDH-H | | | |
| | | Renal carcinoma antigen NY-REN-46 | | | |
| 37 | LGMN | Legumain | LGMN | X | |
| | | Protease, cysteine 1 | | | |
| | | Asparaginyl endopeptidase | | | |
| 38 | LRIG3 | Leucine-rich repeats and immunoglobulin-like domains protein 3 | LRIG3 | X | X |
| 39 | Macrophage mannose receptor | Macrophage mannose receptor 1 | MRC1 | X | |
| | | MMR | | | |
| | | C-type lectin domain family 13 member D CD_antigen = CD206 | | | |
| 40 | MEK1 | Dual specificity mitogen-activated protein kinase kinase 1 | MAP2K1 | X | X |
| | | MAPK/ERK kinase 1 | | | |
| | | ERK activator kinase 1 | | | |
| 41 | METAP1 | Methionine aminopeptidase 1 | METAP1 | X | |
| | | MetAP 1 | | | |
| | | MAP 1 | | | |
| | | Peptidase M1 | | | |
| 42 | Midkine | Neurite outgrowth-promoting protein | MDK | | X |
| | | Neurite outgrowth-promoting factor 2 | | | |
| | | Midgestation and kidney protein | | | |
| | | Amphiregulin-associated protein | | | |
| | | ARAP | | | |
| 43 | MIP-5 | C-C motif chemokine 15 | MIP5 | | X |
| | | Small-inducible cytokine A15 | | | |
| | | Macrophage inflammatory protein 5 | | | |
| | | Chemokine CC-2 | | | |
| | | HCC-2 | | | |
| | | NCC-3 | | | |
| | | MIP-1 delta | | | |
| | | Leukotactin-1 | | | |
| | | LKN-1 | | | |
| | | Mrp-2b | | | |
| 44 | MK13 | Mitogen-activated protein kinase 13 | MAPK13 | X | |
| | | MAP kinase p38 delta | | | |
| | | Mitogen-activated protein kinase p38 delta | | | |
| | | Stress-activated protein kinase 4 | | | |
| 45 | MMP-7 | Matrilysin | MMP7 | X | |
| | | Pump-1 protease | | | |
| | | Uterine metalloproteinase | | | |
| | | Matrix metalloproteinase-7 | | | |
| | | MMP-7 | | | |
| | | Matrin | | | |
| 46 | NACA | Nascent polypeptide-associated complex subunit alpha | NACA | X | |
| | | NAC-alpha | | | |
| | | Alpha-NAC | | | |
| | | Allergen = Hom s 2 | | | |
| 47 | NAGK | N-acetylglucosamine kinase | NAGK | X | |
| | | GlcNAc kinase | | | |
| 48 | PARC | C-C motif chemokine 18 | CCL18 | | X |
| | | Small-inducible cytokine A18 | | | |
| | | Macrophage inflammatory protein 4 | | | |
| | | MIP-4 | | | |
| | | Pulmonary and activation-regulated chemokine | | | |
| | | CC chemokine PARC | | | |

TABLE 1-continued

Lung Cancer Biomarkers

| Column #1 Biomarker # | Column #2 Biomarker Designation | Column #3 Alternate Protein Names | Column #4 Gene Designation (Entrez Gene Link) | Column #5 Benign Nodule versus NSCLC | Column #6 Smokers versus NSCLC |
|---|---|---|---|---|---|
| | | Alternative macrophage activation-associated CC chemokine 1<br>AMAC-1<br>Dendritic cell chemokine 1<br>DC-CK1 | | | |
| 49 | Proteinase-3 | Proteinase-3<br>PR-3<br>AGP7<br>P29<br>Myeloblastin<br>Leukocyte proteinase 3<br>Wegener's autoantigen<br>Neutrophil proteinase 4<br>NP4<br>C-ANCA antigen | PRTN3 | X | |
| 50 | Prothrombin | Prothrombin<br>(Coagulation factor II) | F2 | X | X |
| 51 | PTN | Pleiotrophin<br>Heparin-binding growth-associated molecule<br>HB-GAM<br>Heparin-binding growth factor 8<br>HBGF-8<br>Osteoblast-specific factor 1<br>OSF-1<br>Heparin-binding neurite outgrowth-promoting factor 1 HBNF-1<br>Heparin-binding brain mitogen<br>HBBM | PTN | | X |
| 52 | RAC1 | Ras-related C3 botulinum toxin substrate 1<br>p21-Rac1<br>Ras-like protein TC25<br>Cell migration-inducing gene 5 protein | RAC1 | | X |
| 53 | Renin | Renin<br>Angiotensinogenase | REN | | X |
| 54 | RGM-C | Hemojuvelin<br>Hemochromatosis type 2 protein<br>RGM domain family member C | HFE2 | X | |
| 55 | SCF sR | Mast/stem cell growth factor receptor<br>(SCFR; Proto-oncogene tyrosine-protein kinase Kit; c-kit;<br>CD_antigen = CD117) | KIT | X | X |
| 56 | sL-Selectin | sL-Selectin<br>Leukocyte adhesion molecule-1<br>Lymph node homing receptor<br>LAM-1<br>L-Selectin<br>L-Selectin, soluble<br>Leukocyte surface antigen Leu-8<br>TQ1<br>gp90-MEL<br>Leukocyte-endothelial cell adhesion molecule 1<br>LECAM1<br>CD62 antigen-like family member L | SELL | | X |
| 57 | TCTP | Translationally-controlled tumor protein<br>p23<br>Histamine-releasing factor<br>HRF<br>Fortilin | TPT1 | | X |
| 58 | UBE2N | Ubiquitin-conjugating enzyme E2 N<br>Ubiquitin-protein ligase N<br>Ubiquitin carrier protein N<br>Ubc13<br>Bendless-like ubiquitin-conjugating enzyme | UBE2N | | X |

TABLE 1-continued

Lung Cancer Biomarkers

| Column #1 Biomarker # | Column #2 Biomarker Designation | Column #3 Alternate Protein Names | Column #4 Gene Designation (Entrez Gene Link) | Column #5 Benign Nodule versus NSCLC | Column #6 Smokers versus NSCLC |
|---|---|---|---|---|---|
| 59 | Ubiquitin + 1 | Ubiquitin | RPS27A | | X |
| 60 | VEGF | Vascular endothelial growth factor A<br>VEGF-A<br>Vascular permeability factor | VEGFA | X | |
| 61 | YES | Proto-oncogene tyrosine-protein kinase Yes<br>c-Yes<br>p61-Yes | YES | X | |

TABLE 2

Aptamer Concentrations

| Target | Final Aptamer Conc (nM) |
|---|---|
| AMPM2 | 0.5 |
| Apo A-I | 0.25 |
| b-ECGF | 2 |
| BLC | 0.25 |
| BMP-1 | 1 |
| BTK | 0.25 |
| C1s | 0.25 |
| C9 | 1 |
| Cadherin E | 0.25 |
| Cadherin-6 | 0.5 |
| Calpain I | 0.5 |
| Catalase | 0.5 |
| CATC | 0.5 |
| Cathepsin H | 0.5 |
| CD30 Ligand | 0.5 |
| CDK5/p35 | 0.5 |
| CK-MB | 1 |
| CNDP1 | 0.5 |
| Contactin-5 | 1 |
| CSK | |
| Cyclophilin A | 0.5 |
| Endostatin | 1 |
| ERBB1 | 0.5 |
| FYN | 0.25 |
| GAPDH, liver | 0.25 |
| HMG-1 | 0.5 |
| HSP 90a | 0.5 |
| HSP 90b | 0.5 |
| IGFBP-2 | 1 |
| IL-15 Ra | 0.5 |
| IL-17B | 0.5 |
| IMB1 | 1 |
| Kallikrein 7 | 0.5 |
| KPCI | 0.25 |
| LDH-H 1 | 0.5 |
| LGMN | 0.5 |
| LRIG3 | 0.25 |
| Macrophage mannose receptor | 2 |
| MEK1 | 0.5 |
| METAP1 | 0.25 |
| Midkine | 0.5 |
| MIP-5 | 1 |
| MK13 | 1 |
| MMP-7 | 0.25 |
| NACA | 0.5 |
| NAGK | 0.5 |
| PARC | 0.5 |
| Proteinase-3 | 1 |
| Prothrombin | 0.5 |
| PTN | 0.25 |
| RAC1 | 0.5 |
| Renin | 0.25 |

TABLE 2-continued

Aptamer Concentrations

| Target | Final Aptamer Conc (nM) |
|---|---|
| RGM-C | 0.5 |
| SCF sR | 1 |
| sL-Selectin | 0.5 |
| TCTP | 0.5 |
| UBE2N | 0.5 |
| Ubiquitin + 1 | 0.5 |
| VEGF | 1 |
| YES | 0.5 |

TABLE 3

| Site | NSCLC | Benign Nodule | Asymptomatic Smokers |
|---|---|---|---|
| 1 | 32 | 0 | 47 |
| 2 | 63 | 176 | 128 |
| 3 | 70 | 195 | 94 |
| 4 | 54 | 49 | 83 |
| Sum | 213 | 420 | 352 |
| Males | 51% | 46% | 49% |
| Females | 49% | 54% | 51% |
| Median Age | 68 | 60 | 57 |
| Median Pack Years | 40 | 42 | 34 |
| Median FEV1 | 1.94 | 2.43 | 2.58 |
| Median FEV 1% | 74 | 88 | 90 |
| Median FEV1/FVC | 70 | 72 | 73 |

TABLE 4

Biomarkers Identified in Benign Nodule-NSCLC in Aggregated Data

| | | |
|---|---|---|
| SCF sR | CNDP1 | Stress-induced-phosphoprotein 1 |
| RGM-C | MEK1 | LRIG3 |
| ERBB1 | MDHC | ERK-1 |
| Cadherin E | Catalase | Cyclophilin A |
| CK-MB | BMP-1 | Caspase-3 |
| METAP1 | ART | UFM1 |
| HSP90a | C9 | RAC1 |
| IGFBP-2 | TCPTP | Peroxiredoxin-1 |
| Calpain I | RPS6KA3 | PAFAHbeta subunit |

TABLE 4-continued

Biomarkers Identified in Benign Nodule-NSCLC in Aggregated Data

| | | |
|---|---|---|
| KPCI | IMB1 | MK01 |
| MMP-7 | UBC9 | Integrina1b1 |
| β-ECGF | Ubiquitin + 1 | IDE |
| HSP90b | Cathepsin H | CAMK2A |
| NAGK | CSK21 | BLC |
| FGF-17 | BTK | BARK1 |
| Macrophage mannose receptor | Thrombin | eIF-5 |
| MK13 | LYN | UFC1 |
| NACA | HSP70 | RS7 |
| GAPDH | UBE2N | PRKACA |
| CSK | TCTP | AMPM2 |
| Activin A | RabGDPdissociation inhibitor beta | Stress-induced-phosphoprotein 1 |
| Prothrombin | MAPKAPK3 | |

TABLE 5

Biomarkers Identified in Smoker-NSCLC in Aggregated Data

| | | |
|---|---|---|
| SCF sR | Renin | Caspase-3 |
| PTN | CSK | AMPM2 |
| HSP90a | Contactin-5 | RS7 |
| Kallikrein 7 | UBE2N | OCAD1 |
| LRIG3 | MPIF-1 | HSP70 |
| IGFBP-2 | PRKACA | GSK-3alpha |
| PARC | granzymeA | FSTL3 |
| CD30 Ligand | Ubiquitin + 1 | PAFAH beta subunit |
| Prothrombin | NAGK | Integrin a1b1 |
| ERBB1 | Cathepsin S | ERK-1 |
| KPCI | TCTP | CSK21 |
| BTK | UBC9 | CATC |
| GAPDH, liver | MK13 | MK01 |
| CK-MB | Cystatin C | pTEN |
| LDH-H1 | RPS6KA3 | b2-Microglobulin |
| CNDP1 | IL-15Ra | UFM1 |
| RAC1 | Calpain I | UFC1 |
| C9 | MAPKAPK3 | Peroxiredoxin-1 |
| FGF-17 | IMB1 | PKB |
| Endostatin | BARK1 | IDE |
| Cyclophilin A | Cathepsin H | HSP90b |
| C1s | Macrophage mannose receptor | BGH3 |
| CD30 | Dtk | BLC |
| BMP-1 | NACA | XPNPEP1 |
| SBDS | RabGDPdissociation inhibitor beta | TNFsR-I |
| MIP-5 | LYN | DUS3 |
| CCL28 | METAP1 | |
| MMP-7 | MK12 | |

TABLE 6

Biomarkers Identified in Benign Nodule-NSCLC by Site

| | |
|---|---|
| ERBB1 | FGF-17 |
| LRIG3 | CD30Ligand |
| HMG-1 | LGMN |
| YES | Proteinase-3 |
| C9 | MEK1 |
| MK13 | BLC |
| Macrophage mannose receptor | IL-17B |
| ApoA-I | CATC |
| CNDP1 | Cadherin-6 |
| BMP-1 | |

TABLE 7

Biomarkers Identified in Smoker-NSCLC by Site

| | | |
|---|---|---|
| Kallikrein 7 | CSK | Azurocidin |
| SCF sR | FYN | b2-Microglobulin |
| ERBB1 | BLC | OCAD1 |
| C9 | TCTP | LGMN |
| LRIG3 | Midkine | PKB |
| AMPM2 | FGF-17 | XPNPEP1 |
| HSP90a | MEK1 | Cadherin-6 |
| sL-Selectin | BMP-1 | pTEN |
| BTK | LYN | LYNB |
| CNDP1 | Integrin a1b1 | DUS3 |
| CDK5-p35 | PKB gamma | Carbonic anhydrase XIII |

TABLE 8

Biomarkers Identified in Benign Nodule-NSCLC in Blended Data Set

| | | | |
|---|---|---|---|
| YES | Catalase | PAFAH beta subunit | eIF-5 |
| MK13 | Prothrombin | AMPM2 | TNFsR-I |
| LRIG3 | BTK | TCPTP | BLC |
| HMG-1 | DRG-1 | BGH3 | MAPKAPK3 |
| ERBB1 | UBE2N | Ubiquitin + 1 | b2-Microglobulin |
| Cadherin E | Activin A | BARK1 | SOD |
| CK-MB | TCTP | LYN | GSK-3 alpha |
| C9 | UBC9 | PRKACA | Fibrinogen |
| SCFsR | NAGK | LGMN | ERK-1 |
| CNDP1 | Calpain I | Integrin a1b1 | Cadherin-6 |
| RGM-C | GAPDH | HSP70 | IDE |
| METAP1 | UFM1 | XPNPEP1 | UFC1 |
| Macrophage mannose receptor | Caspase-3 | Stress-induced-phosphoprotein1 | PSA-ACT |
| BMP-1 | b-ECGF | RPS6KA3 | CATC |
| KPCI | RAC1 | SHP-2 | pTEN |
| IGFBP-2 | MDHC | CEA | PSA |
| CSK | Proteinase-3 | OCAD1 | CATE |
| NACA | MK01 | Cyclophilin A | Peroxiredoxin-1 |
| IMB1 | MEK1 | RabGDP dissociation inhibitor beta | SBDS |
| Cathepsin H | HSP90a | DUS3 | RS7 |
| MMP-7 | Thrombin | CAMK2A | Carbonic anhydrase XIII |
| VEGF | FGF-17 | CaMKKalpha | |
| HSP90b | ART | CSK21 | |

TABLE 9

Biomarkers Identified in Smoker-NSCLC in Blended Data Set

| | | | |
|---|---|---|---|
| SCFsR | UBE2N | CystatinC | GSK-3alpha |
| LRIG3 | MIP-5 | LYN | CATC |
| HSP90a | Contactin-5 | MPIF-1 | SBDS |
| ERBB1 | Ubiquitin + 1 | GCP-2 | PAFAH beta subunit |
| C9 | Macrophage mannose receptor | KPCI | IMB1 |
| AMPM2 | PRKACA | MK12 | CSK21 |
| Kallikrein 7 | Cathepsin S | MAPKAPK3 | PKB |
| PTN | BMP-1 | Integrin a1b1 | Dtk |
| PARC | Cyclophilin A | HSP70 | DUS3 |
| CD30 Ligand | CCL28 | RPS6KA3 | Calpain I |
| Prothrombin | Endostatin | NACA | TNFsR-I |
| CSK | Cathepsin H | RS7 | PTP-1B |
| CK-MB | Granzyme A | Peroxiredoxin-1 | IDE |
| BTK | GAPDH, liver | MMP-7 | HSP90b |
| C1s | FGF-17 | pTEN | Fibrinogen |
| IGFBP-2 | BARK1 | UFM1 | Caspase-3 |
| LDH-H1 | BLC | UBC9 | PSA-ACT |
| RAC1 | RabGDP dissociation inhibitor beta | FSTL3 | OCAD1 |
| Renin | CD30 | BGH3 | SOD |
| CNDP1 | MK13 | UFC1 | METAP1 |

TABLE 9-continued

Biomarkers Identified in Smoker-NSCLC in Blended Data Set

| | | | |
|---|---|---|---|
| TCTP | NAGK | MK01 | PSA |
| IL-15Ra | b2-Microglobulin | ERK-1 | |

TABLE 10

| Biomarkers for Lung Cancer | Benign Nodule | Smokers |
|---|---|---|
| AMPM2 | YES | SCFsR |
| BMP-1 | MK13 | LRIG3 |
| BTK | LRIG3 | HSP90a |
| C1s | HMG-1 | ERBB1 |
| C9 | ERBB1 | C9 |
| Cadherin E | CadherinE | AMPM2 |
| Catalase | CK-MB | Kallikrein7 |
| Cathepsin H | C9 | PTN |
| CD30Ligand | SCFsR | PARC |
| CK-MB | CNDP1 | CD30Ligand |
| CNDP1 | RGM-C | Prothrombin |
| Contactin-5 | METAP1 | CSK |
| CSK | Macrophage mannose receptor | CK-MB |
| ERBB1 | BMP-1 | BTK |
| HMG-1 | KPCI | C1s |
| HSP90a | IGFBP-2 | IGFBP-2 |
| HSP90b | CSK | LDH-H1 |
| IGFBP-2 | NACA | RAC1 |
| IL-15Ra | IMB1 | Renin |
| IMB1 | CathepsinH | CNDP1 |
| Kallikrein7 | MMP-7 | TCTP |
| KPCI | VEGF | IL-15Ra |
| LDH-H1 | HSP90b | UBE2N |
| LRIG3 | Catalase | MIP-5 |
| Macrophage mannose receptor | Prothrombin | Contactin-5 |
| METAP1 | ApoA-I | Ubiquitin + 1 |
| MIP-5 | b-ECGF | BLC |
| MK13 | BLC | BMP-1 |
| MMP-7 | Cadherin-6 | CDK5-p35 |
| NACA | Calpain I | Cyclophilin A |
| PARC | CATC | Endostatin |
| Prothrombin | CD30Ligand | FGF-17 |
| PTN | FGF-17 | FYN |
| RAC1 | GAPDH | GAPDH |
| Renin | HSP90a | KPCI |
| RGM-C | IL-17B | MEK1 |
| SCF sR | LGMN | Midkine |
| TCTP | MEK1 | sL-Selectin |
| UBE2N | NAGK | |
| Ubiquitin + 1 | Proteinase-3 | |
| VEGF | | |
| YES | | |
| ApoA-I | | |
| b-ECGF | | |
| BLC | | |
| Cadherin-6 | | |
| Calpain I | | |
| CATC | | |
| CDK5-p35 | | |
| CyclophilinA | | |
| Endostatin | | |
| FYN | | |
| FGF-17 | | |
| GAPDH | | |
| IL-17B | | |
| LGMN | | |
| MEK1 | | |
| Midkine | | |
| NAGK | | |
| Proteinase-3 | | |
| sL-Selectin | | |

TABLE 11

| Aptamer To Designated Biomarker | Solution $K_d$ (M) | Assay LLOQ (M) | Up or Down Regulated |
|---|---|---|---|
| AMPM2 | $3 \times 10^{-10}$ | NM | Up |
| Apo A-I | $9 \times 10^{-09}$ | $2 \times 10^{-11}$ | Down |
| β-ECGF | $1 \times 10^{-10}$ (pool) | NM | Up |
| BLC | $5 \times 10^{-10}$ (pool) | $7 \times 10^{-14}$ | Up |
| BMP-1 | $2 \times 10^{-10}$ | $9 \times 10^{-13}$ | Down |
| BTK | $8 \times 10^{-10}$ (pool) | $2 \times 10^{-13}$ | Up |
| C1s | $8 \times 10^{-09}$ | $7 \times 10^{-12}$ | Up |
| C9 | $1 \times 10^{-11}$ | $1 \times 10^{-14}$ | Down |
| Cadherin E | $3 \times 10^{-10}$ | $2 \times 10^{-12}$ | Down |
| Cadherin-6 | $2 \times 10^{-09}$ | $2 \times 10^{-12}$ | Up |
| Calpain I | $2 \times 10^{-11}$ | $7 \times 10^{-14}$ | Up |
| Catalase | $7 \times 10^{-10}$ (pool) | $8 \times 10^{-14}$ | Up |
| CATC | $8 \times 10^{-08}$ | NM | Up |
| Cathepsin H | $1 \times 10^{-09}$ (pool) | $8 \times 10^{-13}$ | Up |
| CD30 Ligand | $2 \times 10^{-09}$ (pool) | $7 \times 10^{-13}$ | Up |
| CDK5/p35 | $2 \times 10^{-10}$ | NM | Up |
| CK-MB | $1 \times 10^{-08}$ (pool) | NM | Down |
| CNDP1 | $3 \times 10^{-08}$ | NM | Down |
| Contactin-5 | $3 \times 10^{-11}$ | NM | Down |
| CSK | $3 \times 10^{-10}$ | $5 \times 10^{-13}$ | Up |
| Cyclophilin A | $1 \times 10^{-09}$ (pool) | $2 \times 10^{-13}$ | Up |
| Endostatin | $5 \times 10^{-10}$ | $1 \times 10^{-13}$ | Up |
| ERBB1 | $1 \times 10^{-10}$ | $4 \times 10^{-14}$ | Down |
| FGF-17 | $5 \times 10^{-10}$ (pool) | NM | Up |
| FYN | $3 \times 10^{-09}$ | NM | Up |
| GAPDH | $8 \times 10^{-12}$ | $4 \times 10^{-13}$ | Up |
| HMG-1 | $2 \times 10^{-10}$ | $1 \times 10^{-12}$ | Up |
| HSP 90α | $1 \times 10^{-10}$ | $1 \times 10^{-12}$ | Up |
| HSP90β | $2 \times 10^{-10}$ | $4 \times 10^{-12}$ | Up |
| IGFBP-2 | $6 \times 10^{-10}$ | $9 \times 10^{-13}$ | Up |
| IL-15 Rα | $4 \times 10^{-11}$ | $1 \times 10^{-13}$ | Up |
| IL-17B | $3 \times 10^{-11}$ (pool) | $4 \times 10^{-13}$ | Up |
| IMB1 | $8 \times 10^{-08}$ (pool) | NM | Up |
| Kallikrein 7 | $6 \times 10^{-11}$ | $2 \times 10^{-12}$ | Down |
| KPCI | $9 \times 10^{-09}$ | NM | Up |
| LDH-H1 | $1 \times 10^{-09}$ | $8 \times 10^{-13}$ | Up |
| LGMN | $7 \times 10^{-09}$ | NM | Up |
| LRIG3 | $3 \times 10^{-11}$ | $8 \times 10^{-14}$ | Down |
| Macrophage mannose receptor | $1 \times 10^{-09}$ | $1 \times 10^{-11}$ | Up |
| MEK1 | $6 \times 10^{-10}$ | NM | Up |
| METAP1 | $7 \times 10^{-11}$ | $9 \times 10^{-13}$ | Up |
| Midkine | $2 \times 10^{-10}$ | $4 \times 10^{-11}$ | Up |
| MIP-5 | $9 \times 10^{-09}$ (pool) | $2 \times 10^{-13}$ | Up |
| MK13 | $2 \times 10^{-09}$ | NM | Up |
| MMP-7 | $7 \times 10^{-11}$ | $3 \times 10^{-13}$ | Up |
| NACA | $2 \times 10^{-11}$ | NM | Up |
| NAGK | $2 \times 10^{-09}$ (pool) | NM | Up |
| PARC | $9 \times 10^{-11}$ | $1 \times 10^{-13}$ | Up |
| Proteinase-3 | $5 \times 10^{-09}$ (pool) | $4 \times 10^{-12}$ | Up |
| Prothrombin | $5 \times 10^{-09}$ | $1 \times 10^{-12}$ | Down |
| PTN | $4 \times 10^{-11}$ | $5 \times 10^{-12}$ | Up |
| RAC1 | $7 \times 10^{-11}$ | NM | Up |
| Renin | $3 \times 10^{-11}$ | $3 \times 10^{-13}$ | Up |
| RGM-C | $3 \times 10^{-11}$ | NM | Down |
| SCF sR | $5 \times 10^{-11}$ | $3 \times 10^{-12}$ | Down |
| sL-Selectin | $2 \times 10^{-10}$ (pool) | $2 \times 10^{-13}$ | Down |

TABLE 11-continued

| Aptamer To Designated Biomarker | Solution $K_d$ (M) | Assay LLOQ (M) | Up or Down Regulated |
|---|---|---|---|
| TCTP | $2 \times 10^{-11}$ (pool) | NM | Up |
| UBE2N | $6 \times 10^{-11}$ (pool) | NM | Up |
| Ubiquitin + 1 | $2 \times 10^{-10}$ | $1 \times 10^{-12}$ | Up |
| VEGF | $4 \times 10^{-10}$ | $9 \times 10^{-14}$ | Up |
| YES | $2 \times 10^{-09}$ | NM | Up |

TABLE 12

Parameters for Smoker Control Group

| Biomarker # from Table 1 | Biomarker | $\mu_c$ | $\sigma_c^2$ | $\mu_d$ | $\sigma_d^2$ | KS | p-value | AUC |
|---|---|---|---|---|---|---|---|---|
| 1 | AMPM2 | 3.05 | 1.07E−02 | 3.20 | 3.62E−02 | 0.45 | 5.55E−24 | 0.75 |
| 4 | BLC | 2.58 | 1.23E−02 | 2.72 | 3.97E−02 | 0.37 | 8.72E−17 | 0.74 |
| 5 | BMP-1 | 4.13 | 1.32E−02 | 4.00 | 2.01E−02 | 0.38 | 1.21E−17 | 0.75 |
| 6 | BTK | 3.12 | 2.44E−01 | 3.51 | 2.45E−01 | 0.35 | 3.25E−15 | 0.72 |
| 7 | C1s | 4.01 | 3.47E−03 | 4.06 | 4.23E−03 | 0.31 | 4.68E−12 | 0.69 |
| 8 | C9 | 5.31 | 3.54E−03 | 5.38 | 5.37E−03 | 0.43 | 3.49E−22 | 0.75 |
| 15 | CD30 Ligand | 3.21 | 2.86E−03 | 3.26 | 4.42E−03 | 0.31 | 1.08E−11 | 0.70 |
| 16 | CDK5-p35 | 2.98 | 3.48E−03 | 3.02 | 4.75E−03 | 0.25 | 1.63E−07 | 0.67 |
| 17 | CK-MB | 3.25 | 5.18E−02 | 3.07 | 4.89E−02 | 0.33 | 1.42E−13 | 0.71 |
| 18 | CNDP1 | 3.65 | 1.97E−02 | 3.52 | 3.07E−02 | 0.36 | 4.14E−16 | 0.73 |
| 19 | Contactin-5 | 3.66 | 9.35E−03 | 3.59 | 1.33E−02 | 0.31 | 1.67E−11 | 0.68 |
| 20 | CSK | 3.25 | 6.59E−02 | 3.54 | 1.10E−01 | 0.41 | 1.33E−20 | 0.76 |
| 21 | CyclophilinA | 4.42 | 6.04E−02 | 4.65 | 6.80E−02 | 0.38 | 2.17E−17 | 0.73 |
| 22 | Endostatin | 4.61 | 4.29E−03 | 4.67 | 1.07E−02 | 0.32 | 1.42E−12 | 0.69 |
| 23 | ERBB1 | 4.17 | 2.25E−03 | 4.10 | 5.18E−03 | 0.47 | 9.39E−27 | 0.78 |
| 24 | FGF-17 | 3.08 | 1.12E−03 | 3.11 | 1.31E−03 | 0.32 | 1.07E−12 | 0.71 |
| 25 | FYN | 3.18 | 6.88E−02 | 3.24 | 7.99E−02 | 0.13 | 1.53E−02 | 0.58 |
| 26 | GAPDH | 3.26 | 7.32E−02 | 3.51 | 1.62E−01 | 0.40 | 2.02E−19 | 0.68 |
| 28 | HSP90a | 4.45 | 1.86E−02 | 4.61 | 1.86E−02 | 0.50 | 3.09E−30 | 0.80 |
| 30 | IGFBP-2 | 4.30 | 3.42E−02 | 4.48 | 4.17E−02 | 0.37 | 5.40E−17 | 0.74 |
| 31 | IL-15 Ra | 3.03 | 9.74E−03 | 3.12 | 2.10E−02 | 0.31 | 7.31E−12 | 0.69 |
| 34 | Kallikrein 7 | 3.52 | 8.67E−03 | 3.44 | 1.21E−02 | 0.36 | 2.47E−15 | 0.70 |
| 35 | KPCI | 2.58 | 2.92E−03 | 2.66 | 1.01E−02 | 0.40 | 2.30E−19 | 0.74 |
| 36 | LDH-H1 | 3.60 | 8.03E−03 | 3.67 | 1.45E−02 | 0.32 | 3.70E−12 | 0.68 |
| 38 | LRIG3 | 3.55 | 3.10E−03 | 3.50 | 3.60E−03 | 0.36 | 1.39E−15 | 0.72 |
| 40 | MEK1 | 2.81 | 1.54E−03 | 2.84 | 2.75E−03 | 0.28 | 1.96E−09 | 0.67 |
| 42 | Midkine | 3.21 | 3.13E−02 | 3.24 | 5.58E−02 | 0.13 | 1.90E−02 | 0.56 |
| 43 | MIP-5 | 3.60 | 3.65E−02 | 3.77 | 5.88E−02 | 0.34 | 8.40E−14 | 0.70 |
| 48 | PARC | 4.90 | 1.94E−02 | 5.01 | 2.13E−02 | 0.34 | 7.01E−14 | 0.71 |
| 50 | Prothrombin | 4.68 | 5.37E−02 | 4.53 | 4.31E−02 | 0.32 | 1.09E−12 | 0.68 |
| 51 | PTN | 3.73 | 7.08E−03 | 3.80 | 7.36E−03 | 0.34 | 3.97E−14 | 0.72 |
| 52 | RAC1 | 3.85 | 6.13E−02 | 4.09 | 7.31E−02 | 0.40 | 4.60E−19 | 0.72 |
| 53 | Renin | 3.25 | 2.52E−02 | 3.39 | 6.36E−02 | 0.30 | 4.23E−11 | 0.68 |
| 55 | SCF sR | 3.79 | 1.11E−02 | 3.68 | 1.48E−02 | 0.37 | 9.90E−17 | 0.75 |
| 56 | sL-Selectin | 4.46 | 5.63E−03 | 4.40 | 9.30E−03 | 0.30 | 6.24E−11 | 0.69 |
| 57 | TCTP | 4.19 | 4.69E−02 | 4.44 | 7.43E−02 | 0.43 | 9.69E−22 | 0.76 |
| 58 | UBE2N | 4.42 | 9.30E−02 | 4.67 | 9.53E−02 | 0.34 | 6.56E−14 | 0.72 |
| 59 | Ubiquitin + 1 | 4.25 | 1.75E−02 | 4.34 | 1.43E−02 | 0.31 | 1.55E−11 | 0.68 |

TABLE 13

Parameters for benign nodules control group

| Biomarker # from Table 1 | Biomarker | $\mu_c$ | $\sigma_c^2$ | $\mu_d$ | $\sigma_d^2$ | KS | p-value | AUC |
|---|---|---|---|---|---|---|---|---|
| 2 | ApoA-I | 3.83 | 1.04E−02 | 3.77 | 1.56E−02 | 0.24 | 1.67E−07 | 0.65 |
| 3 | b-ECGF | 3.03 | 1.27E−03 | 3.06 | 1.53E−03 | 0.30 | 7.50E−12 | 0.68 |
| 4 | BLC | 2.60 | 1.50E−02 | 2.72 | 3.97E−02 | 0.31 | 1.77E−12 | 0.70 |
| 5 | BMP-1 | 4.11 | 1.39E−02 | 4.00 | 2.01E−02 | 0.32 | 2.00E−13 | 0.72 |
| 8 | C9 | 5.31 | 4.84E−03 | 5.38 | 5.37E−03 | 0.39 | 9.42E−20 | 0.75 |
| 9 | Cadherin E | 4.51 | 5.91E−03 | 4.43 | 9.86E−03 | 0.37 | 1.93E−17 | 0.74 |
| 10 | Cadherin-6 | 2.91 | 3.79E−03 | 2.98 | 1.12E−02 | 0.36 | 1.42E−16 | 0.72 |
| 11 | Calpain I | 4.37 | 1.33E−02 | 4.50 | 2.32E−02 | 0.40 | 7.63E−21 | 0.75 |

TABLE 13-continued

Parameters for benign nodules control group

| Biomarker # from Table 1 | Biomarker | $\mu_c$ | $\sigma_c^2$ | $\mu_d$ | $\sigma_d^2$ | KS | p-value | AUC |
|---|---|---|---|---|---|---|---|---|
| 12 | Catalase | 4.27 | 2.09E−02 | 4.37 | 1.30E−02 | 0.34 | 4.30E−15 | 0.72 |
| 13 | CATC | 2.80 | 5.83E−03 | 2.86 | 7.63E−03 | 0.31 | 8.55E−13 | 0.69 |
| 14 | Cathepsin H | 4.59 | 3.24E−03 | 4.63 | 7.54E−03 | 0.30 | 4.29E−12 | 0.66 |
| 15 | CD30 Ligand | 3.21 | 4.19E−03 | 3.26 | 4.42E−03 | 0.26 | 4.70E−09 | 0.68 |
| 17 | CK-MB | 3.23 | 4.47E−02 | 3.07 | 4.89E−02 | 0.32 | 2.76E−13 | 0.70 |
| 18 | CNDP1 | 3.65 | 2.03E−02 | 3.52 | 3.07E−02 | 0.35 | 2.04E−15 | 0.72 |
| 20 | CSK | 3.25 | 7.98E−02 | 3.54 | 1.10E−01 | 0.41 | 2.35E−21 | 0.76 |
| 23 | ERBB1 | 4.17 | 2.76E−03 | 4.10 | 5.18E−03 | 0.46 | 1.22E−26 | 0.77 |
| 24 | FGF-17 | 3.08 | 1.26E−03 | 3.11 | 1.31E−03 | 0.31 | 9.59E−13 | 0.71 |
| 26 | GAPDH | 3.22 | 7.96E−02 | 3.51 | 1.62E−01 | 0.40 | 7.88E−21 | 0.69 |
| 27 | HMG-1 | 4.01 | 4.57E−02 | 4.19 | 7.55E−02 | 0.30 | 1.99E−11 | 0.70 |
| 28 | HSP90a | 4.43 | 2.23E−02 | 4.61 | 1.86E−02 | 0.51 | 1.26E−33 | 0.81 |
| 29 | HSP90b | 3.06 | 3.70E−03 | 3.14 | 9.67E−03 | 0.42 | 2.73E−22 | 0.75 |
| 30 | IGFBP-2 | 4.32 | 3.57E−02 | 4.48 | 4.17E−02 | 0.35 | 2.30E−15 | 0.73 |
| 32 | IL-17B | 2.19 | 3.73E−03 | 2.23 | 4.16E−03 | 0.28 | 3.65E−10 | 0.68 |
| 33 | IMB1 | 3.47 | 2.21E−02 | 3.67 | 5.45E−02 | 0.42 | 2.04E−22 | 0.75 |
| 35 | KPCI | 2.57 | 3.26E−03 | 2.66 | 1.01E−02 | 0.43 | 3.57E−23 | 0.75 |
| 37 | LGMN | 3.13 | 2.03E−03 | 3.17 | 4.15E−03 | 0.30 | 1.15E−11 | 0.69 |
| 38 | LRIG3 | 3.55 | 3.59E−03 | 3.50 | 3.60E−03 | 0.33 | 9.00E−14 | 0.71 |
| 39 | Macrophage mannose receptor | 4.10 | 1.51E−02 | 4.22 | 2.48E−02 | 0.36 | 7.24E−17 | 0.72 |
| 40 | MEK1 | 2.81 | 1.77E−03 | 2.84 | 2.75E−03 | 0.31 | 3.79E−12 | 0.69 |
| 41 | METAP1 | 2.67 | 2.45E−02 | 2.89 | 5.83E−02 | 0.44 | 2.99E−24 | 0.75 |
| 44 | MK13 | 2.79 | 3.38E−03 | 2.85 | 4.88E−03 | 0.36 | 6.16E−17 | 0.74 |
| 45 | MMP-7 | 3.64 | 3.24E−02 | 3.82 | 4.85E−02 | 0.37 | 1.89E−17 | 0.73 |
| 46 | NACA | 3.11 | 8.28E−03 | 3.21 | 2.63E−02 | 0.34 | 4.91E−15 | 0.70 |
| 47 | NAGK | 3.71 | 2.04E−02 | 3.84 | 2.63E−02 | 0.38 | 7.50E−19 | 0.73 |
| 49 | Proteinase-3 | 3.95 | 9.09E−02 | 4.18 | 1.23E−01 | 0.30 | 2.22E−11 | 0.69 |
| 50 | Prothrombin | 4.67 | 4.19E−02 | 4.53 | 4.31E−02 | 0.32 | 2.17E−13 | 0.68 |
| 54 | RGM-C | 4.44 | 4.85E−03 | 4.38 | 6.13E−03 | 0.30 | 1.00E−11 | 0.69 |
| 55 | SCF sR | 3.77 | 9.71E−03 | 3.68 | 1.48E−02 | 0.35 | 1.96E−15 | 0.72 |
| 60 | VEGF | 3.55 | 8.80E−03 | 3.62 | 1.14E−02 | 0.30 | 1.27E−11 | 0.69 |
| 61 | YES | 2.97 | 9.54E−04 | 3.00 | 1.73E−03 | 0.29 | 7.59E−11 | 0.67 |

TABLE 14

Sensitivity + Specificity for Exemplary Combinations of Biomarkers

| # | | | | | | | | | Sensitivity | Specificity | Sensitivity + Specificity | AUC |
|---|---|---|---|---|---|---|---|---|---|---|---|---|
| 1 | SCFsR | | | | | | | | 0.629 | 0.727 | 1.356 | 0.75 |
| 2 | SCFsR | HSP90a | | | | | | | 0.761 | 0.753 | 1.514 | 0.84 |
| 3 | SCFsR | HSP90a | ERBB1 | | | | | | 0.775 | 0.827 | 1.602 | 0.87 |
| 4 | SCFsR | HSP90a | ERBB1 | PTN | | | | | 0.784 | 0.861 | 1.645 | 0.89 |
| 5 | SCFsR | HSP90a | ERBB1 | PTN | BTK | | | | 0.84 | 0.844 | 1.684 | 0.9 |
| 6 | SCFsR | HSP90a | ERBB1 | PTN | BTK | CD30 Ligand | | | 0.822 | 0.869 | 1.691 | 0.9 |
| 7 | SCFsR | HSP90a | ERBB1 | PTN | BTK | CD30 Ligand | Kallikrein7 | | 0.845 | 0.875 | 1.72 | 0.91 |
| 8 | SCFsR | HSP90a | ERBB1 | PTN | BTK | CD30 Ligand | Kallikrein7 | LRIG3 | 0.859 | 0.864 | 1.723 | 0.91 |
| 9 | SCFsR | HSP90a | ERBB1 | PTN | BTK | CD30 Ligand | Kallikrein7 | LRIG3 | LDH-H1 | 0.869 | 0.872 | 1.741 | 0.91 |
| 10 | SCFsR | HSP90a | ERBB1 | PTN | BTK | CD30 Ligand | Kallikrein7 | LRIG3 | LDH-H1 | PARC | 0.873 | 0.878 | 1.751 | 0.91 |

TABLE 15

Parameters derived from training set for naïve Bayes classifier.

| Biomarker | $\mu_c$ | $\mu_d$ | $\sigma_c$ | $\sigma_d$ | $\tilde{x}$ | p (c\|$\tilde{x}$) | p (d\|$\tilde{x}$) | ln (p(c\|$\tilde{x}$)/p(d\|$\tilde{x}$)) |
|---|---|---|---|---|---|---|---|---|
| C9 | 11.713 | 11.934 | 0.199 | 0.210 | 11.667 | 1.946 | 0.843 | 0.836 |
| LRIG3 | 7.409 | 7.307 | 0.090 | 0.084 | 7.372 | 4.058 | 3.511 | 0.145 |
| GAPDH | 9.027 | 9.385 | 0.511 | 0.230 | 9.000 | 0.780 | 0.428 | 0.599 |

TABLE 15-continued

Parameters derived from training set for naïve Bayes classifier.

| Biomarker | $\mu_c$ | $\mu_d$ | $\sigma_c$ | $\sigma_d$ | $\tilde{x}$ | $p(c|\tilde{x})$ | $p(d|\tilde{x})$ | $\ln(p(c|\tilde{x})/p(d|\tilde{x}))$ |
|---|---|---|---|---|---|---|---|---|
| MMP12 | 6.139 | 6.346 | 0.096 | 0.255 | 6.129 | 4.115 | 1.087 | 1.332 |
| KLK7 | 8.130 | 7.979 | 0.230 | 0.298 | 8.419 | 0.789 | 0.450 | 0.562 |

TABLE 16

Naïve Bayes parameters for all markers in Table 21 for both tissue and serum

| Biomarker | Tissue $\mu_c$ | Tissue $\mu_d$ | Tissue $\sigma_c$ | Tissue $\sigma_d$ | Serum $u_c$ | Serum $\mu_d$ | Serum $\sigma_c$ | Serum $\sigma_d$ |
|---|---|---|---|---|---|---|---|---|
| Activin A | 5.927 | 6.713 | 0.124 | 0.816 | 6.990 | 7.060 | 0.089 | 0.120 |
| Adiponectin | 9.357 | 8.560 | 0.456 | 0.154 | 8.986 | 9.141 | 0.406 | 0.391 |
| AMPM2 | 9.352 | 9.916 | 0.393 | 0.313 | 7.067 | 7.079 | 0.091 | 0.107 |
| Apo A-I | 6.554 | 6.573 | 0.312 | 0.271 | 8.699 | 8.593 | 0.139 | 0.130 |
| b-ECGF | 6.731 | 7.256 | 0.606 | 0.739 | 6.205 | 6.160 | 0.056 | 0.072 |
| BGN | 7.989 | 6.821 | 0.653 | 0.168 | 7.140 | 7.067 | 0.125 | 0.077 |
| BLC | 6.283 | 7.776 | 0.253 | 0.971 | 7.065 | 7.058 | 0.066 | 0.072 |
| BMP-1 | 5.149 | 5.377 | 0.071 | 0.239 | 8.766 | 8.548 | 0.213 | 0.234 |
| BTK | 8.782 | 7.757 | 0.547 | 1.303 | 7.567 | 7.856 | 0.464 | 0.304 |
| C1s | 7.989 | 7.973 | 0.206 | 0.298 | 8.532 | 8.540 | 0.106 | 0.121 |
| C9 | 11.488 | 11.417 | 0.325 | 0.380 | 11.715 | 11.936 | 0.189 | 0.223 |
| Cadherin-6 | 7.129 | 7.502 | 0.034 | 0.265 | 7.971 | 7.959 | 0.087 | 0.067 |
| Cadherin E | 7.370 | 7.916 | 0.458 | 0.349 | 9.252 | 9.050 | 0.200 | 0.181 |
| Calpain I | 9.641 | 9.962 | 0.503 | 0.553 | 10.358 | 10.466 | 0.132 | 0.143 |
| Carbonic anhydrase III | 9.096 | 7.504 | 0.288 | 0.890 | 8.552 | 8.687 | 0.474 | 0.351 |
| Caspase-3 | 6.758 | 7.426 | 0.248 | 0.110 | 7.097 | 7.136 | 0.338 | 0.367 |
| Catalase | 11.253 | 10.581 | 0.127 | 0.633 | 10.051 | 10.243 | 0.392 | 0.276 |
| CATC | 7.839 | 7.783 | 0.457 | 0.385 | 7.248 | 7.229 | 0.088 | 0.088 |
| Cathepsin H | 12.452 | 11.758 | 0.158 | 0.410 | 9.485 | 9.585 | 0.124 | 0.210 |
| CD30 Ligand | 6.655 | 6.911 | 0.069 | 0.168 | 7.622 | 7.605 | 0.038 | 0.035 |
| CD36 ANTIGEN | 7.026 | 6.262 | 0.478 | 0.175 | 8.252 | 8.224 | 0.114 | 0.141 |
| CDK5/p35 | 6.581 | 6.741 | 0.210 | 0.215 | 6.986 | 7.044 | 0.083 | 0.075 |
| CK-MB | 8.912 | 8.564 | 0.703 | 0.611 | 7.515 | 7.230 | 0.317 | 0.307 |
| CNDP1 | 7.293 | 7.292 | 0.062 | 0.189 | 9.995 | 9.754 | 0.295 | 0.375 |
| Contactin-5 | 5.793 | 5.777 | 0.063 | 0.146 | 6.749 | 6.689 | 0.109 | 0.141 |
| CSK | 8.526 | 8.181 | 0.370 | 0.736 | 6.809 | 7.186 | 0.388 | 0.245 |
| CXCL16, soluble | 8.216 | 7.559 | 0.517 | 0.449 | 9.660 | 9.744 | 0.185 | 0.230 |
| Cyclophilin A | 11.751 | 11.668 | 0.159 | 0.123 | 8.586 | 8.784 | 0.323 | 0.233 |
| Endostatin | 8.669 | 8.096 | 0.233 | 0.374 | 8.763 | 8.876 | 0.125 | 0.162 |
| ERBB1 | 7.041 | 7.263 | 0.134 | 0.336 | 10.578 | 10.428 | 0.119 | 0.135 |
| ESAM | 8.659 | 7.451 | 0.376 | 0.473 | 9.022 | 9.033 | 0.151 | 0.142 |
| FGF-17 | 6.111 | 5.998 | 0.036 | 0.066 | 6.897 | 6.902 | 0.062 | 0.069 |
| Fibronectin | 9.681 | 10.795 | 0.452 | 1.097 | 11.288 | 11.105 | 0.253 | 0.269 |
| FYN | 8.003 | 7.834 | 0.149 | 0.262 | 8.002 | 8.033 | 0.123 | 0.086 |
| GAPDH, liver | 12.703 | 12.713 | 0.123 | 0.152 | 9.033 | 9.410 | 0.536 | 0.194 |
| HMG-1 | 11.639 | 11.541 | 0.545 | 0.615 | 8.430 | 8.546 | 0.133 | 0.096 |
| HSP 90a | 11.569 | 11.820 | 0.479 | 0.279 | 9.165 | 9.343 | 0.226 | 0.182 |
| HSP 90b | 8.509 | 9.422 | 0.974 | 0.960 | 7.635 | 7.653 | 0.053 | 0.059 |
| IDE | 8.426 | 9.023 | 0.362 | 0.302 | 7.670 | 7.728 | 0.096 | 0.106 |
| IGFBP-2 | 7.715 | 9.591 | 0.416 | 1.413 | 8.514 | 9.006 | 0.417 | 0.448 |
| IGFBP-5 | 7.619 | 9.347 | 0.282 | 1.263 | 9.705 | 9.675 | 0.126 | 0.138 |
| IGFBP-7 | 8.999 | 9.843 | 0.717 | 0.307 | 9.251 | 9.156 | 0.148 | 0.172 |
| IL-15 Ra | 6.088 | 6.577 | 0.123 | 0.318 | 7.068 | 7.066 | 0.056 | 0.071 |
| IL-17B | 5.441 | 5.531 | 0.051 | 0.139 | 6.267 | 6.257 | 0.052 | 0.066 |
| IL-8 | 7.037 | 8.206 | 0.145 | 0.631 | 7.114 | 7.109 | 0.052 | 0.066 |
| IMB1 | 5.867 | 6.218 | 1.300 | 1.010 | 7.326 | 7.390 | 0.150 | 0.152 |
| Kallikrein 7 | 5.990 | 6.152 | 0.146 | 0.447 | 8.132 | 7.964 | 0.221 | 0.295 |
| KPCI | 6.589 | 6.821 | 0.244 | 0.420 | 6.195 | 6.194 | 0.053 | 0.046 |
| LDH-H 1 | 12.527 | 12.640 | 0.135 | 0.169 | 7.221 | 7.261 | 0.140 | 0.198 |
| LGMN | 7.964 | 8.124 | 0.084 | 0.101 | 8.404 | 8.377 | 0.074 | 0.070 |
| LRIG3 | 6.198 | 6.213 | 0.383 | 0.336 | 7.411 | 7.301 | 0.090 | 0.092 |
| Macrophage mannose receptor | 6.738 | 5.654 | 0.394 | 0.440 | 8.132 | 8.233 | 0.203 | 0.253 |
| MEK1 | 6.543 | 6.657 | 0.305 | 0.505 | 5.979 | 5.966 | 0.039 | 0.048 |
| METAP1 | 9.004 | 9.807 | 0.540 | 0.412 | 7.955 | 7.982 | 0.095 | 0.081 |
| Midkine | 6.619 | 7.223 | 0.770 | 1.112 | 7.714 | 7.714 | 0.298 | 0.193 |
| MIP-5 | 5.582 | 5.657 | 0.041 | 0.090 | 8.560 | 8.659 | 0.262 | 0.233 |
| MK13 | 7.195 | 7.793 | 0.260 | 0.491 | NA | NA | NA | NA |
| MMP-12 | 5.822 | 8.677 | 0.182 | 1.045 | 6.129 | 6.323 | 0.100 | 0.260 |
| MMP-7 | 6.800 | 8.224 | 0.440 | 0.215 | 8.881 | 9.232 | 0.235 | 0.182 |
| NACA | 6.480 | 6.738 | 0.207 | 0.183 | 7.774 | 7.791 | 0.111 | 0.108 |
| NAGK | 9.469 | 9.986 | 0.328 | 0.457 | 7.385 | 7.476 | 0.203 | 0.216 |
| NAP-2 | 10.672 | 9.447 | 0.357 | 0.842 | 7.765 | 7.775 | 0.286 | 0.342 |

TABLE 16-continued

Naïve Bayes parameters for all markers in Table 21 for both tissue and serum

| Biomarker | Tissue $\mu_c$ | Tissue $\mu_d$ | Tissue $\sigma_c$ | Tissue $\sigma_d$ | Serum $u_c$ | Serum $\mu_d$ | Serum $\sigma_c$ | Serum $\sigma_d$ |
|---|---|---|---|---|---|---|---|---|
| PARC | 9.519 | 9.315 | 0.537 | 0.169 | 10.087 | 10.291 | 0.424 | 0.369 |
| Proteinase-3 | 7.667 | 6.963 | 0.789 | 0.850 | 8.340 | 8.394 | 0.461 | 0.504 |
| Prothrombin | 7.245 | 7.400 | 0.443 | 0.390 | NA | NA | NA | NA |
| P-Selectin | 7.947 | 6.593 | 0.263 | 0.508 | 9.937 | 9.944 | 0.278 | 0.199 |
| PTN | 7.363 | 7.301 | 0.492 | 0.531 | 8.149 | 8.250 | 0.116 | 0.152 |
| RAC1 | 11.522 | 11.299 | 0.109 | 0.220 | 8.408 | 8.697 | 0.378 | 0.323 |
| Renin | 5.964 | 5.894 | 0.039 | 0.080 | 7.675 | 7.797 | 0.338 | 0.506 |
| RGM-C | 6.677 | 6.646 | 0.049 | 0.084 | 9.765 | 9.700 | 0.164 | 0.180 |
| SCF sR | 6.607 | 6.639 | 0.163 | 0.175 | 9.603 | 9.503 | 0.139 | 0.141 |
| SLPI | 10.635 | 9.435 | 0.676 | 0.476 | NA | NA | NA | NA |
| sL-Selectin | 6.524 | 6.827 | 0.149 | 0.166 | NA | NA | NA | NA |
| sRAGE | 11.154 | 7.304 | 0.619 | 0.912 | 7.001 | 6.845 | 0.333 | 0.297 |
| TCTP | 10.524 | 10.395 | 0.087 | 0.127 | 8.847 | 9.137 | 0.290 | 0.224 |
| Thrombospondin-1 | 9.012 | 10.305 | 0.520 | 1.093 | 9.187 | 8.950 | 0.558 | 0.349 |
| TPSB2 | 10.798 | 9.138 | 0.668 | 1.055 | 7.714 | 7.435 | 0.346 | 0.441 |
| TrATPase | 11.031 | 8.887 | 0.993 | 0.703 | 9.099 | 9.168 | 0.204 | 0.148 |
| TSP2 | 6.569 | 7.837 | 0.085 | 0.627 | 7.468 | 7.562 | 0.162 | 0.218 |
| UBE2N | 10.654 | 10.725 | 0.166 | 0.140 | 9.234 | 9.487 | 0.521 | 0.288 |
| Ubiquitin + 1 | 10.948 | 10.860 | 0.249 | 0.275 | 9.218 | 9.284 | 0.249 | 0.171 |
| uPA | 5.747 | 6.564 | 0.119 | 0.445 | 6.868 | 6.874 | 0.104 | 0.126 |
| URB | 7.180 | 8.539 | 0.283 | 0.699 | 8.689 | 8.756 | 0.173 | 0.202 |
| VEGF | 6.313 | 7.593 | 0.088 | 1.074 | 7.699 | 7.769 | 0.096 | 0.145 |
| vWF | 7.927 | 7.193 | 0.263 | 0.139 | 10.531 | 10.684 | 0.236 | 0.200 |
| YES | 7.086 | 7.723 | 0.386 | 0.314 | 6.593 | 6.605 | 0.065 | 0.067 |

TABLE 17

Patient demographics, resection location and tumor types for the eight NSCLC samples

| Age | Sex | Smoking History | Location | Stage | Tissue Dx |
|---|---|---|---|---|---|
| 47 | F | Smoker | Left Upper Lobe | pT3pN1pMx stage IIIA | Poorly differentiated non-small cell CA with focal Squamous differentiation |
| 73 | F | Smoker | Left Lower Lobe | pT2pN0pMx stage IB | Poorly differentiated Squamous cell carcinoma |
| 48 | M | Smoker | Right Upper Lobe | pT2pN1pMx stage IIIA | Poorly differentiated Squamous cell carcinoma |
| 60 | F | Smoker | Left Upper Lobe | T4 N1 M0 stage IIIB—note T4 distinction based on clinical lung collapse; tumor was pT2 by size criteria | Poorly differentiated Squamous cell carcinoma |
| 51 | F | Smoker | Right Upper Lobe | pT2pN0pMx stage IB | Moderately differentiated Adenocarcinoma |
| 71 | F | Smoker | Right Upper Lobe | pT2pN0pMx stage IB | Well differentiated Adenocarcinoma |
| 75 | F | Smoker | Right Lower Lobe | pT1N0Mx Stage IA | Well differentiated Adenocarcinoma |
| 73 | M | Smoker | Left Upper Lobe | pT1bN0Mx Stage IA | Atypical Carcinoid Tumor (i.e. neuroendocrine, IHC positive for chromogranin) |

TABLE 18

Differentially Expressed Biomarkers Between Tumor and Normal Tissue

| Biomarker # | Biomarker Designation | Alternate Protein Names | Gene | Up/Down Regulated |
|---|---|---|---|---|
| 1 | Activin A | Inhibin beta A chain<br>Activin beta-A chain<br>Erythroid differentiation protein<br>EDF | INHBA | up |
| 2 | Adiponectin | 30 kDa adipocyte complement-related protein<br>Adipocyte complement-related 30 kDa protein<br>ACRP30<br>Adipocyte, C1q and collagen domain-containing protein | ADIPOQ | down |

TABLE 18-continued

Differentially Expressed Biomarkers Between Tumor and Normal Tissue

| Biomarker # | Biomarker Designation | Alternate Protein Names | Gene | Up/Down Regulated |
|---|---|---|---|---|
| 3 | BCA-1* | Adipose most abundant gene transcript 1 protein<br>apM-1<br>Gelatin-binding protein<br>Adipolean<br>C—X—C motif chemokine 13<br>Angie<br>B cell-attracting chemokine 1<br>B lymphocyte chemoattractant<br>CXC chemokine BLC<br>Small-inducible cytokine B13<br>BLC | CXCL13 | up |
| 4 | Biglycan | Bone/cartilage proteoglycan I<br>PG-S1 | BGN | down |
| 5 | Cadherin-1* | CAM 120/80<br>Epithelial cadherin<br>E-cadherin<br>Uvomorulin<br>CD324 | CDH1 | up |
| 6 | Carbonic anhydrase III | Carbonic anhydrase 3<br>Carbonate dehydratase III<br>CA-III | CA3 | down |
| 7 | Caspase-3 | CASP-3<br>Apopain<br>Cysteine protease CPP32<br>CPP-32<br>Protein Yama<br>SREBP cleavage activity 1<br>SCA-1 | CASP3 | up |
| 8 | Catalase* | | CAT | down |
| 9 | CD36 Antigen | Platelet glycoprotein 4<br>Fatty acid translocase<br>FAT<br>Glycoprotein IIIb<br>GPIIIB<br>Leukocyte differentiation antigen CD36<br>PAS IV<br>PAS-4<br>Platelet collagen receptor<br>Platelet glycoprotein IV<br>GPIV<br>Thrombospondin receptor | CD36 | down |
| 10 | CXCL16, soluble | C—X—C motif chemokine 16<br>Scavenger receptor for phosphatidylserine and oxidized low density lipoprotein<br>SR-PSOX<br>Small-inducible cytokine B16<br>Transmembrane chemokine CSCL16 | CXCL16 | down |
| 11 | Endostatin* | | COL18A1 | down |
| 12 | ESAM | Endothelial cell-selective adhesion molecule | ESAM | down |
| 13 | Fibronectin | FN<br>Cold-insoluble globulin<br>CIG<br>FNT | FN1 | up |
| 14 | Insulysin | Insulin-degrading enzyme<br>Abeta-degrading protease<br>Insulin protease<br>Insulinase | IDE | up |
| 15 | IGFBP-2* | Insulin-like growth factor-binding protein 2<br>IBP-2<br>IGF-binding protein 2 | IGFBP2 | up |
| 16 | IGFBP-5 | Insulin-like growth factor-binding protein 5<br>IBP-5<br>IGF-binding protein 5 | IGFBP5 | up |
| 17 | IGFBP-7 | Insulin-like growth factor-binding protein 7<br>IBP-7<br>IGF-binding protein 7<br>IGFBP-rP1<br>MAC25 protein<br>PGI2-stimulating factor<br>Prostacyclin-stimulating factor<br>Tumor-derived adhesion factor<br>TAF | IGFBP7 | up |
| 18 | IL-8 | Interleukin-8<br>C—X—C motif chemokine 8<br>Emoctakin | IL8 | up |

TABLE 18-continued

Differentially Expressed Biomarkers Between Tumor and Normal Tissue

| Biomarker # | Biomarker Designation | Alternate Protein Names | Gene | Up/Down Regulated |
|---|---|---|---|---|
| | | Granulocyte chemotactic protein 1<br>GCP-1<br>Monocyte-derived neutrophil chemotactic factor<br>MDNCF<br>Monocyte-derived neutrophil-activating peptide<br>MONAP<br>Neutrophil-activating protein<br>NAP-1<br>Protein 3-10C<br>T-cell chemotactic factor | | |
| 19 | MRC1* | Macrophage mannose receptor 1<br>MMR<br>C-type lectin domain family 13 member D<br>C-type lectin domain family 13 member D-like<br>Macrophage mannose receptor 1-like protein 1<br>CD206 | MRC1 | down |
| 20 | MAPK13* | Mitogen-activated protein kinase 13<br>MAP kinase 13<br>Mitogen-activated protein kinase p38 delta<br>MAP kinase p38 delta<br>Stress-activated protein kinase 4 | MAPK13 | up |
| 21 | MMP-7* | Matrilysin<br>Matrin<br>Matrix metalloproteinase-7<br>Pump-1 protease<br>Uterine metalloproteinase | MMP7 | up |
| 22 | MMP-12* | Macrophage metalloelastase<br>MME<br>Macrophage elastase<br>ME<br>hME<br>Matrix metalloproteinase-12 | MMP12 | up |
| 23 | NAGK* | N-acetyl-D-glucosamine kinase<br>N-acetylglucosamine kinase<br>GlcNAc kinase | NAGK | up |
| 24 | NAP-2 | Neutrophil-activating peptide 2 | PPBP | down |
| 25 | P-Selectin | CD62 antigen-like family member P<br>Granule membrane protein 140<br>GMP-140<br>Leukocyte-endothelial cell adhesion molecule 3<br>LECAM-3<br>Platelet activation dependent granule-external membrane protein<br>PADGEM<br>CD62P | SELP | down |
| 26 | SLPI | Antileukoproteinase<br>ALP<br>BLPI<br>HUSI-1<br>Mucus proteinase inhibitor<br>MPI<br>Protease inhibitor WAP4<br>Secretory leukocyte protease inhibitor<br>Seminal proteinase inhibitor<br>WAP four-disulfide core domain protein 4 | SLPI | down |
| 27 | sRAGE | Advanced glycosylation end product-specific receptor<br>Receptor for advanced glycosylation end products | AGER | down |
| 28 | Thrombospondin-1 | TSP-1 | THBS1 | up |
| 29 | Thrombospondin-2 | TSP-2 | THBS1 | up |
| 30 | TrATPase | Tartrate-resistant acid phosphatase type 5<br>TR-AP<br>Tartrate-resistant acid ATPase<br>Type 5 acid phosphatase | ACP5 | down |
| 31 | Tryptase β-2 | Tryptase beta-2<br>Tryptase-2<br>Tryptase II<br>TRYB2 | TPSB2 | down |
| 32 | uPA | Urokinase-type plasminogen activator<br>U-plasminogen activator<br>Urokinase | PLAU | up |
| 33 | URB | Coiled-coil domain-containing protein 80<br>Down-regulated by oncogenes protein 1<br>Up-regulated in BRS-3 deficient mouse | CCDC80 | up |

TABLE 18-continued

Differentially Expressed Biomarkers Between Tumor and Normal Tissue

| Biomarker # | Biomarker Designation | Alternate Protein Names | Gene | Up/Down Regulated |
|---|---|---|---|---|
| 34 | VEGF* | homolog<br>Vascular endothelial growth factor A<br>VEGF-A<br>Vascular permeability factor<br>VPF | VEGFA | up |
| 35 | vWF | von Willebrand factor | VWF | down |
| 36 | YES* | Tyrosine-protein kinase Yes<br>Proto-oncogene c-Yes<br>P61-Yes | YES1 | up |

*Overlap of Biomarkers Expressed in both Serum and Tumor Tissue

TABLE 19

Categorization of NSCLC tissue biomarkers into biological processes

| Angiogenesis | Growth and Metabolism | Inflammation & Apoptosis | Invasion, Metastasis (ECM) |
|---|---|---|---|
| VEGF | Adiponectin* | Activin A | Biglycan* |
| Endostatin | Carbonic anhydrase III* | BCA-1* | Cadherin-1 |
| Thrombospondin-1 | IGFBP-2 | Catalase | CD36 Antigen |
| Thrombospondin-2 | IGFBP-5 | CXCL16, soluble* | ESAM |
|  | IGFBP-7 | IL-8 | Fibronectin* |
|  | Insulysin* | MRC1* | MMP-7 |
|  | NAGK* | NAP-2 | MMP-12 |
|  | TrATPase* | sRAGE | P-Selectin* |
|  | Tryptase b-2 | SLPI | URB* |
|  | MAPK13* | uPA | vWF |
|  |  | Caspase-3 | Thrombospondin-1 |
|  |  |  | Thrombospondin-2 |
|  |  |  | YES |

*Novel NSCLC Biomarker

TABLE 20

Biomarkers Identified in NSCLC Tissue*

| Biomarker # | Biomarker Designation |
|---|---|
| 1 | Activin A |
| 2 | Adiponectin |
| 3 | Biglycan |
| 4 | Carbonic anhydrase III |
| 5 | Caspase-3 |
| 6 | CD36 Antigen |
| 7 | CXCL16, soluble |
| 8 | ESAM |
| 9 | Fibronectin |
| 10 | Insulysin |
| 11 | IGFBP-5 |
| 12 | IGFBP-7 |
| 13 | IL-8 |
| 14 | MMP-12 |
| 15 | NAP-2 |
| 16 | P-Selectin |
| 17 | SLPI |
| 18 | sRAGE |
| 19 | Thrombospondin-1 |
| 20 | Thrombospondin-2 |
| 21 | TrATPase |
| 22 | Tryptase β-2 |
| 23 | uPA |
| 24 | URB |
| 25 | vWF |

*This list excludes biomarkers which were identified in both tissue and serum samples

TABLE 21

Biomarkers Identified in Serum and Tissue

| Biomarker | Biomarker Designation |
|---|---|
| 1 | Activin A |
| 2 | Adiponectin |
| 3 | AMPM2 |
| 4 | Apo A-I |
| 5 | Biglycan |
| 6 | b-ECGF |
| 7 | BLC* |
| 8 | BMP-1 |
| 9 | BTK |
| 10 | C1s |
| 11 | C9 |
| 12 | Cadherin E* |
| 13 | Cadherin-6 |
| 14 | Calpain I |
| 15 | Carbonic anhydrase III |
| 16 | Caspase-3 |
| 17 | Catalase* |
| 18 | CATC |
| 19 | Cathepsin H |
| 20 | CD30 Ligand |
| 21 | CD36 Antigen |
| 22 | CDK5-p35 |
| 23 | CK-MB |
| 24 | CNDP1 |
| 25 | Contactin-5 |
| 26 | CSK |
| 27 | CXCL16, soluble |
| 28 | Cyclophilin A |
| 29 | Endostatin* |
| 30 | ERBB1 |
| 31 | ESAM |
| 32 | FGF-17 |
| 33 | Fibronectin |
| 34 | FYN |
| 35 | GAPDH, liver |
| 36 | HMG-1 |
| 37 | HSP 90a |
| 38 | HSP 90b |
| 39 | IGFBP-2* |
| 40 | IGFBP-5 |
| 41 | IGFBP-7 |
| 42 | IL-8 |
| 43 | IL-15 Ra |

TABLE 21-continued

Biomarkers Identified in Serum and Tissue

| Biomarker | Biomarker Designation |
|---|---|
| 44 | IL-17B |
| 45 | IMB1 |
| 46 | Insulysin |
| 47 | Kallikrein 7 |
| 48 | KPCI |
| 49 | LDH-H 1 |
| 50 | LGMN |
| 51 | LRIG3 |
| 52 | Macrophage mannose receptor* |
| 53 | MEK1 |
| 54 | METAP1 |
| 55 | Midkine |
| 56 | MIP-5 |
| 57 | MK13* |
| 58 | MMP-7* |
| 59 | MMP-12* |
| 60 | NACA |
| 61 | NAGK* |
| 62 | NAP-2 |
| 63 | PARC |
| 64 | P-Selectin |
| 65 | Proteinase-3 |
| 66 | Prothrombin |
| 67 | PTN |
| 68 | RAC1 |
| 69 | Renin |
| 70 | RGM-C |
| 71 | SCF sR |
| 72 | SLPI |
| 73 | sL-Selectin |
| 74 | sRAGE |
| 75 | TCTP |
| 76 | Thrombospondin-1 |
| 77 | Thrombospondin-2 |
| 78 | TrATPase |
| 79 | Tryptase β-2 |
| 80 | UBE2N |
| 81 | Ubiquitin + 1 |
| 82 | uPA |
| 83 | URB |
| 84 | VEGF* |
| 85 | vWF |
| 86 | YES* |

*Biomarkers identified in both serum in tissue

TABLE 22

81 Panels of two biomarkers including MMP-12

| | Markers | | AUC |
|---|---|---|---|
| 1 | CSK | MMP-12 | 0.848 |
| 2 | GAPDH, liver | MMP-12 | 0.842 |
| 3 | Cyclophilin A | MMP-12 | 0.832 |
| 4 | TCTP | MMP-12 | 0.831 |
| 5 | C9 | MMP-12 | 0.828 |
| 6 | LRIG3 | MMP-12 | 0.826 |
| 7 | MMP-7 | MMP-12 | 0.824 |
| 8 | BMP-1 | MMP-12 | 0.823 |
| 9 | SCF sR | MMP-12 | 0.823 |
| 10 | ERBB1 | MMP-12 | 0.822 |
| 11 | RAC1 | MMP-12 | 0.822 |
| 12 | Kallikrein 7 | MMP-12 | 0.822 |
| 13 | HSP 90a | MMP-12 | 0.817 |
| 14 | CDK5/p35 | MMP-12 | 0.815 |
| 15 | IGFBP-2 | MMP-12 | 0.812 |
| 16 | HMG-1 | MMP-12 | 0.809 |
| 17 | Cadherin E | MMP-12 | 0.808 |
| 18 | b-ECGF | MMP-12 | 0.807 |
| 19 | Calpain I | MMP-12 | 0.805 |
| 20 | RGM-C | MMP-12 | 0.804 |
| 21 | IMB1 | MMP-12 | 0.802 |
| 22 | UBE2N | MMP-12 | 0.802 |
| 23 | LGMN | MMP-12 | 0.801 |
| 24 | Catalase | MMP-12 | 0.801 |
| 25 | CK-MB | MMP-12 | 0.800 |
| 26 | BTK | MMP-12 | 0.799 |
| 27 | Endostatin | MMP-12 | 0.791 |
| 28 | BGN | MMP-12 | 0.791 |
| 29 | PTN | MMP-12 | 0.790 |
| 30 | CD30 Ligand | MMP-12 | 0.789 |
| 31 | Activin A | MMP-12 | 0.785 |
| 32 | vWF | MMP-12 | 0.784 |
| 33 | TSP2 | MMP-12 | 0.784 |
| 34 | IL-8 | MMP-12 | 0.782 |
| 35 | Adiponectin | MMP-12 | 0.781 |
| 36 | Thrombospondin-1 | MMP-12 | 0.779 |
| 37 | NAGK | MMP-12 | 0.777 |
| 38 | MIP-5 | MMP-12 | 0.776 |
| 39 | VEGF | MMP-12 | 0.776 |
| 40 | NACA | MMP-12 | 0.773 |
| 41 | LDH-H 1 | MMP-12 | 0.771 |
| 42 | CNDP1 | MMP-12 | 0.770 |
| 43 | IGFBP-7 | MMP-12 | 0.770 |
| 44 | Proteinase-3 | MMP-12 | 0.769 |
| 45 | TPSB2 | MMP-12 | 0.769 |
| 46 | Apo A-I | MMP-12 | 0.768 |
| 47 | Macrophage mannose receptor | MMP-12 | 0.768 |
| 48 | Ubiquitin + 1 | MMP-12 | 0.767 |
| 49 | IDE | MMP-12 | 0.767 |
| 50 | Cathepsin H | MMP-12 | 0.766 |
| 51 | CXCL16, soluble | MMP-12 | 0.763 |
| 52 | TrATPase | MMP-12 | 0.762 |
| 53 | Caspase-3 | MMP-12 | 0.757 |
| 54 | Cadherin-6 | MMP-12 | 0.757 |
| 55 | Contactin-5 | MMP-12 | 0.756 |
| 56 | BLC | MMP-12 | 0.756 |
| 57 | FGF-17 | MMP-12 | 0.755 |
| 58 | Fibronectin | MMP-12 | 0.754 |
| 59 | NAP-2 | MMP-12 | 0.754 |
| 60 | HSP 90b | MMP-12 | 0.754 |
| 61 | C1s | MMP-12 | 0.753 |
| 62 | AMPM2 | MMP-12 | 0.752 |
| 63 | IL-17B | MMP-12 | 0.752 |
| 64 | IL-15 Ra | MMP-12 | 0.751 |
| 65 | uPA | MMP-12 | 0.750 |
| 66 | PARC | MMP-12 | 0.749 |
| 67 | IGFBP-5 | MMP-12 | 0.748 |
| 68 | Renin | MMP-12 | 0.745 |
| 69 | KPCI | MMP-12 | 0.742 |
| 70 | METAP1 | MMP-12 | 0.742 |
| 71 | Carbonic anhydrase III | MMP-12 | 0.740 |
| 72 | CATC | MMP-12 | 0.740 |
| 73 | MEK1 | MMP-12 | 0.740 |
| 74 | URB | MMP-12 | 0.736 |
| 75 | CD36 ANTIGEN | MMP-12 | 0.735 |
| 76 | Midkine | MMP-12 | 0.735 |
| 77 | sRAGE | MMP-12 | 0.731 |
| 78 | ESAM | MMP-12 | 0.729 |
| 79 | YES | MMP-12 | 0.728 |
| 80 | P-Selectin | MMP-12 | 0.723 |
| 81 | FYN | MMP-12 | 0.707 |

TABLE 23

100 Panels of three biomarkers including MMP-12

| | Markers | | | AUC |
|---|---|---|---|---|
| 1 | C9 | GAPDH, liver | MMP-12 | 0.879 |
| 2 | MMP-7 | GAPDH, liver | MMP-12 | 0.876 |
| 3 | C9 | CSK | MMP-12 | 0.875 |
| 4 | BMP-1 | CSK | MMP-12 | 0.869 |
| 5 | BMP-1 | GAPDH, liver | MMP-12 | 0.868 |
| 6 | LRIG3 | GAPDH, liver | MMP-12 | 0.867 |
| 7 | Kallikrein 7 | GAPDH, liver | MMP-12 | 0.867 |

TABLE 23-continued

100 Panels of three biomarkers including MMP-12

| | Markers | | | AUC |
|---|---|---|---|---|
| 8 | MMP-7 | CSK | MMP-12 | 0.867 |
| 9 | RAC1 | C9 | MMP-12 | 0.865 |
| 10 | CSK | Kallikrein 7 | MMP-12 | 0.865 |
| 11 | IGFBP-2 | GAPDH, liver | MMP-12 | 0.864 |
| 12 | CDK5/p35 | GAPDH, liver | MMP-12 | 0.862 |
| 13 | C9 | TCTP | MMP-12 | 0.862 |
| 14 | C9 | Cyclophilin A | MMP-12 | 0.862 |
| 15 | LRIG3 | CSK | MMP-12 | 0.862 |
| 16 | SCF sR | CSK | MMP-12 | 0.861 |
| 17 | SCF sR | GAPDH, liver | MMP-12 | 0.861 |
| 18 | IGFBP-2 | CSK | MMP-12 | 0.860 |
| 19 | MMP-7 | TCTP | MMP-12 | 0.860 |
| 20 | b-ECGF | GAPDH, liver | MMP-12 | 0.860 |
| 21 | ERBB1 | CSK | MMP-12 | 0.859 |
| 22 | RAC1 | BMP-1 | MMP-12 | 0.858 |
| 23 | LRIG3 | TCTP | MMP-12 | 0.858 |
| 24 | ERBB1 | GAPDH, liver | MMP-12 | 0.857 |
| 25 | BMP-1 | TCTP | MMP-12 | 0.857 |
| 26 | RGM-C | CSK | MMP-12 | 0.857 |
| 27 | CSK | b-ECGF | MMP-12 | 0.856 |
| 28 | RAC1 | Kallikrein 7 | MMP-12 | 0.856 |
| 29 | CDK5/p35 | CSK | MMP-12 | 0.856 |
| 30 | HMG-1 | MMP-7 | MMP-12 | 0.856 |
| 31 | CK-MB | GAPDH, liver | MMP-12 | 0.855 |
| 32 | RAC1 | CDK5/p35 | MMP-12 | 0.855 |
| 33 | CSK | Thrombospondin-1 | MMP-12 | 0.854 |
| 34 | C9 | BTK | MMP-12 | 0.854 |
| 35 | RAC1 | LRIG3 | MMP-12 | 0.854 |
| 36 | HSP 90a | C9 | MMP-12 | 0.854 |
| 37 | Activin A | GAPDH, liver | MMP-12 | 0.854 |
| 38 | HSP 90a | BMP-1 | MMP-12 | 0.854 |
| 39 | Endostatin | CSK | MMP-12 | 0.853 |
| 40 | CSK | GAPDH, liver | MMP-12 | 0.853 |
| 41 | BMP-1 | Cyclophilin A | MMP-12 | 0.853 |
| 42 | ERBB1 | TCTP | MMP-12 | 0.853 |
| 43 | GAPDH, liver | TCTP | MMP-12 | 0.853 |
| 44 | LGMN | GAPDH, liver | MMP-12 | 0.853 |
| 45 | HSP 90a | LRIG3 | MMP-12 | 0.853 |
| 46 | C9 | Kallikrein 7 | MMP-12 | 0.852 |
| 47 | SCF sR | LRIG3 | MMP-12 | 0.852 |
| 48 | Calpain I | C9 | MMP-12 | 0.852 |
| 49 | C9 | Catalase | MMP-12 | 0.852 |
| 50 | HMG-1 | C9 | MMP-12 | 0.852 |
| 51 | C9 | LRIG3 | MMP-12 | 0.852 |
| 52 | LRIG3 | Kallikrein 7 | MMP-12 | 0.852 |
| 53 | SCF sR | TCTP | MMP-12 | 0.851 |
| 54 | SCF sR | Cyclophilin A | MMP-12 | 0.851 |
| 55 | BMP-1 | UBE2N | MMP-12 | 0.851 |
| 56 | Kallikrein 7 | TCTP | MMP-12 | 0.851 |
| 57 | MMP-7 | UBE2N | MMP-12 | 0.851 |
| 58 | MMP-7 | RAC1 | MMP-12 | 0.851 |
| 59 | Kallikrein 7 | Cyclophilin A | MMP-12 | 0.850 |
| 60 | MIP-5 | GAPDH, liver | MMP-12 | 0.850 |
| 61 | CSK | CK-MB | MMP-12 | 0.850 |
| 62 | MMP-7 | Cyclophilin A | MMP-12 | 0.850 |
| 63 | CSK | LGMN | MMP-12 | 0.850 |
| 64 | RGM-C | GAPDH, liver | MMP-12 | 0.850 |
| 65 | CDK5/p35 | TCTP | MMP-12 | 0.850 |
| 66 | PTN | GAPDH, liver | MMP-12 | 0.850 |
| 67 | Adiponectin | GAPDH, liver | MMP-12 | 0.850 |
| 68 | LRIG3 | UBE2N | MMP-12 | 0.849 |
| 69 | Thrombospondin-1 | GAPDH, liver | MMP-12 | 0.849 |
| 70 | SCF sR | C9 | MMP-12 | 0.849 |
| 71 | CSK | Catalase | MMP-12 | 0.849 |
| 72 | Endostatin | GAPDH, liver | MMP-12 | 0.849 |
| 73 | SCF sR | RAC1 | MMP-12 | 0.849 |
| 74 | RAC1 | b-ECGF | MMP-12 | 0.849 |
| 75 | TPSB2 | GAPDH, liver | MMP-12 | 0.849 |
| 76 | C9 | UBE2N | MMP-12 | 0.849 |
| 77 | b-ECGF | TCTP | MMP-12 | 0.849 |
| 78 | C9 | IMB1 | MMP-12 | 0.849 |
| 79 | Calpain I | GAPDH, liver | MMP-12 | 0.848 |
| 80 | CSK | IL-8 | MMP-12 | 0.848 |
| 81 | CSK | Adiponectin | MMP-12 | 0.848 |
| 82 | Kallikrein 7 | IMB1 | MMP-12 | 0.848 |
| 83 | Calpain I | CSK | MMP-12 | 0.848 |
| 84 | Macrophage mannose receptor | GAPDH, liver | MMP-12 | 0.848 |
| 85 | SCF sR | CDK5/p35 | MMP-12 | 0.848 |
| 86 | IGFBP-2 | Cyclophilin A | MMP-12 | 0.848 |
| 87 | CDK5/p35 | BTK | MMP-12 | 0.848 |
| 88 | Macrophage mannose receptor | CSK | MMP-12 | 0.847 |
| 89 | Cadherin E | IGFBP-2 | MMP-12 | 0.847 |
| 90 | Thrombospondin-1 | TCTP | MMP-12 | 0.847 |
| 91 | ERBB1 | C9 | MMP-12 | 0.847 |
| 92 | RAC1 | RGM-C | MMP-12 | 0.847 |
| 93 | ERBB1 | Cyclophilin A | MMP-12 | 0.847 |
| 94 | CXCL16, soluble | GAPDH, liver | MMP-12 | 0.847 |
| 95 | RGM-C | Cyclophilin A | MMP-12 | 0.847 |
| 96 | LRIG3 | Cyclophilin A | MMP-12 | 0.847 |
| 97 | ERBB1 | RAC1 | MMP-12 | 0.847 |
| 98 | Kallikrein 7 | UBE2N | MMP-12 | 0.847 |
| 99 | MMP-7 | LRIG3 | MMP-12 | 0.847 |
| 100 | BMP-1 | BTK | MMP-12 | 0.847 |

TABLE 24

100 Panels of four biomarkers including MMP-12

| | Markers | | | | AUC |
|---|---|---|---|---|---|
| 1 | MMP-7 | C9 | GAPDH, liver | MMP-12 | 0.892 |
| 2 | C9 | LRIG3 | GAPDH, liver | MMP-12 | 0.890 |
| 3 | MMP-7 | LRIG3 | GAPDH, liver | MMP-12 | 0.889 |
| 4 | SCF sR | C9 | GAPDH, liver | MMP-12 | 0.889 |
| 5 | IGFBP-2 | C9 | GAPDH, liver | MMP-12 | 0.889 |
| 6 | C9 | LGMN | GAPDH, liver | MMP-12 | 0.889 |
| 7 | IGFBP-2 | MMP-7 | GAPDH, liver | MMP-12 | 0.889 |
| 8 | MMP-7 | BMP-1 | GAPDH, liver | MMP-12 | 0.889 |
| 9 | C9 | Kallikrein 7 | GAPDH, liver | MMP-12 | 0.889 |
| 10 | C9 | BMP-1 | GAPDH, liver | MMP-12 | 0.888 |
| 11 | ERBB1 | C9 | GAPDH, liver | MMP-12 | 0.887 |
| 12 | MMP-7 | CDK5/p35 | GAPDH, liver | MMP-12 | 0.886 |
| 13 | C9 | b-ECGF | GAPDH, liver | MMP-12 | 0.886 |
| 14 | Cadherin E | MMP-7 | GAPDH, liver | MMP-12 | 0.885 |
| 15 | MMP-7 | TPSB2 | GAPDH, liver | MMP-12 | 0.885 |
| 16 | Macrophage mannose receptor | C9 | GAPDH, liver | MMP-12 | 0.885 |
| 17 | MMP-7 | IGFBP-7 | GAPDH, liver | MMP-12 | 0.885 |
| 18 | MMP-7 | CSK | GAPDH, liver | MMP-12 | 0.884 |

TABLE 24-continued

| | | 100 Panels of four biomarkers including MMP-12 | | | |
|---|---|---|---|---|---|
| | | Markers | | | AUC |
| 19 | MMP-7 | b-ECGF | GAPDH, liver | MMP-12 | 0.884 |
| 20 | C9 | Adiponectin | GAPDH, liver | MMP-12 | 0.884 |
| 21 | C9 | TPSB2 | GAPDH, liver | MMP-12 | 0.884 |
| 22 | HMG-1 | MMP-7 | CSK | MMP-12 | 0.884 |
| 23 | SCF sR | MMP-7 | GAPDH, liver | MMP-12 | 0.884 |
| 24 | MMP-7 | Thrombospondin-1 | GAPDH, liver | MMP-12 | 0.883 |
| 25 | CXCL16, soluble | C9 | GAPDH, liver | MMP-12 | 0.883 |
| 26 | MMP-7 | Kallikrein 7 | GAPDH, liver | MMP-12 | 0.883 |
| 27 | C9 | MIP-5 | GAPDH, liver | MMP-12 | 0.883 |
| 28 | SCF sR | BMP-1 | GAPDH, liver | MMP-12 | 0.883 |
| 29 | C9 | CSK | LGMN | MMP-12 | 0.883 |
| 30 | C9 | GAPDH, liver | LDH-H 1 | MMP-12 | 0.882 |
| 31 | C9 | RGM-C | GAPDH, liver | MMP-12 | 0.882 |
| 32 | Macrophage mannose receptor | MMP-7 | GAPDH, liver | MMP-12 | 0.882 |
| 33 | Endostatin | C9 | GAPDH, liver | MMP-12 | 0.882 |
| 34 | MMP-7 | RGM-C | GAPDH, liver | MMP-12 | 0.882 |
| 35 | LRIG3 | Kallikrein 7 | GAPDH, liver | MMP-12 | 0.882 |
| 36 | C9 | Cadherin-6 | GAPDH, liver | MMP-12 | 0.882 |
| 37 | MMP-7 | LRIG3 | CSK | MMP-12 | 0.882 |
| 38 | MMP-7 | GAPDH, liver | TCTP | MMP-12 | 0.882 |
| 39 | C9 | CSK | Kallikrein 7 | MMP-12 | 0.881 |
| 40 | MMP-7 | GAPDH, liver | LDH-H 1 | MMP-12 | 0.881 |
| 41 | MMP-7 | LGMN | GAPDH, liver | MMP-12 | 0.881 |
| 42 | ERBB1 | MMP-7 | GAPDH, liver | MMP-12 | 0.881 |
| 43 | HMG-1 | MMP-7 | GAPDH, liver | MMP-12 | 0.881 |
| 44 | IGFBP-2 | Kallikrein 7 | GAPDH, liver | MMP-12 | 0.881 |
| 45 | C9 | Thrombospondin-1 | GAPDH, liver | MMP-12 | 0.881 |
| 46 | C9 | CDK5/p35 | GAPDH, liver | MMP-12 | 0.881 |
| 47 | ERBB1 | C9 | CSK | MMP-12 | 0.881 |
| 48 | MMP-7 | BMP-1 | CSK | MMP-12 | 0.881 |
| 49 | Cadherin E | MMP-7 | CSK | MMP-12 | 0.881 |
| 50 | SCF sR | CDK5/p35 | GAPDH, liver | MMP-12 | 0.881 |
| 51 | C9 | RGM-C | CSK | MMP-12 | 0.881 |
| 52 | C9 | GAPDH, liver | NACA | MMP-12 | 0.880 |
| 53 | C9 | LRIG3 | CSK | MMP-12 | 0.880 |
| 54 | MMP-7 | Adiponectin | GAPDH, liver | MMP-12 | 0.880 |
| 55 | C9 | CSK | GAPDH, liver | MMP-12 | 0.880 |
| 56 | LRIG3 | BMP-1 | GAPDH, liver | MMP-12 | 0.880 |
| 57 | MMP-7 | PTN | GAPDH, liver | MMP-12 | 0.880 |
| 58 | C9 | CSK | Thrombospondin-1 | MMP-12 | 0.880 |
| 59 | Activin A | C9 | GAPDH, liver | MMP-12 | 0.880 |
| 60 | Endostatin | C9 | CSK | MMP-12 | 0.880 |
| 61 | IGFBP-2 | BMP-1 | GAPDH, liver | MMP-12 | 0.880 |
| 62 | IGFBP-2 | LRIG3 | GAPDH, liver | MMP-12 | 0.880 |
| 63 | SCF sR | MMP-7 | CSK | MMP-12 | 0.880 |
| 64 | Cadherin E | C9 | GAPDH, liver | MMP-12 | 0.880 |
| 65 | SCF sR | LRIG3 | GAPDH, liver | MMP-12 | 0.880 |
| 66 | Calpain I | C9 | GAPDH, liver | MMP-12 | 0.879 |
| 67 | RAC1 | C9 | Kallikrein 7 | MMP-12 | 0.879 |
| 68 | C9 | LRIG3 | TCTP | MMP-12 | 0.879 |
| 69 | C9 | CDK5/p35 | CSK | MMP-12 | 0.879 |
| 70 | C9 | CSK | LDH-H 1 | MMP-12 | 0.879 |
| 71 | ERBB1 | MMP-7 | CSK | MMP-12 | 0.879 |
| 72 | Activin A | MMP-7 | GAPDH, liver | MMP-12 | 0.879 |
| 73 | IGFBP-2 | Thrombospondin-1 | GAPDH, liver | MMP-12 | 0.879 |
| 74 | C9 | Proteinase-3 | GAPDH, liver | MMP-12 | 0.878 |
| 75 | vWF | C9 | GAPDH, liver | MMP-12 | 0.878 |
| 76 | MMP-7 | CNDP1 | GAPDH, liver | MMP-12 | 0.878 |
| 77 | C9 | BMP-1 | CSK | MMP-12 | 0.878 |
| 78 | C9 | CK-MB | GAPDH, liver | MMP-12 | 0.878 |
| 79 | IGFBP-2 | MMP-7 | CSK | MMP-12 | 0.878 |
| 80 | MMP-7 | GAPDH, liver | Fibronectin | MMP-12 | 0.878 |
| 81 | MMP-7 | CD30 Ligand | GAPDH, liver | MMP-12 | 0.878 |
| 82 | C9 | CDK5/p35 | TCTP | MMP-12 | 0.878 |
| 83 | C9 | CNDP1 | GAPDH, liver | MMP-12 | 0.878 |
| 84 | Calpain I | C9 | CSK | MMP-12 | 0.878 |
| 85 | MMP-7 | C9 | CSK | MMP-12 | 0.877 |
| 86 | MMP-7 | CK-MB | GAPDH, liver | MMP-12 | 0.877 |
| 87 | Calpain I | MMP-7 | GAPDH, liver | MMP-12 | 0.877 |
| 88 | SCF sR | C9 | CSK | MMP-12 | 0.877 |
| 89 | MMP-7 | Cadherin-6 | GAPDH, liver | MMP-12 | 0.877 |
| 90 | MMP-7 | Catalase | GAPDH, liver | MMP-12 | 0.877 |
| 91 | MMP-7 | CDK5/p35 | CSK | MMP-12 | 0.877 |
| 92 | MMP-7 | RAC1 | GAPDH, liver | MMP-12 | 0.877 |
| 93 | SCF sR | Kallikrein 7 | GAPDH, liver | MMP-12 | 0.877 |

TABLE 24-continued

100 Panels of four biomarkers including MMP-12

| | Markers | | | | AUC |
|---|---|---|---|---|---|
| 94 | C9 | Catalase | GAPDH, liver | MMP-12 | 0.877 |
| 95 | C9 | FGF-17 | GAPDH, liver | MMP-12 | 0.877 |
| 96 | HMG-1 | MMP-7 | TCTP | MMP-12 | 0.877 |
| 97 | ERBB1 | C9 | TCTP | MMP-12 | 0.877 |
| 98 | MMP-7 | GAPDH, liver | NACA | MMP-12 | 0.877 |
| 99 | ERBB1 | BMP-1 | GAPDH, liver | MMP-12 | 0.877 |
| 100 | HSP 90a | C9 | LRIG3 | MMP-12 | 0.877 |

TABLE 25

100 Panels of five biomarkers including MMP-12

| | Markers | | | | | AUC |
|---|---|---|---|---|---|---|
| 1 | C9 | LRIG3 | Kallikrein 7 | GAPDH, liver | MMP-12 | 0.900 |
| 2 | MMP-7 | C9 | LRIG3 | GAPDH, liver | MMP-12 | 0.900 |
| 3 | SCF sR | C9 | LRIG3 | GAPDH, liver | MMP-12 | 0.900 |
| 4 | SCF sR | C9 | BMP-1 | GAPDH, liver | MMP-12 | 0.898 |
| 5 | IGFBP-2 | MMP-7 | LRIG3 | GAPDH, liver | MMP-12 | 0.898 |
| 6 | IGFBP-2 | C9 | Kallikrein 7 | GAPDH, liver | MMP-12 | 0.897 |
| 7 | MMP-7 | C9 | BMP-1 | GAPDH, liver | MMP-12 | 0.897 |
| 8 | MMP-7 | C9 | TPSB2 | GAPDH, liver | MMP-12 | 0.897 |
| 9 | IGFBP-2 | MMP-7 | Thrombospondin-1 | GAPDH, liver | MMP-12 | 0.897 |
| 10 | MMP-7 | C9 | RGM-C | GAPDH, liver | MMP-12 | 0.897 |
| 11 | HMG-1 | MMP-7 | C9 | GAPDH, liver | MMP-12 | 0.897 |
| 12 | Macrophage mannose receptor | C9 | LRIG3 | GAPDH, liver | MMP-12 | 0.897 |
| 13 | C9 | LRIG3 | LGMN | GAPDH, liver | MMP-12 | 0.897 |
| 14 | C9 | Kallikrein 7 | LGMN | GAPDH, liver | MMP-12 | 0.897 |
| 15 | Cadherin E | MMP-7 | BMP-1 | GAPDH, liver | MMP-12 | 0.897 |
| 16 | Macrophage mannose receptor | C9 | Kallikrein 7 | GAPDH, liver | MMP-12 | 0.897 |
| 17 | MMP-7 | C9 | Kallikrein 7 | GAPDH, liver | MMP-12 | 0.896 |
| 18 | Cadherin E | IGFBP-2 | MMP-7 | GAPDH, liver | MMP-12 | 0.896 |
| 19 | MMP-7 | C9 | b-ECGF | GAPDH, liver | MMP-12 | 0.896 |
| 20 | IGFBP-2 | C9 | Thrombospondin-1 | GAPDH, liver | MMP-12 | 0.896 |
| 21 | SCF sR | C9 | CDK5/p35 | GAPDH, liver | MMP-12 | 0.896 |
| 22 | C9 | BMP-1 | LGMN | GAPDH, liver | MMP-12 | 0.896 |
| 23 | MMP-7 | LRIG3 | BMP-1 | GAPDH, liver | MMP-12 | 0.896 |
| 24 | MMP-7 | C9 | CDK5/p35 | GAPDH, liver | MMP-12 | 0.896 |
| 25 | SCF sR | MMP-7 | CDK5/p35 | GAPDH, liver | MMP-12 | 0.896 |
| 26 | SCF sR | MMP-7 | BMP-1 | GAPDH, liver | MMP-12 | 0.896 |
| 27 | IGFBP-2 | C9 | LRIG3 | GAPDH, liver | MMP-12 | 0.896 |
| 28 | SCF sR | MMP-7 | C9 | GAPDH, liver | MMP-12 | 0.895 |
| 29 | Macrophage mannose receptor | ERBB1 | C9 | GAPDH, liver | MMP-12 | 0.895 |
| 30 | IGFBP-2 | MMP-7 | Kallikrein 7 | GAPDH, liver | MMP-12 | 0.895 |
| 31 | IGFBP-2 | MMP-7 | CDK5/p35 | GAPDH, liver | MMP-12 | 0.895 |
| 32 | MMP-7 | C9 | GAPDH, liver | LDH-H 1 | MMP-12 | 0.895 |
| 33 | IGFBP-2 | MMP-7 | C9 | GAPDH, liver | MMP-12 | 0.895 |
| 34 | Macrophage mannose receptor | MMP-7 | C9 | GAPDH, liver | MMP-12 | 0.895 |
| 35 | MMP-7 | IGFBP-7 | BMP-1 | GAPDH, liver | MMP-12 | 0.895 |
| 36 | C9 | BMP-1 | Kallikrein 7 | GAPDH, liver | MMP-12 | 0.895 |
| 37 | SCF sR | MMP-7 | LRIG3 | GAPDH, liver | MMP-12 | 0.895 |
| 38 | SCF sR | IGFBP-2 | MMP-7 | GAPDH, liver | MMP-12 | 0.895 |
| 39 | C9 | b-ECGF | LGMN | GAPDH, liver | MMP-12 | 0.895 |
| 40 | MMP-7 | C9 | LGMN | GAPDH, liver | MMP-12 | 0.895 |
| 41 | SCF sR | HMG-1 | MMP-7 | CSK | MMP-12 | 0.895 |
| 42 | IGFBP-2 | MMP-7 | IGFBP-7 | GAPDH, liver | MMP-12 | 0.895 |
| 43 | Cadherin E | MMP-7 | CDK5/p35 | GAPDH, liver | MMP-12 | 0.895 |
| 44 | MMP-7 | C9 | Thrombospondin-1 | GAPDH, liver | MMP-12 | 0.895 |
| 45 | Macrophage mannose receptor | MMP-7 | LRIG3 | GAPDH, liver | MMP-12 | 0.895 |
| 46 | MMP-7 | IGFBP-7 | LRIG3 | GAPDH, liver | MMP-12 | 0.895 |
| 47 | IGFBP-2 | MMP-7 | BMP-1 | GAPDH, liver | MMP-12 | 0.895 |
| 48 | MMP-7 | BMP-1 | CSK | GAPDH, liver | MMP-12 | 0.895 |
| 49 | MMP-7 | LRIG3 | Kallikrein 7 | GAPDH, liver | MMP-12 | 0.895 |
| 50 | IGFBP-2 | MMP-7 | TPSB2 | GAPDH, liver | MMP-12 | 0.895 |
| 51 | MMP-7 | BMP-1 | GAPDH, liver | LDH-H 1 | MMP-12 | 0.894 |
| 52 | C9 | Kallikrein 7 | TPSB2 | GAPDH, liver | MMP-12 | 0.894 |
| 53 | Cadherin E | MMP-7 | b-ECGF | GAPDH, liver | MMP-12 | 0.894 |
| 54 | SCF sR | C9 | Kallikrein 7 | GAPDH, liver | MMP-12 | 0.894 |

TABLE 25-continued

100 Panels of five biomarkers including MMP-12

| | Markers | | | | | AUC |
|---|---|---|---|---|---|---|
| 55 | IGFBP-2 | MMP-7 | GAPDH, liver | LDH-H 1 | MMP-12 | 0.894 |
| 56 | SCF sR | C9 | Thrombospondin-1 | GAPDH, liver | MMP-12 | 0.894 |
| 57 | MMP-7 | BMP-1 | Thrombospondin-1 | GAPDH, liver | MMP-12 | 0.894 |
| 58 | MMP-7 | C9 | CSK | GAPDH, liver | MMP-12 | 0.894 |
| 59 | Endostatin | C9 | LRIG3 | GAPDH, liver | MMP-12 | 0.894 |
| 60 | C9 | LRIG3 | Thrombospondin-1 | GAPDH, liver | MMP-12 | 0.894 |
| 61 | C9 | LRIG3 | BMP-1 | GAPDH, liver | MMP-12 | 0.894 |
| 62 | IGFBP-2 | MMP-7 | b-ECGF | GAPDH, liver | MMP-12 | 0.894 |
| 63 | IGFBP-2 | MMP-7 | LGMN | GAPDH, liver | MMP-12 | 0.894 |
| 64 | MMP-7 | C9 | Cadherin-6 | GAPDH, liver | MMP-12 | 0.894 |
| 65 | Cadherin E | MMP-7 | C9 | GAPDH, liver | MMP-12 | 0.894 |
| 66 | HMG-1 | MMP-7 | C9 | CSK | MMP-12 | 0.894 |
| 67 | SCF sR | C9 | Adiponectin | GAPDH, liver | MMP-12 | 0.894 |
| 68 | CXCL16, soluble | C9 | LRIG3 | GAPDH, liver | MMP-12 | 0.894 |
| 69 | IGFBP-2 | MMP-7 | CSK | GAPDH, liver | MMP-12 | 0.894 |
| 70 | SCF sR | Macrophage mannose receptor | C9 | GAPDH, liver | MMP-12 | 0.894 |
| 71 | MMP-7 | C9 | Adiponectin | GAPDH, liver | MMP-12 | 0.894 |
| 72 | Cadherin E | MMP-7 | TPSB2 | GAPDH, liver | MMP-12 | 0.894 |
| 73 | C9 | LRIG3 | Cadherin-6 | GAPDH, liver | MMP-12 | 0.894 |
| 74 | MMP-7 | LRIG3 | CSK | GAPDH, liver | MMP-12 | 0.894 |
| 75 | MMP-7 | LRIG3 | Thrombospondin-1 | GAPDH, liver | MMP-12 | 0.894 |
| 76 | ERBB1 | MMP-7 | C9 | GAPDH, liver | MMP-12 | 0.894 |
| 77 | ERBB1 | C9 | BMP-1 | GAPDH, liver | MMP-12 | 0.894 |
| 78 | ERBB1 | C9 | LGMN | GAPDH, liver | MMP-12 | 0.894 |
| 79 | C9 | Adiponectin | LGMN | GAPDH, liver | MMP-12 | 0.894 |
| 80 | MMP-7 | BMP-1 | CDK5/p35 | GAPDH, liver | MMP-12 | 0.893 |
| 81 | MMP-7 | BMP-1 | LGMN | GAPDH, liver | MMP-12 | 0.893 |
| 82 | C9 | LRIG3 | GAPDH, liver | NACA | MMP-12 | 0.893 |
| 83 | C9 | Kallikrein 7 | GAPDH, liver | LDH-H 1 | MMP-12 | 0.893 |
| 84 | C9 | Kallikrein 7 | Adiponectin | GAPDH, liver | MMP-12 | 0.893 |
| 85 | IGFBP-2 | MMP-7 | Cadherin-6 | GAPDH, liver | MMP-12 | 0.893 |
| 86 | IGFBP-2 | C9 | LGMN | GAPDH, liver | MMP-12 | 0.893 |
| 87 | MMP-7 | BMP-1 | TPSB2 | GAPDH, liver | MMP-12 | 0.893 |
| 88 | C9 | LRIG3 | Adiponectin | GAPDH, liver | MMP-12 | 0.893 |
| 89 | C9 | TPSB2 | LGMN | GAPDH, liver | MMP-12 | 0.893 |
| 90 | MMP-7 | C9 | CD30 Ligand | GAPDH, liver | MMP-12 | 0.893 |
| 91 | Cadherin E | MMP-7 | LRIG3 | GAPDH, liver | MMP-12 | 0.893 |
| 92 | SCF sR | IGFBP-2 | C9 | GAPDH, liver | MMP-12 | 0.893 |
| 93 | HMG-1 | IGFBP-2 | MMP-7 | GAPDH, liver | MMP-12 | 0.893 |
| 94 | SCF sR | Cadherin E | MMP-7 | GAPDH, liver | MMP-12 | 0.893 |
| 95 | SCF sR | MMP-7 | Thrombospondin-1 | GAPDH, liver | MMP-12 | 0.893 |
| 96 | IGFBP-2 | C9 | BMP-1 | GAPDH, liver | MMP-12 | 0.893 |
| 97 | MMP-7 | LRIG3 | GAPDH, liver | TCTP | MMP-12 | 0.893 |
| 98 | C9 | LRIG3 | GAPDH, liver | LDH-H 1 | MMP-12 | 0.893 |
| 99 | SCF sR | C9 | TPSB2 | GAPDH, liver | MMP-12 | 0.893 |
| 100 | IGFBP-2 | Macrophage mannose receptor | MMP-7 | GAPDH, liver | MMP-12 | 0.893 |

What is claimed is:

1. A method comprising the following steps:
   a) contacting a biological sample from a human with a set of N capture reagents, wherein N is any integer from 5 to 20, wherein the biological sample is selected from the group consisting of whole blood, plasma, and serum, further wherein the capture reagents are aptamers comprising a 5-position pyrimidine modification, further wherein each capture reagent specifically binds to a different protein of the set of proteins comprising at least ERBB1, SCFsR, WIMP-12, C9 and MMP-7;
   b) measuring the level of each protein of the set of proteins based on measurement of the capture reagents;
   c) applying a trained nave Bayes classifier, trained with data from a lung cancer negative group and a lung cancer positive group, to the measured level of each of the different proteins in order to calculate an individual log-likelihood ratio for each of the different proteins;
   d) determining a risk level of the human for having lung cancer based on the sum of each log-likelihood ratio for each of the different proteins plus a term to account for the prevalence of lung cancer in a population comprising the human; and
   e) administering a treatment selected from the group consisting of a cancer vaccine, radiation, drug therapy, surgery and a combination thereof to the subject.

2. The method of claim 1, wherein measurement of the protein levels comprises performing an in vitro assay.

3. The method of claim 1, wherein the biological sample is serum.

4. The method of claim 1, wherein the human is a smoker.

5. The method of claim 1, wherein the human has a pulmonary nodule.

* * * * *

UNITED STATES PATENT AND TRADEMARK OFFICE
CERTIFICATE OF CORRECTION

PATENT NO. : 11,221,340 B2
APPLICATION NO. : 15/993132
DATED : January 11, 2022
INVENTOR(S) : Sheri K. Wilcox et al.

Page 1 of 1

It is certified that error appears in the above-identified patent and that said Letters Patent is hereby corrected as shown below:

In the Claims

In Claim 1, at Column 117, Line 56, "WIMP-12" should read --MMP-12--; and

In Claim 1, at Column 117, Line 59, "nave" should read --naïve--.

Signed and Sealed this
Nineteenth Day of April, 2022

Katherine Kelly Vidal
*Director of the United States Patent and Trademark Office*